(12) United States Patent
Rhodes et al.

(10) Patent No.: US 11,746,379 B2
(45) Date of Patent: Sep. 5, 2023

(54) GENE FUSIONS AND GENE VARIANTS ASSOCIATED WITH CANCER

(71) Applicant: Life Technologies Corporation, Carlsbad, CA (US)

(72) Inventors: Daniel Rhodes, Ann Arbor, MI (US); Seth Sadis, Ann Arbor, MI (US); Peter Wyngaard, Ann Arbor, MI (US); Nikolay Khazanov, Ann Arbor, MI (US); Santhoshi Bandla, Northville, MI (US); Mark Tomilo, Ann Arbor, MI (US); Sean Eddy, Ann Arbor, MI (US); Emma Bowden, Ann Arbor, MI (US); Jia Li, Northville, MI (US)

(73) Assignee: Life Technologies Corporation, Carlsbad, CA (US)

(*) Notice: Subject to any disclaimer, the term of this patent is extended or adjusted under 35 U.S.C. 154(b) by 283 days.

(21) Appl. No.: 16/103,516

(22) Filed: Aug. 14, 2018

(65) Prior Publication Data

US 2019/0040472 A1  Feb. 7, 2019

Related U.S. Application Data

(60) Division of application No. 14/672,066, filed on Mar. 27, 2015, now Pat. No. 10,072,298, which is a continuation-in-part of application No. 14/214,300, filed on Mar. 14, 2014, now abandoned.

(60) Provisional application No. 62/092,898, filed on Dec. 17, 2014, provisional application No. 62/004,727, filed on May 29, 2014, provisional application No. 61/993,732, filed on May 15, 2014, provisional application No. 61/971,455, filed on Mar. 27, 2014, (Continued)

(51) Int. Cl.
| | | |
|---|---|---|
| C12Q 1/6886 | (2018.01) | |
| G16B 20/20 | (2019.01) | |
| G16B 20/00 | (2019.01) | |
| G16B 30/00 | (2019.01) | |
| G16B 40/00 | (2019.01) | |

(52) U.S. Cl.
CPC .......... *C12Q 1/6886* (2013.01); *G16B 20/20* (2019.02); *C12Q 2600/156* (2013.01); *C12Q 2600/158* (2013.01); *C12Q 2600/16* (2013.01); *G16B 20/00* (2019.02); *G16B 30/00* (2019.02); *G16B 40/00* (2019.02)

(58) Field of Classification Search
CPC .................................................. C12Q 1/6886
See application file for complete search history.

(56) References Cited

U.S. PATENT DOCUMENTS

| 7,687,247 B1 | 3/2010 | Hartley et al. |
|---|---|---|
| 2009/0111097 A1 | 4/2009 | Kopreski et al. |
| 2014/0288116 A1 | 9/2014 | Bandla et al. |

FOREIGN PATENT DOCUMENTS

| CN | 101466721 | 6/2009 |
|---|---|---|
| CN | 102234681 | 11/2011 |

(Continued)

OTHER PUBLICATIONS

Ahern, H. The Scientist 9(15):20. (Year: 1995).*
(Continued)

*Primary Examiner* — Diana B Johannsen
(74) *Attorney, Agent, or Firm* — Klarquist Sparkman, LLP

(57) ABSTRACT

The disclosure provides gene fusions, gene variants, and novel associations with disease states, as well as kits, probes, and methods of using the same.

5 Claims, 13 Drawing Sheets

Specification includes a Sequence Listing.

Gene Fusion RNASeq data processing workflow

Related U.S. Application Data provisional application No. 61/940,226, filed on Feb. 14, 2014, provisional application No. 61/935,650, filed on Feb. 4, 2014, provisional application No. 61/915,392, filed on Dec. 12, 2013, provisional application No. 61/907,939, filed on Nov. 22, 2013, provisional application No. 61/860,115, filed on Jul. 30, 2013, provisional application No. 61/824,253, filed on May 16, 2013, provisional application No. 61/813,465, filed on Apr. 18, 2013, provisional application No. 61/813,182, filed on Apr. 17, 2013.

(56) References Cited

FOREIGN PATENT DOCUMENTS

| CN | 102533945 A | 7/2012 | |
|---|---|---|---|
| CN | 102575287 | 7/2012 | |
| CN | 103468813 A | 12/2013 | |
| WO | WO-9947706 A1 * | 9/1999 | ........... C12Q 1/6874 |
| WO | WO-2008/127248 A1 | 10/2008 | |
| WO | WO-2010/132888 | 11/2010 | |
| WO | WO-2010/132888 A2 | 11/2010 | |
| WO | WO-2013/006195 | 1/2013 | |
| WO | WO-2013/059740 | 4/2013 | |
| WO | WO-2013/089882 | 6/2013 | |

OTHER PUBLICATIONS

Bijapur, J. et al. Nucleic Acids Research 27(8):1802-1809. (Year: 1999).*
Cheuk, W. et al., "Timely Topic: Anaplastic Lymphoma Kinase (ELk) Spreads its Influence", *Pathology*, vol. 33, No. 1, Jan. 1, 2001, 7-12.
EP18189042.7, , "EP Search Report", dated Oct. 22, 2018, 1-4.
Thompson, Floyd H. et al., "Amplification of 19q13.1-q13.2 Sequences in Ovarian Cancer", *Cancer Genetics and Cytogenetics*, vol. 87, No. 1, Mar. 1, 1996, 55-62.
Kelly L.M., et al., "Identification of the Transforming STRN-ALK Fusion as a Potential Therapeutic Target in the Aggressive Forms of Thyroid Cancer", PNAS, vol. 111, No. 11, Mar. 18, 2014, pp. 4233-4238.
Kim J., et al., "NTRK1 Fusion in Glioblastoma Multiforme", PLoS One, Mar. 19, 2014, vol. 9, No. 3, pp. e91940, doi: 10.1371/journal.pone.0091940.
Armstrong, Florence et al., "TPM3-ALK expression induces changes in cytoskeleton organisation and confers higher metastatic capacities than other ALK fusion proteins", Armstrong, F., et al, *TPM3-ALK expression induces changes in cytoskeleton organisation and confers higher metastatic capacities than other ALK fusion proteins, European Journal of Cancer* 43 (2007) 640-646, Feb. 2, 2007, 640-646.
Bridge, J. et al., "Short Communication: Fusion of the ALK Gene to the Clathrin Heavy Chain Gene, CLTC, in Inflammatory Myofibroblastic Tumor", *American Journal of Pathology*, vol. 159 (2), Aug. 2001, 411-415.
Davies, et al., "Molecular pathways: ROS1 fusion proteins in cancer.", *Clinical Cancer Research*, vol. 19, No. 15, Aug. 1, 2013, 4040-4045.
Giacomini, et al., "Breakpoint Analysis of Transcriptional and Genomic Profiles Uncovers Novel Gene Fusions Spanning Multiple Human Cancer Types", *PLOS Genetics*, vol. 9, No. 4, Apr. 2013, 1-19 (e1003464).
Halbritter, J. et al., "High-throughput mutation analysis in patients with a nephronophthisis-associated ciliopathy applying multiplexed barcoded array-based PCR amplification and next-generation sequencing", *J. Med. Genet.*, 49, 2012, 756-767.

Heist, R. S. et al., "SnapShot: Non-Small Cell Lung Cancer", *Cancer Cell*, vol. 21, Mar. 20, 2012, 448-448.e2.
Invitrogen, , "Platinum® SYBR® Green qPCR SuperMix-UDG", Cat. No. 11733-038 Cat. n. 11733-046, Jun. 1, 2010.
Jones, M.A. et al., "Targeted polymerase chain reaction-based enrichment and next generation sequencing for diagnostic testing of congenital disorders of glycosylation", *Genetics in Medicine*, vol. 13, Nov. 2011, 921-932.
Kikuchi, M. et al., "Clinical significance of minimal residual disease in adult acute lymphoblastic Teukemia", *Int. J. Hematol*, vol. 92, Sep. 10, 2010, 481-489.
Kutyavin, I. , "Use of Base Modifications in Primers and Amplicons to Improve Nucleic Acids Detection in the Real-Time Snake Polymerase Chain Reaction", *ASSAY and Drug Development Technologies*, vol. 9 (1), Feb. 2011, 58-68.
Lamant, L. et al., "A new fusion gene TPM3-ALK in anaplastic large cell lymphoma created by a (1:2) (q25;p23) translocation", *Blood*, vol. 93 (9), May 1, 1999, 3088-3095.
Lawrence, Brandon et al., "TPM3-ALK and TPM4-ALK Oncogenes in Inflammatory Myofibroblastic Tumors", Lawrence, B. et al., *TPM3-ALK and TPM4-ALK Oncogenes in Inflammatory Myofibroblastic Tumors, American Journal of Pathology*, 157 (2000) 377-384, Aug. 2000, 377-384.
Li, C. et al., "Spectrum of Oncogenic Driver Mutations in Lung Adenocarcinomas from East Asian Never Smokers", *PLoS One*, vol. 6, No. 11, Nov. 30, 2011, 1-6.
Lin, E. et al., "Exon Array Profiling Detects EML4-ALK Fusion in Breast, Colorectal, and Non-Small Cell Lung Cancers", *Molecular Cancer Research*, vol. 7, Sep. 8, 2009, 1466-1476.
Ma, Z. et al., "Fusion of ALK to the Ran-Binding Protein 2 (RANBP2) Gene in Inflammatory Myofibroblastic Tumor", *Genes, Chromosomes & Cancer*, vol. 37, 2003, 98-105.
Makretsov, M. et al., "A fluorescence in situ hybridization study of ETV6-NTRK3 fusion gene in secretory breast carcinoma", *Genes, Chromosomes & Cancer*, vol. 40, 2004, 152-157.
Meech, S.J. et al., "Unusual childhood extramedullary hematologic malignancy with natural killer cell properties that contains tropomyosin 4-anaplastic lymphoma kinase gene fusion", *Blood*, vol. 98 (4), Aug. 15, 2001, 1209-1216.
Monma, F. et al., "Fluorescent In Situ Hybridization Analysis of Philadelphia Chromosome-Negative Chronic Myeloid Leukemia with the bcr/abl Fusion Gene", *International Journal of Hematology*, vol. 80, 2004, 155-158.
Nanostring Technologies, , "nCounter Leukemia Fusion Gene Expression Assay Overview", Jul. 18, 2011, 1-5.
Pao, W. et al., "Chipping Away at the Lung Cancer Genome", *Nature Medicine*, vol. 18, No. 3, Mar. 2012, 349-351.
PCT/US2014/029592, , "International Search Report and Written Opinion dated Apr. 13, 2015", dated Apr. 13, 2015, 24 Pages.
PCT/US2015/023197, , "International Search Report and Written Opinion", dated Nov. 17, 2015, 16 Pages.
Seo, J. S. et al., "The Transcriptional Landscape and Mutational Profile of Lung Adenocarcinoma", *Genome Research*, vol. 22, No. 11, Sep. 13, 2012, 2109-2119.
Takeuchi, K. et al., "Multiplex Reverse Transcription-PCR Screening for EML4-ALK Fusion Transcripts", *Clinical Cancer Research*, vol. 14, Oct. 16, 2008, 6618-6624.
Vindin, Howard et al., "Cytoskeletal Tropomyosins: choreographers of actin filament functional diversity", *Journal of Muscle Research and Cell Motility, Chapman, London*, vol. 34, No. 3, Aug. 1, 2013, 261-274.
Voelkerding, et al., "Next Generation Sequencing for Clinical Diagnostics—Principles and Application to Targeted Resequencing for Hypertrophic Cardiomyopathy", *Journal of Molecular Diagnostics*, vol. 12, No. 5, 2010, 539-551.
Wan, T. et al., "Diagnostic utility of dual fusion PML/RARa translocation DNA probe (D-FISH) in acute promyelocytic leukemia", *Oncology Reports*, vol. 17, 2007, 799-805.

* cited by examiner

| Variant position | Human Genome Build and Nucleic Acid Start Positions of Variant Alleles | Pan-cancer Patient Count |
| --- | --- | --- |
| p.R273 | 36_7517845, 36_7517846, 37_7577120, 37_7577121 | 134 |
| p.R248 | 36_7518263, 36_7518264, 37_7577538, 37_7577539 | 95 |
| p.R175 | 36_7519131, 36_7519132, 37_7578406, 37_7578407 | 69 |
| p.G245 | 36_7518272, 36_7518273, 37_7577547, 37_7577548 | 45 |
| p.R213 | 36_7518937, 37_7578212 | 41 |
| p.H179 | 36_7519118, 36_7519119, 37_7578393, 37_7578394, 37_7578395 | 40 |
| p.Y220 | 36_7518915, 37_7578190, 37_7578191 | 38 |
| p.H193 | 36_7518996, 36_7518997, 37_7578271, 37_7578272 | 34 |
| p.R282 | 36_7517819, 37_7577093, 37_7577094 | 34 |
| p.R196 | 36_7518988, 37_7578263 | 33 |
| p.R249 | 36_7518259, 36_7518261, 37_7577534, 37_7577535, 37_7577536 | 30 |
| p.R158 | 36_7519183, 37_7578457, 37_7578458 | 27 |
| p.R195 | 36_7518990, 36_7518991, 37_7578264, 37_7578265, 37_7578266 | 24 |
| p.C176 | 36_7519128, 37_7578403, 37_7578404 | 23 |
| p.G266 | 36_7517866, 36_7517867, 37_7577141, 37_7577142 | 22 |
| p.P278 | 36_7517830, 36_7517831, 37_7577105, 37_7577106 | 22 |
| p.T125 | 36_7520037, 36_7520038, 37_7579312, 37_7579313 | 21 |
| p.C238 | 36_7518293, 37_7577567, 37_7577568, 37_7577569 | 20 |
| p.V157 | 36_7519186, 37_7578460, 37_7578461 | 19 |
| p.V173 | 36_7519138, 37_7578412, 37_7578413 | 19 |
| p.R306 | 36_7517747, 37_7577022 | 18 |
| p.R280 | 36_7517824, 36_7517825, 37_7577098, 37_7577099, 37_7577100 | 16 |
| p.Y163 | 36_7519167, 36_7519168, 37_7578442, 37_7578443 | 16 |
| p.K132 | 36_7519259, 36_7519260, 36_7519261, 37_7578534, 37_7578535, 36_7578536 | 15 |
| p.S241 | 36_7518284, 37_7577559, 37_7577560 | 15 |
| p.Y234 | 36_7518305, 36_7518306, 37_7577580 | 15 |
| p.R337 | 36_7514743, 37_7574017, 37_7574018 | 14 |
| p.V216 | 36_7518927, 36_7518928, 37_7578202, 37_7578203 | 14 |

Frequent TP53 mutations by amino acid position

FIG. 9A

| Variant Classification | Overall Frequency (n=5,309 patients) | Frequency Relative to All Observed TP53 Mutations (n=1,985 total TP53 mutations) |
|---|---|---|
| Missense_Mutation | 2.52% | 6.75% |
| Missense_Mutation | 1.79% | 4.79% |
| Missense_Mutation | 1.30% | 3.48% |
| Missense_Mutation | 0.85% | 2.27% |
| Nonsense_Mutation | 0.77% | 2.07% |
| Missense_Mutation | 0.75% | 2.02% |
| Missense_Mutation | 0.72% | 1.91% |
| Missense_Mutation | 0.64% | 1.71% |
| Missense_Mutation | 0.64% | 1.71% |
| Nonsense_Mutation | 0.62% | 1.66% |
| Missense_Mutation | 0.57% | 1.51% |
| Missense_Mutation | 0.51% | 1.36% |
| Missense_Mutation | 0.45% | 1.21% |
| Missense_Mutation | 0.43% | 1.16% |
| Missense_Mutation | 0.41% | 1.11% |
| Missense_Mutation | 0.41% | 1.11% |
| Splice_Site | 0.40% | 1.06% |
| Missense_Mutation | 0.38% | 1.01% |
| Missense_Mutation | 0.36% | 0.96% |
| Missense_Mutation | 0.36% | 0.96% |
| Nonsense_Mutation | 0.34% | 0.91% |
| Missense_Mutation | 0.30% | 0.81% |
| Missense_Mutation | 0.30% | 0.81% |
| Missense_Mutation | 0.28% | 0.76% |
| Missense_Mutation | 0.28% | 0.76% |
| Missense_Mutation | 0.28% | 0.76% |
| Missense_Mutation | 0.26% | 0.71% |
| Missense_Mutation | 0.26% | 0.71% |

Frequent TP53 mutations by amino acid position

FIG. 9B

| Variant position | Human Genome Build and Nucleic Acid Start Positions of Variant Alleles | Patient Count |
|---|---|---|
| p.P177 | 36_7519107, 37_7578384 | 4 |
| p.I255 | 36_7518239, 37_7577515 | 2 |
| p.L252 | 37_7577519, 37_7577525 | 2 |
| p.P128 | 37_7578540, 37_7578542 | 2 |
| p.P191 | 36_7519000 | 2 |
| p.T155 | 37_7578446, 37_7578456 | 2 |
| p.A138 | 37_7578505 | 1 |
| p.A161 | 37_7578444 | 1 |
| p.C277 | 37_7577107 | 1 |
| p.F113 | 37_7579346 | 1 |
| p.G112 | 37_7579343 | 1 |
| p.I162 | 37_7578443 | 1 |
| p.I162 | 37_7578443 | 1 |
| p.K139 | 37_7578506 | 1 |
| p.L264 | 36_7517871 | 1 |
| p.M237 | 36_7518288 | 1 |
| p.N239 | 37_7577558 | 1 |
| p.R110 | 37_7579356 | 1 |
| p.R267 | 37_7577120 | 1 |
| p.R273 | 37_7577102 | 1 |
| p.T253 | 36_7518239 | 1 |
| p.V218 | 37_7578195 | 1 |
| p.V274 | 37_7577115 | 1 |

TP53 in-frame insertion and deletion mutations were rare

FIG. 10A

| Variant Classification | Overall Frequency (n=5,309 patients) | Frequency Relative to All Observed TP53 Mutations (n=1,985 total TP53 mutations) |
|---|---|---|
| In_Frame_Del | 0.08% | 0.20% |
| In_Frame_Del | 0.04% | 0.10% |
| In_Frame_Del | 0.04% | 0.10% |
| In_Frame_Del | 0.04% | 0.10% |
| In_Frame_Del | 0.04% | 0.10% |
| In_Frame_Del | 0.04% | 0.10% |
| In_Frame_Del | 0.02% | 0.05% |
| In_Frame_Del | 0.02% | 0.05% |
| In_Frame_Del | 0.02% | 0.05% |
| In_Frame_Del | 0.02% | 0.05% |
| In_Frame_Del | 0.02% | 0.05% |
| In_Frame_Del | 0.02% | 0.05% |
| In_Frame_Ins | 0.02% | 0.05% |
| In_Frame_Del | 0.02% | 0.05% |
| In_Frame_Ins | 0.02% | 0.05% |
| In_Frame_Del | 0.02% | 0.05% |
| In_Frame_Del | 0.02% | 0.05% |
| In_Frame_Del | 0.02% | 0.05% |
| In_Frame_Del | 0.02% | 0.05% |
| In_Frame_Del | 0.02% | 0.05% |
| In_Frame_Del | 0.02% | 0.05% |
| In_Frame_Del | 0.02% | 0.05% |
| In_Frame_Ins | 0.02% | 0.05% |

TP53 in-frame insertion and deletion mutations were rare

FIG. 10B

GENE FUSIONS AND GENE VARIANTS ASSOCIATED WITH CANCER

RELATED APPLICATIONS

This application is a divisional application under 35 U.S.C. § 120 of allowed U.S. application Ser. No. 14/672, 066, filed Mar. 27, 2015, which application claims the benefit under 35 U.S.C. § 119(e) of U.S. Provisional Application No. 62/092,898, filed Dec. 17, 2014; and U.S. Provisional Application No. 62/004,727, filed May 29, 2014; and U.S. Provisional Application No. 61/993,732, filed May 15, 2014; and U.S. Provisional Application No. 61/971,455, filed Mar. 27, 2014; and U.S. application Ser. No. 14/672, 066 is a Continuation-in-Part of U.S. application Ser. No. 14/214,300, filed Mar. 14, 2014, now abandoned, which application claims the benefit under 35 U.S.C. § 119(e) of U.S. Provisional Application No. 61/940,226, filed Feb. 14, 2014; and U.S. Provisional Application No. 61/935,650, filed Feb. 4, 2014; and U.S. Provisional Application No. 61/915,392, filed Dec. 12, 2013; and U.S. Provisional Application No. 61/907,939, filed Nov. 22, 2013; and U.S. Provisional Application No. 61/860,115, filed Jul. 30, 2013; and U.S. Provisional Application No. 61/824,253, filed May 16, 2013; and U.S. Provisional Application No. 61/813,465, filed Apr. 18, 2013; and U.S. Provisional Application No. 61/813,182 filed Apr. 17, 2013. The entire contents of the aforementioned applications are incorporated by reference herein.

SEQUENCE LISTING

This application hereby incorporates by reference the material of the electronic Sequence Listing filed concurrently herewith. The material in the electronic Sequence Listing is submitted as a text (.txt) file entitled "LT00802_1_2ST25.txt" created on Mar. 27, 2015, last modified Feb. 12, 2018 which has a file size of 103,558, and is herein incorporated by reference in its entirety.

FIELD OF INVENTION

The present invention relates generally to gene fusions and gene variants that are associated with cancer.

BACKGROUND

Aberrations such as chromosomal translocations and gene variants are frequently found in human cancer cells. Chromosomal translocations may result in a chimeric gene expressing a fusion transcript which is then translated into a fusion protein that affects normal regulatory pathways and stimulates cancer cell growth. Gene variants may also result in aberrant proteins that affect normal regulatory pathways.

The identification of new fusion genes, new variants of known fusion genes, and gene variants or alleles provides an opportunity for additional diagnostics and cancer treatment targets.

BRIEF SUMMARY OF THE INVENTION

The disclosure provides novel gene fusion variants and gene fusion-disease state associations. The gene fusions provided herein are associated with certain cancers. The disclosure further provides probes, such as amplification primer sets and detection probes, as well as methods and systems of detection, diagnosis, and treatment and kits that include or detect the gene fusions disclosed herein.

In certain embodiments, novel mutations and fusions associated with cancer are disclosed in Tables 41-44.

The disclosure further provides reaction mixtures, sets of probes, kits, methods, isolated nucleic acids comprising or to detect the novel mutations and fusion events of Tables 41-44.

In one embodiment, the disclosure provides a reaction mixture comprising a probe or a set of probes that specifically recognize a gene fusion selected from Table 1-Table 3, Table 19, and Table 22. The set of probes can be, for example a set of amplification primers. In another embodiment, provided herein is a reaction mixture that includes a set of primers that flank a gene fusion selected from Table 1-Table 3, Table 19, and Table 22 in a target nucleic acid. For example, the set of primers can each bind to a target sequence in the human genome within 1000, 750, 500, 250, 100, 90, 80, 75, 70, 65, 50, or 25 nucleotides of opposite sides of the one of the fusion breakpoints identified in Tables 4-6, 20, and 23. The reaction mixture of this embodiment can further include a detector probe that binds to either side of a breakpoint in a gene fusion selected from Table 1-Table 3, Table 19, and Table 22, or that binds a binding region that spans the breakpoint in a gene fusion selected from Table 1-Table 3, Table 19, and Table 22, including specific embodiments where the breakpoint is identified in Tables 4-6, 20, and 23. In exemplary embodiments, the detector probe binds to a target sequence in the human genome within 1000, 750, 500, 250, 100, 90, 80, 75, 70, 60, 50, or 25 nucleotides of one of the fusion breakpoints identified in Tables 4-6, 20, and 23. The reaction mixture that includes a detector probe, or does not include a detector probe, can further include a polymerase, a reverse transcriptase, dNTPs, and/or a uracil DNA deglycosylase (UDG). The polymerase, the reverse transcriptase, and the UDG are typically not from human origin. The polymerase in illustrative embodiments is a thermostable polymerase such as a Taq polymerase. In certain embodiments, the dNTPs in the reaction mixture include dUTP, and the reaction mixture can in certain examples, be devoid of dTTP. Furthermore, the reaction mixture can include an amplicon, such as a DNA amplicon that includes one or more deoxyuridine ("dU") residues. In certain embodiments the reaction mixture includes a DNA amplicon that includes one or more dU residues for every deoxythymidine residue in the corresponding human genomic sequence. In certain embodiments, the amplicon includes a segment for which a corresponding sequence is not found in the human genome, such as, for example, a DNA barcode sequence. The non-human segment can be for example, 5-10,000, 5-5000, 5-1000, 5-500, 5-100, 5-50, 5-25, 5-10, 10-10,000, 10-5000, 10-1000, 10-500, 10-100, 10-50, or 10-25 nucleotides in length. In certain embodiments, the amplicon includes segment that corresponds to the region of the human genome that spans an intron, but the amplicon does not include a segment corresponding to the intron. The reaction mixture can further include a target nucleic acid, for example a human target nucleic acid. The human target nucleic acid can be, for example, isolated from a biological sample from a person suspected of having a cancer selected from: BLCA=bladder carcinoma, BRCA=breast carcinoma, CESC=cervical cell carcinoma, COAD=colon adenocarcinoma, GBM=glioblastoma multiforme, HNSC=head and neck squamous cell carcinoma, KIRK=clear cell renal cell carcinoma, KIRP=kidney renal papillary cell carcinoma, LAML=acute myeloid leukemia, LGG=brain lower grade glioma, LIHC=liver hepatocellular carcinoma, LUAD=lung adenocarcinoma, LUSC=squamous cell lung carcinoma, OV=ovarian serous adenocarcinoma, PRAD=prostate adenocarcinoma, READ=rectal adenocarcinoma, SKCM=cutaneous melanoma, STAD=stomach adenocarcinoma, THCA=thyroid carcinoma, and UCEC=uterine corpus endometrioid carcinoma. In certain embodiments, the target nucleic acid is from a tumor, for example a tumor of one of the cancer types listed in the preceding sentence.

In another embodiment, a set of probes that specifically recognizes a nucleic acid comprising at least one of SEQ ID NOs: 1-289 (gene fusions) is provided. In another embodiment, provided herein is a set of primers that specifically amplify a target nucleic acid that includes at least 25, 30, 40, 50, 75, 100, 125, 150, 200, or all of SEQ ID NOs: 1-289, or that amplifies up to 25, 30, 40, 50, 75, 100, 125, 150, 200, or all of SEQ ID NOs: 1-289. In another embodiment, provided herein is a qPCR assay, such as a TaqMan™ assay or a Molecular Beacons™ assay, that specifically amplifies and detects a target nucleic acid that includes at least 25, 30, 40, 50, 75, 100, 125, 150, 200, or all of SEQ ID NOs: 1-289.

The disclosure also provides an isolated nucleic acid comprising at least one sequence selected from a segment that includes at least 25, 30, 40, 50, 75, 100, 125, 150 200, or all of SEQ ID NOs: 1-289 or that includes up to 25, 30, 40, 50, 75, 100, 125, 150, 200, or all of SEQ ID NOs: 1-289. The isolated nucleic acid can include a first primer on a 5' end. Furthermore, the nucleic acid can be single stranded or double stranded. In certain embodiments, the isolated nucleic acid includes a segment for which a corresponding sequence is not found in the human genome, such as, for example, a DNA barcode sequence. The segment can be for example, 5-10,000, 5-5000, 5-1000, 5-500, 5-100, 5-50, 5-25, 5-10, 10-10,000, 10-5000, 10-1000, 10-500, 10-100, 10-50, or 10-25 nucleotides in length.

The disclosure, in other embodiments, provides a kit that includes a detector probe and/or a set of probes, for example, a set of amplification primers, that specifically recognize a nucleic acid comprising a breakpoint for a gene fusion selected from Table 1-Table 3, Table 19, and Table 22. For example, in certain embodiments the detector probe or set of amplification primers are designed to amplify and/or detect a nucleic acid that includes up to 25, 30, 40, 50, 75, 100, 125, 150, 200, or all of at least one of SEQ ID NOs: 1-289. The kit can further include, in one or more separate or in the same vessel, at least one component from an amplification reaction mixture, such as a polymerase, dNTPs, a reverse transcriptase, and/or UDG, typically the reverse transcriptase, polymerase and UDG are not from human origin. In certain embodiments, the dNTPs include dUTP, and in illustrative examples are devoid of dTTP. The polymerase in illustrative embodiments is a thermostable polymerase such as a Taq polymerase. Furthermore, the kit can include a control nucleic acid. For example the control nucleic acid can include a sequence that includes the break point in a gene fusion selected from Table 1-Table 3, Table 19, and Table 22, such as a nucleic acid that includes at least 25, 30, 40, 50, 75, 100, 125, 150, 200, or all of SEQ ID NOs: 1-289 or a nucleic acid that includes up to 25, 30, 40, 50, 75, 100, 125, 150, 200, or all of SEQ ID NOs: 1-289.

A method of detecting a cancer is provided comprising amplifying a nucleic acid that spans a breakpoint in a gene fusion selected from Table 1-Table 3, Table 19, and Table 22, for example the nucleic acid can include a sequence selected from SEQ ID NOs: 1-289, and detecting the presence of the nucleic acid, wherein the presence of the nucleic acid indicates a cancer is present in the sample. In another method, provided herein is a method of detecting a cancer selected from, bladder, colon, breast, endometrial, melanoma, ovarian, glioblastoma, glioma, leukemia, renal cell carcinoma, thyroid, and prostate adenocarcinoma that includes generating an amplicon that includes a sequence selected from SEQ ID NOs: 1-289 and detecting the presence of the amplicon, wherein the presence of the amplicon indicates bladder, colon, melanoma, ovarian, glioblastoma, lung, glioma, leukemia, renal cell carcinoma, thyroid, endometrial endometrioid adenocarcinoma, breast and prostate adenocarcinoma is present in the sample. The amplicon typically includes primers that were extended to form the amplicon. The cancer is selected from bladder urothelial carcinoma, breast carcinoma, endometrial endometrioid adenocarcinoma, colon adenocarcinoma, glioblastoma multiforme, clear cell renal cell carcinoma, papillary renal cell carcinoma, acute myeloid leukemia, brain lower grade glioma, lung adenocarcinoma, ovarian serous cystadenocarcinoma, prostate adenocarcinoma, rectal cutaneous melanoma, and thyroid gland carcinoma. The amplicon that is generated, in certain illustrative embodiments is a DNA amplicon that includes dU residues, and in certain examples includes no dT residues. In the methods provided in this paragraph, the amplicon can be generated using reaction mixtures provided herein. In certain embodiments, the method includes detecting expression of a nucleic acid that spans a breakpoint in a gene fusion selected from Table 1-Table 3, Table 19, and Table 22. Methods for detecting expression typically include a step of isolating RNA from a sample, such as a tumor sample, which can be a formalin fixed sample in illustrative embodiments.

In one embodiment, the reaction mixture includes a dye selected from SYBR Green, SBYR Greener, Fluorescein, Oregon Green, FAM, TET, JOE, VIC, Yakima Yellow, HEX, Cy3, Bodipy TMR, NED, TAMRA, Cy3.5, ROX, Texas Red, LightCycler Red, Bodipy 630/650, Alexa Fluor 647, Cy5, Alexa Fluor 660, or Cy 5.5. In certain embodiments, the dye is attached to a detably-labeled probe in the reaction mixture. In other embodiments, the dye is bound to the amplicon directly or through a detectably-labeled probe.

A kit comprising a probe or a set of probes, for example, a detectable probe or a set of amplification primers that specifically recognize a nucleic acid comprising a break point from Tables 4-6, 20, and 23 is provided. The kit can further include, in the same vessel, or in certain preferred embodiments, in a separate vessel, a component from an amplification reaction mixture, such as a polymerase, typically not from human origin, dNTPs, and/or UDG. Furthermore, the kit can include a control nucleic acid. For example the control nucleic acid can include a sequence that includes a break point selected from Tables 4-6, 20, and 23.

In another embodiment, provided herein a gene fusion that includes the gene fusions identified in Tables 1-3, 19, and 22. In illustrative embodiments, the gene fusions include one of the breakpoints identified in Tables 4-6, 20, and 23. Accordingly, provided herein is an isolated gene fusion nucleic acid of between 100 and 10,000 nucleotides in length and comprising at least 25 nucleotides on either side of one of the break points in Tables 4-6, 20, and 23.

In a related embodiment, provided herein is an isolated gene fusion nucleic acid comprising at least one of the break points in Tables 4-6, 20, and 23. In certain embodiments, the isolated gene fusion nucleic acid comprises at least 25, 30, 40, 50, 75, 100, 125, 150, 200, or all of SEQ ID NOs: 1-289 or a nucleic acid that includes up to 25, 30, 40, 50, 75, 100, 125, 150, 200, or all of SEQ ID NOs: 1-289. The isolated gene fusion nucleic acid can have a length, for example, of between 50 and 100,000 nucleotides, between 100 and 50,000 nucleotides, between 100 and 25,000 nucleotides, between 100 and 10,000 nucleotides, between 100 and 5,000 nucleotides, between 100 and 2500 nucleotides, between 100 and 1,000 nucleotides, between 100 and 500 nucleotides, between 100 and 250 nucleotides, between 100 and 200 nucleotides, between 250 and 10,000 nucleotides, between 250 and 5,000 nucleotides, between 250 and 1,000 nucleotides, or between 250 and 500 nucleotides. In certain aspects, the isolated gene fusion nucleic acid is DNA. In certain illustrative embodiments, the isolated nucleic gene fusion is devoid of intron sequences but spans a region that in the genome includes one or more introns. In certain embodiments, the isolated gene fusion nucleic acid is a cDNA.

In another embodiment, an isolated gene fusion nucleic acid is provided comprising at least one of the break points in Tables 4-6, 20, and 23.

In another embodiment is a method to detect a cancer selected from bladder urothelial carcinoma, breast carcinoma, endometrial endometrioid adenocarcinoma, colon adenocarcinoma, glioblastoma multiforme, clear cell renal cell carcinoma, papillary renal cell carcinoma, acute myeloid leukemia, brain lower grade glioma, lung adenocarcinoma, ovarian serous cystadenocarcinoma, prostate adenocarcinoma, rectal cutaneous melanoma, and thyroid gland carcinoma in a sample by detecting the presence of a gene fusion selected from Table 1-Table 3, Table 19, and Table 22.

The disclosure provides novel gene variants and gene variant-disease state associations. The gene variants can have one or more mutations that result in a variant protein. The gene variants provided herein are associated with certain cancers. The gene variants result in protein variants. The disclosure further provides probes, such as amplification primer sets and detection probes, as well as methods of detection, diagnosis, and treatment and kits that include or detect the gene variants disclosed herein.

In one embodiment, the disclosure provides a composition and a kit comprising a set of probes that specifically recognize the nucleotide sequence that encodes a gene variant selected from Table 7 and/or Table 11. The set of probes can be, for example a set of amplification primers. In another embodiment, provided herein is a composition that includes a set of primers that flank a gene variant that encodes one or more variants in Table 7 and/or Table 11. The reaction mixture of this embodiment can further include a detector probe that binds to a nucleotide sequence including a gene variant selected from Table 7 and/or Table 11. The reaction mixture that includes a detector probe or does not include a detector probe, can further include a polymerase, dNTPs, and/or a uracil DNA deglycosylase (UDG). The polymerase and UDG are typically not from a human origin. The reaction mixture can further include a target nucleic acid, for example a human target nucleic acid. The human target nucleic acid can be, for example, isolated from a biological sample from a person suspected of having a cancer. The cancer can be selected from: BLCA=bladder carcinoma, BRCA=breast carcinoma, CESC=cervical cell carcinoma, COAD=colon adenocarcinoma, GBM=glioblastoma multiforme, HNSC=head and neck squamous cell carcinoma, KIRK=clear cell renal cell carcinoma, KIRP=kidney renal papillary cell carcinoma, LAML=acute myeloid leukemia, LGG=brain lower grade glioma, LIHC=liver hepatocellular carcinoma, LUAD=lung adenocarcinoma, LUSC=squamous cell lung carcinoma, OV=ovarian serous adenocarcinoma, PRAD=prostate adenocarcinoma, READ=rectal adenocarcinoma, SKCM=cutaneous melanoma, STAD=stomach adenocarcinoma, THCA=thyroid carcinoma, and UCEC=uterine corpus endometrioid carcinoma.

The nucleotide sequence that encodes one or more gene variants in Table 7 and/or Table 11 can be any size that encompasses the variation. For example, the nucleotide sequence can be any size that can be easily copied using a primer and/or detected using a probe.

In another embodiment, a set of probes that specifically recognize a nucleic acid coding for a gene variant selected from Table 7 and/or Table 11 (gene variants) is provided. In another embodiment, provided herein is a set of primers that specifically amplify a target nucleic acid that codes for a gene variant selected from Table 7 and/or Table 11. In another embodiment, provided herein is a qPCR assay, such as, but not limited to, a TaqMan™ assay, a Scorpions assay, or a Molecular Beacons™ assay that specifically amplifies and detects a target nucleic acid that codes for a gene variant selected from Table 7 and/or Table 11.

The disclosure also provides an isolated nucleic acid comprising at least one sequence that codes for one or more gene variants selected from Table 7 and/or Table 11. The isolated nucleic acid can include a first primer on a 5' end. Furthermore, the nucleic acid can be single stranded or double stranded.

The disclosure, in other embodiments, provides a kit that includes a detector probe and/or a set of probes, for example, a set of amplification primers that specifically recognize a nucleic acid that codes for a gene variant selected from Table 7 and/or Table 11. For example, in certain embodiments the detector probe or set of amplification primers are designed to amplify and/or detect a nucleic acid that codes for a variant in Table 7 and/or Table 11. The kit can further include, in a separate or in the same vessel, a component from an amplification reaction mixture, such as a polymerase, typically not from human origin, dNTPs, and/or UDG. Furthermore, the kit can include a control nucleic acid. For example the control nucleic acid can include a sequence that includes the gene variant selected from Table 7 and/or Table 11.

A method of detecting a cancer is provided comprising amplifying a nucleic acid that encodes a gene variant selected from Table 7 and/or Table 11, for example the nucleic can include a sequence from one of the accession numbers in Table 7 and/or Table 11 except that the sequence contains the variant that codes for the gene variants in Table 7 and/or Table 11, and detecting the presence of the nucleic acid, wherein the presence of the nucleic acid indicates a cancer is present in the sample. In another method, provided herein is a method of detecting a cancer that includes generating an amplicon that includes a sequence encoding a variant selected from Table 7 and/or Table 11, and detecting the presence of the nucleic acid, wherein the presence of the nucleic acid indicates a cancer or cancer cell is present in the sample. The amplicon typically includes primers that are extended to form the amplicon. The cancer is selected from bladder carcinoma, breast carcinoma, cervical cell carcinoma, colon adenocarcinoma, glioblastoma multiforme, head and neck squamous cell carcinoma, clear cell renal cell carcinoma, kidney renal papillary cell carcinoma, acute myeloid leukemia, brain lower grade glioma, liver hepatocellular carcinoma, lung adenocarcinoma, squamous cell lung carcinoma, ovarian serous adenocarcinoma, prostate adenocarcinoma, rectal adenocarcinoma, cutaneous melanoma, stomach adenocarcinoma, thyroid carcinoma, and uterine corpus endometrioid carcinoma.

A kit comprising a set of probes, for example, a set of amplification primers that specifically recognize a nucleic acid comprising a gene variant from Table 7 and/or Table 11 is provided. The kit can further include, in a separate or in the same vessel, a component from an amplification reaction mixture, such as a polymerase, typically not from human origin, dNTPs, and/or UDG. Furthermore, the kit can include a control nucleic acid. For example the control nucleic acid can include a sequence that includes the gene variant from Table 7 and/or Table 11.

In certain embodiments, a set of probes that specifically recognize a nucleic acid comprising a gene variant from Table 7 and/or Table 11 is provided.

In another embodiment, a gene variant is provided comprising at least one of the gene variants in Table 7 and/or Table 11.

In another embodiment is a method to detect a cancer selected from bladder carcinoma, breast carcinoma, cervical cell carcinoma, colon adenocarcinoma, glioblastoma multiforme, head and neck squamous cell carcinoma, clear cell renal cell carcinoma, kidney renal papillary cell carcinoma, acute myeloid leukemia, brain lower grade glioma, liver hepatocellular carcinoma, lung adenocarcinoma, squamous cell lung carcinoma, ovarian serous adenocarcinoma, prostate adenocarcinoma, rectal adenocarcinoma, cutaneous melanoma, stomach adenocarcinoma, thyroid carcinoma, and uterine corpus endometrioid carcinoma in a sample by detecting the presence of a gene variant selected from Table 7 and/or Table 11. Gene variants can include, but are not limited to, ZNF479 variants R110, R295K, R295T, R295I, R345I, R345T, K438T, and T466K.

In another embodiment, a method of delivering a drug to a subject is provided, wherein the method includes detecting a genetic event identified in Table 15, and treating the subject with a drug, wherein the drug is believed to positively affect the clinical outcome of patients having the genetic event. In illustrative embodiments, the genetic event is associated with a gene found in Table 8 and the drug is listed in Table 8 as a companion for that gene. In another embodiment, provided herein is a method for determining if a subject receives a drug, the method includes detecting a genetic event identified in Table 15, and then delivering a drug to the subject if the detected genetic event is listed in Table 15 as associated with a poor prognosis, wherein the drug is believed to positively affect the clinical outcome of patients having the genetic event. In illustrative embodiments, the genetic event is associated with a gene found in Table 8 and the drug is listed in Table 8 as a companion for that gene.

In one embodiment, a kit is provided, wherein the kit comprises a set of probes, wherein each probe specifically hybridizes to a nucleic acid comprising a breakpoint from Tables 4-6, 20, and 23.

In one embodiment, a method is provided, the method comprising: amplifying a nucleic acid comprising at least one gene fusion from Tables 1-3, 19, and 22 from a sample; and detecting the presence of the at least one gene fusion by at least one of: contacting the composition with at least one probe, wherein each probe specifically hybridizes to the nucleic acid, or observing the presence of a non-natural or non-native chemical structure in the nucleic acid; wherein detecting the presence of the at least one gene fusion indicates that at least one cancer from Tables 1-3, 19, and 22 is present in the sample.

In one embodiment, a system is provided, the system comprising a nucleic acid amplifier configured to amplify a nucleic acid comprising at least one gene fusion from Tables 1-3, 19, and 22 from a sample, to yield an amplified nucleic acid; a detector configured to detect the presence of the at least one gene fusion in the amplified nucleic acid by at least one of (i) contacting the composition with at least one probe, wherein each probe specifically hybridizes to the nucleic acid, or (ii) observing the presence of a non-natural or non-native chemical structure in the nucleic acid, and further configured to transmit a detection indication; and a computer system configured to receive the detection indication and determine that at least one cancer from Tables 1-3, 19, and 22 is present in the sample, based on the detection indication.

In one embodiment, a non-transitory computer readable program storage unit is provided, the non-transitory computer readable program storage unit encoded with instructions that, when executed by a computer, perform a method, comprising receiving an input comprising at least a cancer type and an event type, wherein the cancer type is selected from Table 15 and the event type is selected from Table 15; querying a database for at least one entry comprising a plurality of fields, wherein the plurality of fields comprises at least one of the cancer type and the event type; and transmitting an output comprising at least one field of the plurality from the at least one entry, wherein the at least one field comprises at least one gene, at least one druggable gene, at least one drug targeting the at least one druggable gene, or a prognosis.

In one embodiment, a method is provided, wherein the method comprises administering to a patient having at least one gene fusion selected from the gene fusions listed in Tables 1-3, 19, and 22 at least one drug selected from the drugs listed in Tables 8, 16-17, 21, and 24.

In one embodiment, a method is provided, wherein the method comprises contacting a nucleic acid sample from a patient with a reaction mixture comprising a first primer complementary to a first gene and a second primer complementary to a second gene, wherein a fusion of the first gene and the second gene is detectable by the presence of an amplicon generated by the first primer and the second primer, wherein the fusion comprises a breakpoint selected from the breakpoints listed in Tables 4-6, 20, and 23.

In one embodiment, a non-transitory computer readable program storage unit is provided, the non-transitory computer readable program storage unit encoded with instructions that, when executed by a computer, perform a method, comprising receiving RNA sequence data from at least one cancer cell line; running at least one gene fusion caller on the sequence data, to identify possible breakpoints between fused genes in the processed data; filtering said possible breakpoints, to retain candidate breakpoints, wherein each candidate breakpoint is in a 5' untranslated region (UTR) or a coding DNA sequence (CDS) of a functional gene region and each candidate breakpoint does not occur in an intron; and annotating the candidate breakpoints with at least one annotation useful in determining a relevance of a gene fusion for at least one of cancer diagnosis, cancer prognosis, or cancer treatment, wherein the gene fusion comprises the candidate breakpoint.

In one embodiment, a non-transitory computer readable program storage unit is provided, the non-transitory computer readable program storage unit encoded with instructions that, when executed by a computer, perform a method, comprising receiving mutation data from at least one cancer cell line; annotating the mutation data with at least one of variant classification, variant position, or variant change, to yield annotated mutation data; filtering the annotated mutation data, to yield gene region mutation data; classifying the gene region mutation data as hotspot, deleterious, or other; and nominating a gene comprising the gene region mutation as a gain of function, loss of function, or recurrent other gene, based on the relative frequency of mutations in the gene and the classifications of all gene region mutations in the gene.

In one embodiment, a method is provided, the method comprising detecting one or more gene fusions in a sample from a subject, to yield gene fusion detection data, wherein at least one of the gene fusions is selected from the gene fusions listed in Tables 1-3, 19, and 22, receiving by a computer system the gene fusion detection data, and identifying by the computer system at least one therapeutic option recommended for the subject, based on the gene fusion detection data.

In one embodiment, a system is provided, the system comprising a detector configured to (i) detect one or more gene fusions in a sample from a subject, to yield gene fusion detection data, wherein at least one of the gene fusions is selected from the gene fusions listed in Tables 1-3, 19, and 22 and (ii) transmit the gene fusion detection data; and a computer system configured to receive the gene fusion detection data and identify at least one therapeutic option recommended for the subject, based on the gene fusion detection data.

In another embodiment, a novel TP53 WT gene signature is provided as well as methods of detecting expression levels of one or more of the TP53 WT gene signature genes in Table 40.

DESCRIPTION OF THE DRAWINGS

FIGS. 9 A-B is a table of frequent TP53 mutations by amino acid position. Mutations displayed that occur with overall frequency in patients of >0.25% in the pan-cancer analysis. A recurrent splice site mutation was identified at the intron-exon junction affecting T-125

FIGS. 10 A-B is a table of Tp53 in-frame insertion and deletion mutations. The maximum detected in-frame insertion-deletions identified was 21 bp. Greater than 99% of non-transposon indels across the genome are <100 bp.

DETAILED DESCRIPTION

Figure 1:
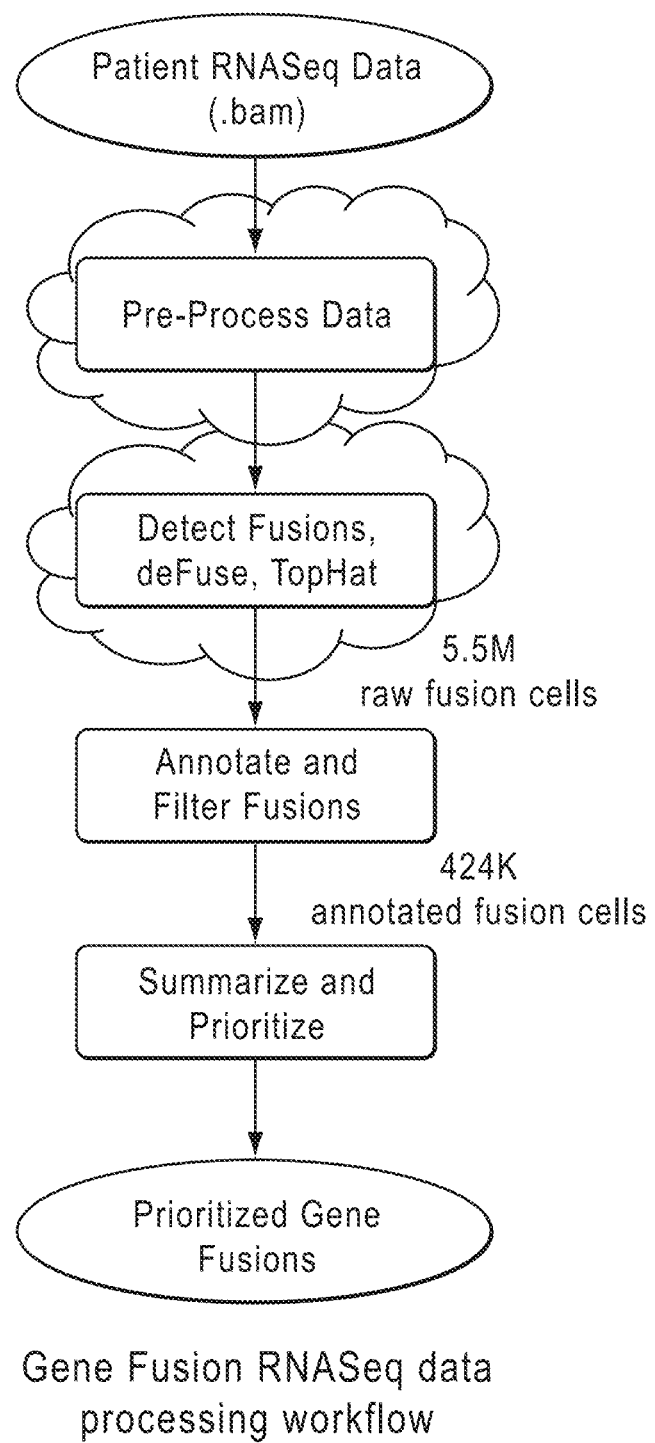
FIG. 1 provides a workflow for gene fusion RNASeq data processing.

The disclosure provides novel gene fusions and variants, as well as novel associations of gene fusions and/or gene variants with certain types of cancers. Further provided are probes, reaction mixtures, assays and kits that relate to the gene fusions and/or variants disclosed herein.

Definitions

The term "marker" or "biomarker" refers to a molecule (typically protein, nucleic acid, carbohydrate, or lipid) that is expressed in the cell, expressed on the surface of a cancer cell or secreted by a cancer cell in comparison to a non-cancer cell, and which is useful for the diagnosis of cancer, for providing a prognosis, and for preferential targeting of a pharmacological agent to the cancer cell. Oftentimes, such markers are molecules that are overexpressed in a cancer cell in comparison to a non-cancer cell, for instance, 1-fold overexpression, 2-fold overexpression, 3-fold overexpression or more in comparison to a normal cell. Further, a marker can be a molecule that is inappropriately synthesized in the cancer cell, for instance, a molecule that contains deletions, additions or mutations in comparison to the molecule expressed on a normal cell. Alternatively, such biomarkers are molecules that are underexpressed in a cancer cell in comparison to a non-cancer cell, for instance, 1-fold underexpression, 2-fold underexpression, 3-fold underexpression, or more. Further, a marker can be a molecule that is inappropriately synthesized in cancer, for instance, a molecule that contains deletions, additions or mutations in comparison to the molecule expressed on a normal cell.

It will be understood by the skilled artisan that markers may be used in combination with other markers or tests for any of the uses, e.g., prediction, diagnosis, or prognosis of cancer, disclosed herein.

"Biological sample" includes sections of tissues such as biopsy and autopsy samples, and frozen sections taken for histologic purposes. For example, the biological sample can include a Fresh-Frozen Paraffin-Embedded (FFPE) sample. Alternatively, a biological sample can include blood and blood fractions or products (e.g., serum, plasma, platelets, red blood cells, and the like), sputum, bronchoalveolar lavage, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., lung etc.), the size and type of the tumor, among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue from within the tumor. A diagnosis or prognosis made by endoscopy or radiographic guidance can require a "core-needle biopsy", or a "fine-needle aspiration biopsy" which generally obtains a suspension of cells from within a target tissue. Biopsy techniques are discussed, for example, in Harrison's Principles of Internal Medicine, Kasper, et al., eds., 16th ed., 2005, Chapter 70, and throughout Part V.

The terms "overexpress," "overexpression," or "overexpressed" interchangeably refer to a protein or nucleic acid (RNA) that is translated or transcribed at a detectably greater level, usually in a cancer cell, in comparison to a normal cell. The term includes overexpression due to transcription, post transcriptional processing, translation, post-translational processing, cellular localization (e.g., organelle, cytoplasm, nucleus, cell surface), and RNA and protein stability, as compared to a normal cell. Overexpression can be detected using conventional techniques for detecting mRNA (i.e., RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold or more higher levels of transcription or translation in comparison to a normal cell.

The terms "underexpress," "underexpression," or "underexpressed" or "downregulated" interchangeably refer to a protein or nucleic acid that is translated or transcribed at a detectably lower level in a cancer cell, in comparison to a normal cell. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., RT-PCR, PCR, hybridization) or proteins (i.e., ELISA, immunohistochemical techniques). Underexpression can be 10%, 20%, 30%, 40%, 50%, 60%, 70%, 80%, 90% or less in comparison to a control. In certain instances, underexpression is 1-fold, 2-fold, 3-fold, 4-fold or more lower levels of transcription or translation in comparison to a control.

The term "differentially expressed" or "differentially regulated" refers generally to a protein or nucleic acid that is overexpressed (upregulated) or underexpressed (downregulated) in one sample compared to at least one other sample, generally in a cancer patient compared to a sample of non-cancerous tissue in the context of the present invention.

The term "system" sets forth a set of components, real or abstract, comprising a whole where each component interacts with or is related to at least one other component within the whole.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serino (S), Threonine (T); and 8) Cysteine (C), Methionine (M). See, e.g., Creighton, Proteins (1984).

The phrase "specifically (or selectively) binds" when referring to a protein, nucleic acid, antibody, or small molecule compound refers to a binding reaction that is determinative of the presence of the protein or nucleic acid, such as the differentially expressed genes of the present invention, often in a heterogeneous population of proteins or nucleic acids and other biologics. In the case of antibodies, under designated immunoassay conditions, a specified antibody may bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

The phrase "functional effects" in the context of assays for testing compounds that modulate a marker protein includes the determination of a parameter that is indirectly or directly under the influence of a biomarker of the invention, e.g., a chemical or phenotypic. A functional effect therefore includes ligand binding activity, transcriptional activation or repression, the ability of cells to proliferate, the ability to migrate, among others. "Functional effects" include in vitro, in vivo, and ex vivo activities.

By "determining the functional effect" is meant assaying for a compound that increases or decreases a parameter that is indirectly or directly under the influence of a biomarker of the invention, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the marker; measuring changes in enzymatic activity; the ability to increase or decrease cellular proliferation, apoptosis, cell cycle arrest, measuring changes in cell surface markers. The functional effects can be evaluated by many means known to those skilled in the art, e.g., microscopy for quantitative or qualitative measures of alterations in morphological features, measurement of changes in RNA or protein levels for other genes expressed in placental tissue, measurement of RNA stability, identification of downstream or reporter gene expression (CAT, luciferase, β-gal, GFP and the like), e.g., via chemiluminescence, fluorescence, colorimetric reactions, antibody binding, inducible markers, etc.

"Inhibitors," "activators," and "modulators" of the markers are used to refer to activating, inhibitory, or modulating molecules identified using in vitro and in vivo assays of cancer biomarkers. Inhibitors are compounds that, e.g., bind to, partially or totally block activity, decrease, prevent, delay activation, inactivate, desensitize, or down regulate the activity or expression of cancer biomarkers. "Activators" are compounds that increase, open, activate, facilitate, enhance activation, sensitize, agonize, or up regulate activity of cancer biomarkers, e.g., agonists. Inhibitors, activators, or modulators also include genetically modified versions of cancer biomarkers, e.g., versions with altered activity, as well as naturally occurring and synthetic ligands, antagonists, agonists, antibodies, peptides, cyclic peptides, nucleic acids, antisense molecules, ribozymes, RNAi and siRNA molecules, small organic molecules and the like. Such assays for inhibitors and activators include, e.g., expressing cancer biomarkers in vitro, in cells, or cell extracts, applying putative modulator compounds, and then determining the functional effects on activity, as described above.

A "probe" or "probes" refers to a polynucleotide that is at least eight (8) nucleotides in length and which forms a hybrid structure with a target sequence, due to complementarity of at least one sequence in the probe with a sequence in the target region. The polynucleotide can be composed of DNA and/or RNA. Probes in certain embodiments, are detectably labeled, as discussed in more detail herein. Probes can vary significantly in size. Generally, probes are, for example, at least 8 to 15 nucleotides in length. Other probes are, for example, at least 20, 30 or 40 nucleotides long. Still other probes are somewhat longer, being at least, for example, 50, 60, 70, 80, 90 nucleotides long. Yet other probes are longer still, and are at least, for example, 100, 150, 200 or more nucleotides long. Probes can be of any specific length that falls within the foregoing ranges as well. Preferably, the probe does not contain a sequence complementary to the sequence(s) used to prime for a target sequence during the polymerase chain reaction.

The terms "complementary" or "complementarity" are used in reference to polynucleotides (that is, a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Alternatively, there may be "complete" or "total" complementarity between the nucleic acids. The degree of complementarity between nucleic acid strands has significant effects on the efficiency and strength of hybridization between nucleic acid strands.

"Oligonucleotide" or "polynucleotide" refers to a polymeric form of nucleotides of any length, either deoxyribonucleotide or ribonucleotide. These terms include, but are not limited to, a single-, double- or triple-stranded DNA, genomic DNA, cDNA, RNA, DNA-RNA hybrid, or a polymer comprising purine and pyrimidine bases or other natural chemically, biochemically modified non-natural or derivatized nucleotide bases.

"Amplification detection assay" refers to a primer pair and matched probe wherein the primer pair flanks a region of a target nucleic acid, typically a target gene that defines an amplicon, and wherein the probe binds to the amplicon.

The terms "genetic variant" and "nucleotide variant" are used herein interchangeably to refer to changes or alterations to the reference human gene or cDNA sequence at a particular locus, including, but not limited to, nucleotide base deletions, insertions, inversions, and substitutions in the coding and noncoding regions. Deletions may be of a single nucleotide base, a portion or a region of the nucleotide sequence of the gene, or of the entire gene sequence. Insertions may be of one or more nucleotide bases. The "genetic variant" or "nucleotide variant" may occur in transcriptional regulatory regions, untranslated regions of mRNA, exons, introns, or exon/intron junctions. The "genetic variant" or "nucleotide variant" may or may not result in stop codons, frame shifts, deletions of amino acids, altered gene transcript splice forms or altered amino acid sequence.

The term "gene" refers to a polynucleotide (e.g., a DNA segment), that encodes a polypeptide and includes regions preceding and following the coding regions as well as intervening sequences (introns) between individual coding segments (exons). Parent genes or protein sequences are presented as Entrez Gene IDs or accession numbers. For example, the ZNF479 Entrez Gene ID is 90827. If any changes have been made to the sequence in the Gene ID in Entrez, the change is indicated after the Gene ID with a decimal and the number of the change (e.g., 90827.1). Further, for example, TPM1 has the accession number NM_004304.

The term "allele" or "gene allele" is used herein to refer generally to a naturally occurring gene having a reference sequence or a gene containing a specific nucleotide variant.

As used herein, "haplotype" is a combination of genetic (nucleotide) variants in a region of an mRNA or a genomic DNA on a chromosome found in an individual. Thus, a haplotype includes a number of genetically linked polymorphic variants which are typically inherited together as a unit.

As used herein, the term "amino acid variant" is used to refer to an amino acid change to a reference human protein sequence resulting from "genetic variant" or "nucleotide variant" to the reference human gene encoding the reference protein. The term "amino acid variant" is intended to encompass not only single amino acid substitutions, but also amino acid deletions, insertions, and other significant changes of amino acid sequence in the reference protein. Variants of the invention are described by the following nomenclature: [original amino acid residue/position/substituted amino acid residue]. For example, the substitution of leucine for arginine at position 76 is represented as R76L.

The term "genotype" as used herein means the nucleotide characters at a particular nucleotide variant marker (or locus) in either one allele or both alleles of a gene (or a particular chromosome region). With respect to a particular nucleotide position of a gene of interest, the nucleotide(s) at that locus or equivalent thereof in one or both alleles form the genotype of the gene at that locus. A genotype can be homozygous or heterozygous. Accordingly, "genotyping" means determining the genotype, that is, the nucleotide(s) at a particular gene locus. Genotyping can also be done by determining the amino acid variant at a particular position of a protein which can be used to deduce the corresponding nucleotide variant(s).

A set of probes typically refers to a set of primers, usually primer pairs, and/or detectably-labeled probes that are used to detect the target genetic variations. The primer pairs are used in an amplification reaction to define an amplicon that spans a region for a target genetic variation for each of the aforementioned genes. The set of amplicons are detected by a set of matched probes. In an exemplary embodiment, the invention is a set of TaqMan™ (Roche Molecular Systems, Pleasanton, Calif.) assays that are used to detect a set of target genetic variations used in the methods of the invention.

In one embodiment, the set of probes are a set of primers used to generate amplicons that are detected by a nucleic acid sequencing reaction, such as a next generation sequencing reaction. In these embodiments, for example, AmpliSEQ™ (Life Technologies/Ion Torrent, Carlsbad, Calif.) or TruSEQ™ (Illumina, San Diego, Calif.) technology can be employed. In other embodiments, the two or more probes are primer pairs.

A modified ribonucleotide or deoxyribonucleotide refers to a molecule that can be used in place of naturally occurring bases in nucleic acid and includes, but is not limited to, modified purines and pyrimidines, minor bases, convertible nucleosides, structural analogs of purines and pyrimidines, labeled, derivatized and modified nucleosides and nucleotides, conjugated nucleosides and nucleotides, sequence modifiers, terminus modifiers, spacer modifiers, and nucleotides with backbone modifications, including, but not limited to, ribose-modified nucleotides, phosphoramidates, phosphorothioates, phosphonamidites, methyl phosphonates, methyl phosp7horamidites, methyl phosphonamidites, 5'-β-cyanoethyl phosphoramidites, methylenephosphonates, phosphorodithioates, peptide nucleic acids, achiral and neutral internucleotidic linkages.

"Hybridize" or "hybridization" refers to the binding between nucleic acids. The conditions for hybridization can be varied according to the sequence homology of the nucleic acids to be bound. Thus, if the sequence homology between the subject nucleic acids is high, stringent conditions are used. If the sequence homology is low, mild conditions are used. When the hybridization conditions are stringent, the hybridization specificity increases, and this increase of the hybridization specificity leads to a decrease in the yield of non-specific hybridization products. However, under mild hybridization conditions, the hybridization specificity decreases, and this decrease in the hybridization specificity leads to an increase in the yield of non-specific hybridization products.

"Stringent conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in *Biochemistry and Molecular Biology*—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$, is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed.

Hybridization between nucleic acids can occur between a DNA molecule and a DNA molecule, hybridization between a DNA molecule and a RNA molecule, and hybridization between a RNA molecule and a RNA molecule.

A "mutein" or "variant" refers to a polynucleotide or polypeptide that differs relative to a wild-type or the most prevalent form in a population of individuals by the exchange, deletion, or insertion of one or more nucleotides or amino acids, respectively. The number of nucleotides or amino acids exchanged, deleted, or inserted can be 1, 2, 3, 4, 5, 6, 7, 8, 9, 10, 11, 12, 13, 14, 15, 16, 17, 18, 19, 20 or more such as 25, 30, 35, 40, 45 or 50. The term mutein can also encompass a translocation, for example the fusion of the polypeptides encoded by the ALK and TPM1 genes (TPM1/ALK).

"Gene fusion" refers to a chimeric genomic DNA resulting from the fusion of at least a portion of a first gene to a portion of a second gene. The point of transition between the sequence from the first gene in the fusion to the sequence from the second gene in the fusion is referred to as the "breakpoint" or "fusion point."

Transcription of the gene fusion results in a chimeric mRNA.

"Single nucleotide polymorphism" or "SNP" refers to a DNA sequence variation that occurs when a single nucleotide (A, T, G, or C) in the genome differs between members of a biological species or paired chromosomes in a human.

"Mutation" is defined herein as a specific change at a genomic location, i.e.: Chromosome, start, stop, reference base, alternate base, variant type (SNP, INS, DEL) etc.

"Annotation" is defined herein as a transcript-specific set of properties that describe the effect of the mutation, i.e.: Gene, transcript, variant classification, variant change, variant codon position, etc.

A "primer" or "primer sequence" refers to an oligonucleotide that hybridizes to a target nucleic acid sequence (for example, a DNA template to be amplified) to prime a nucleic acid synthesis reaction. The primer may be a DNA oligonucleotide, a RNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3-4 nucleotides long) do not form thermodynamically stable duplexes with target nucleic acids under such hybridization conditions. The upper limit is often determined by the possibility of having a duplex formation in a region other than the pre-determined nucleic acid sequence in the target nucleic acid. Generally, suitable primer lengths are in the range of about 10 to about 40 nucleotides long. In certain embodiments, for example, a primer can be 10-40, 15-30, or 10-20 nucleotides long. A primer is capable of acting as a point of initiation of synthesis on a polynucleotide sequence when placed under appropriate conditions.

The primer will be completely or substantially complementary to a region of the target polynucleotide sequence to be copied. Therefore, under conditions conducive to hybridization, the primer will anneal to the complementary region of the target sequence. Upon addition of suitable reactants, including, but not limited to, a polymerase, nucleotide triphosphates, etc., the primer is extended by the polymerizing agent to form a copy of the target sequence. The primer may be single-stranded or alternatively may be partially double-stranded.

"Detection," "detectable" and grammatical equivalents thereof refers to ways of determining the presence and/or quantity and/or identity of a target nucleic acid sequence. In some embodiments, detection occurs amplifying the target nucleic acid sequence. In other embodiments, sequencing of the target nucleic acid can be characterized as "detecting" the target nucleic acid. A label attached to the probe can include any of a variety of different labels known in the art that can be detected by, for example, chemical or physical means. Labels that can be attached to probes may include, for example, fluorescent and luminescence materials.

"Amplifying," "amplification," and grammatical equivalents thereof refers to any method by which at least a part of a target nucleic acid sequence is reproduced in a template-dependent manner, including without limitation, a broad range of techniques for amplifying nucleic acid sequences, either linearly or exponentially. Exemplary means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), recombinase-polymerase amplification (RPA)(TwistDx, Cambridg, UK), and self-sustained sequence replication (3SR), including multiplex versions or combinations thereof, for example but not limited to, OLA/PCR, PCR/OLA, LDR/PCR, PCR/PCR/LDR, PCR/LDR, LCR/PCR, PCR/LCR (also known as combined chain reaction-CCR), and the like. Descriptions of such techniques can be found in, among other places, Sambrook et al. Molecular Cloning, 3$^{rd}$ Edition; Ausbel et al.; PCR Primer: A Laboratory Manual, Diffenbach, Ed., Cold Spring Harbor Press (1995); The Electronic Protocol Book, Chang Bioscience (2002), Msuih et al., *J. Clin. Micro.* 34:501-07 (1996); The Nucleic Acid Protocols Handbook, R. Rapley, ed., Humana Press, Totowa, N.J. (2002).

Analysis of nucleic acid markers can be performed using techniques known in the art including, without limitation, sequence analysis, and electrophoretic analysis. Non-limiting examples of sequence analysis include Maxam-Gilbert sequencing, Sanger sequencing, capillary array DNA sequencing, thermal cycle sequencing (Sears et al., Biotechniques, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nat. Biotechnol.*, 16:381-384 (1998)), and sequencing by hybridization. Chee et al., *Science*, 274:610-614 (1996); Drmanac et al., *Science*, 260: 1649-1652 (1993); Drmanac et al., *Nat. Biotechnol.*, 16:54-58 (1998). Non-limiting examples of electrophoretic analysis include slab gel electrophoresis such as agarose or polyacrylamide gel electrophoresis, capillary electrophoresis, and denaturing gradient gel electrophoresis. Additionally, next generation sequencing methods can be performed using commercially available kits and instruments from companies such as the Life Technologies/Ion Torrent PGM or Proton, the Illumina HiSEQ or MiSEQ, and the Roche/454 next generation sequencing system.

In some embodiments, the amount of probe that gives a fluorescent signal in response to an excited light typically relates to the amount of nucleic acid produced in the amplification reaction. Thus, in some embodiments, the amount of fluorescent signal is related to the amount of product created in the amplification reaction. In such embodiments, one can therefore measure the amount of amplification product by measuring the intensity of the fluorescent signal from the fluorescent indicator.

"Detectably labeled probe" or "detector probe" refers to a molecule used in an amplification reaction, typically for quantitative or real-time PCR analysis, as well as end-point analysis. Such detector probes can be used to monitor the amplification of the target nucleic acid sequence. In some embodiments, detector probes present in an amplification reaction are suitable for monitoring the amount of amplicon(s) produced as a function of time. Such detector probes include, but are not limited to, the 5'-exonuclease assay (TAQMAN® probes described herein (see also U.S. Pat. No. 5,538,848) various stem-loop molecular beacons (see for example, U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355, 421 and 6,593,091), linear PNA beacons (see, for example, Kubista et al., 2001, SPIE 4264:53-58), non-FRET probes (see, for example, U.S. Pat. No. 6,150,097), Sunrise®/Amplifluor™ probes (U.S. Pat. No. 6,548,250), stem-loop and duplex Scorpion probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383, 752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem. Res. Toxicol. 15:118-126; and Yu et al., 2001, J. Am. Chem. Soc 14:11155-11161.

Detector probes can also include quenchers, including without limitation black hole quenchers (Biosearch), Iowa Black (IDT), QSY quencher (Molecular Probes), and Dabsyl and Dabcel sulfonate/carboxylate Quenchers (Epoch).

Detector probes can also include two probes, wherein for example a fluor is on one probe, and a quencher is on the other probe, wherein hybridization of the two probes together on a target quenches the signal, or wherein hybridization on the target alters the signal signature via a change in fluorescence. Detector probes can also comprise sulfonate derivatives of fluorescenin dyes with $SO_3$ instead of the carboxylate group, phosphoramidite forms of fluorescein, phosphoramidite forms of CY 5 (commercially available for example from Amersham). In some embodiments, interchelating labels are used such as ethidium bromide, SYBR® Green I (Molecular Probes), and PicoGreen® (Molecular Probes), thereby allowing visualization in real-time, or end point, of an amplification product in the absence of a detector probe. In some embodiments, real-time visualization can comprise both an intercalating detector probe and a sequence-based detector probe can be employed. In some embodiments, the detector probe is at least partially quenched when not hybridized to a complementary sequence in the amplification reaction, and is at least partially unquenched when hybridized to a complementary sequence in the amplification reaction. In some embodiments, the detector probes of the present teachings have a Tm of 63-69° C., though it will be appreciated that guided by the present teachings routine experimentation can result in detector probes with other Tms. In some embodiments, probes can further comprise various modifications such as a minor groove binder (see for example U.S. Pat. No. 6,486, 308) to further provide desirable thermodynamic characteristics.

In some embodiments, detection can occur through any of a variety of mobility dependent analytical techniques based on differential rates of migration between different analyte species. Exemplary mobility-dependent analysis techniques include electrophoresis, chromatography, mass spectroscopy, sedimentation, for example, gradient centrifugation, field-flow fractionation, multi-stage extraction techniques, and the like. In some embodiments, mobility probes can be hybridized to amplification products, and the identity of the target nucleic acid sequence determined via a mobility dependent analysis technique of the eluted mobility probes, as described for example in Published P.C.T. Application WO04/46344 to Rosenblum et al., and WO01/92579 to Wenz et al. In some embodiments, detection can be achieved by various microarrays and related software such as the Applied Biosystems Array System with the Applied Biosystems 1700 Chemiluminescent Microarray Analyzer and other commercially available array systems available from Affymetrix, Agilent, Illumina, and Amersham Biosciences, among others (see also Gerry et al., J. Mol. Biol. 292:251-62, 1999; De Bellis et al., Minerva Biotec 14:247-52, 2002; and Stears et al., Nat. Med. 9:14045, including supplements, 2003). It will also be appreciated that detection can comprise reporter groups that are incorporated into the reaction products, either as part of labeled primers or due to the incorporation of labeled dNTPs during an amplification, or attached to reaction products, for example but not limited to, via hybridization tag complements comprising reporter groups or via linker arms that are integral or attached to reaction products. Detection of unlabeled reaction products, for example using mass spectrometry, is also within the scope of the current teachings.

"Aberration" Means a genomic structural variation or alteration of DNA. Examples include: over-/under-expression; copy number amplification/deletion; mutation; gene fusion; etc.

"Driver Event" means a genomic aberration, representing a Gain of Function (GoF) mutation, a fusion, or copy number peak.

"Recurrent" means occurrence of an event in 3 or more tumor samples.

"Mitelman" means a database of Chromosome Aberrations and Gene Fusions in Cancer manually curated from literature. goo.gl/PnXMT Gene Fusions

TABLE 1

Gene Fusions

| Cancer Type | Gene A Symbol | Gene B Symbol | orientation | Druggable gene |
|---|---|---|---|---|
| Bladder Urothelial Carcinoma | ALK | TPM1 | TPM1/ALK | ALK |
| Colon Adenocarcinoma | ALK | PRKAR1A | PRKAR1A/ALK | ALK |
| Cutaneous Melanoma | ALK | NCOA1 | NCOA1/ALK | ALK |
| Ovarian Serous Cystadenocarcinoma | CASR | LPP | LPP/CASR | CASR |
| Glioblastoma | EGFR | MDM2 | MDM2/EGFR | EGFR |
| Lower Grade Glioma | ELAVL3 | FGFR3 | FGFR3/ELAVL3 | FGFR3 |
| Acute Myeloid Leukemia | B2M | GNAS | B2M/GNAS | GNAS |
| Clear Cell Renal Cell Carcinoma | DOCK8 | JAK2 | DOCK8/JAK2 | JAK2 |
| Papillary Renal Cell Carcinoma | HNF1B | NOTCH1 | HNF1B/NOTCH1 | NOTCH1 |
| Glioblastoma | NFASC | NTRK1 | NFASC/NTRK1 | NTRK1 |
| Thyroid Gland Carcinoma | NTRK1 | SSBP2 | SSBP2/NTRK1 | NTRK1 |
| Thyroid Gland Carcinoma | NTRK1 | SQSTM1 | SQSTM1/NTRK1 | NTRK1 |
| Prostate Adenocarcinoma | PIK3CA | TBL1XR1 | TBL1XR1/PIK3CA | PIK3CA |
| Thyroid Gland Carcinoma | AKAP13 | RET | AKAP13/RET | RET |
| Thyroid Gland Carcinoma | FKBP15 | RET | FKBP15/RET | RET |
| Thyroid Gland Carcinoma | RET | TBL1XR1 | TBL1XR1/RET | RET |
| Glioblastoma | CEP85L | ROS1 | CEP85L/ROS1 | ROS1 |

TABLE 1-continued

Gene Fusions

| Cancer Type | Gene A Symbol | Gene B Symbol | orientation | Druggable gene |
|---|---|---|---|---|
| Thyroid Gland Carcinoma | ALK | GTF2IRD1 | GTF2IRD1/ALK | ALK |
| Ovarian Serous Cystadenocarcinoma | BRS3 | HTATSF1 | HTATSF1/BRS3 | BRS3 |
| Invasive Breast Carcinoma | CCDC132 | CDH1 | CDH1/CCDC132; CCDC132/CDH1 | CDH1 |
| Invasive Breast Carcinoma | ERBB2 | SLC29A3 | ERBB2/SLC29A3 | ERBB2 |
| Thyroid Gland Carcinoma | MET | TFG | MET/TFG; TFG/MET | MET |
| Ovarian Serous Cystadenocarcinoma | MNDA | NOTCH2 | NOTCH2/MNDA | NOTCH2 |
| Thyroid Gland Carcinoma | IRF2BP2 | NTRK1 | IRF2BP2/NTRK1 | NTRK1 |
| Ovarian Serous Cystadenocarcinoma | EIF2C2 | PTK2 | EIF2C2/PTK2 | PTK2 |
| Invasive Breast Carcinoma | HOXB3 | RARA | RARA/HOXB3 | RARA |
| Prostate Adenocarcinoma | ETV4 | STAT3 | STAT3/ETV4 | STAT3 |
| Invasive Breast Carcinoma | C17orf64 | TOP1 | TOP1/C17orf64 | TOP1 |
| Prostate Adenocarcinoma | KIAA0753 | TP53 | TP53/KIAA0753 | TP53 |
| Glioblastoma | GFAP | VIM | GFAP/VIM; VIM/GFAP | VIM |
| Thyroid Gland Carcinoma | LTK | UACA | UACA/LTK | LTK |
| Papillary Renal Cell Carcinoma | ALK | STRN | STRN/ALK | ALK |
| Thyroid Gland Carcinoma | ALK | STRN | STRN/ALK | ALK |
| Cutaneous Melanoma | BRAF | CDC27 | CDC27/BRAF | BRAF |
| Thyroid Gland Carcinoma | BRAF | MACF1 | MACF1/BRAF | BRAF |
| Thyroid Gland Carcinoma | BRAF | MKRN1 | MKRN1/BRAF | BRAF |
| Cutaneous Melanoma | BRAF | TAX1BP1 | TAX1BP1/BRAF | BRAF |
| Prostate Adenocarcinoma | BRAF | JHDM1D | JHDM1D/BRAF | BRAF |

TABLE 2

Gene Fusions

| Cancer Type | Gene A Symbol | Gene B Symbol | Orientation | Druggable gene |
|---|---|---|---|---|
| Cutaneous Melanoma | CLCN6 | RAF1 | CLCN6/RAF1 | RAF1 |
| Cutaneous Melanoma | TRAK1 | RAF1 | TRAK/RAF1 | RAF1 |
| Colon Adenocarcinoma | AKT1 | PRKACA | PRKACA/AKT1 | AKT1 |
| Endometrial Endometrioid Adenocarcinoma | AKT1 | PRKACA | PRKACA/AKT1 | AKT1 |
| Colon Adenocarcinoma | AKT2 | PRKACA | PRKACA/AKT2 | AKT2 |
| Lung Adenocarcinoma | FYN | MLL | MLL/FYN | FYN |
| Lung Adenocarcinoma | ECHD1 | FYN | ECHD1/FYN | FYN |
| Invasive Breast Carcinoma | JAK2 | TTC13 | TTC13/JAK2 | JAK2 |
| Gastric Adenocarcinoma | CAB39 | ERBB2 | CAB39/ERBB2 | ERBB2 |
| Endometrial Endometrioid Adenocarcinoma | BRAF | EXOC4 | EXOC4/BRAF | BRAF |
| Invasive Breast Carcinoma | HOOK3 | IKBKB | HOOK3/IKBKB | IKBKB |
| Invasive Breast Carcinoma | CDK6 | KRIT1 | KRIT1/CDK6 | CDK6 |
| Gastric Adenocarcinoma | CAPZA2 | MET | CAPZA2/MET | MET |
| Invasive Breast Carcinoma | ACE | MLLT6 | MLLT6/ACE | ACE |
| Endometrial Endometrioid Adenocarcinoma | HLA-C | MUC16 | HLA-C/MUC16 | MUC16 |
| Head and Neck Squamous Cell Carcinoma | LYN | NTRK3 | LYN/NTRK3 | LYN, NTRK3 |
| Ovarian Serous Cystadenocarcinoma | MUC16 | OR7G2 | MUC16/OR7G2 | MUC16 |
| Ovarian Serous Cystadenocarcinoma | MDK | RAB11B | RAB11B/MDK | MDK |
| Squamous Cell Lung Carcinoma | GADD45GIP1 | RB1 | RB1/GADD45GIP1 | RB1 |
| Gastric Adenocarcinoma | PRKAR2A | RHOA | PRKAR2A/RHOA | RHOA |
| Cutaneous Melanoma | MAPK1 | SHANK3 | SHANK3/MAPK1 | MAPK1 |
| Thyroid Gland Carcinoma | RET | SPECC1L | SPECC1L/RET | RET |
| Ovarian Serous Cystadenocarcinoma | IGFBP2 | SPP1 | IGFBP2/SPP1 | IGFBP2, SPP1 |
| Invasive Breast Carcinoma | PAPD7 | SRD5A1 | PAPD7/SRD5A1; SRD5A1/PAPD7 | SRD5A1 |
| Glioblastoma | RARA | TAOK1 | TAOK1/RARA | RARA |
| Gastric Adenocarcinoma | CDK12 | THRA | THRA/CDK12 | THRA |
| Invasive Breast Carcinoma | NARS2 | TOP1 | NARS2/TOP1 | TOP1 |
| Gastric Adenocarcinoma | PTK2 | TRAPPC9 | PTK2/TRAPPC9; TRAPPC9/PTK2 | PTK2 |
| Invasive Breast Carcinoma | CBL | UBE4A | CBL/UBE4A | CBL |
| Lower Grade Glioma | GFAP | VIM | GFAP/VIM; VIM/GFAP | VIM |

TABLE 2-continued

Gene Fusions

| Cancer Type | Gene A Symbol | Gene B Symbol | Orientation | Druggable gene |
|---|---|---|---|---|
| Invasive Breast Carcinoma | ADAM9 | WRN | WRN/ADAM9 | ADAM9 |
| Colon and Rectal Adenocarcinoma | MAP2K2 | YWHAE | YWHAE/MAP2K2 | MAP2K2 |
| Head and Neck Squamous Cell Carcinoma | ALK | CLIP4 | CLIP4/ALK | ALK |
| Squamous Cell Lung Carcinoma | ALK | CLIP4 | CLIP4/ALK | ALK |
| Thyroid Gland Carcinoma | ALK | MEMO1 | MEMO1/ALK | ALK |
| Thyroid Gland Carcinoma | BRAF | SND1 | BRAF/SND1; SND1/BRAF | BRAF |
| Thyroid Gland Carcinoma | BRAF | ZC3HAV1 | ZC3HAV1/BRAF | BRAF |

TABLE 3

Gene Fusions

| Cancer Type | Gene A Symbol | Gene B Symbol | orientation | Druggable gene | Cancer type precedent |
|---|---|---|---|---|---|
| Thyroid Gland Carcinoma | NOTCH1 | SEC16A | SEC16A-NOTCH1 | NOTCH1 | breast cancer |
| Invasive Breast Carcinoma | ERC1 | RET | ERC1-RET | RET | thyroid cancer |
| Ovarian Serous Cystadenocarcinoma | CCDC170 | ESR1 | ESR1/CCDC170 | ESR1 | Invasive Breast Carcinoma |
| Head and Neck Squamous Cell Carcinoma | RPS6KB1 | VMP1 | RPS6KB1/VMP1; VMP1/RPS6KB1 | RPS6KB1 | Invasive Breast Carcinoma |
| Lung Adenocarcinoma | RPS6KB1 | VMP1 | RPS6KB1/VMP1 | RPS6KB1 | Invasive Breast Carcinoma |
| Squamous Cell Lung Carcinoma | RPS6KB1 | VMP1 | RPS6KB1/VMP1 | RPS6KB1 | Invasive Breast Carcinoma |
| Ovarian Serous Cystadenocarcinoma | RPS6KB1 | VMP1 | RPS6KB1/VMP1 | RPS6KB1 | Invasive Breast Carcinoma |
| Cutaneous Melanoma | RPS6KB1 | VMP1 | RPS6KB1/VMP1 | RPS6KB1 | Invasive Breast Carcinoma |
| Gastric Adenocarcinoma | RPS6KB1 | VMP1 | RPS6KB1/VMP1 | RPS6KB1 | Invasive Breast Carcinoma |

TABLE 4

| Table 4 Fusion Name | 5' Gene Symbol | 5' Gene Chromosome | 5' Accession | 5' Gene Breakpoint | 3' Gene Chrom | 3' Gene Symbol | 3' Accession | 3' Gene Breakpoint | Breakpoint Sequence | SEQ ID NO: |
|---|---|---|---|---|---|---|---|---|---|---|
| TPM1/ ALK | TPM1 | chr15 | NM_000366 | 63,354,844 | chr2 | ALK | NM_004304 | 29446394 | TGCGGAGAGGTCAGTAACTAAATTG GAGAAAGCATTGATGACTTAGAA G\|TGTACCGCCGGAAGCACCAGGAG CTGCAAGCCATGCAGATGAGCTGC AG | 1 |
| PRKAR1/ ALK | PRKAR1A | chr17 | NM_002734 | 66,511,717 | chr2 | ALK | NM_004304 | 29446263 | CTGAGAGACCCATGGCATTCCTCAG GGAATACTTTGAGAGGTTGGAGAA G\|ACCTCCTCCATCAGTGACCTGAAG GAGGTGCCGCGGAAAAACATCACC CT | 2 |
| NCOA1/ ALK | NCOA1 | chr2 | NM_003743 | 24,991,142 | chr2 | ALK | NM_004304 | 30143047 | GTGCAACAGGTTCAGTGTTTGCTG ACGTCCAGTGTACAGTGAATCTGGT\| AGGCGGCTGTGGGGCTGCTCCAGTT CAATCTCAGCGAGCTGTTCAGTTGG | 3 |
| LPP/ CASR | LPP | chr3 | NM_005578 | 188,202,492 | chr3 | CASR | NM_000388 | 121972795 | GAAACTTTCCTCCTCCACCACCTCTT GATGAAGAGGCTTTCAAAGTACAG\| AAGGCATCACAGGAGGCCTCTGCAT GATGTGGCTTCCAAAGACTCAAGGA | 4 |
| MDM2/ EGFR | MDM2 | chr12 | NM_002392 | 69,203,072 | chr7 | EGFR | NM_005228 | 55231426 | GATGGTGCTGTAACCACCTCACAGA TTCCAGCTTCGAACAAGAGACCCT\| GTGAGCCAAGGAGTTTGTGAGA ACTCTGAGTGCATACAGTGCCACCCA | 5 |
| FGFR3/ ELAVL3 | FGFR3 | chr4 | NM_000142 | 1,808,638 | chr19 | ELAVL3 | NM_001420 | 11577572 | GCCCTCCCAGAGGCCCACCTTCAAG CAGCTGGTGGAGGACCTGGACCGTG\|TCCTTGGTACAAATGGAGCCACTGA CGACAGCAAGACCAACCTCATCGTC | 6 |
| B2M/ GNAS | B2M | chr15 | NM_004048 | 45,003,811 | chr20 | GNAS | NM_000516 | 57470667 | TAGCTGTGCTGCGCTACTCTCTCTT TCTGGCCTGGAGGCTATCCAGCGT\|G CTGGAGAATCTGGTAAAAGCACCAT TGTGAAGCAGATGAGGATCCTGCA | 7 |
| DOCK8/ JAK2 | DOCK8 | chr9 | NM_203447 | 340,321 | chr9 | JAK2 | NM_004972 | 5050686 | GAGATTTGGAATTTCCAACACGAG AAGTATATGTCCCTCCACACTGTGTA\| CAGTGCGCCATGATGATTTTGTCACG GATGGATAAAAGTACCTGTGACTCA | 8 |

TABLE 4-continued

Breakpoint Sequence for Table 1

| Table 4 Fusion Name | 5' Gene Chromosome | 5' Gene Symbol | 5' Accession | 5' Gene Breakpoint | 3' Gene Chrom | 3' Gene Symbol | 3' Accession | 3' Gene Breakpoint | Breakpoint Sequence | SEQ ID NO: |
|---|---|---|---|---|---|---|---|---|---|---|
| HNF1B/ NOTCH1 | chr17 | HNF1B | NM_000458 | 36,099,431 | chr9 | NOTCH1 | NM_017617 | 139396940 | TGCCGCTCTGTACACCTGGTACGTC AGAAGCAACAGAGATCTCTCGA C\|GTGAGACCGTGGAGCCGCCCCG CCGGCGCAGCTGCACTTCATGTACG TG | 9 |
| NFASC/ NTRK1 | chr1 | NFASC | NM_015090 | 204,951,148 | chr1 | NTRK1 | NM_002529 | 156844363 | GGGAAGGGCCCTGAGCCAGAGTCC GTCATCGGTTACTCCGGAGAGATT A\|CACTAACAGCACATCTGGAGACC CGGTGGAGAAGGACGAAACAC CTT | 10 |
| SSBP2/ NTRK1 | chr5 | SSBP2 | NM_012446 | 80,742,687 | chr1 | NTRK1 | NM_002529 | 156845312 | TCCAGGAGGTGGAGGGCCACCAGG AACACCCATGCTAGTCCAGCA G\|GCCCGGCTGTGCTGGCTCCAGAG GATGGGCTGGCCATGCTCCCTGCATT TC | 11 |
| SQSTM1/ NTRK1 | chr5 | SQSTM1 | NM_003900 | 179,252,226 | chr1 | NTRK1 | NM_002529 | 156844363 | TTTCCTGAAGAACGTTGGGAGAGT GTGGCAGCTGCCCTTAGCCCTCTGG\| ACACTAACAGCACATCTGGAGACCC GGTGGAGAAGGACGAAACACCT | 12 |
| TBL1XR1/ PIK3CA | chr3 | TBL1XR1 | NM_024665 | 176,914,909 | chr3 | PIK3CA | NM_006218 | 178916538 | CATATAAAACTACTTTAAGGAATTA GATGTATGGTGTCCCAAAGCAGAA\| ACCTTGGAAACGGTGGCCTCCAACG CCGCTCCCCCCTCCCGGAATGGAGG | 13 |
| AKAP13/ RET | chr15 | AKAP13 | NM_006738 | 86,286,839 | chr10 | RET | NM_020630 | 43612067 | CGCCATCTGCACCTTCCATAGCCAA ATCAGGGTCATTGGACTCAGAACTT\| GGTTCTTGGAAAACTCTAGGAGAA GGCGAATTTGAAAAGTGGTCAAGG | 14 |
| FKBP15/ RET | chr9 | FKBP15 | NM_015258 | 115,932,802 | chr10 | RET | NM_020630 | 43612032 | AATCTTACAATGGCAGGACCATTCT GGAACCATGAATACGATCAA G\|GAGAATCCAAAGTGGGAATTCCC TCGGAAGAACTTGGTTCTTGGAAAA AC | 15 |
| TBL1XR1/ RET | chr3 | TBL1XR1 | NM_024665 | 176,765,103 | chr10 | RET | NM_020630 | 43610136 | GCCCTATATTTGCATTAAAATGGAA TAAGAAGGAAATTTCATCCTAAGT \|GCTGGACTCCATGGAGAACCAGT CTCCGTGGATGCCTTCAAGATCCTGG | 16 |
| CEP85L/ ROS1 | chr6 | CEP85L | 387119 | 118,802,942 | chr6 | ROS1 | NM_002944 | 117641193 | TTAATATGCCAGAAAAAGAAGAA AAGGAGTTAGTAACTACCGTTCAGA | 17 |

TABLE 4-continued

Breakpoint Sequence for Table 1

| Table 4 Fusion Name | 5' Gene Symbol | 5' Accession | 5' Gene Chromosome | 5' Gene Breakpoint | 3' Gene Symbol | 3' Accession | 3' Gene Chrom | 3' Gene Breakpoint | Breakpoint Sequence | SEQ ID NO: |
|---|---|---|---|---|---|---|---|---|---|---|
| | | | | | | | | | G\|TACTCTTCAACCCAAGAGAGA TTGAAAATCTTCCTGCCTTCCCTGGG | 30 |
| CCDC132/ CDH1 | NM_017667 | chr7 | CCDC132 | 92,940,584 | CDH1 | NM_004360 | chr16 | 68,857,494 | GAATGCACCTATCTTAACAAATACA ACATTGAACGTCATAAGACTTGTTG\| TTCTGGGGATTCTTGGAGGAATTCT TGCTTTGCTAATTCTGATTCTGCTG | 31 |
| CDH1/ CCDC132 | NM_004360 | chr16 | CDH1 | 68,857,529 | CCDC132 | NM_017667 | chr7 | 92,952,923 | AACATCAAAGCAATTGGCTTAAGA ATGTTCATCATCTGCATATATTTTC\|T TAGCAAAGCAAGAATTCCTCCAAGA ATCCCCAGAATGGCAGGAATTTGC | 32 |
| CDH1/ CCDC132 | NM_004360 | chr16 | CDH1 | 68,857,529 | CCDC132 | NM_017667 | chr7 | 92,952,923 | GCAAATTCCTGCCATTCTGGGGATT CTTGGAGGAATTCTTGCTTTGCTAA\| GAAAATATATGCAGATGATGAACAT TCTTAAGCCAATTGCCTTTGATGTT | 33 |
| EIF2C2/ PTK2 | NM_012154 | chr8 | EIF2C2 | 141,645,584 | PTK2 | NM_005607 | chr8 | 141,685,598 | GCTGCAGGATCTGGTTTACCCACAG GCTGATATATGTTGGTTTCCAAT\| CGGGGCCGGCTCCCGAGTACATGGT GGCGCCGAGGGGCTCCGGGGCC | 34 |
| EIF2C2/ PTK2 | NM_012154 | chr8 | EIF2C2 | 141,645,584 | PTK2 | NM_005607 | chr8 | 141,685,598 | GGGCCCCGGAGCCCCTCGGCCGCGCC ACCATGTACTCGGGAGCCCGGCCCCG\| ATTGGAAACCAACATATATATCAG CCTGTGGGTAAACCAGATCCTGCAG | 35 |
| EIF2C2/ PTK2 | NM_012154 | chr8 | EIF2C2 | 141,645,584 | PTK2 | NM_005607 | chr8 | 141,712,806 | CCCCGGAGCCCCTCGGCGGCGGCCAC CATGTACTCGGGAGCCGGCCCCGGT\| TTCTGGCTACCCTGGTTCACATGGA ATCACAGCCATGGCTGGCAGCATCT | 36 |
| EIF2C2/ PTK2 | NM_012154 | chr8 | EIF2C2 | 141,645,584 | PTK2 | NM_005607 | chr8 | 141,762,415 | CGAAGTACAGTTTTACATGTTTA ATTGCAACCGCCAAAGCTGGATTCT\| CCGGGGCCGGCTCCCGAGTACATGG TGGCGCCGCCGGAGGGGCTCCGGGG | 37 |
| EIF2C2/ PTK2 | NM_012154 | chr8 | EIF2C2 | 141,645,584 | PTK2 | NM_005607 | chr8 | 141,675,096 | GGCCCCGGAGCCCCTCGGCGGCGCC ACCATGTACTCGGGAGCCCGGCCCCG\| GAAGTCGGCTTGGCCCTGAGGACA TTATTGGCCCACTGTGGATGAGACCAT | |

TABLE 4-continued

Breakpoint Sequence for Table 1

| Table 4 Fusion Name | 5' Gene Symbol | 5' Gene Accession | 5' Chromosome | 5' Gene Breakpoint | 3' Gene Symbol | 3' Gene Accession | 3' Chrom | 3' Gene Breakpoint | Breakpoint Sequence | SEQ ID NO: |
|---|---|---|---|---|---|---|---|---|---|---|
| ERBB2/ SLC29A3 | ERBB2 | NM_004448 | chr17 | 37,883,211 | SLC29A3 | NM_018344 | chr10 | 73,115,986 | ACACATGGGCGCAAGAACAGGCC TCATGTAGTACCTGGCATACTCCAG C\|GCCCGGGCAGGTCTGGACAGA AGAAGCCTGCTGGGGTACCAGATA CT | 38 |
| ERBB2/ SLC29A3 | ERBB2 | NM_004448 | chr17 | 37,883,548 | SLC29A3 | NM_018344 | chr10 | 73,121,774 | GGGGCTGGGGCATGGTCCACCAC AGGCACCGCAGCTCATCTACCAGA \|CTCCCTCAGTGCCCCTTCGGTGGCC TCCAGATTCATTGATTCCCACACAC | 39 |
| ERBB2/ SLC29A3 | ERBB2 | NM_004448 | chr17 | 37,883,598 | SLC29A3 | NM_018344 | chr10 | 73,121,726 | GTGGCGGTGGGGACCTGACACTAG GGCTGGAGCCCTCTGAAGAGAGG CC\|TGTTCTTGCGGCCCATGTGTTT CTGGTGAAGAGGAGCTTCCCCAGGA CT | 40 |
| ERBB2/ SLC29A3 | ERBB2 | NM_004448 | chr17 | 37,883,205 | SLC29A3 | NM_018344 | chr10 | 73,115,911 | CTGAGGAGTATCTGTACCCCAGCA GGGCTTCTTCTGTCCAGACCCTGCC\| CAGCGCCCTGCCCTTCTTCCTGACG GCCACTGTCTTCCTCGTGCTCTGCA | 41 |
| ERBB2/ SLC29A3 | ERBB2 | NM_004448 | chr17 | 37,882,078 | SLC29A3 | NM_018344 | chr10 | 73,115,911 | TGCAGAGCACGAGGAAGACAGTGG CCGTCAGGAAGAAGGCCAGGCGC TG\|GGTGCAGATGGGGGCTGGGGC AGCCGCTCCCCCTTTTCCAGCAGGT CAG | 42 |
| GFAP/ VIM | GFAP | NM_002055 | chr17 | 42,987,987 | VIM | NM_003380 | chr10 | 17,277,377 | AGGAGAACCGATCACCATTCCCGT GCAGACCTTCTCCAACCTGCAGATT\| CGAGGAGAGCAGGATTCTCTGCCTC TTCCAAACTTTTCCTCCCCTGAACCT | 43 |
| GFAP/ VIM | GFAP | NM_002055 | chr17 | 42,988,732 | VIM | NM_003380 | chr10 | 17,277,285 | ACGTGCGGGAGGCGGCCAGTTATCA GGAGGCGCTGGCGCGGCTGAGGA A\|ATGCTCGTCACCTTCGTGAATAC CAAGACCTGCTCAATGTTAAGATGGC | 44 |
| GFAP/ VIM | GFAP | NM_002055 | chr17 | 42,987,987 | VIM | NM_003380 | chr10 | 17,277,377 | AGGAGAACCGATCACCATTCCCGT GCAGACCTTCTCCAACCTGCAGATT\| CGAGGAGAGCAGGATTCTCTGCCTT CTTCCAAACTTTTCCTCCCCTGAACC | 45 |

TABLE 4-continued

Breakpoint Sequence for Table 1

| Table 4 Fusion Name | 5' Gene Chromosome | 5' Gene Symbol | 5' Accession | 5' Gene Breakpoint | 3' Gene Chrom | 3' Gene Symbol | 3' Accession | 3' Gene Breakpoint | Breakpoint Sequence | SEQ ID NO: |
|---|---|---|---|---|---|---|---|---|---|---|
| GFAP/VIM | GFAP | NM_002055 | chr17 | 42,988,622 | VIM | NM_003380 | chr10 | 17,277,371 | AATGTCAAGCTGGCCTGGACATCG AGATCGCCACCTACAGGAAGCTGCT \| GGAAGGCGAGGAGCAGGATTTC TCTGCCTCTTCCAAACTTTCCTCCC | 46 |
| GFAP/VIM | GFAP | NM_002055 | chr17 | 42,985,511 | VIM | NM_003380 | chr10 | 17,277,237 | ATCACCATTCCGTGCAGACCTTCT CCAACCTGCAGATTCGAGAAACCAG \|GACACTATTGCCGCCTGCAGGAT GAGATTCAGAATATGAAGGAGGAA AT | 47 |
| GFAP/VIM | GFAP | NM_001131019 | chr17 | 42,987,602 | VIM | NM_003380 | chr10 | 17,277,286 | CTTCTCCAACCTGCAGATTCGAGGG GGCAAAAGCACCAAAGACGGGGAA A\|TGGCTCGTCACCTTCGTGAATACC AAGACCTGCTCAATGTTAAGATGGCC | 48 |
| GFAP/VIM | GFAP | NM_002055 | chr17 | 42,987,983 | VIM | NM_003380 | chr10 | 17,278,298 | GAACCGGATCACCATTCCCGTGCAG ACCTTCTCCAACCTGCAGATTCGAG\| AATCTGGATTCACTCCCTCTGGTTG ATACCCACTCAAAAGGACACTTCT | 49 |
| GFAP/VIM | GFAP | NM_002055 | chr17 | 42,992,594 | VIM | NM_003380 | chr10 | 17,271,785 | CAGAGATGATGGAGCTCAATGACC GCTTTGCCAGTTACATCGAGAAGGT T\|CGCTTCCTGGAGCAGAATAA GATCCTGCTGCCGAGCTCGAGCAG CT | 50 |
| GFAP/VIM | GFAP | NM_002055 | chr17 | 42,985,469 | VIM | NM_003380 | chr10 | 17,277,285 | GAAACCAGCTGGACACCAAGTCTG TGTCAGAAGGCCACCTCAAGAGGA A\|ATGGCTCGTCACCTTCGTGAATAC CAAGACCTGCTCAATGTTAAGATGGC | 51 |
| GFAP/VIM | GFAP | NM_002055 | chr17 | 42,988,779 | VIM | NM_003380 | chr10 | 17,277,168 | CACGAACGAGTCCCTGGAGAGGCA GATGCCGAGCAGGAGGAGCGGCA CG\|AATGAGTCCCTGAACGCCAGA TGCGTGAAATGGAAGAGAACTTTGC CGT | 52 |
| GFAP/VIM | GFAP | NM_002055 | chr17 | 42,988,637 | VIM | NM_003380 | chr10 | 17,277,351 | GGCAGAGAAATCCTGCTCTCCTCGC CTTCCAGCAGTTCCTCTGTAGGTGGC\| GTGGCCATTCGATGTCCAGGGCCA GCTTGACATTGAGCAGTCCTGGTA | 53 |

TABLE 4-continued

Breakpoint Sequence for Table 1

| Table 4 Fusion Name | 5' Gene Chromosome | 5' Gene Symbol | 5' Accession | 5' Gene Breakpoint | 3' Gene Chrom | 3' Gene Symbol | 3' Accession | 3' Gene Breakpoint | Breakpoint Sequence | SEQ ID NO: |
|---|---|---|---|---|---|---|---|---|---|---|
| GFAP/VIM | GFAP | NM_002055 | chr17 | 42,992,627 | VIM | NM_003380 | chr10 | 17,271,752 | CTGGCTTCAAGGAGACCCGGCCAGTGAGCGGGCAGAGATGAGAGCTC\|AATGACCGCTTCGCCAACTACATCGACAAGGTGCGCTTCCTGGAGCAGCA | 54 |
| GFAP/VIM | GFAP | NM_002055 | chr17 | 42,988,742 | VIM | NM_003380 | chr10 | 17,277,351 | GAGGAGCGGCACGTGCGGGAGGCGGCCAGTTATCAGGAGGCGCTGGCGCG\|GCCACCTACAGGAAGCTGCTGGAAGGCGAGGAGCAGGATTTCTCTGCC | 55 |
| GFAP/VIM | GFAP | NM_002055 | chr17 | 42,988,025 | VIM | NM_003380 | chr10 | 17,276,771 | CATCGAGATCGCCACTACAGGAAGCTGCTAGAGGGCGAGGAGAACCGGA\|GACAGGTGCAGTCCCTCACCTGTGAAGTGGATGCCCTTAAAGGAACCAAT | 56 |
| GFAP/VIM | GFAP | NM_002055 | chr17 | 42,988,742 | VIM | NM_003380 | chr10 | 17,277,367 | GAGGAGCGGCACGTGCGGGAGGCGGCCAGTTATCAGGAGGCGCTGGCGC\|TGCTGGAAGGCGAGGAGCAGGATTTCTCTGCCTCTTCCAAACTTTTCC | 57 |
| GFAP/VIM | GFAP | NM_002055 | chr17 | 42,988,642 | VIM | NM_003380 | chr10 | 17,277,351 | GGCAGAGAAATCCTGCTCTCCTCGCCTTCCAGCAGCTTCCTGTAGTGGC\|GATCTCGATGTCCAGGCCAGCTTGACATTGAGCAGGTCCTGGTACTCCT | 58 |
| GFAP/VIM | GFAP | NM_002055 | chr17 | 42,988,642 | VIM | NM_003380 | chr10 | 17,277,351 | AGGAGTACCAGGACCTGCTCAATGTCAAGCTGGCCCTGGACATCGAGATC\|GCCACCTACAGGAAGCTGCTGGAAGGCGAGGAGCAGGATTTCTCTGC | 59 |
| GFAP/VIM | GFAP | NM_002055 | chr17 | 42,992,612 | VIM | NM_003380 | chr10 | 17,271,824 | CCCGGCCAGTGAGCGGCAGAGATGATGGAGCTCAATGACCGCTTTGCC\|CTCGAGCAGCTCAAGGGCCAAGGCAAGTCGCGCCTGGGGGACCTCTACGA | 60 |
| GFAP/VIM | GFAP | NM_002055 | chr17 | 42,992,610 | VIM | NM_003380 | chr10 | 17,271,769 | CGGGCCAGTGAGCGGGCAGAGATGATGGAGCTCAATGACCGCTTTGCCAG\|CTACATCGACAAGGTGCGCTTCCTGGAGCAGCAGAATAAGATCCTGCTGG | 61 |

TABLE 4-continued

Breakpoint Sequence for Table 1

| Table 4 Fusion Name | 5' Gene Symbol | 5' Accession | 5' Gene Chromosome | 5' Gene Breakpoint | 3' Gene Symbol | 3' Gene Chrom | 3' Accession | 3' Gene Breakpoint | Breakpoint Sequence | SEQ ID NO: |
|---|---|---|---|---|---|---|---|---|---|---|
| GTF2IRD1/ ALK | GTF2IRD1 | NM_005685 | chr7 | 73,935,627 | ALK | chr2 | NM_004304 | 29,446,394 | ACGTCCATGCTCCAAGCGCATTCT CTTCCCATCCTCCATGACAAGTCA\|GTGTACCGCCGGAAGCACCAGGAG CTGCAAGCCATGCAGATGGAGCTGCA | 62 |
| HTATSF1/ BRS3 | HTATSF1 | NM_014500 | chrX | 135,586,622 | BRS3 | chrX | NM_001727 | 135,572,292 | CCATGAGCGAGTTGTCATCATCAAG AATATGTTTCATCCTATGGATTTTG\|AGATACAAGGCAGTTGTGAAGCCA CTTGAGCGACAGCCCTCCAATGCCAT | 63 |
| IRF2BP2/ NTRK1 | IRF2BP2 | NM_182972 | chr1 | 234,744,241 | NTRK1 | chr1 | NM_002529 | 156,844,363 | CTCGGGGCCCTTCGAGAGCAAGTTT AAGAAGGAGCCGGCCCTGACTGCA G\|ACACTAACAGCACATCTGGAGAC CCGGTGGAGAAGGACGACGAAACA CCT | 64 |
| IRF2BP2/ NTRK1 | IRF2BP2 | NM_182972 | chr1 | 234,744,241 | NTRK1 | chr1 | NM_002529 | 156,844,363 | AGGTGTTTCGTCCTTCTTCCACCG GGTCTCCAGATGTGCTGTTAGTGT\|C TGCAGTCAGGGCCGGCCTCCTTCTTA AACTTGCTCTCGAAGGGCCCCCGAG | 65 |
| MET/ TFG | MET | NM_000245 | chr7 | 116,412,043 | TFG | chr3 | NM_006070 | 100,455,420 | AGAAATGGTTTCAAATGAATCTGTA GACTACCGAGCTACTTTTCCAGAAG GGCCACCCAGTGCTCCTGCAGAAGA TCGTTCAGGAGAACACCCGACAGCATT | 66 |
| MET/ TFG | MET | NM_000245 | chr7 | 116,412,013 | TFG | chr3 | NM_006070 | 100,455,435 | TGTAAGTGCCCGAAGTGTAAGCCA ACTACAGAAATGGTTTCAAATGAAT\|CTGCAGAAGATCGTTCAGGAACAC CCGACAGCATTGCTTCCTCCTCCTCA | 67 |
| MET/ TFG | MET | NM_000245 | chr7 | 116,414,937 | TFG | chr3 | NM_006070 | 100,455,447 | AATGGTTTCAAATGAATCTGTAGAC TACCGAGCTACTTTTCCAGAGATC\|GTTCAGGAACACCCGACAGCATTGC TTCCTCCTCCTCAGCAGCTCACCCA | 68 |
| MET/ TFG | MET | NM_000245 | chr7 | 116,415,078 | TFG | chr3 | NM_006070 | 100,455,435 | TATATCCAGTCCATTACTGCAAAT ACTGTCCACATTGACCTCAGTGCTC\|CTGCAGAAGATCGTTCAGGAACACC CGACAGCATTGCTTCCTCCTCCTCA | 69 |
| NOTCH2/ MNDA | NOTCH2 | NM_024408 | chr1 | 120,478,095 | MNDA | chr1 | NM_002432 | 158,815,377 | TATTGACCTTGTGAACCATTTCAAG TGCTCTTGCCCACCAGGCACTCGGG\|AATCAGGAAACCCAGCCCAACGG CAGGTGGATGCAAGAAGAAATGTT CC | 70 |

TABLE 4-continued

Breakpoint Sequence for Table 1

| Table 4 Fusion Name | 5' Gene Symbol | 5' Gene Accession | 5' Chromosome | Gene Breakpoint | 3' Gene Symbol | 3' Gene Chrom | 3' Accession | 3' Gene Breakpoint | Breakpoint Sequence | SEQ ID NO: |
|---|---|---|---|---|---|---|---|---|---|---|
| NOTCH2/MNDA | NOTCH2 | NM_024408 | chr1 | 120,478,095 | MNDA | NM_002432 | chr1 | 58,815,377 | GTATTGACCTTGTGAACCATTTCAA GTGCTCTTGCCCACCAGGCACTCGG GAATCAGGAAACCCAGGCCCAACG GCAGGTGGATCAAGAAGAAATGT TC | 71 |
| RARA/HOXB3 | RARA | NM_000964 | chr17 | 38,508,759 | HOXB3 | NM_002146 | chr17 | 46,632,980 | CCATCCCCGACCAGATCACCCTCCT CAAGGCTGCCTGCCTGACATCCTG GAGGGAGATTTGTCCCTGCCGCT CGCTCTGGGGCTCGATGTGAATATA | 72 |
| STAT3/ETV4 | STAT3 | NM_003150 | chr17 | 40,468,807 | ETV4 | NM_001986 | chr17 | 41,611,353 | GTTTGAAATAATGGTGAAGGTGCT GAACCCTCAGCAGGAGGGCAGTTTG TAGCTTTCCACAGCCCACCACCAG GATCAAGAAGGAGCCCCAGAGTCCC | 73 |
| STAT3/ETV4 | STAT3 | NM_003150 | chr17 | 40,468,860 | ETV4 | NM_001986 | chr17 | 41,613,825 | AGCAATACCATTGACCTGCCATGT CCCCCGCACTTTAGATTCATTGAT GCAGTTTGTTCCTGATTTCATTCAG AAAACCTAGCTTTCCACAGCCCCA | 74 |
| STAT3/ETV4 | STAT3 | NM_003150 | chr17 | 40,468,846 | ETV4 | NM_001986 | chr17 | 41,610,042 | CCTGCCGATGTCCCCCGCACTTTA GATTCATTGATGCAGTTTGGAAATA GATGTCACCGGTGCCATCAATGT ACTCCACACAGAGGCTTCTCTGG | 75 |
| TFG/MET | TFG | NM_006070 | chr3 | 100,451,516 | MET | NM_000245 | chr7 | 116,414,935 | ATCAATAAAAATGTTATGTCAGCGT TTGGCTTAACAGATGATCAGGTTTC AGATCAGTTTCCTAATTCATCTCAG AACGGTTCATGCCGACAAGTGCAGT | 76 |
| TOP1/C17orf64 | TOP1 | NM_003286 | chr20 | 39,729,993 | C17orf64 | NM_181707 | chr17 | 58,503,144 | CATCCAAGGTTCCATTAAATACATC ATGCTTAACCCTAGTTCACGAATCA AGGTGACAAATGTCATGCCTGGA GACAAGCTCCAGCGCCAGCCTGCT | 77 |
| TOP1/C17orf64 | TOP1 | NM_003286 | chr20 | 39,729,993 | C17orf64 | NM_181707 | chr17 | 58,503,144 | CCAAGGTTCCATTAAATACATCATG CTTAACCCTAGTTCACGAATCAAGG TGACAAATGTCATGCCTGGAGAC AAGCTCCAGCGCCAGCCCTGCTAGA | 78 |
| TOP1/C17orf64 | TOP1 | NM_003286 | chr20 | 39,728,797 | C17orf64 | NM_181707 | chr17 | 58,503,167 | TGGCATGGCGCATGAGCGAGTCTCT AGCAGGGCTGGCGCTGGAGCTTGTC TCCAGGAGGCTCTATCTTGAAGTTA GCAATCCTCTTTGTGGTTATCCA | 79 |

TABLE 4-continued

Breakpoint Sequence for Table 1

| Table 4 Fusion Name | 5' Gene Symbol | 5' Gene Chromosome | 5' Accession | 5' Gene Breakpoint | 3' Gene Symbol | 3' Gene Chrom | 3' Accession | 3' Gene Breakpoint | Breakpoint Sequence | SEQ ID NO: |
|---|---|---|---|---|---|---|---|---|---|---|
| TP53/ KIAA0753 | TP53 | NM_000546 | chr17 | 7,590,695 | KIAA0753 | NM_014804 | chr17 | 6,498,373 | TCAGCATATGGATTTATTATATCT TGACGAACAGACTCCTGGTATTT\|C AATCCAGGAAGCGTCACCGTC GTGGAAAGCACGCTCCCAGCCGA | 80 |
| TP53/ KIAA0753 | TP53 | NM_000546 | chr17 | 7,579,529 | KIAA0753 | NM_014804 | chr17 | 6,493,323 | TCCCAAGCAATGGATGATTTGATGC TGTCCCCGACGATATTGAACAAT TTCCCTGGATGAAAGTGTGGGAACA GAGGAAGGATCAGAGAAAAGAGAGG | 81 |
| TP53/ KIAA0753 | TP53 | NM_000546 | chr17 | 7,590,695 | KIAA0753 | NM_014804 | chr17 | 6,498,373 | TTCGGGCTGGGAGCTGCTTTCCAC GACGGTGACACGCTTCCCTGGATTG\| GAAATACCAGGAGTCTGTTGTCAA AGATATAATAAAATCCATATGCTG | 82 |
| VIM/ GFAP | VIM | NM_003380 | chr10 | 17,277,255 | GFAP | NM_002055 | chr17 | 42,987,987 | GAACTTTGCCGTTGAAGCTGCTAAC TACCAAGACACTATTGCCGCCTGC\| TCGAGAACCAGCCTGACACCAA GTCTGTCTCAGAAGGCCACCTCAAGA | 83 |
| VIM/ GFAP | VIM | NM_003380 | chr10 | 17,277,325 | GFAP | NM_002055 | chr17 | 42,988,666 | AAGGAGGAAATGGCTGCTCACCTTC GTGAATACCAAGACCTGCTCAATGT\| CAAGCTGGCCCTGACAATCGAGATC GCCACCTACAGGAAGCTGCTAGAGG | 84 |
| VIM/ GFAP | VIM | NM_003380 | chr10 | 17,277,255 | GFAP | NM_002055 | chr17 | 42,987,987 | TTGAAGCTGCTAACTACCAAGACAC TATTGCCGCCTGC\|TCGAGAAACCA GCCTGACACCAAGTCTGTGTCAGA AGGCCACCTCAAGA | 85 |
| VIM/ GFAP | VIM | NM_003380 | chr10 | 17,277,370 | GFAP | NM_002055 | chr17 | 42,988,621 | AATGTTAAGATGGCCCTTGACATTG AGATTGCCACCTACAGGAAGCTGCT\| AGAGGGCGAGGAGAACCGGATCAC CATTCCCGTGCAGACCTTCTCCAACC | 86 |
| VIM/ GFAP | VIM | NM_003380 | chr10 | 17,271,830 | GFAP | NM_002055 | chr17 | 42,992,688 | GGTGCGCTTCTGGAGCAGCAGAAT AAGATCCTGTGGCCCAGCTCGAGC\| GGGCACTCAATGCTGGCTTCAAGG AGACCCGGGCCAGTGAGCGGGCAG AG | 87 |
| VIM/ GFAP | VIM | NM_003380 | chr10 | 17,277,350 | GFAP | NM_002055 | chr17 | 42,988,641 | GTGAATACCAAGACCTGCTCAATGT TAAGATGGCCCTTGACATTGAGATT\| GCCACCTACAGGAAGCTGCTAGAG GCGAGGAGAACCGGATCACCATT CC | 88 |

TABLE 4-continued

Breakpoint Sequence for Table 1

| Table 4 Fusion Name | 5' Gene Chromosome | 5' Gene Symbol | 5' Accession | 5' Gene Breakpoint | 3' Gene Chrom | 3' Gene Symbol | 3' Accession | 3' Gene Breakpoint | Breakpoint Sequence | SEQ ID NO: |
|---|---|---|---|---|---|---|---|---|---|---|
| VIM/ GFAP | VIM | VIM | NM_003380 | 17,277,877 | GFAP | NM_002055 | chr17 | 42,988,655 | GAAGGCGGAGGAGAGCAGGATTCT CTGCCTCTTCCAAACTTTCCTCCCT\|TGGACATCGAGATCGCCACCTACAG GAAGCTGCTAGAGGGCGAGGAGAAC | 89 |
| VIM/ GFAP | VIM | VIM | NM_003380 | 17,277,877 | GFAP | NM_002055 | chr17 | 42,988,655 | GGAAGGCGAGGAGAGCAGGATTCT CTGCCTCTTCCAAACTTTCCTCCCT\|TGGACATCGAGATCGCCACCTACAG GAAGCTGCTAGAGGGCGAGGAGAAC | 90 |
| UACA/ LTK | chr15 | UACA | NM_018003 | 70,957,001 | chr15 | LTK | NM_002344 | 41799372 | TGATTGACACTCTGCAGCACCAAGT GAAATCTCTGGAGCAACAGCTGGCC \|GTGGGGCTTGGCCCGGCCCAGTCCT GGCCTCTGCCACCAGTGTCACCGA | 184 |
| STRN/ ALK | chr2 | STRN | NM_003162 | 37,143,221 | chr2 | ALK | NM_004304 | 29446394 | TACGGGACAGAATTGAATCAGGGA GATATGAAGCTCCAAGCTATGATT C\|TGTGTACCGCCGGAAGCACCAGG AGCTGCAAGCCATGCAGATGGAGCT GC | 185 |
| STRN/ ALK | chr2 | STRN | NM_003162 | 37,143,221 | chr2 | ALK | NM_004304 | 29446394 | TACGGGACAGAATTGAATCAGGGA GATATGAAGCTCCAAGCTATGATT C\|TGTGTACCGCCGGAAGCACCAGG AGCTGCAAGCCATGCAGATGGAGCT GC | 186 |
| JHDM1D/ BRAF | chr7 | JHDM1D | NM_030647 | 139,810,895 | chr7 | BRAF | NM_004333 | 140481493 | TAGAACCTGGACACCTTATTAAAGAA CTTTCTAAAGTAATTCGAGCAATAG\|AGAAAACACTTGGTAGACGGGACT CGAGTGATGATTGGGAGATTCCTGAT | 187 |
| JHDM1D/ BRAF | chr7 | JHDM1D | NM_030647 | 139,810,895 | chr7 | BRAF | NM_004333 | 140481493 | GACCTGGACACCTTATTAAAGAACT TCTAAAGTAATTCGAGCAATAGA \|AAAACACTTGGTAGACGGACTCG AGTGATGATTGGGAGATTCCTGATGG | 188 |

TABLE 4-continued

Breakpoint Sequence for Table 1

| Table 4 Fusion Gene Name | 5' Gene Chromosome | 5' Gene Symbol | 5' Accession | 5' Gene Breakpoint | 3' Gene Chrom | 3' Gene Symbol | 3' Accession | 3' Gene Breakpoint | Breakpoint Sequence | SEQ ID NO: |
|---|---|---|---|---|---|---|---|---|---|---|
| TAX1BP1/ BRAF | chr7 | TAX1BP1 | NM_006024 | 27,827,222 | chr7 | BRAF | NM_004333 | 140481493 | CTGAAAAGGAAAATCTGCAAAGAA CTTTCCTGCTTACAACCTCAAGTAA A\|AAACACTTGGTAGACGGGACTC GAGTGATGATTGGGAGATTCCTGAT GG | 189 |
| MKRN1/ BRAF | chr7 | MKRN1 | NM_013446 | 140,158,807 | chr7 | BRAF | NM_004333 | 140487384 | TGCAGTCCTGCATCCAATGATGC TGCCCAGAGATCGCAGCATATCAAA \|GACTTGATTAGAGACCAAGGATTTC GTGGTGATGGAGGATCAACCACAGG | 190 |
| MACF1/ BRAF | chr1 | MACF1 | NM_012090 | 39,896,580 | chr7 | BRAF | NM_004333 | 140487384 | TTGGACAAAGGGTGGATGAAATTG ATGCTCTATTCAGAGATCACAACA G\|GACTTGATTAGAGACCAAGGATT TCGTGGTGATGGAGGATCAACCACA GG | 191 |
| CDC27/ BRAF | chr17 | CDC27 | NM_001256 | 45,206,816 | chr7 | BRAF | NM_004333 | 140487365 | CAGAGAAGGCTTTGATACCCTAAA CAAAGCCATTGTCATTGATCCCAAG\| GATTTCGTGGTGATGGAGGATCAAC CACAGTTTGTCTGCTACCCCCCT | 192 |

TABLE 5

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Melanoma | CLCN6/ RAF1 | chr1 | CLCN6 | NM_001286 | 11867247 | chr3 | RAF1 | NM_002880 | 12641914 | GAGAAACACAGGAGG AGGAGGATGAGATTC TTCCAAGGAAAGACT ATGAG\|GATGCAATTC GAAGTCACAGCGAAT CAGCCTCACCTTCAGC CCTGTCCAG SEQ ID NO: 18 |
| Melanoma | TRAK1/ RAF1 | chr3 | TRAK1 | NM_014965 | 42235390 | chr3 | RAF1 | NM_002880 | 12641914 | TCCAGCATCTGGGGG CTGCTAAGGATGCCC AGCGGCAGCTCACAG CCGAG\|GATGCAATTC GAAGTCACAGCGAAT CAGCCTCACCTTCAGC CCTGTCCAG SEQ ID NO: 19 |
| Colon adenocarcinoma | PRKACA/ AKT1 | chr19 | PRKACA | NM_002730 | 14208406 | chr14 | AKT1 | NM_005163 | 1.05E+08 | AGGGCCGCACTTGGA CCTTGTGCGGCACCCG TGAGTACCTGCCCCT GAG\|GTGCTGGAGGAC AATGACTACGCCGT GCAGTGGACTGGTGG GGGCTGGG SEQ ID NO: 20 |
| Colon adenocarcinoma | PRKACA/ AKT1 | chr19 | PRKACA | NM_002730 | 14208406 | chr14 | AKT1 | NM_005163 | 1.05E+08 | AGGGCCGCACTTGGA CCTTGTGCGGCACCCG TGAGTACCTGCCCCT GAG\|GTGCTGGAGGAC AATGACTACGCCGT GCAGTGGACTGGTGG GGGCTGGG SEQ ID NO: 21 |
| Colon adenocarcinoma | PRKACA/ AKT1 | chr19 | PRKACA | NM_002730 | 14208406 | chr14 | AKT1 | NM_005163 | 1.05E+08 | AGGGCCGCACTTGGA CCTTGTGCGGCACCCG TGAGTACCTGCCCCT GAG\|GTGCTGGAGGAC AATGACTACGCCGT GCAGTGGACTGGTGG GGGCTGGG SEQ ID NO: 22 |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Endometrial endometriosis | PRKACA/ AKT1 | chr19 | PRKACA | NM_002730 | 14208406 | chr14 | AKT1 | NM_005163 | 1.05E+08 | AGGGCCGCACTTGGA CCTTGTGCGGCACCCC TGAGTACCTGCCCCT GAG\|GTGCTGGAGGAC AATGACTACGCCGT GCAGTGGACTGGTGG GGGCTGGG SEQ ID NO: 23 |
| Colon adenocarcinoma | PRKACA/ AKT2 | chr19 | PRKACA | NM_002730 | 14208406 | chr19 | AKT2 | NM_001626 | 40742011 | AGGGCCGCACTTGGA CCTTGTGCGGCACCCC TGAGTACCTGCCCCT GAG\|GTGCTGGAGGAC AATGACTATGCCGG GCCGTGGACTGGTGG GGGCTGGG SEQ ID NO: 24 |
| Lung adenocarcinoma | MLL/FYN | chr11 | MLL | NM_005933 | 1.18E+08 | chr6 | FYN | NM_002037 | 1.12E+08 | CCAGGAAGCTCGATC AAATGCCCGCCTAAA GCAGCTCTCATTTGCA GGTG\|GTACTTTGAA AACTTGGCCGAAAAG ATGCTGAGCGACAGC TATTGTCCT SEQ ID NO: 25 |
| Lung adenocarcinoma | ECHDC1/ FYN | chr6 | ECHDC1 | NM_001002030 | 1.28E+08 | chr6 | FYN | NM_002037 | 1.12E+08 | CAAGGTTGGGCATTG GGTGGAGGAGCAGAA TTTACTACAGCATGTG ATTT\|CAGGGAAGGAG ATTGGTGGGAAGCCC GCTCCTTGACAACTGG AGAGACAG SEQ ID NO: 26 |
| Breast carcinoma | TTC13/JAK2 | chr1 | TTC13 | NM_024525 | 2.31E+08 | chr9 | JAK2 | NM_004972 | 5055786 | CTTCATATATCAGAGGA CTATGCAACAGCCCA TGAAGACTTTCAGCA GTCCT\|CTGAAAATTG AACTTAGCTCATTAAG GGAAGCTTTGTCTTTC GTGTCATT SEQ ID NO: 27 |
| Gastric Adenocarcinoma | CAB39/ ERBB2 | chr2 | CAB39 | NM_016289 | 231,577,945 | chr17 | ERBB2 | NM_004448 | 37,863,243 | GGGGACGCAGCGACGAC GCGGAGGCAGAGAAG |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Gastric Adenocarcinoma | CAPZA2/MET | chr7 | CAPZA2 | NM_006136 | 116,502,704 | chr7 | MET | NM_000245 | 116,435,709 | GGAACGCCCGCCCA GCCCC\|TGTGCACCGG CACAGACATGAAGCT GCGGCTCCCTGCCAGT CCCGAGACC SEQ ID NO: 91 CCAGAAGGAGGAAGATGG CGGATCTGGAGGAGC AGTTGTCTGATGAAG AGAAG\|TGGTCCTTTG GCGTGCTCCTCTGGGA GCTGATGACAAGAGG AGCCCCACC SEQ ID NO: 92 |
| Invasive Breast Carcinoma | CBL/UBE4A | chr11 | CBL | NM_005188 | 119,158,656 | chr11 | UBE4A | NM_004788 | 118,261,372 | CAAAATCAAACCTTC CTCATCTGCCAATGCC ATTTATTCTGGCTG CCA\|GGGATGAGGAGA ATTTCTGTGCCACTGT GCCCAAGGATGACG TTCCTAT SEQ ID NO: 93 |
| Endometrial Endometrioid Adenocarcinoma | EXOC4/BRAF | chr7 | EXOC4 | NM_021807 | 133,164,892 | chr7 | BRAF | NM_004333 | 140,434,570 | TCTGCGAGAACAGAG AAGGAGCTCTATAG TCGGAGTGGAGAACT GCAAG\|ATTCTCGCCT CTATTGAGCTGCTGGC CCGCTCATTGCCAAA AATTCACCG SEQ ID NO: 94 |
| Low Grade Glioma | VM/GFAP | chr10 | VIM | NM_003380 | 17,271,860 | chr17 | GFAP | NM_002055 | 42,992,778 | CCTGCTGGCCCAGCTC GAGCAGCTCAAGGGC CAAGGCAAGTCGCGC CTGG\|CTCCTGGCCGC CGTCTGGGTCCTGGCA CCCGCCTCTCCCTGGC TCGAATG SEQ ID NO: 95 |
| Low Grade Glioma | VM/GFAP | chr10 | VIM | NM_003380 | 17,276,745 | chr17 | GFAP | NM_002055 | 42,988,692 | CTGACCTCTCTGAGGC TGCCAACCGGAACAA TGACGCCCTGCGCCA GGCA\|CAGGAGTACCA |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Low Grade Glioma | | | | | | | | | | GGACCTGCTCAATGTC AAGCTGGCCCTGGAC ATCGAGAT SEQ ID NO: 96 |
| Low Grade Glioma | VM/GFAP | chr10 | VIM | NM_003380 | 17,276,789 | chr17 | GFAP | NM_002055 | 42,990,649 | CAGGCAAAGCAGGAG TCCACTGAGTACCGG AGACAGGTGCAGTCC CTCAC\|GTACCGCTCC AAGTTTGCAGACCTG ACAGACGCTGCTGCC CGCAACGCGG SEQ ID NO: 97 |
| Low Grade Glioma | VM/GFAP | chr10 | VIM | NM_003380 | 17,276,817 | chr17 | GFAP | NM_002055 | 42,988,824 | TTTGCCGTTGAAGCTG CTAACTACCAAGACA CTATTGGCCGCCTGCA GGA\|GTACCAGGACCT GCTCAATGTCAAGCT GGCCCTGGACATCGA GATCGCCA SEQ ID NO: 98 |
| Low Grade Glioma | VM/GFAP | chr10 | VIM | NM_003380 | 17,276,817 | chr17 | GFAP | NM_002055 | 42,988,824 | CATTGAGATTGCCACC TACAGGAAGCTGCTG GAAGGCGAGGAGAGC AGGA\|GTACCAGGACC TGCTCAATGTCAAGCT GGCCCTGGACATCGA GATCGCCA SEQ ID NO: 99 |
| Low Grade Glioma | VM/GFAP | chr10 | VIM | NM_003380 | 17,277,255 | chr17 | GFAP | NM_002055 | 42,987,988 | GAACTTTGCCGTTGAA GCTGCTAACTACCAA GACACTATTGGCCGC CTGC\|TTCGAGAAACC AGCCTGGACACCAAG TCTGTGTCAGAAGGC CACCTCAAG SEQ ID NO: 100 |
| Low Grade Glioma | VM/GFAP | chr10 | VIM | NM_003380 | 17,277,259 | chr17 | GFAP | NM_002055 | 42,988,687 | TTTGCCGTTGAAGCTG CTAACTACCAAGACA CTATTGCCCGCCTGCA GGA\|GTACCAGGACCT GCTCAATGTCAAGCT GGCCCTGGACATCGA |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Low Grade Glioma | VM/GFAP | chr10 | VIM | NM_003380 | 17,277,2259 | chr17 | GFAP | NM_002055 | 42,988,687 | GATCGCCA SEQ ID NO: 101 |
| Low Grade Glioma | VM/GFAP | chr10 | VIM | NM_003380 | 17,277,323 | chr17 | GFAP | NM_002055 | 42,988,623 | TTTGCCGTTGAAGCTG CTAACTACCAAGACA CTATTGGCCGCCTGCA GGA\|GTACCAGGACCT GCTCAATGTCAAGCT GGCCCTGGACATCGA GATCGCCA SEQ ID NO: 102 |
| Low Grade Glioma | VM/GFAP | chr10 | VIM | NM_003380 | 17,277,325 | chr17 | GFAP | NM_002055 | 42,988,666 | TGAAGGAGGAAATGG CTCGTCACCTTCGTGA ATACCAAGACCTGCT CAAT\|CTAGAGGGCGA GGAGAACCGGATCAC CATTCCCGTGCAGACC TTCTCCAA SEQ ID NO: 103 |
| Low Grade Glioma | VM/GFAP | chr10 | VIM | NM_003380 | 17,277,370 | chr17 | GFAP | NM_002055 | 42,988,621 | AAGGAGGAAATGGCT CGTCACCTTCGTGAAT ACCAAGACCTGCTCA ATGT\|CAAGCTGGCCC TGGACATCGAGATCG CCACCTACGAAGC TGCTAGAGG SEQ ID NO: 104 |
| Low Grade Glioma | VM/GFAP | chr10 | VIM | NM_003380 | 17,277,370 | chr17 | GFAP | NM_002055 | 42,988,621 | AATGTTAAGATGGCC CTTGACATTGAGATTG CCACCTACAGGAAGC TGCT\|AGAGGGCGAGG AGAACCGGATCACCA TTCCCGTGCAGACCTT CTCCAACC SEQ ID NO: 105 |
| Low Grade Glioma | VM/GFAP | chr10 | VIM | NM_003380 | 17,277,370 | chr17 | GFAP | NM_002055 | 42,988,621 | AATGTTAAGATGGCC CTTGACATTGAGATTG CCACCTACAGGAAGC TGCT\|AGAGGGCGAGG AGAACCGGATCACCA TTCCCGTGCAGACCTT CTCCAACC SEQ ID NO: 106 |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Low Grade Glioma | VM/GFAP | chr10 | VIM | NM_003380 | 17,277,370 | chr17 | GFAP | NM_002055 | 42,988,621 | AATGTTAAGATGGCC CTTGACATTGAGATTG CCACTACAGGAAGC TGCT\|AGAGGGCGAGG AGAACCGGATCACCA TTCCCGTGCAGACCTT CTCCAACC SEQ ID NO: 107 |
| Low Grade Glioma | VM/GFAP | chr10 | VIM | NM_003380 | 17,277,370 | chr17 | GFAP | NM_002055 | 42,988,621 | AATGTTAAGATGGCC CTTGACATTGAGATTG CCACTACAGGAAGC TGCT\|AGAGGGCGAGG AGAACCGGATCACCA TTCCCGTGCAGACCTT CTCCAACC SEQ ID NO: 108 |
| Low Grade Glioma | VM/GFAP | chr10 | VIM | NM_003380 | 17,277,375 | chr17 | GFAP | NM_002055 | 42,988,777 | TAAGATGGCCCTTGA CATTGAGATTGCCACC TACAGGAAGCTGCTG GAAG\|GCGGGAGGCG GCCAGTTATCAGGAG GCGCTGGCGCGGCTG GAGGAAGAGG SEQ ID NO: 109 |
| Low Grade Glioma | VM/GFAP | chr10 | VIM | NM_003380 | 17,277,877 | chr17 | GFAP | NM_002055 | 42,988,655 | GAAGGCGAGGAGAGC AGGATTCTCTGCCTC TTCCAAACTTTTCCTC CCT\|TGGACATCGAGA TCGCCACCTACAGGA AGCTGCTACAGGGCG AGGAGAAC SEQ ID NO: 110 |
| Low Grade Glioma | VM/GFAP | chr10 | VIM | NM_003380 | 17,277,877 | chr17 | GFAP | NM_002055 | 42,988,655 | GAAGGCGAGGAGAGC AGGATTCTCTGCCTC TTCCAAACTTTTCCTC CCT\|TGGACATCGAGA TCGCCACCTACAGGA AGCTGCTAGAGGGCG AGGAGAAC SEQ ID NO: 111 |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Low Grade Glioma | GFAP/VIM | chr17 | GFAP | NM_002055 | 42,984,756 | chr10 | VIM | NM_003380 | 17,278,322 | CCTCAAGAGAACAT CGTGGTGAAGACCGT GGAGATGCGGATGG AGAGG\|GATACCCACT CAAAAGGACACTTC TGATTAAGACGGTTG AAACTAGAGA SEQ ID NO: 112 |
| Low Grade Glioma | GFAP/VIM | chr17 | GFAP | NM_002055 | 42,985,436 | chr10 | VIM | NM_003380 | 17,277,187 | GGCCACCTCAAGAGG AACATCGTGGTGAAG ACCGTGGAGATGCGG GATGG\|AGATGCGTGA AATGGAAGAGAACTT TGCCGTTGAAGCTGCT AACTACCAA SEQ ID NO: 113 |
| Low Grade Glioma | GFAP/VIM | chr17 | GFAP | NM_002055 | 42,985,438 | chr10 | VIM | NM_003380 | 17,277,380 | AAGGCCACCTCAAGA GGAACATCGTGGTGA AGACCGTGGAGATGC GGGAT\|GGAGAGCAGG ATTTCTGCCTCTTC CAAACTTTCCTCCCT GAACCTGA SEQ ID NO: 114 |
| Low Grade Glioma | GFAP/VIM | chr17 | GFAP | NM_002055 | 42,985,452 | chr10 | VIM | NM_003380 | 17,277,278 | CAAGTCTGTGTCAGA AGGCCACCTCAAGAG GAACATCGTGGTGAA GACCG\|GGAGGAAATG GCTCGTCACCTTCGTG AATACCAAGACCTGC TCAATGTTA SEQ ID NO: 115 |
| Low Grade Glioma | GFAP/VIM | chr17 | GFAP | NM_001131019 | 42,987,510 | chr10 | VIM | NM_003380 | 17,277,303 | TTATACCAATACAGG CTCACCAGATTGTAA ATGGAACGCGCCGG CTCGC\|GAATACCAAG ACCTGCTCAATGTTAA GATGGCCCTTGACATT GAGATTGC SEQ ID NO: 116 |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Low Grade Glioma | GFAP/VIM | chr17 | GFAP | NM_002055 | 42,987,987 | chr10 | VIM | NM_003380 | 17,277,377 | AGGAGAACCGATCACCATTCCCGTGCAGACCTTCTCCAACCTGCAGATT\|CGAGGAGACCAGGATTTCTCTGCCTCTTCCAAACTTTTCCTCCCTGAACC SEQ ID NO: 117 |
| Low Grade Glioma | GFAP/VIM | chr17 | GFAP | NM_002055 | 42,987,987 | chr10 | VIM | NM_003380 | 17,277,377 | AGGAGAACCGATCACCATTCCCGTGCAGACCTTCTCCAACCTGCAGATT\|CGAGGAGACCAGGATTTCTCTGCCTCTTCCAAACTTTTCCTCCCTGAACC SEQ ID NO: 118 |
| Low Grade Glioma | GFAP/VIM | chr17 | GFAP | NM_002055 | 42,988,642 | chr10 | VIM | NM_003380 | 17,277,351 | AGGAGTACCAGGACCTGCTCAATGTCAAGCTGGCCCTGGACATGAGATC\|GCCACCTACAGAAGCTGCTGAAGGCAGGAGAGCAGGATTTCTCTGCC SEQ ID NO: 119 |
| Low Grade Glioma | GFAP/VIM | chr17 | GFAP | NM_002055 | 42,988,655 | chr10 | VIM | NM_003380 | 17,277,336 | GCCCGCCACTTGCAGGAGTACCAGGACCTGCTCAATGTCAAGCTGGCCCT\|CTTGACATTGAGATTGCCACCTACAGGAAGCTGCTGAAGGCGAGGAGAG SEQ ID NO: 120 |
| Endometrial Endometrioid Adenocarcinoma | HLA-C/MUC16 | chr6 | HLA-C | NM_002117 | 31,237,270 | chr19 | MUC16 | NM_024690 | 8,959,665 | GCATTTTCTTCCCACAGGTGGAAAAGGAGGGAGCTGCTCTCAGGCTGCGT\|CCAGCAACAGTGCCCAGGCTACTACCAGTCACACCTAGACCTGGAGGATC SEQ ID NO: 121 |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Endometrial Endometrioid Adenocarcinoma | HLA-C/MUC16 | chr6 | HLA-C | NM_002117 | 31,237,270 | chr19 | MUC16 | NM_024690 | 8,959,665 | GCATTTTCTTCCCACA GGTGGAAAAGGAGGG AGCTGCTCTCAGGCTG CGT\|CCAGCAACAGTG CCCAGGCTACTACCA GTCACACCTAGACCT GGAGGATC SEQ ID NO: 122 |
| Endometrial Endometrioid Adenocarcinoma | HLA-C/MUC16 | chr6 | HLA-C | NM_002117 | 31,237,270 | chr19 | MUC16 | NM_024690 | 8,959,665 | GCATTTTCTTCCCACA GGTGGAAAAGGAGGG AGCTGCTCTCAGGCTG CGT\|CCAGCAACAGTG CCCAGGCTACTACCA GTCACACCTAGACCT GGAGGATC SEQ ID NO: 123 |
| Endometrial Endometrioid Adenocarcinoma | HLA-C/MUC16 | chr6 | HLA-C | NM_002117 | 31,237,270 | chr19 | MUC16 | NM_024690 | 8,959,665 | GCATTTTCTTCCCACA GGTGGAAAAGGAGGG AGCTGCTCTCAGGCTG CGT\|CCAGCAACAGTG CCCAGGCTACTACCA GTCACACCTAGACCT GGAGGATC SEQ ID NO: 124 |
| Endometrial Endometrioid Adenocarcinoma | HLA-C/MUC16 | chr6 | HLA-C | NM_002117 | 31,237,270 | chr19 | MUC16 | NM_024690 | 8,959,665 | GCATTTTCTTCCCACA GGTGGAAAAGGAGGG AGCTGCTCTCAGGCTG CGT\|CCAGCAACAGTG CCCAGGCTACTACCA GTCACACCTAGACCT GGAGGATC SEQ ID NO: 125 |
| Endometrial Endometrioid Adenocarcinoma | HLA-C/MUC16 | chr6 | HLA-C | NM_002117 | 31,237,270 | chr19 | MUC16 | NM_024690 | 8,959,665 | GCATTTTCTTCCCACA GGTGGAAAAGGAGGG AGCTGCTCTCAGGCTG CGT\|CCAGCAACAGTG CCCAGGCTACTACCA GTCACACCTAGACCT GGAGGATC SEQ ID NO: 126 |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Endometrial Endometrioid Adenocarcinoma | HLA-C/MUC16 | chr6 | HLA-C | NM_002117 | 31,237,270 | chr19 | MUC16 | NM_024690 | 8,959,665 | GCATTTTCTTCCCACA GGTGGAAAAGGAGGG AGCTGCTCTCAGGCTG CGT\|CCAGCAACAGTG CCCAGGCTACTACCA GTCACACCTAGACCT GGAGGATC SEQ ID NO: 127 |
| Endometrial Endometrioid Adenocarcinoma | HLA-C/MUC16 | chr6 | HLA-C | NM_002117 | 31,237,270 | chr19 | MUC16 | NM_024690 | 8,959,665 | GCATTTTCTTCCCACA GGTGGAAAAGGAGGG AGCTGCTCTCAGGCTG CGT\|CCAGCAACAGTG CCCAGGCTACTACCA GTCACACCTAGACCT GGAGGATC SEQ ID NO: 128 |
| Endometrial Endometrioid Adenocarcinoma | HLA-C/MUC16 | chr6 | HLA-C | NM_002117 | 31,237,270 | chr19 | MUC16 | NM_024690 | 8,959,665 | GCATTTTCTTCCCACA GGTGGAAAAGGAGGG AGCTGCTCTCAGGCTG CGT\|CCAGCAACAGTG CCCAGGCTACTACCA GTCACACCTAGACCT GGAGGATC SEQ ID NO: 129 |
| Endometrial Endometrioid Adenocarcinoma | HLA-C/MUC16 | chr6 | HLA-C | NM_002117 | 31,237,270 | chr19 | MUC16 | NM_024690 | 8,959,665 | GCATTTTCTTCCCACA GGTGGAAAAGGAGGG AGCTGCTCTCAGGCTG CGT\|CCAGCAACAGTG CCCAGGCTACTACCA GTCACACCTAGACCT GGAGGATC SEQ ID NO: 130 |
| Invasive Breast Carcinoma | HOOK3/IKBKB | chr8 | HOOK3 | NM_032410 | 42,798,568 | chr8 | IKBKB | NM_001556 | 42,147,725 | GATGCAGCAGAGCTT GGAAGGATGCTTCAG CTCATCTTAGGCTGTG CTGT\|GAACTTGGCGC CCAATGACCTGCCCCT GCTGGCCATGGAGTA CTGCCAAG SEQ ID NO: 131 |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Invasive Breast Carcinoma | HOOK3/ IKBKB | chr8 | HOOK3 | NM_032410 | 42,798,588 | chr8 | IKBKB | NM_001556 | 42,162,705 | GGATGCTTCAGCTCAT CTTAGCTGTGTCTGTG AACTGTGAACAGAAG CAA\|GCCTCTGCGCTT AGATACCTTCATGAA AACAGAATCATCCAT CGGGATCT SEQ ID NO: 132 |
| Ovarian Serous Cystadenocarcinoma | IGFBP2/ SPP1 | chr2 | IGFBP2 | NM_000597 | 217,528,783 | chr4 | SPP1 | NM_000582 | 88,896,866 | GGGAGCCCCACCAT CCGGGGGACCCCGA GTGTCATCTCTTCTAC AATG\|AGCAGCAGGAG GAGGCAGAGCACAGC ATCGTCGGGACCAGA CTCGTCTCA SEQ ID NO: 133 |
| Ovarian Serous Cystadenocarcinoma | IGFBP2/ SPP1 | chr2 | IGFBP2 | NM_000597 | 217,528,783 | chr4 | SPP1 | NM_000582 | 88,896,866 | TGAGACGAGTCTGGT CCCGACGATGCTGTG CTCTGCTCCTCCCTGC TGCT\|CATTGTAGAAG AGATGACACTCGGG TCCCCCGGATGGTG GGGCTCCC SEQ ID NO: 134 |
| Invasive Breast Carcinoma | KRIT1/ CDK6 | chr7 | KRIT1 | NM_004912 | 91,842,555 | chr7 | CDK6 | NM_001259 | 92,462,486 | ATATTTACAAAGGCA AGCCCCAGCAATCAT AAAGTCATCCCTGTGT ATGT\|AGGAGGGCATG CCGCTCTCCACCATCC GCGAGGTGGGCGTGC TGAGGCAC SEQ ID NO: 135 |
| Head and Neck Squamous Cell Carcinoma | LYN/NTRK3 | chr8 | LYN | NM_002350 | 56,866,524 | chr15 | NTRK3 | NM_002530 | 88,670,398 | AGATCCCCCGGGAGT CCATCAAGTTGGTGA AAAGCTTGCGCTG GGCAG\|TTTGGGGTAT CCATAGCAGTTGGAC TTGCTGCTTTTGCCTG TGTCCTGTT SEQ ID NO: 136 |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Invasive Breast Carcinoma | MLLT6/ACE | chr17 | MLLT6 | NM_005937 | 36,868,267 | chr17 | ACE | NM_000789 | 61,573,755 | CCACCGCAGCAGGAGA AGCACCCCACCCACC ACGAGAGGGCCAGA AGAAG\|GTACTTTGTC AGCTTCATCATCCAGT TCCAGTTCCACGAGG CACTGTGCC SEQ ID NO: 137 |
| Invasive Breast Carcinoma | MLLT6/ACE | chr17 | MLLT6 | NM_005937 | 36,868,267 | chr17 | ACE | NM_000789 | 61,573,755 | CCTGGCACAGTGCCTC GTGGAACTGGAACTG GATGATGAAGCTGAC AAAG\|TACCTTCTTCTG GCCCCTCTCGTGGTGG GTGGGGTGCTTCTCCT GCTGCG SEQ ID NO: 138 |
| Ovarian Serous Cystadenocarcinoma | MUC16/ OR7G2 | chr19 | MUC16 | NM_024690 | 9,024,134 | chr19 | OR7G2 | NM_001005193 | 9,213,932 | AGTGGATCTCAGAAC CTCAGGGACTCCATCC TCCCTCTCCAGCCCCA CAA\|ATTCATCATCAA CAGCATGGAAGCGAG AAACCAAACAGCTAT TTCAAAT SEQ ID NO: 139 |
| Ovarian Serous Cystadenocarcinoma | MUC16/ OR7G2 | chr19 | MUC16 | NM_024690 | 9,045,564 | chr19 | OR7G2 | NM_001005193 | 9,213,935 | ATTTTGAAATAGCTGT TTGGTTTCTCGCTTCC ATGCTGTTGATGATGA AT\|TTGTTCTTGAGGTC ACACTCTCAGAGGCC AAGGTGGACATCCCA GGTGTG SEQ ID NO: 140 |
| Invasive Breast Carcinoma | NARS2/ TOP1 | chr11 | NARS2 | NM_024678 | 78,189,672 | chr20 | TOP1 | NM_003286 | 39,721,138 | GGAACTGTTCAAGGC TACAACAATGATGGT TCTCTCAAATGTCCT GAAG\|GCATCAAGTGG AAATTCCTAGAACAT AAAGGTCCAGTATTT GCCCCACCA SEQ ID NO: 141 |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Breakpoint | 3' Gene Chromosome | 3' Gene | 3' Accession | 3' Gene Breakpoint | Breakpoint Sequence |
|---|---|---|---|---|---|---|---|---|---|---|---|
| Invasive Breast Carcinoma | SRD5A1/ PAPD7 | chr5 | SRD5A1 | NM_001047 | 6,633,982 | | chr5 | PAPD7 | NM_006999 | 6,738,796 | GCGCCCAACTGCATC CTCCTGGCCATGTTCC TCGTCCACTACGGGC ATCG\|GTACAGATATT TGGCAGCTTTAGTACA GGTCTTTATCTTCCAA CTAGCGA SEQ ID NO: 142 |
| Invasive Breast Carcinoma | PAPD7/ SRD5A1 | chr5 | PAPD7 | NM_006999 | 6,746,451 | | chr5 | SRD5A1 | NM_001047 | 6,662,933 | GGGAGAAATTTTAAT TACTTGAAAACCGGT ATTAGAATCAAAGAA GGAGG\|CTTATTTGAA TACGTAACTGCAGCC AACTATTTTGGAGAA ATCATGGAGT SEQ ID NO: 143 |
| Gastric Adenocarcinoma | PRKAR2A/ RHOA | chr3 | PRKAR2A | NM_004157 | 48,845,082 | | chr3 | RHOA | NM_001664 | 49,405,981 | GACGAGGACTTGGAA GTTCCAGTTCCTAGCA GATTTAATAGACGAG TATC\|AGGTAGAGTTG GCTTTGTGGGACACA GCTGGGCAGGAAGAT TATGATCGC SEQ ID NO: 144 |
| Gastric Adenocarcinoma | TRAPPC9/ PTK2 | chr8 | TRAPPC9 | NM_031466 | 141,460,889 | | chr8 | PTK2 | NM_005607 | 141,900,868 | CTCTGTGTCCCGTTTG AGAAAAGGACTTTG TAGGACTGGACACAG ACAG\|CAGATATGAC AGATACCTAGCATCT AGCAAAATAATGGCA GCTGCTTAC SEQ ID NO: 145 |
| Gastric Adenocarcinoma | PTK2/TRAPPC9 | chr8 | PTK2 | NM_005607 | 142,011,224 | | chr8 | TRAPPC9 | NM_031466 | 141,034,176 | CCGCCCCGTGTCGTC TGCCTTCGCTTCACGG CGCCGAGCCGCGGTC CGA\|ACCCTGAAGCT GTCCTGAATTTCAAAT ACTCTGAGGCCGG GCCACAC SEQ ID NO: 146 |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Ovarian Serous Cystadenocarcinoma | RAB11B/MDK | chr19 | RAB11B | NM_004218 | 8,468,319 | chr11 | MDK | NM_002391 | 46,404,173 | AGGAAGCATTCAAGA ACATCCTCACAGAGA TCTACCGCATCGTGTC ACAG\|GTGATGGGGC ACAGGCACCAAAGTC CGCCAAGGCACCCTG AAGAAGGCG SEQ ID NO: 147 |
| Ovarian Serous Cystadenocarcinoma | RAB11B/MDK | chr19 | RAB11B | NM_004218 | 8,468,374 | chr11 | MDK | NM_002391 | 46,404,248 | GATCGCAGACCGCGC TGCCCACGACGAGTC CCCGGGAACAACGT GGTGG\|CCATCCGCGT CACCAAGCCCTGCAC CCCAAGACCAAAGC AAAGGCCAAA SEQ ID NO: 148 |
| Squamous Cell Lung Carcinoma | RB1/GADD45GIP1 | chr13 | RB1 | NM_000321 | 48,955,574 | chr19 | GADD45GIP1 | NM_052850 | 13,065,313 | AAAACATTTAGAACG ATGTGAACATCGAAT CATGGAATCCCTGCA TGGC\|CAAGATGCCAC AGATGATTGTGAACT GGCAGCAGCAGCAGC GGGAGACT SEQ ID NO: 149 |
| Cutaneous Melanoma | SHANK3/ MAPK1 | chr22 | SHANK3 | NM_033517 | 51,115,121 | chr22 | MAPK1 | NM_002745 | 22,153,417 | TTTATGCCCAGAACCT CATCGATGATAAGCA GTTTGCAAAGCTTCAC ACA\|AAGATCTGTGAC TTTGGCCTGGCCCGTG TTGCAGATCCAGACC ATGATCA SEQ ID NO: 150 |
| Thyroid Gland Carcinoma | SPECC1L/ RET | chr22 | SPECC1L | NM_015330 | 24,734,416 | chr10 | RET | NM_020630 | 43,610,055 | TGCAGCTGCAATTCCT CGAACGCCCCTGAGC CCAAGTCCTATGAAA ACCC\|CTCCTCAGCTG AGATGACCTTCCGGA GGCCCCCAGGCCT TCCCGGTCA SEQ ID NO: 151 |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Glioblastoma | TAOK1/ RARA | chr17 | TAOK1 | NM_020791 | 27,718,042 | chr17 | RARA | NM_000964 | 38,504,568 | GGGAGGGCTGGGCAC TATCTCTTCAGAACTG CTGCTCTGGGTCTCAA TGG\|CCTTTCGCCGAC AGGTCTGGGCGGAG CAGGCAGGCGCAGCC CCCTGCAG SEQ ID NO: 152 |
| Gastric Adenocarcinoma | THRA/CDK12 | chr17 | THRA | NM_003250 | 38,245,586 | chr17 | CDK12 | NM_015083 | 37,686,884 | CAACACCGCAAACA CAACATTCCGCACTTC TGGCCCAAGCTGCTG ATGA\|AGAGAAGAGGC CCCTGAGCCCCCG GACCTCCACCGCGC CACCTCCAC SEQ ID NO: 153 |
| Invasive Breast Carcinoma | WRN/ADAM9 | chr8 | WRN | NM_000553 | 30,982,516 | chr8 | ADAM9 | NM_003816 | 38,871,484 | TCCTTGGAATTATGG GAACTGAAAATGCT GTGATAATTGCAGGT CCAG\|AGACCTTTTGC CTGAAGATTTTGTGT TTATACTTACAACAAG GAAGGGA SEQ ID NO: 154 |
| Colon and Rectal Adenocarcinoma | YWHAE/ MAP2K2 | chr17 | YWHAE | NM_006761 | 1,303,359 | chr19 | MAP2K2 | NM_030662 | 4,123,868 | CGCTATGGATGATCG AGAGGATCTGTGTA CCAGGCGAAGCTGGC CGAGC\|TGGCCCGGAG GAAGCCGGTGCTGCC GGCGCTCACCATCAA CCCTACCATC SEQ ID NO: 155 |
| Thyroid Gland Carcinoma | ZC3HAV1/ BRAF | chr7 | ZC3HAV1 | NM_020119 | 138,758,639 | chr7 | BRAF | NM_004333 | 140482825 | ACCAAGCCAGCCA ATTCTGTCTTCACC ACCAAATGGATTTG GTATTG\|GAAT GAAAACACTTGGTA GACGGGACTCGAG TGATGATTGGGAGA TTCCT SEQ ID NO: 193 |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Thyroid Gland Carcinoma | BRAF/SND1 | chr7 | SND1 | NM_014390 | 127,361,454 | chr7 | BRAF | NM_004333 | 140487384 | TTCACCTGTCCAGC ATCCGACCACCGAG GCTGGAGGGGGAG AACACCCAGTGACT TGATTAGAGACCAA GGATTTCGTGGTGA TGGAGGATCAACC ACAGG SEQ ID NO: 194 |
| Thyroid Gland Carcinoma | BRAF/SND1 | chr7 | BRAF | NM_004333 | 140,487,348 | chr7 | SND1 | NM_014390 | 127724776 | GTCAATATTGATGA CTTGATTAGAGACC AAGGATTTCGTGGT GATGGAGG\|CACCC AGTTGAGAAGCT GATGGAGAACATG CGCAATGACATTGC CAGTC SEQ ID NO: 195 |
| Thyroid Gland Carcinoma | SND1/BRAF | chr7 | SND1 | NM_014390 | 127,361,454 | chr7 | BRAF | NM_004333 | 140487384 | CACCTGTCCAGCAT CCGACCACCGAGG CTGGAGGGGAGA ACACCCAGGA\|CTT GATTAGAGACCAA GGATTTCGTGGTGA TGGAGGATCAACC ACAGTT SEQ ID NO: 196 |
| Thyroid Gland Carcinoma | MEMO1/ALK | chr2 | MEMO1 | NM_015955 | 32,168,371 | chr2 | ALK | NM_004304 | 29543748 | GGCTTTCACAAGTA CAGTCTACAAAAA GACCTGCTAGAGCC ATTATTGCC\|CCGGA AACTGCCTGTGGGT TTTTACTGCAACTT TGAAGATGGCTTCT GTG SEQ ID NO: 197 |

TABLE 5-continued

Breakpoint sequences for Table 2

| Table 5 Cancer | Fusion Name | 5' Gene Chromosome | 5' Gene Symbol | 5' Accession | 5' Gene Breakpoint | 3' Gene Chromosome | 3' Gene | 3' Accession | 3' Gene Breakpoint | Breakpoint Sequence |
|---|---|---|---|---|---|---|---|---|---|---|
| Head and Neck Squamous Cell Carcinoma | CLIP4/ALK | chr2 | CLIP4 | NM_024692 | 29,404,563 | chr2 | ALK | NM_004304 | 29462609 | GAGGGGTCTCAGGT CCTGCTCACGAGCT CCAATGAGATGGGT ACTGTTAG\|GTTGA AGATGCCCAGCAC AGACACGCCGTGG GACCGCATCATGGT GTTCT SEQ ID NO: 198 |
| Squamous Cell Lung Carcinoma | CLIP4/ALK | chr2 | CLIP4 | NM_024692 | 29,404,561 | chr2 | ALK | NM_004304 | 29462607 | ACGAGGGGTCTCA GGTCCTGCTCACGA GCTCCAATGAGATG GGTACTGTT\|AGGTT GAAGATGCCCAGC ACAGACACGCCGT GGGACCGCATCATG GTGTT SEQ ID NO: 199 |

TABLE 6 breakpoint sequences for Table 3

| Table 6 Fusion Name | 5' Gene Symbol | 5' Gene Chrom | 5' Gene Symbol Accession | 5' Gene Breakpoint | 3' Gene Chromosome | 3' Gene Symbol | 3' Accession | 3' Gene Breakpoint | Breakpoint Sequence | SEQ ID NO: |
|---|---|---|---|---|---|---|---|---|---|---|
| SEC16A-NOTCH1 | SEC16A | chr9 | NM_014866 | 139357445 | chr9 | NOTCH1 | NM_017617 | 1.39E+08 | ATTGATTTCACGAATG AGGCAGTGGAGCAGG TGGAAGAGGAGGAGT CTGG\|CCCCGGATGCT CCCAGCCCGGTGAGA CCTGCCTGAATGCCG GGAAGTGTG | 28 |
| ERC1-RET | ERC1 | chr12 | NM_178039 | 1,250,953 | chr10 | RET | NM_020630 | 43612032 | GGACATGTTGGATGT GAAGGAGCGGAAGT TAATGTTCTTCAGAAG AAGG\|AGGATCCAAAG TGGGAATTCCCTCGG AAGAACTTGGTTCTTG GAAAAACT | 29 |
| ESR1/CCDC170 | ESR1 | chr6 | NM_000125 | 152,332,929 | chr6 | CCDC170 | NM_025059 | 151,907,024 | CATGGAGCACCCAGG GAAGCTACTGTTTGCT CCTAACTTGCTCTTGG ACA\|GATGGTCTCCCA GCTTGAAGCCCAAAT ATCTGAGCTTGTTGAA CAGTTGG | 156 |
| RPS6KB1/VMP1 | RPS6KB1 | chr17 | NM_003161 | 57,990,165 | chr17 | VMP1 | NM_030938 | 57,915,656 | CAGAATGTTTTGAGCT ACTTCGGGTACTTGGT AAAGGGGCTATGGA AAG\|TGCTGTCCCCGG CATAGGTCCATCTCTG CAGAAGCCATTTCAG GAGTACC | 157 |
| VMP1/RPS6KB1 | VMP1 | chr17 | NM_030938 | 57,915,758 | chr17 | RPS6KB1 | NM_003161 | 57,987,923 | GTTCATATGGTCCAAC TCCCCATGGTCCATG CTTTCATTTAACTGAC CC\|TGTGGTGTGCCCA TTTCGCTTTTGTGTG AAGCTTCTGCCGTTGA GCCTC | 158 |
| RPS6KB1/VMP1 | RPS6KB1 | chr17 | NM_003161 | 57,970,686 | chr17 | VMP1 | NM_030938 | 57,915,656 | AGACCTGGACCAGCC AGAGGACGCGGGCTC TGAGGATGAGCTGGA GGAGG\|GGTGCTGTCC CCGGCATAGGTCCAT | 159 |

TABLE 6-continued breakpoint sequences for Table 3

| Table 6 Fusion Name | 5' Gene Chrom | 5' Gene Symbol | 5' Accession | 5' Gene Breakpoint | 3' Gene Chromosome | 3' Gene Symbol | 3' Accession | 3' Gene Breakpoint | Breakpoint Sequence | SEQ ID NO: |
|---|---|---|---|---|---|---|---|---|---|---|
| VMP1/RPS6KB1 | chr17 | VMP1 | NM_030938 | 57,915,758 | chr17 | RPS6KB1 | NM_003161 | 57,987,923 | CTCTGCAGAAGCCAT TTCAGGAGTA | 160 |
| RPS6KB1/VMP1 | chr17 | RPS6KB1 | NM_003161 | 57,970,606 | chr17 | VMP1 | NM_030938 | 57,915,656 | AAGTTCATATGGTCCA ACTCCCCATGGTCCA TGCTTTCATTTAACTG AC\|CCTGTGGTGTGCC CATTTCGCTTTTGTGG TGAAGCTTCTGCCGTT GAGCC | 161 |
| RPS6KB1/VMP1 | chr17 | RPS6KB1 | NM_003161 | 57,992,064 | chr17 | VMP1 | NM_030938 | 57,915,656 | GGTACTCCTGAAATG GCTTCTGCAGAGATG GACCTATGCCGGGGA CAGCA\|CTTCCCTGTCT CGGAAGTCCGGGGCT GGGTAAAAGCCCGTCC CGCCTCCTT | 162 |
| RPS6KB1/VMP1 | chr17 | RPS6KB1 | NM_003161 | 58,003,943 | chr17 | VMP1 | NM_030938 | 57,915,656 | GTAACAGGAGCAAAT ACTGGGAAAATATTT GCCATGAAGGTGCTT AAAAA\|GTGCTGTCCC CGGCATAGTTCCATC TCTGCAGAAGCCATTT CAGGAGTAC | 163 |
| RPS6KB1/VMP1 | chr17 | RPS6KB1 | NM_003161 | 57,970,686 | chr17 | VMP1 | NM_030938 | 57,917,129 | GCCTTTCAGACTGTG GAAAACTCTACCTCA TCCTTGAGTATCTCAG TGG\|GAGAAAACTGGT TGTCCTGATGTTTGA AAAGTTGGTCGTTGTC ATGGTG | 164 |
| RPS6KB1/VMP1 | chr17 | RPS6KB1 | NM_003161 | 57,990,165 | chr17 | VMP1 | NM_030938 | 57,915,656 | AGACCTGGACCAGCC AGAGGACGCGGGTC TGAGGATGAGCTGGA GGAGG\|GGTGCTGTCC CCGGCATAGGTCCAT CTCTGCAGAAGCCAT TTCAGGAGTA | 165 |
| RPS6KB1/VMP1 | chr17 | RPS6KB1 | NM_003161 | 57,990,165 | chr17 | VMP1 | NM_030938 | 57,915,656 | CAGAATGTTTTGAGCT ACTTCGGGTACTTGGT AAGGGGCTATGA AAG\|TGCTGTCCCCGG | 165 |

TABLE 6-continued breakpoint sequences for Table 3

| Table 6 Fusion Name | 5' Gene Chrom | 5' Gene Symbol | 5' Accession | 5' Gene Breakpoint | 3' Gene Chromosome | 3' Gene Symbol | 3' Accession | 3' Gene Breakpoint | Breakpoint Sequence | SEQ ID NO: |
|---|---|---|---|---|---|---|---|---|---|---|
| | | | | | | | | | CATAGGTCCATCTCTG CAGAAGCCATTTCAG GAGTACC | |
| RPS6KB1/VMP1 | chr17 | RPS6KB1 | NM_003161 | 58,003,943 | chr17 | VMP1 | NM_030938 | 57,917,129 | ATGCCTTTCAGACTGG TGGAAAACTTCACCT CATCCTTGAGTATCTC AGT\|GGGAGAAACTG GTTGTCCTGGATGTTT GAAAAGTTGGTCGTT GTCATGG | 166 |
| RPS6KB1/VMP1 | chr17 | RPS6KB1 | NM_003161 | 58,009,009 | chr17 | VMP1 | NM_030938 | 57,917,215 | ATATTTATGGAAGAC ACTGCCTGCTTTTACT TGGCAGAAATCTCCA TGGC\|ACAAAGTTATG CCAAACGAATCCAGC AGCGGTTGAACTCAG AGGAGAAAA | 167 |
| RPS6KB1/VMP1 | chr17 | RPS6KB1 | NM_003161 | 58,009,061 | chr17 | VMP1 | NM_030938 | 57,895,132 | TGGGGCATTTACATCA AAAGGGGATCATCTA CAGAGACCTGAAGCC GGAG\|TGGTGCTGTCC CCGGCATAGGTCCAT CTCTGCAGAAGCCAT TTCAGGAGT | 168 |
| RPS6KB1/VMP1 | chr17 | RPS6KB1 | NM_003161 | 57,970,625 | chr17 | VMP1 | NM_030938 | 57,915,703 | TACCCAGCCCCGGAC TTCCGAGACAGGGAA GCTGAGGACATGGCA GGAGT\|ACCTGGAGGC TCAACGGCAGAAGCT TCACCACAAAAGCGA AATGGGCACA | 169 |
| RPS6KB1/VMP1 | chr17 | RPS6KB1 | NM_003161 | 57,970,643 | chr17 | VMP1 | NM_030938 | 57,915,710 | CCTGTGGTGTGCCCAT TTCGCTTTTGTGGTGA AGCTTCTGCCGTTGAG CC\|TCCAGTCTATGT CAAACACTCCTGCCA TGTCCTCAGCTTCCT GTCTCG | 170 |
| RPS6KB1/VMP1 | chr17 | RPS6KB1 | NM_003161 | 57,992,064 | chr17 | VMP1 | NM_030938 | 57,886,157 | AACAGGAGCAAATAC TGGGAAAATATTTGC CATGAAGGTGCTTAA | 171 |

TABLE 6-continued breakpoint sequences for Table 3

| Table 6 Fusion Name | 5' Gene Symbol | 5' Gene Chrom | 5' Accession | 5' Gene Breakpoint | 3' Gene Chromosome | 3' Gene Symbol | 3' Accession | 3' Gene Breakpoint | Breakpoint Sequence | SEQ ID NO: |
|---|---|---|---|---|---|---|---|---|---|---|
| RPS6KB1/VMP1 | RPS6KB1 | chr17 | NM_003161 | 58,007,535 | chr17 | VMP1 | NM_030938 | 57,915,656 | AAAGG\|ACTTTGCCTC CCGGGCCAAACTGGC AGTTCAAAACTAGT ACAGAAAGTT | 172 |
| RPS6KB1/VMP1 | RPS6KB1 | chr17 | NM_003161 | 57,970,625 | chr17 | VMP1 | NM_030938 | 57,915,703 | CTATTTATGCAGTTAG AAAGAGGGAATAT TTATGGAAGACACTG CCTG\|TGCTGTCCCCG GCATAGGTCCATCTCT GCAGAAGCCATTTCA GGAGTACC | 173 |
| RPS6KB1/VMP1 | RPS6KB1 | chr17 | NM_003161 | 57,990,165 | chr17 | VMP1 | NM_030938 | 57,917,129 | TGTGCCCATTTCGCTT TTGTGGTGAAGCTTCT GCCGTTGAGCCTCCA GGT\|ACTCCTGCCATG TCCTCAGCTTCCCTGT CTCGGAAGTCCGGGG CTGGGTA | 174 |
| RPS6KB1/VMP1 | RPS6KB1 | chr17 | NM_003161 | 57,992,037 | chr17 | VMP1 | NM_030938 | 57,851,147 | CCAGAATGTTTTGAGC TACTTCGGTACTTGG TAAAGGGGCTATGG AAA\|GGGAGAAACT GGTTGTCCTGGATGTT TGAAAAGTTGGTCGTT GTCATGG | 175 |
| RPS6KB1/VMP1 | RPS6KB1 | chr17 | NM_003161 | 57,970,686 | chr17 | VMP1 | NM_030938 | 57,889,031 | ATGAAAGTTTTTCA AGTACGAAAAGTAAC AGGAGCAAATACTGG GAAA\|ATATTTCATGG CCAGACAGCTCGCC TCTCAGGTGCTGCC CAGATGATG | 176 |
| RPS6KB1/VMP1 | RPS6KB1 | chr17 | NM_003161 | 57,970,686 | chr17 | VMP1 | NM_030938 | 57,886,157 | ACCTGGACCAGCCAG AGGACGCGGGCTCTG AGGATGAGCTGGAGG AGGGG\|ATTCCAAATC CTTTATTTGATCTGGC TGGAATAACGTGTGG ACACTTTCT | 177 |
| RPS6KB1/VMP1 | RPS6KB1 | chr17 | NM_003161 | | chr17 | VMP1 | NM_030938 | | ACCTGGACCAGCCAG AGGACGCGGGCTCTG | |

TABLE 6-continued breakpoint sequences for Table 3

| Table 6 Fusion Name | 5' Gene Chrom | 5' Gene Symbol | 5' Accession | 5' Gene Breakpoint | 3' Gene Chromosome | 3' Gene Symbol | 3' Accession | 3' Gene Breakpoint | Breakpoint Sequence | SEQ ID NO: |
|---|---|---|---|---|---|---|---|---|---|---|
| | | | | | | | | | AGGATGAGCTGGAGG AGGGG\|GACTTTGCCT CCCGGCCAAACTGG CAGTTCAAAAACTAG TACAGAAAGT | |
| RPS6KB1/VMP1 | chr17 | RPS6KB1 | NM_003161 | 57,970,686 | chr17 | VMP1 | NM_030938 | 57,889,031 | GAAAGTGTCCACACG TTATTCCAGCCAGATC AAATAAAGGATTTGG AATC\|CCCTCCTCCAG CTCATCCTCAGAGCCC GCGTCCTCTGGCTGGT CCAGGTC | 178 |
| RPS6KB1/VMP1 | chr17 | RPS6KB1 | NM_003161 | 57,970,686 | chr17 | VMP1 | NM_030938 | 57,886,157 | CTGGACCAGCCAGAG GACGCGGGCTCTGAG GATGAGCTGGAGAG GGGGA\|CTTTGCCTCC CGGGCCAAACTGGCA GTTCAAAAACTAGTA CAGAAAGTTG | 179 |
| RPS6KB1/VMP1 | chr17 | RPS6KB1 | NM_003161 | 57,970,686 | chr17 | VMP1 | NM_030938 | 57,886,157 | CCTGGACCAGCCAGA GGACGCGGGCTCTGA GGATGAGCTGGAGGA GGGGG\|ACTTTGCCTC | 180 |

TABLE 6-continued breakpoint sequences for Table 3

| Table 6 Fusion Name | 5' Gene Chrom | 5' Gene Symbol | 5' Accession | 5' Gene Breakpoint | 3' Gene Chromosome | 3' Gene Symbol | 3' Accession | 3' Gene Breakpoint | Breakpoint Sequence | SEQ ID NO: |
|---|---|---|---|---|---|---|---|---|---|---|
| RPS6KB1/VMP1 | chr17 | RPS6KB1 | NM_003161 | 57,970,686 | chr17 | VMP1 | NM_030938 | 57,886,157 | CCGGGCCAAACTGGC AGTTCAAAAACTAGT ACAGAAAGT | 181 |
| RPS6KB1/VMP1 | chr17 | RPS6KB1 | NM_003161 | 57,970,686 | chr17 | VMP1 | NM_030938 | 57,886,157 | ACCTGGACCAGCCAG AGGACGCGGGCTCTG AGGATGAGCTGGAGG AGGGG\|GACTTTGCCT CCCGGCCAAACTGG CAGTTCAAAAACTAG TACAGAAAGT | 182 |
| RPS6KB1/VMP1 | chr17 | RPS6KB1 | NM_003161 | 57,992,064 | chr17 | VMP1 | NM_030938 | 57,915,656 | CGCGGGCTCTGAGGA TGAGCTGGAGGAGGG GGA\|CTTTGCCTCCCG GGCCAAACTGGCAGT TCAAAACTAGTACA GAAAGTTG | 183 |
| RPS6KB1/VMP1 | chr17 | RPS6KB1 | NM_003161 | 57,992,064 | chr17 | VMP1 | NM_030938 | 57,915,656 | AGTAACAGAGCAAA TACTGGGAAAATATTT GCCATGAAGGTGCTT AAAA\|AGTGCTGTCCC CGGCATAGTCCATC TCTGCAGAAGCCATTT CAGGAGTA | |

The disclosure provides novel gene fusions and gene fusion variants (ie, varying breakpoint locations on one or both of the partner genes) selected from those shown in Table 1-Table 3, Table 19, and Table 22 of gene fusions such as TPM1/ALK, PRKAR1A/ALK, NCOA1/ALK, LPP/ CASR, MDM2/EGFR, FGFR3/ELAVL3, B2M/GNAS, DOCK8/JAK2, HNF1B/NOTCH1, NFASC/NTRK1, SSBP2/NTRK1, SQSTM1/NTRK1, TBL1XR1/PIK3CA, AKAP13/RET, FKBP15/RET, TBL1XR1/RET, CEP85L/ ROS1, CLCN6/RAF1, TRAK1/RAF1, PRKACA/AKT1, PRKACA/AKT2, MLL/FYN, ECHD1/FYN, TTC13/JAK2, SEC16A/NOTCH1, ERC1/RET, GTF2IRD1/ALK, HTATSF1/BRS3, CDH1/CCDC132, CCDC132/CDH1, ERBB2/SLC29A3, MET/TFG; TFG/MET, NOTCH2/ MNDA, IRF2BP2/NTRK1, EIF2C2/PTK2, RARA/ HOXB3, STAT3/ETV4,and GFAP/VIM; VIM/GFAP, TOP1/C17orf64, and TP53/KIAA0753. As a result of these discoveries, the disclosure provides isolated gene fusion nucleic acids and sequences complementary thereto, amplicons, transcripts, reaction mixtures, as well as probes that specifically recognize the nucleic acid sequences of the gene fusions, sequences complementary thereto, amplicons, and transcripts. The disclosure further contemplates antisense nucleotides for use in the treatment of the associated disease.

Table 1-Table 3, Table 19, and Table 22 provide a list of the gene fusions (Gene A/Gene B) indicating the genes involved (Gene A and Gene B), the chromosome locations, the breakpoint locations, the fusion types and the distance. The gene fusions are shown with the associated TOGA disease (The Cancer Genome Atlas). The cancers are shown with 3-4 letter abbreviations which are explained in more detail in the diagnostics section.

Generally, Tables 1-3, 19, and 22 provide one or more novel gene fusions and/or associations of gene fusions with TOGA diseases. For example, Table 19 presents novel gene fusions, and Table 22 presents novel associations of gene fusions with TOGA diseases.

Tables 4-6, 20, and 23 provide the breakpoint sequences for the gene fusions in Tables 1-3, 19, and 22. The breakpoint sequences are identified as SEQ ID NO:1-289.

Assays and Kits

In certain embodiments, assays and methods of detection are provided. Methods for detecting gene fusions provided herein are known in the art. As non-limiting examples, such assays can include 5' nuclease PCR assays (Applied Biosystems, Foster City, Calif.), next generation sequencing assays (Ion Torrent, Carlsbad Calif.; Illumina, San Diego, Calif.), or microarray assays (Skotheim et al., *Molecular Cancer* 2009, 8:5). In at least one embodiment, the assays or methods include at least one primer or probe that is complementary to or encodes a gene fusion and/or breakpoint in Tables 1-6.

In at least one embodiment, assays and methods of quantitating the amount of expression of a gene fusion are provided. The methods may involve quantitating expression of one or more exons. For example, TaqMan™ Gene Expression Assays can be designed for a set of known fusion transcripts for quantitative analysis. Such assays can be designed such that the primers and probe span the breakpoint region, although in certain illustrative embodiments the primers and probe are not placed directly on the breakpoint.

In certain embodiments, the disclosure provides a primer, a probe or a set of probes or primers that specifically recognize one or more of the gene fusions and/or breakpoints disclosed herein.

In one embodiment, the disclosure provides a composition and a kit comprising a set of probes that specifically recognize a gene fusion selected from Tables 1-3, 19, and 22 and/or a breakpoint in Tables 4-6, 20, and 23. The set of probes can be, for example a set of amplification primers. In another embodiment, provided herein is a composition that includes a set of primers that flank a gene fusion selected from Tables 1-3, 19, and 22 in a target nucleic acid. The reaction mixture of this embodiment can further include a detector probe that binds to either side of a breakpoint in a gene fusion selected from Tables 1-3, 19, and 22, or that binds a binding region that spans the breakpoint in a gene fusion selected from Tables 1-3, 19, and 22. The reaction mixture that includes a detector probe or does not include a detector probe, can further include a polymerase, dNTPs, and/or a uracil DNA deglycosylase (UDG). The polymerase and UDG are typically not from a human origin. The reaction mixture can further include a target nucleic acid, for example a human target nucleic acid. The human target nucleic acid can be, for example, isolated from a biological sample from a person suspected of having a cancer.

In another embodiment, provided herein is a qPCR assay, such as a TaqMan™ assay or a Molecular Beacons™ assay, that specifically amplifies and detects a target nucleic acid that includes SEQ ID NOs: 1-289.

The disclosure also provides an isolated nucleic acid comprising at least one sequence selected from SEQ ID NOs: 1-289. The isolated nucleic acid can include a first primer on a 5' end. Furthermore, the nucleic acid can be single stranded or double stranded.

The disclosure, in other embodiments, provides a kit that includes a detector probe and/or a set of probes, for example, a set of amplification primers that specifically recognize a nucleic acid comprising a breakpoint for a gene fusion selected from Tables 1-3, 19, and 22. For example, in certain embodiments the detector probe or set of amplification primers are designed to amplify and/or detect a nucleic acid that includes at least one of SEQ ID NOs:1-289. The kit can further include, in a separate or in the same vessel, a component from an amplification reaction mixture, such as a polymerase, typically not from human origin, dNTPs, and/or UDG. Furthermore, the kit can include a control nucleic acid. For example the control nucleic acid can include a sequence that includes the break point in a gene fusion selected from Tables 1-3, 19, and 22.

In some embodiments there is provided a kit encompassing at least 2 primer pairs and 2 detectably labeled probes. In these non-limiting embodiments, the 2 primer pairs and/or 2 detectably labeled probes form 2 amplification detection assays.

The kits of the present invention may also comprise instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

In some embodiments, the kits and assays comprise one or more probes that specifically recognize a target, such as a gene fusion nucleic acid sequence. In at least one embodiment, the kits and assays are diagnostic kits and assays.

A kit comprising a set of probes, for example, a set of amplification primers that specifically recognize a nucleic acid comprising a break point from Tables 4-6, 20, and 23 is provided. The kit can further include, in a separate or in the same vessel, a component from an amplification reaction mixture, such as a polymerase, typically not from human origin, dNTPs, and/or UDG. Furthermore, the kit can include a control nucleic acid. For example the control nucleic acid can include a sequence that includes the break point selected from Tables 4-6, 20, and 23.

In another embodiment, a gene fusion is provided comprising at least one of the break points in Tables 4-6, 20, and 23.

In some embodiments, a reaction mixture and a kit are provided. In some embodiments, the kit encompasses a detectable probe that selectively binds a gene fusion. In some embodiments, the gene fusion is any one of the gene fusions in Table 4, Table 5, Table 6, Table 20, or Table 23.

Thus, in some embodiments are provided a kit encompassing a reaction mixture and a detectable probe that selectively binds a gene fusion, the gene fusion being any one of the gene fusions in Table 4, Table 5, Table 6, Table 20, or Table 23.

Diagnostics

Methods of diagnosing, treating, and detecting gene fusions and associated disease are contemplated herein. The methods can include detecting gene fusions in a subject sample.

A subject sample can be any bodily tissue or fluid that includes nucleic acids from the subject. In certain embodiments, the sample will be a blood sample comprising circulating tumor cells or cell free DNA. In other embodiments, the sample can be a tissue, such as a cancerous tissue. The cancerous tissue can be from a tumor tissue and may be fresh frozen or formalin-fixed, paraffin-embedded (FFPE).

The disease can be a cancer or tumor. Cancers can include, but are not limited to, melanoma, cervical cancer, pancreatic cancer, head and neck squamous cancer, lung adenocarcinoma, colon adenocarcinoma, uterine carcinoma, ovarian cancer, glioblastoma, low grade glioma, lung adenocarcinoma, thyroid cancer, and gastric cancer.

Cancers can include but are not limited to, bladder carcinoma, breast carcinoma, cervical cell carcinoma, colon adenocarcinoma, glioblastoma multiforme, head and neck squamous cell carcinoma, clear cell renal cell carcinoma, kidney renal papillary cell carcinoma, acute myeloid leukemia, brain lower grade glioma, liver hepatocellular carcinoma, lung adenocarcinoma, squamous cell lung carcinoma, ovarian serous adenocarcinoma, prostate adenocarcinoma, rectal adenocarcinoma, cutaneous melanoma, stomach adenocarcinoma, thyroid carcinoma, and uterine corpus endometrioid carcinoma. As used herein, BLCA=bladder carcinoma, BRCA=breast carcinoma, CESC=cervical cell carcinoma, COAD=colon adenocarcinoma, GBM=glioblastoma multiforme, HNSC=head and neck squamous cell carcinoma, KIRK=clear cell renal cell carcinoma, KIRP=kidney renal papillary cell carcinoma, LAML=acute myeloid leukemia, LGG=brain lower grade glioma, LIHC=liver hepatocellular carcinoma, LUAD=lung adenocarcinoma, LUSC=squamous cell lung carcinoma, OV=ovarian serous adenocarcinoma, PRAD=prostate adenocarcinoma, READ=rectal adenocarcinoma, SKCM=cutaneous melanoma, STAD=stomach adenocarcinoma, THCA=thyroid carcinoma, and UCEC=uterine corpus endometrioid carcinoma.

In some embodiments, a method of detecting novel gene variants or gene fusions is provided, the method encompassing a reaction mixture, wherein the novel gene variant or gene fusion is detected by the generation of an extension product.

In another embodiment, the disclosure provides diagnostics and treatment targets utilizing the disclosed gene fusions and gene variants. The gene fusions, gene variants and associated disease states provide targets for both diagnosis and treatment. For instance, the presence, absence, or increased or decreased expression of a gene fusion target or a gene variant can be used to diagnose a disease state or may be used to prognose or detect a disease state. In at least one embodiment, the gene fusion or gene variant can have a high prevalence (frequency) in a particular cancer, a medium prevalence or a low prevalence. In at least one embodiment, the gene fusion or gene variant can have a high frequency in one cancer or tumor and a low or medium prevalence in another. In at least one embodiment, the gene fusion or gene variant can have a medium or low frequency association with a cancer or tumor. In at least one embodiment, a low or medium frequency gene fusion or gene variant can be used in combination with one or more different high frequency biomarkers of cancers to help to diagnose, prognose or identify a predisposition for a disease. The methods can be used for screening for cancer in a patient or predicting the relative prospects of a particular outcome of a cancer. For example, the presence of BRCA1 or BRCA2 mutations can be analyzed in combination with the gene fusion JAK2/TTC13 for breast cancer.

A method of detecting a cancer is provided comprising amplifying a nucleic acid that spans a breakpoint in a gene fusion selected from Tables 1-3, 19, and 22, for example the nucleic acid can include a sequence selected from SEQ ID NOs: 1-289, and detecting the presence of the nucleic acid, wherein the presence of the nucleic acid indicates a cancer is present in the sample. In another method, provided herein is a method of detecting a cancer that includes generating an amplicon that includes a sequence selected from SEQ ID NOs: 1-289, and detecting the presence of the nucleic acid, wherein the presence of the nucleic acid indicates the cancer or cancer cell is present in the sample. The amplicon typically includes primers that are extended to form the amplicon. The cancer is selected from bladder carcinoma, breast carcinoma, cervical cell carcinoma, colon adenocarcinoma, glioblastoma multiforme, head and neck squamous cell carcinoma, clear cell renal cell carcinoma, kidney renal papillary cell carcinoma, acute myeloid leukemia, brain lower grade glioma, liver hepatocellular carcinoma, lung adenocarcinoma, squamous cell lung carcinoma, ovarian serous adenocarcinoma, prostate adenocarcinoma, rectal adenocarcinoma, cutaneous melanoma, stomach adenocarcinoma, thyroid carcinoma, and uterine corpus endometrioid carcinoma.

In another embodiment is a method to detect a cancer selected from bladder carcinoma, breast carcinoma, cervical cell carcinoma, colon adenocarcinoma, glioblastoma multiforme, head and neck squamous cell carcinoma, clear cell renal cell carcinoma, kidney renal papillary cell carcinoma, acute myeloid leukemia, brain lower grade glioma, liver hepatocellular carcinoma, lung adenocarcinoma, squamous cell lung carcinoma, ovarian serous adenocarcinoma, prostate adenocarcinoma, rectal adenocarcinoma, cutaneous melanoma, stomach adenocarcinoma, thyroid carcinoma, and uterine corpus endometrioid carcinoma in a sample by detecting the presence of a gene fusion selected from Tables 1-3, 19, and 22.

New Gene Fusions

Although some of the gene fusions have been previously reported, provided herein, are numerous variations of the gene fusions in which the break points differ and/or that were not previously known. Nonlimiting examples of gene fusions in which the break points differ and/or were not previously known include:TPM1/ALK, PRKAR1A/ALK, NCOA1/ALK, LPP/CASR, MDM2/EGFR, FGFR3/

ELAVL3, B2M/GNAS, DOCK8/JAK2, HNF1B/NOTCH1, NFASC/NTRK1, SSBP2/NTRK1, SQSTM1/NTRK1, TBL1XR1/PIK3CA, AKAP13/RET, FKBP15/RET, TBL1XR1/RET, CEP85L/ROS1, CLCN6/RAF1, TRAK1/RAF1, PRKACA/AKT1, PRKACA/AKT2, MLL/FYN, ECHD1/FYN and TTC13/JAK2 are novel variants with the breakpoints provided in Tables 4 and 5 as SEQ ID NOs: 1-289.

Also provided herein are numerous gene fusion variants that are associated with one or more cancers.

Cancer Associations

New gene fusion associations with cancer(s) are presented herein. Some of the gene fusions may have been associated with specific cancers or disease states previously. The methods herein have identified new associations that can be used to help diagnose and/or treat the specific cancers. The gene fusions shown in Tables 1-3, 19, and 22 provide the genes involved in the fusion and the association of that gene fusion with one or more specific cancers. For example, the fusion PRKACA/AKT1 is shown to be associated with colon adenocarcinoma and endometrial endometrioid adenocarcinoma.

The gene fusions shown in Table 3 are previously known gene fusions that have been shown to be associated with new cancers. For example, SEC16A/NOTCH1 was previously identified as associated with breast cancer. Current methods identified an association of the gene fusion SEC16A/NOTCH1 with thyroid gland carcinoma. Further, ERC1/RET was previously identified as associated with thyroid cancer. Current methods identified an association of the gene fusion ERC1/RET with invasive breast carcinoma (see Tables 3 and 6).

Reaction Mixtures and Amplicons

In another embodiment, the disclosure provides a reaction mixture comprising a probe or a set of probes that specifically recognize a gene fusion selected from Table 1-Table 3, Table 19, and Table 22. The set of probes can be, for example a set of amplification primers or a labeled probe. In another embodiment, provided herein is a reaction mixture that includes a set of primers that flank a gene fusion selected from Table 1-Table 3, Table 19, and Table 22 in a target nucleic acid. For example, the set of primers can each bind to a target sequence in the human genome within 1000, 750, 500, 250, 100, 90, 80, 75, 70, 65, 50, or 25 nucleotides of opposite sides of the one of the fusion breakpoints identified in Tables 4-6, 20, and 23. The reaction mixture of this embodiment can further include a detector probe that binds to either side of a breakpoint in a gene fusion selected from Table 1-Table 3, Table 19, and Table 22, or that binds a binding region that spans the breakpoint in a gene fusion selected from Table 1-Table 3, Table 19, and Table 22, including specific embodiments where the breakpoint is identified in Tables 4-6, 20, and 23. In exemplary embodiments, the detector probe binds to a target sequence in the human genome within 1000, 750, 500, 250, 100, 90, 80, 75, 70, 60, 50, or 25 nucleotides of one of the fusion breakpoints identified in Tables 4-6, 20, and 23. The reaction mixture that includes a detector probe or does not include a detector probe, can further include a polymerase, a reverse transcriptase, dNTPs, and/or a uracil DNA deglycosylase (UDG). The polymerase, the reverse transcriptase, and the UDG are typically not from human origin. The polymerase in illustrative embodiments is a thermostable polymerase such as a Taq polymerase. In certain embodiments, the dNTPs in the reaction mixture include dUTP, and the reaction mixture can in certain examples, be devoid of dTTP.

The reaction mixture can further include a target nucleic acid, for example a human target nucleic acid. The human target nucleic acid can be, for example, isolated from a biological sample, such as a tumor sample, from a person suspected of having a cancer selected from: BLCA=bladder carcinoma, BRCA=breast carcinoma, CESC=cervical cell carcinoma, COAD=colon adenocarcinoma, GBM=glioblastoma multiforme, HNSC=head and neck squamous cell carcinoma, KIRK=clear cell renal cell carcinoma, KIRP=kidney renal papillary cell carcinoma, LAML=acute myeloid leukemia, LGG=brain lower grade glioma, LIHC=liver hepatocellular carcinoma, LUAD=lung adenocarcinoma, LUSC=squamous cell lung carcinoma, OV=ovarian serous adenocarcinoma, PRAD=prostate adenocarcinoma, READ=rectal adenocarcinoma, SKCM=cutaneous melanoma, STAD=stomach adenocarcinoma, THCA=thyroid carcinoma, and UCEC=uterine corpus endometrioid carcinoma. In certain embodiments, the target nucleic acid is from a tumor, for example a tumor of one of the cancer types listed in the preceding sentence. Furthermore, the target nucleic acid can be extracted from a biological sample from a tumor such as, for example, an FFPE sample.

The reaction mixtures of the present invention can include an amplicon. The amplicon can be for example, an isolated nucleic acid. The amplicon can be between 25 and 2500, between 25 and 2000, between 25 and 1000, between 50 and 1000, between 50 and 500, between 50 and 250, between 50 and 200, between 50 and 150, between 50 and 100, or between 50 and 75 nucleotides in length, for example.

Figure 4:
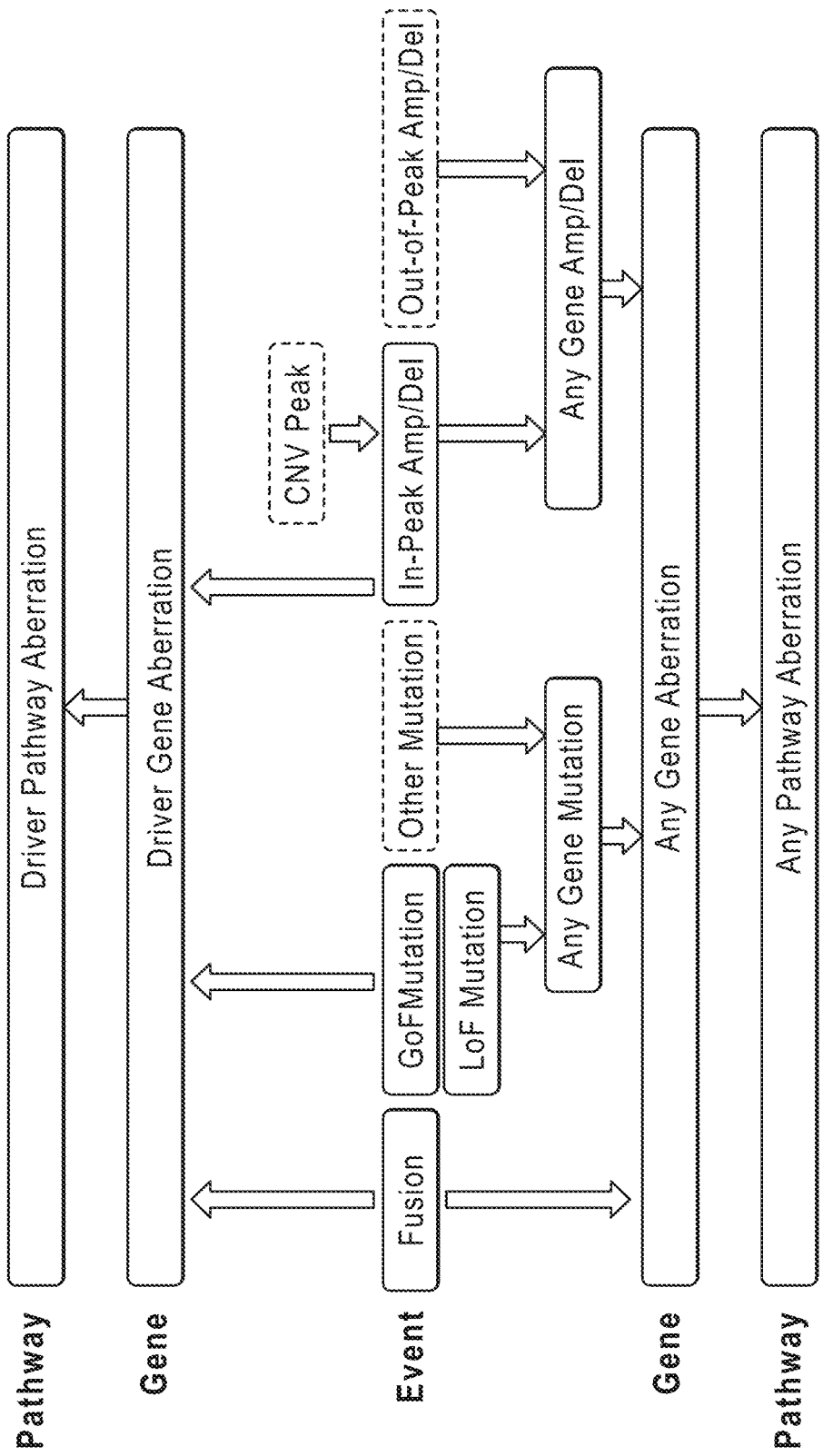
FIG. 4 is a flowchart showing the roll up of genetic events
Figure 5:
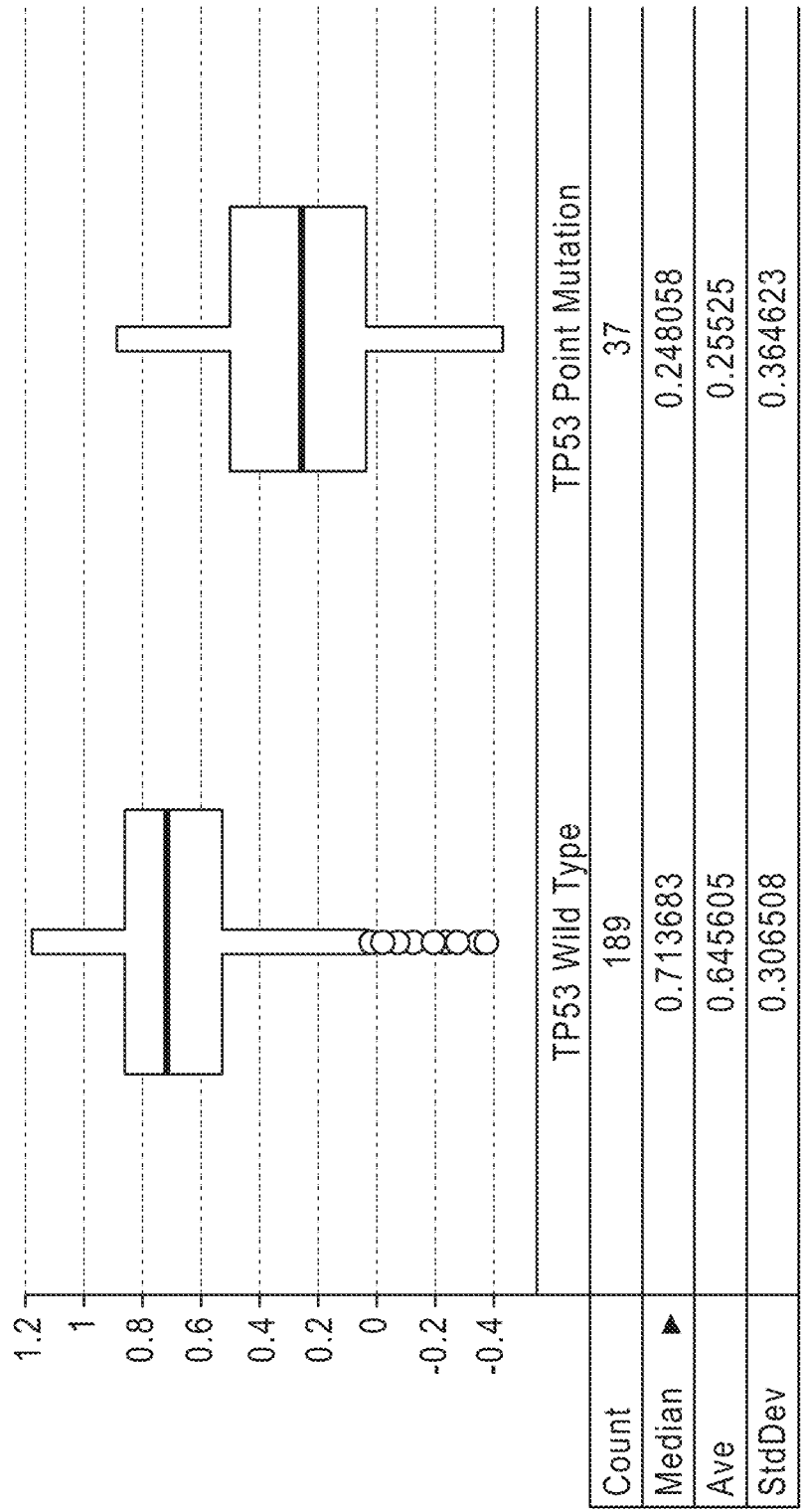
FIG. 5 is a graph showing the TP53 WT expression signature is significantly elevated in TP53 WT breast cancer compared to breast cancer samples harboring a TP53 point mutation.
Figure 6:
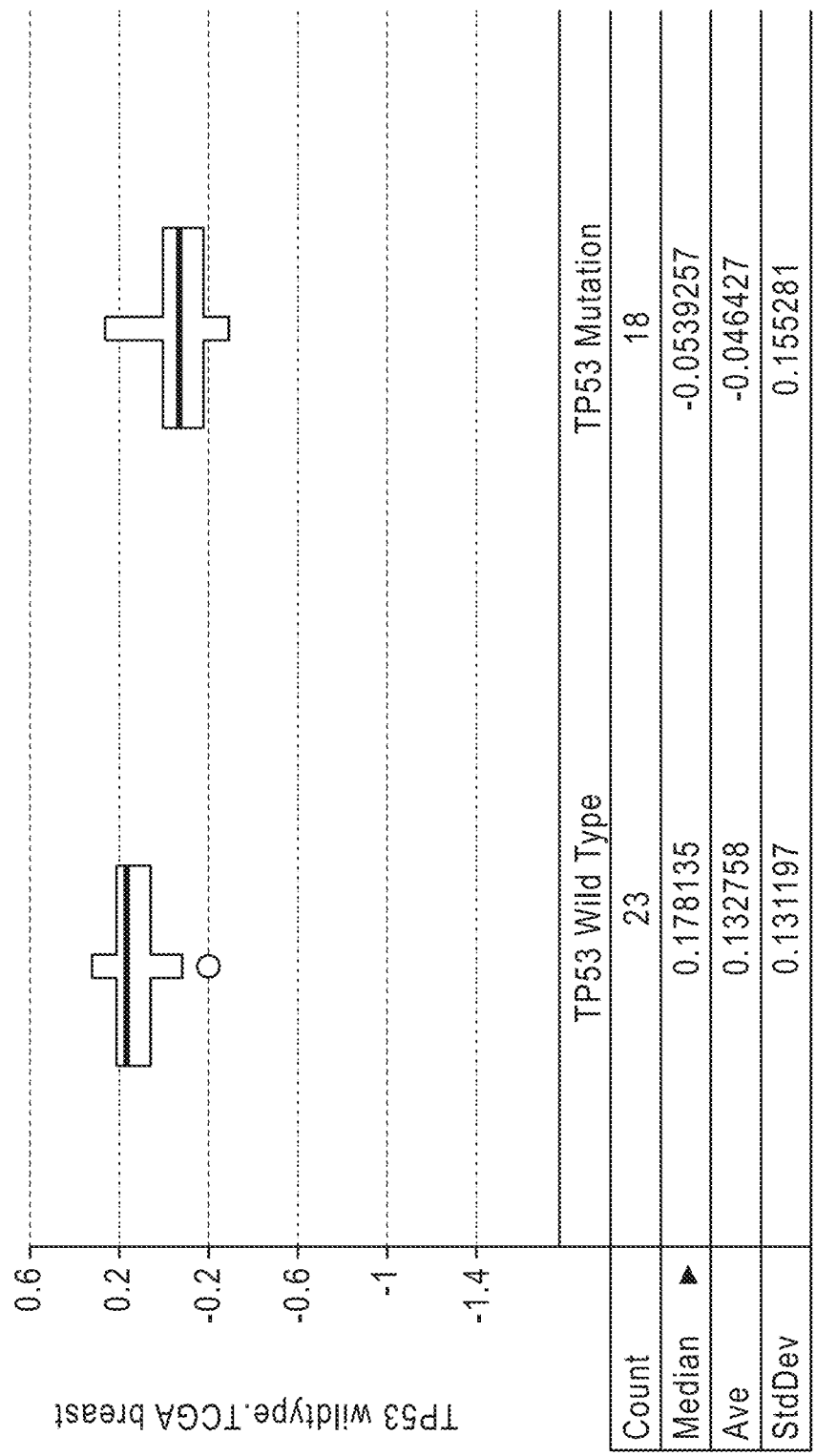
FIG. 6 is a graph showing the TP53 WT expression signature is significantly elevated in TP53 WT lung cancer compared to lung cancer samples harboring a TP53 mutation.
Figure 7:
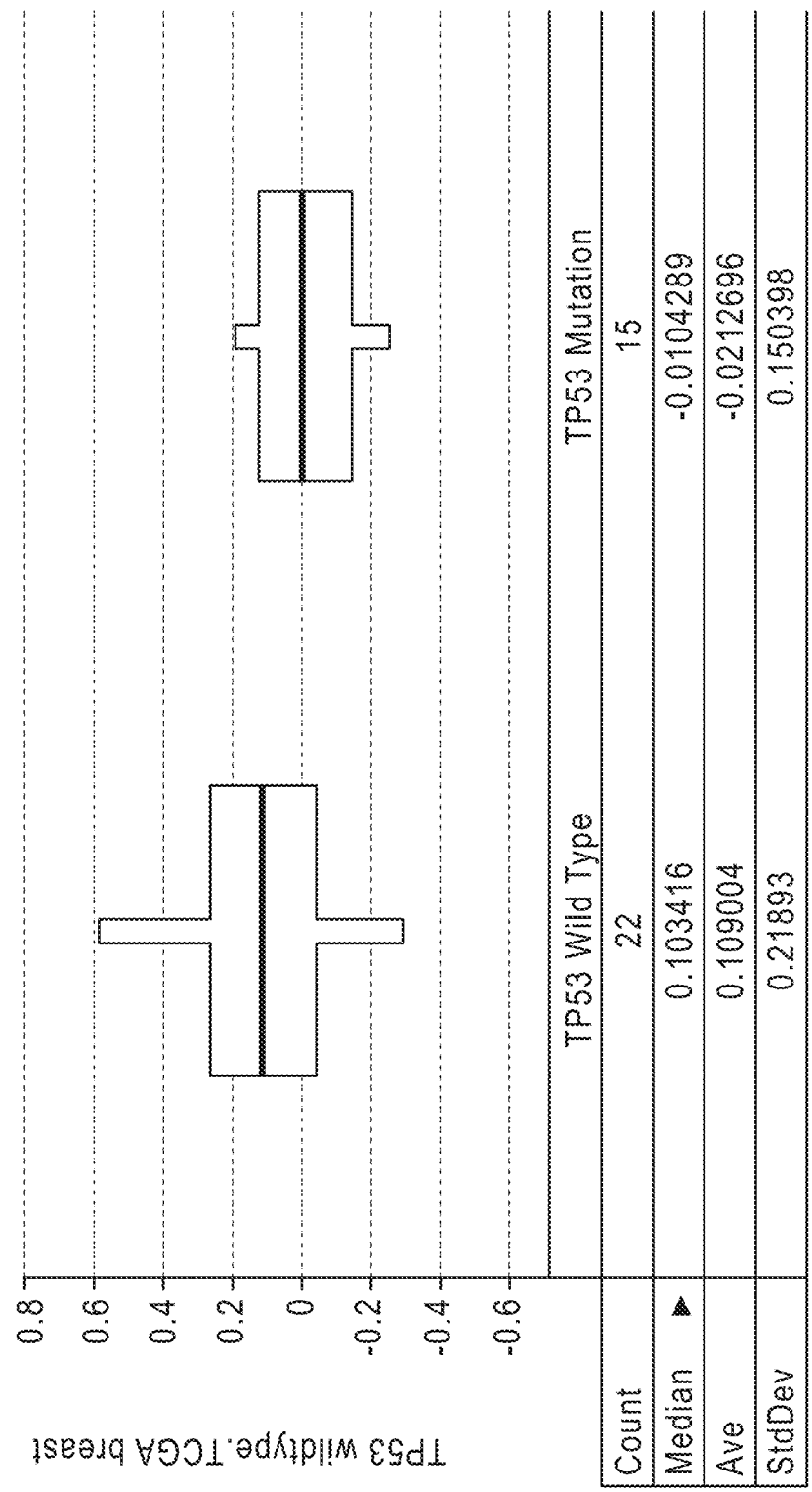
FIG. 7 is a graph showing the TP53 WT expression signature is significantly elevated in HP53 WT ovarian cancer compared to ovarian cancer samples harboring a TP53 mutation.
Figure 8B:
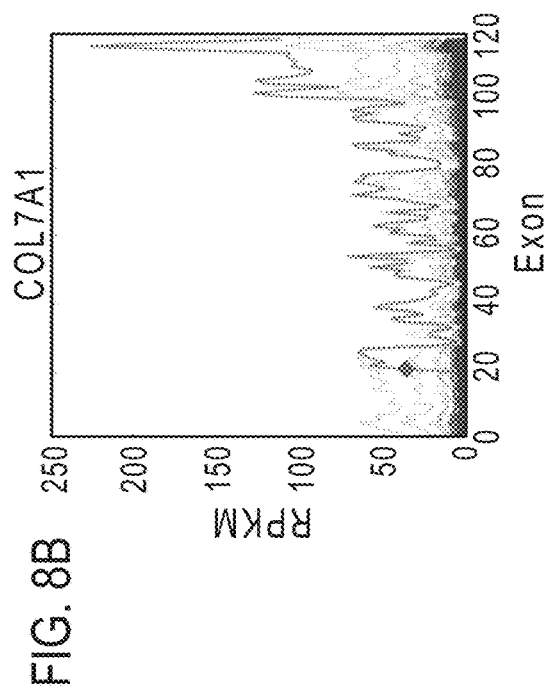
FIG. 8 A-D are graphs depicting is Raw RPKM expression values (A-B) vs. z-score normalized values for PLXNB21 and COL7A1 in Ovarian Serous Carcinoma patients (C-D). The population-wide dips in PLXNB1 expression at exons 12, 17 and 23 are smoothed out in the normalized data. A sample predicted to harbor a fusion between these genes, the red diamond indicates the caller-predicted breakpoint exon.
Figure 8D:
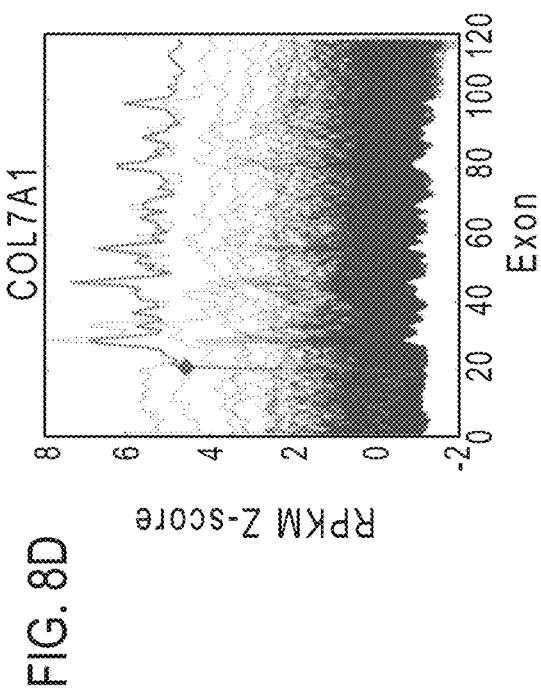
Figure 8A:
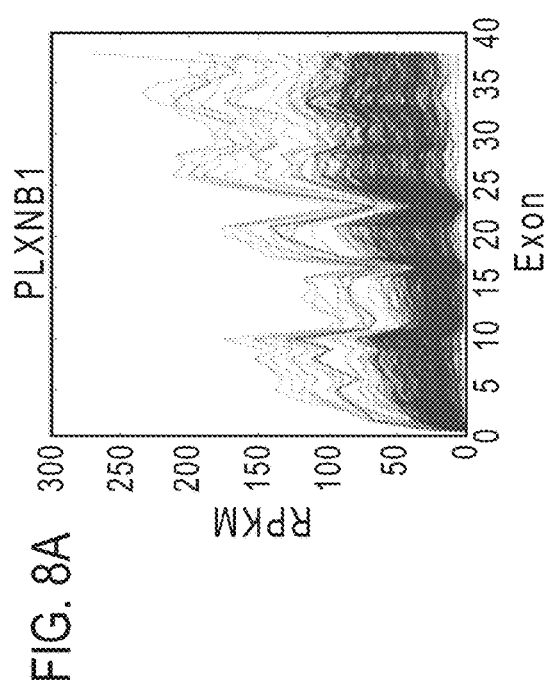
Figure 8C:
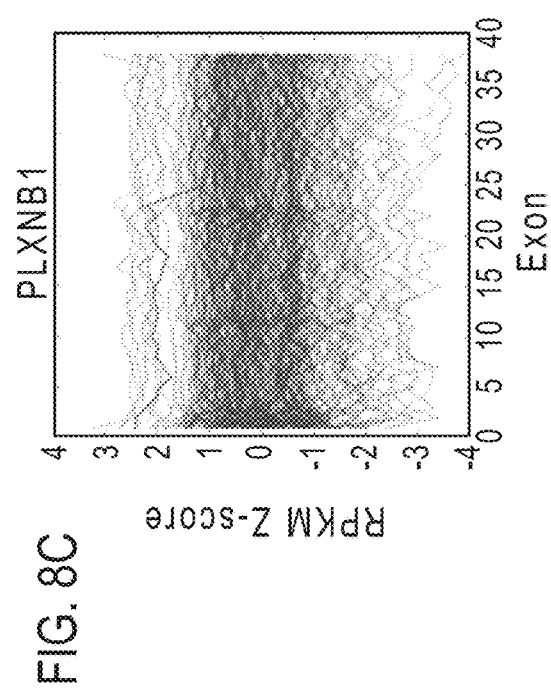

The amplicon can have a nucleotide sequence that is identical or complementary to the target sequence in the human genome within 1000, 750, 500, 250, 100, 90, 80, 75, 70, 65, 50, or 25 nucleotides of opposite sides of the one of the fusion breakpoints identified in Tables 4-6, 20, and 23. In certain embodiments, the amplicon includes 25 to 250, 25 to 100, 25 to 75, 50 to 250, 50 to 200, 50 to 150, 50 to 100, or 50 to 75 of the nucleotide sequence provided in FIGS. 4-6, or a complement thereof. In certain embodiments the amplicons includes sequence variants that occur in nature. For example, the amplicons may include variable nucleotide sequences that correspond to single nucleotide variants or naturally occurring alleles.

Amplicons of the present invention, in certain illustrative embodiments, have a chemical structure that is not found in nature, and/or not found in a mammal, such as a human. For example, certain illustrative amplicons include a base that is not found in nature or not found in a mammal or that may not be found bound to the type of sugar-phosphate backbone of the amplicon. For example, the amplicon might be a DNA amplicon that includes a uracil base bound to the sugar phosphate backbone, thus having a uridine residue at least at one position and in illustrative examples, at all positions that contain a thymidine residue in a template.

Accordingly, the amplicon in illustrative embodiments is a DNA amplicon that includes one or more deoxyuridine ("dU") residues. The dU residue can be added by including such residues in the primers used to generate the amplicon. In certain embodiments the reaction mixture includes a DNA amplicon that includes one or more dU residues for every deoxythymidine residue in the corresponding human genomic sequence. These amplicons can be generated, for example, by using a dNTP mix that includes dUTP instead of dTTP when generating the amplicon using an amplification reaction such as PCR.

In certain embodiments, the amplicon includes a segment for which a corresponding sequence is not found in the human genome, such as, for example, an oligonucleotide sequence, for example a DNA barcode sequence. The non-human segment can be for example, 5-10,000, 5-5000, 5-1000, 5-500, 5-100, 5-50, 5-25, 5-10, 10-10,000, 10-5000, 10-1000, 10-500, 10-100, 10-50, or 10-25 nucleotides in length.

In certain embodiments, the amplicon includes segment that corresponds to the region of the human genome that spans an intron, but the amplicon does not include a segment corresponding to the intron.
Gene Variants (Table 7 and/or Table 11)

TABLE 11

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Prostate Adenocarcinoma | ACOT7 | 1 | 6387379 | SNP | A | G | G | Oncomine | NM_007274 | p.V202A | p.V202 | Missense_Mutation | Hotspot |
| Squamous Cell Lung Carcinoma | ACOT7 | 1 | 6387379 | SNP | A | G | G | Oncomine | NM_007274 | p.V202A | p.V202 | Missense_Mutation | Hotspot |
| Clear Cell Renal Cell Carcinoma | ACOT7 | 1 | 6387379 | SNP | A | G | G | Oncomine | NM_007274 | p.V202A | p.V202 | Missense_Mutation | Hotspot |
| Prostate Adenocarcinoma | ANAPC1 | 2 | 112625621 | SNP | G | C | C | Oncomine | NM_022662 | p.P222A | p.P222 | Missense_Mutation | Hotspot |
| Medulloblastoma | ANAPC1 | 2 | 112625621 | SNP | G | C | C | Oncomine | NM_022662 | p.P222A | p.P222 | Missense_Mutation | Hotspot |
| Gastric Adenocarcinoma | ANAPC1 | 2 | 112625621 | SNP | G | C | C | Oncomine | NM_022662 | p.P222A | p.P222 | Missense_Mutation | Hotspot |
| Lung Adenocarcinoma | ANAPC1 | 2 | 112625621 | SNP | G | C | C | Oncomine | NM_022662 | p.P222A | p.P222 | Missense_Mutation | Hotspot |
| Papillary Renal Cell Carcinoma | ANAPC1 | 2 | 112625621 | SNP | G | C | C | Oncomine | NM_022662 | p.P222A | p.P222 | Missense_Mutation | Hotspot |
| Colorectal Adenocarcinoma | C2orf69 | 2 | 200498052 | SNP | G | A | A | Oncomine | NM_153689 | p.R119H | p.R119 | Missense_Mutation | Hotspot |
| Gastric Adenocarcinoma | C2orf69 | 2 | 200789806 | SNP | C | T | T | Oncomine | NM_153689 | p.R119C | p.R119 | Missense_Mutation | Hotspot |
| Gastric Adenocarcinoma | C2orf69 | 2 | 200789807 | SNP | G | A | A | Oncomine | NM_153689 | p.R119H | p.R119 | Missense_Mutation | Hotspot |
| Cutaneous Melanoma | C4orf22 | 4 | 81791162 | SNP | C | T | T | Oncomine | NM_152770 | p.R117C | p.R117 | Missense_Mutation | Hotspot |
| Cutaneous Melanoma | C4orf22 | 4 | 81791162 | SNP | C | T | T | Oncomine | NM_152770 | p.R117C | p.R117 | Missense_Mutation | Hotspot |
| Cutaneous Melanoma | C4orf22 | 4 | 81504291 | SNP | C | T | T | Oncomine | NM_152770 | p.T96M | p.T96 | Missense_Mutation | Hotspot |
| Thyroid Gland Papillary Carcinoma | C4orf22 | 4 | 81504291 | SNP | C | T | T | Oncomine | NM_152770 | p.T96M | p.T96 | Missense_Mutation | Hotspot |
| Lung Adenocarcinoma | C4orf3 | 4 | 120221638 | SNP | C | T | T | Oncomine | NM_001001701 | p.R18Q | p.R18 | Missense_Mutation | Hotspot |
| Ductal Breast Carcinoma | C4orf3 | 4 | 120221638 | SNP | C | C | G | Oncomine | NM_001001701 | p.R18P | p.R18 | Missense_Mutation | Hotspot |
| Lung Adenocarcinoma | C4orf3 | 4 | 120221638 | SNP | C | T | T | Oncomine | NM_001001701 | p.R18Q | p.R18 | Missense_Mutation | Hotspot |
| Prostate Adenocarcinoma | CACNG3 | 16 | 24373167 | SNP | C | T | T | Oncomine | NM_006539 | p.R311C | p.R311 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Cutaneous Melanoma | CACNG3 | 16 | 24372868 | SNP | C | T | T | Oncomine | NM_006539 | p.S211F | p.S211 | Missense_Mutation | Hotspot |
| Lung Adenocarcinoma | CACNG3 | 16 | 24372930 | SNP | C | T | T | Oncomine | NM_006539 | p.R232W | p.R232 | Missense_Mutation | Hotspot |
| Glioblastoma | CACNG3 | 16 | 24366270 | SNP | G | A | A | Oncomine | NM_006539 | p.A138T | p.A138 | Missense_Mutation | Hotspot |
| Astrocytoma | CACNG3 | 16 | 24373167 | SNP | C | T | T | Oncomine | NM_006539 | p.R311C | p.R311 | Missense_Mutation | Hotspot |
| Colorectal Mucinous Adenocarcinoma | CACNG3 | 16 | 24273772 | SNP | C | T | T | Oncomine | NM_006539 | p.A138V | p.A138 | Missense_Mutation | Hotspot |
| Colorectal Adenocarcinoma | CACNG3 | 16 | 24273771 | SNP | G | A | A | Oncomine | NM_006539 | p.A138T | p.A138 | Missense_Mutation | Hotspot |
| Lung Adenocarcinoma | CACNG3 | 16 | 24372930 | SNP | C | T | T | Oncomine | NM_006539 | p.R232W | p.R232 | Missense_Mutation | Hotspot |
| Squamous Cell Lung Carcinoma | CACNG3 | 16 | 24373168 | SNP | G | C | C | Oncomine | NM_006539 | p.R311P | p.R311 | Missense_Mutation | Hotspot |
| Squamous Cell Lung Carcinoma | CACNG3 | 16 | 24373168 | SNP | G | A | A | Oncomine | NM_006539 | p.R311H | p.R311 | Missense_Mutation | Hotspot |
| Cutaneous Melanoma | CACNG3 | 16 | 24372930 | SNP | C | T | T | Oncomine | NM_006539 | p.R232W | p.R232 | Missense_Mutation | Hotspot |
| Cutaneous Melanoma | CACNG3 | 16 | 24372868 | SNP | C | T | T | Oncomine | NM_006539 | p.S211F | p.S211 | Missense_Mutation | Hotspot |
| Cutaneous Melanoma | CCDC61 | 19 | 46498687 | SNP | G | A | A | Oncomine | NM_001080402 | p.E29K | p.E29 | Missense_Mutation | Hotspot |
| Cutaneous Melanoma | CCDC61 | 19 | 46498700 | SNP | C | T | T | Oncomine | NM_001080402 | p.S33F | p.S33 | Missense_Mutation | Hotspot |
| Cutaneous Melanoma | CCDC61 | 19 | 46498687 | SNP | G | A | A | Oncomine | NM_001080402 | p.E29K | p.E29 | Missense_Mutation | Hotspot |
| Prostate Carcinoma | CDC27 | 17 | 45234367 | SNP | A | T | T | Oncomine | NM_001256 | p.S252T | p.S252 | Missense_Mutation | Hotspot |
| Cutaneous Melanoma | CDC27 | 17 | 45234366 | SNP | G | A | A | Oncomine | NM_001256 | p.S252F | p.S252 | Missense_Mutation | Hotspot |
| Chromophobe Renal Cell Carcinoma | CDC27 | 17 | 45234367 | SNP | A | T | T | Oncomine | NM_001256 | p.S252T | p.S252 | Missense_Mutation | Hotspot |
| Cutaneous Melanoma | CNTN5 | 11 | 100169975 | SNP | G | A | A | Oncomine | NM_014361 | p.E823K | p.E823 | Missense_Mutation | Hotspot |
| Cutaneous Melanoma | CNTN5 | 11 | 100170080 | SNP | G | A | A | Oncomine | NM_014361 | p.G858R | p.G858 | Missense_Mutation | Hotspot |
| Cutaneous Melanoma | CNTN5 | 11 | 99932099 | SNP | C | T | T | Oncomine | NM_014361 | p.S379F | p.S379 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Cutaneous Melanoma | CNTN5 | 11 | 99715827 | SNP | G | A | A | Oncomine | NM_014361 | p.R137Q | p.R137 | Missense_Mutation | Hotspot |
| Colorectal Adenocarcinoma | CNTN5 | 11 | 99221037 | SNP | G | T | T | Oncomine | NM_014361 | p.R137L | p.R137 | Missense_Mutation | Hotspot |
| Colorectal Adenocarcinoma | CNTN5 | 11 | 99221037 | SNP | G | A | A | Oncomine | NM_014361 | p.R137Q | p.R137 | Missense_Mutation | Hotspot |
| Cutaneous Melanoma | CNTN5 | 11 | 99690287 | SNP | C | T | T | Oncomine | NM_014361 | p.S23F | p.S23 | Missense_Mutation | Hotspot |
| Cutaneous Melanoma | CNTN5 | 11 | 100169997 | SNP | G | A | A | Oncomine | NM_014361 | p.E823K | p.E823 | Missense_Mutation | Hotspot |
| Cutaneous Melanoma | CNTN5 | 11 | 99932099 | SNP | C | T | T | Oncomine | NM_014361 | p.S379F | p.S379 | Missense_Mutation | Hotspot |
| Cutaneous Melanoma | CNTN5 | 11 | 100170008 | SNP | G | A | A | Oncomine | NM_014361 | p.G858E | p.G858 | Missense_Mutation | Hotspot |
| Cutaneous Melanoma | CNTN5 | 11 | 99715827 | SNP | G | A | A | Oncomine | NM_014361 | p.R137Q | p.R137 | Missense_Mutation | Hotspot |
| Cutaneous Melanoma | CNTN5 | 11 | 51001262 | SNP | G | A | A | Oncomine | NM_014361 | p.E681K | p.E681 | Missense_Mutation | Hotspot |
| Cutaneous Melanoma | CNTN5 | 11 | 100170080 | SNP | G | A | A | Oncomine | NM_014361 | p.G858R | p.G858 | Missense_Mutation | Hotspot |
| Astrocytoma | CXCR2 | 2 | 219000407 | SNP | G | C | C | Oncomine | NM_001557 | p.A295P | p.A295 | Missense_Mutation | Hotspot |
| Endometrial Endometrioid Adenocarcinoma | CXCR2 | 2 | 218999763 | SNP | G | G | A | Oncomine | NM_001557 | p.R80H | p.R80 | Missense_Mutation | Hotspot |
| Squamous Cell Lung Carcinoma | CXCR2 | 2 | 218999763 | SNP | G | A | A | Oncomine | NM_001557 | p.R80H | p.R80 | Missense_Mutation | Hotspot |
| Cutaneous Melanoma | CXCR2 | 2 | 219000488 | SNP | C | T | T | Oncomine | NM_001557 | p.R322C | p.R322 | Missense_Mutation | Hotspot |
| Cutaneous Melanoma | CXCR2 | 2 | 219000408 | SNP | C | T | T | Oncomine | NM_001557 | p.A295V | p.A295 | Missense_Mutation | Hotspot |
| Cutaneous Melanoma | DCD | 12 | 55039462 | SNP | C | T | T | Oncomine | NM_053283 | p.E43K | p.E43 | Missense_Mutation | Hotspot |
| Cutaneous Melanoma | DCD | 12 | 55039462 | SNP | C | T | T | Oncomine | NM_053283 | p.E43K | p.E43 | Missense_Mutation | Hotspot |
| Cutaneous Melanoma | DSCR6 | 21 | 38390367 | SNP | G | A | A | Oncomine | NM_018962 | p.E145K | p.E145 | Missense_Mutation | Hotspot |
| Lung Adenocarcinoma | DUX4L2 | 10 | 135491125 | SNP | G | A | A | Oncomine | NM_001127386 | p.A246T | p.A246 | Missense_Mutation | Hotspot |
| Lung Adenocarcinoma | DUX4L2 | 10 | 135491123 | SNP | G | A | A | Oncomine | NM_001127386 | p.G245D | p.G245 | Missense_Mutation | Hotspot |
| Infiltrating Bladder Urothelial Carcinoma | DUX4L2 | 10 | 135491113 | SNP | G | T | T | Oncomine | NM_001127386 | p.A242S | p.A242 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Glioblastoma | DUX4L2 | 10 | 135491113 | SNP | G | A | A | Oncomine | NM_001127386 | p.A242T | p.A242 | Missense_Mutation | Hotspot |
| Glioblastoma | DUX4L2 | 10 | 135491125 | SNP | G | A | A | Oncomine | NM_001127386 | p.A246T | p.A246 | Missense_Mutation | Hotspot |
| Glioblastoma | DUX4L2 | 10 | 135491123 | SNP | G | A | A | Oncomine | NM_001127386 | p.G245D | p.G245 | Missense_Mutation | Hotspot |
| Astrocytoma | DUX4L2 | 10 | 135491112 | SNP | C | A | A | Oncomine | NM_001127386 | p.F241L | p.F241 | Missense_Mutation | Hotspot |
| Head and Neck Squamous Cell Carcinoma | DUX4L2 | 10 | 135491123 | SNP | G | A | A | Oncomine | NM_001127386 | p.A246T | p.A246 | Missense_Mutation | Hotspot |
| Head and Neck Squamous Cell Carcinoma | DUX4L2 | 10 | 135491123 | SNP | G | A | A | Oncomine | NM_001127386 | p.G245D | p.G245 | Missense_Mutation | Hotspot |
| Head and Neck Squamous Cell Carcinoma | DUX4L2 | 10 | 135491112 | SNP | C | A | A | Oncomine | NM_001127386 | p.F241L | p.F241 | Missense_Mutation | Hotspot |
| Cutaneous Melanoma | DUX4L2 | 10 | 135491107 | SNP | G | A | A | Oncomine | NM_001127386 | p.A240T | p.A240 | Missense_Mutation | Hotspot |
| Cutaneous Melanoma | DUX4L2 | 10 | 135491123 | SNP | G | A | A | Oncomine | NM_001127386 | p.G245D | p.G245 | Missense_Mutation | Hotspot |
| Cutaneous Melanoma | DUX4L2 | 10 | 135491125 | SNP | G | A | A | Oncomine | NM_001127386 | p.A246T | p.A246 | Missense_Mutation | Hotspot |
| Cutaneous Melanoma | DUX 4L2 | 10 | 135491113 | SNP | G | A | A | Oncomine | NM_001127386 | p.A242T | p.A242 | Missense_Mutation | Hotspot |
| Cutaneous Melanoma | DUX4L2 | 10 | 135491112 | SNP | C | A | A | Oncomine | NM_001127386 | p.F241L | p.F241 | Missense_Mutation | Hotspot |
| Papillary Renal Cell Carcinoma | DUX4L2 | 10 | 135491112 | SNP | C | A | A | Oncomine | NM_001127386 | p.F241L | p.F241 | Missense_Mutation | Hotspot |
| Thyroid Gland Papillary Carcinoma | DUX 4L2 | 10 | 135491125 | SNP | G | A | A | Oncomine | NM_001127386 | p.A246T | p.A246 | Missense_Mutation | Hotspot |
| Thyroid Gland Papillary Carcinoma | DUX4L2 | 10 | 135491107 | SNP | G | A | A | Oncomine | NM_001127386 | p.A240T | p.A240 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Thyroid Gland Papillary Carcinoma | DUX4L2 | 10 | 135491113 | SNP | G | A | A | Oncomine | NM_001127386 | p.A242T | p.A242 | Missense_Mutation | Hotspot |
| Thyroid Gland Papillary Carcinoma | DUX4L2 | 10 | 135491123 | SNP | G | A | A | Oncomine | NM_001127386 | p.G245D | p.G245 | Missense_Mutation | Hotspot |
| Cutaneous Melanoma | EDDM3A | 14 | 21216002 | SNP | G | A | A | Oncomine | NM_006683 | p.R88Q | p.R88 | Missense_Mutation | Hotspot |
| Glioblastoma | EDDM3A | 14 | 21216002 | SNP | G | A | A | Oncomine | NM_006683 | p.R88Q | p.R88 | Missense_Mutation | Hotspot |
| Colorectal Mucinous Adenocarcinoma | EDDM3A | 14 | 20285842 | SNP | G | G | A | Oncomine | NM_006683 | p.R88Q | p.R88 | Missense_Mutation | Hotspot |
| Cutaneous Melanoma | EDDM3A | 14 | 21216002 | SNP | G | A | A | Oncomine | NM_006683 | p.R88Q | p.R88 | Missense_Mutation | Hotspot |
| Ductal Breast Carcinoma | ENDOU | 12 | 48110712 | SNP | G | G | A | Oncomine | NM_006025 | p.P10L3 | p.P130 | Missense_Mutation | Hotspot |
| Endometrial Endometrioid Adenocarcinoma | ENDOU | 12 | 48110712 | SNP | G | G | A | Oncomine | NM_006025 | p.P130L | p.P130 | Missense_Mutation | Hotspot |
| Cutaneous Melanoma | ENDOU | 12 | 48110713 | SNP | G | C | C | Oncomine | NM_006025 | p.P130A | p.P130 | Missense_Mutation | Hotspot |
| Colorectal Adenocarcinoma | ERAS | X | 48572767 | SNP | C | T | T | Oncomine | NM_181532 | p.A97V | p.A97 | Missense_Mutation | Hotspot |
| Endometrial Endometrioid Adenocarcinoma | ERAS | X | 48687822 | SNP | G | G | A | Oncomine | NM_181532 | p.A97T | p.A97 | Missense_Mutation | Hotspot |
| Lung Adenocarcinoma | ERAS | X | 48687822 | SNP | G | A | A | Oncomine | NM_181532 | p.A97T | p.A97 | Missense_Mutation | Hotspot |
| Cutaneous Melanoma | FABP1 | 2 | 88425751 | SNP | C | T | T | Oncomine | NM_001443 | p.E62K | p.E62 | Missense_Mutation | Hotspot |
| Cutaneous Melanoma | FABP1 | 2 | 88425751 | SNP | C | T | T | Oncomine | NM_001443 | p.E62K | p.E62 | Missense_Mutation | Hotspot |
| Medulloblastoma | FAM22F | 9 | 97082793 | DEL | AGA | * | * | Oncomine | NM_017561 | p.S691_in_frame_del | p.S691_in_frame_Del | In_Frame_Del | Hotspot |
| Cervical Squamous Cell Carcinoma | FAM22F | 9 | 97082793 | SNP | C | G | G | Oncomine | NM_017561 | p.K355N | p.K355 | Missense_Mutation | Hotspot |
| Colorectal Adenocarcinoma | FAM22F | 9 | 96122614 | SNP | C | G | G | Oncomine | NM_017561 | p.K355N | p.K355 | Missense_Mutation | Hotspot |
| Cutaneous Melanoma | FAM22F | 9 | 97080945 | DEL | AGA | — | — | Oncomine | NM_017561 | p.S691_in_frame_del | p.S691_in_frame_Del | In_Frame_Del | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Prostate Adenocarcinoma | FAM22F | 9 | 97080945 | DEL | AGA | — | — | Oncomine | NM_017561 | p.S691_in_frame_del | p.S691_in_frame_del | In_Frame_Del | Hotspot |
| Thyroid Gland Carcinoma, NOS | FAM22F | 9 | 97080945 | DEL | AGA | — | — | Oncomine | NM_017561 | p.S691_in_frame_del | p.S691_in_frame_del | In_Frame_Del | Hotspot |
| Ductal Breast Carcinoma | FBXW8 | 12 | 117465850 | SNP | G | G | A | Oncomine | NM_012174 | p.R491H | p.R491 | Missense_Mutation | Hotspot |
| Colorectal Adenocarcinoma | FBXW8 | 12 | 115950233 | SNP | G | A | A | Oncomine | NM_012174 | p.R491H | p.R491 | Missense_Mutation | Hotspot |
| Head and Neck Squamous Cell Carcinoma | FBXW8 | 12 | 117465849 | SNP | C | T | T | Oncomine | NM_012174 | p.R491C | p.R491 | Missense_Mutation | Hotspot |
| Cutaneous Melanoma | FBXW8 | 12 | 117465849 | SNP | C | T | T | Oncomine | NM_012174 | p.R491C | p.R491 | Missense_Mutation | Hotspot |
| Glioblastoma | FBXW8 | 12 | 117465849 | SNP | C | T | T | Oncomine | NM_012174 | p.R491C | p.R491 | Missense_Mutation | Hotspot |
| Lung Adenocarcinoma | FHL3 | 1 | 38463709 | SNP | G | A | A | Oncomine | NM_004468 | p.P143S | p.P143 | Missense_Mutation | Hotspot |
| Thyroid Gland Papillary Carcinoma | FH3L | 1 | 38463709 | SNP | G | A | A | Oncomine | NM_004468 | p.P143S | p.P143 | Missense_Mutation | Hotspot |
| Colorectal Adenocarcinoma | FHL3 | 1 | 38463709 | SNP | G | C | C | Oncomine | NM_004468 | p.P143A | p.P143 | Missense_Mutation | Hotspot |
| Cutaneous Melanoma | GGT1 | 2 | 23340828 | SNP | G | A | A | Oncomine | NM_005265 | p.G84S | p.G84 | Missense_Mutation | Hotspot |
| Cutaneous Melanoma | GK2 | 4 | 80327859 | SNP | C | G | G | Oncomine | NM_033214 | p.R499P | p.R499 | Missense_Mutation | Hotspot |
| Cutaneous Melanoma | GK2 | 4 | 80328367 | SNP | G | A | A | Oncomine | NM_033214 | p.R330C | p.R330 | Missense_Mutation | Hotspot |
| Lung Adenocarcinoma | GK2 | 4 | 80327860 | SNP | G | A | A | Oncomine | NM_033214 | p.R499C | p.R499 | Missense_Mutation | Hotspot |
| Glioblastoma | GK2 | 4 | 80328367 | SNP | G | A | A | Oncomine | NM_033214 | p.R330C | p.R330 | Missense_Mutation | Hotspot |
| Colorectal Adenocarcinoma | GK2 | 4 | 80328891 | SNP | C | A | A | Oncomine | NM_033214 | p.R155L | p.R155 | Missense_Mutation | Hotspot |
| Endometrioid Endometrial Adenocarcinoma | GK2 | 4 | 80547121 | SNP | G | A | A | Oncomine | NM_033214 | p.R420C | p.R420 | Missense_Mutation | Hotspot |
| | GK2 | 4 | 80328892 | SNP | G | A | A | Oncomine | NM_033214 | p.R155C | p.R155 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Head and Neck Squamous Cell Carcinoma | GK2 | 4 | 80327860 | SNP | G | A | A | Oncomine | NM_033214 | p.R499C | p.R499 | Missense_Mutation | Hotspot |
| Lung Adenocarcinoma | GK2 | 4 | 80328679 | SNP | G | A | A | Oncomine | NM_033214 | p.P226S | p.P226 | Missense_Mutation | Hotspot |
| Squamous Cell Lung Carcinoma | GK2 | 4 | 80328678 | SNP | G | A | A | Oncomine | NM_033214 | p.P226L | p.P226 | Missense_Mutation | Hotspot |
| Cutaneous Melanoma | GK2 | 4 | 80328892 | SNP | G | A | A | Oncomine | NM_033214 | p.R155C | p.R155 | Missense_Mutation | Hotspot |
| Cutaneous Melanoma | GK2 | 4 | 80328367 | SNP | G | A | A | Oncomine | NM_033214 | p.R330C | p.R330 | Missense_Mutation | Hotspot |
| Cutaneous Melanoma | GK2 | 4 | 80327860 | SNP | G | A | A | Oncomine | NM_033214 | p.R499C | p.R499 | Missense_Mutation | Hotspot |
| Cutaneous Melanoma | GK2 | 4 | 80328097 | SNP | G | A | A | Oncomine | NM_033214 | p.R420C | p.R420 | Missense_Mutation | Hotspot |
| Cutaneous Melanoma | GK2 | 4 | 80328679 | SNP | G | A | A | Oncomine | NM_033214 | p.P226S | p.P226 | Missense_Mutation | Hotspot |
| Glioblastoma | GOLGA6L10 | 15 | 83014132 | SNP | C | G | G | Oncomine | NM_001164465 | p.E151Q | p.E151 | Missense_Mutation | Hotspot |
| Ductal Breast Carcinoma | GOLGA6L10 | 15 | 83014132 | SNP | C | G | G | Oncomine | NM_001164465 | p.E151Q | p.E151 | Missense_Mutation | Hotspot |
| Head and Neck Squamous Cell Carcinoma | GOLGA6L10 | 15 | 83014132 | SNP | C | G | G | Oncomine | NM_001164465 | p.E151Q | p.E151 | Missense_Mutation | Hotspot |
| Clear Cell Renal Cell Carcinoma | GOLGA6L10 | 15 | 83014132 | SNP | C | G | G | Oncomine | NM_001164465 | p.E151Q | p.E151 | Missense_Mutation | Hotspot |
| Thyroid Gland Papillary Carcinoma | GOLGA6L10 | 15 | 83014132 | SNP | C | G | G | Oncomine | NM_001164465 | p.E151Q | p.E151 | Missense_Mutation | Hotspot |
| Cutaneous Melanoma | GPX7 | 1 | 53072530 | SNP | C | T | T | Oncomine | NM_015696 | p.R105C | p.R105 | Missense_Mutation | Hotspot |
| Head and Neck Squamous Cell Carcinoma | GPX7 | 1 | 53072531 | SNP | G | T | T | Oncomine | NM_015696 | p.R105L | p.R105 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Lung Adenocarcinoma | GPX7 | 1 | 53072531 | SNP | G | A | A | Oncomine | NM_015696 | p.R105H | p.R105 | Missense_Mutation | Hotspot |
| Cutaneous Melanoma | GTSF1 | 12 | 54858877 | SNP | G | A | A | Oncomine | NM_144594 | p.P31S | p.P31 | Missense_Mutation | Hotspot |
| Cutaneous Melanoma | GTSF1 | 12 | 548588 | SNP | G | A | A | Oncomine | NM_144594 | p.P31S | p.P31 | Missense_Mutation | Hotspot |
| Head and Neck Squamous Cell Carcinoma | H3F3A | 1 | 226252059 | SNP | C | T | T | Oncomine | NM_002107 | p.R3C | p.R3 | Missense_Mutation | Hotspot |
| Astrocytoma | H3F3A | 1 | 226252059 | SNP | C | T | T | Oncomine | NM_002107 | p.R3C | p.R3 | Missense_Mutation | Hotspot |
| Cervical Squamous Cell Carcinoma | H3F3A | 1 | 226252059 | SNP | C | T | T | Oncomine | NM_002107 | p.R3C | p.R3 | Missense_Mutation | Hotspot |
| Small Cell Lung Carcinoma | HDDC2 | 6 | 125661566 | SNP | C | G | G | Oncomine | NM_016063 | p.R101P | p.R101 | Missense_Mutation | Hotspot |
| Small Cell Lung Carcinoma | HDDC2 | 6 | 125619867 | SNP | C | G | G | Oncomine | NM_016063 | p.R101P | p.R101 | Missense_Mutation | Hotspot |
| Head and Neck Squamous Cell Carcinoma | HDDC2 | 6 | 125619867 | SNP | C | T | T | Oncomine | NM_016063 | p.R101Q | p.R101 | Missense_Mutation | Hotspot |
| Cutaneous Melanoma | HEXDC | 17 | 80400154 | SNP | A | C | C | Oncomine | NM_173620 | p.T482P | p.T482 | Missense_Mutation | Hotspot |
| Squamous Cell Lung Carcinoma | HEXDC | 17 | 80400154 | SNP | A | C | C | Oncomine | NM_173620 | p.T482P | p.T482 | Missense_Mutation | Hotspot |
| Clear Cell Renal Cell Carcinoma | HEXDC | 17 | 80400154 | SNP | A | C | C | Oncomine | NM_173620 | p.T482P | p.T482 | Missense_Mutation | Hotspot |
| Small Cell Lung Carcinoma | HIST1H4C | 6 | 26112357 | SNP | G | C | C | Oncomine | NM_003542 | p.R68P | p.R68 | Missense_Mutation | Hotspot |
| Head and Neck Squamous Cell Carcinoma | HIST1H4C | 6 | 26104378 | SNP | G | C | C | Oncomine | NM_003542 | p.R68P | p.R68 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Cutaneous Melanoma | HNRNPCL1 | 1 | 12907971 | SNP | C | T | T | Oncomine | NM_001013631 | p.D58N | p.D58 | Missense_Mutation | Hotspot |
| Melanoma | HNRNPCL1 | 1 | 12907847 | SNP | C | T | T | Oncomine | NM_001013631 | p.R99Q | p.R99 | Missense_Mutation | Hotspot |
| Colorectal Adenocarcinoma | HNRNPCL1 | 1 | 12830231 | SNP | G | A | A | Oncomine | NM_001013631 | p.R167W | p.R167 | Missense_Mutation | Hotspot |
| Endometrial Endometrioid Adenocarcinoma | HNRNPCL1 | 1 | 12907644 | SNP | G | G | A | Oncomine | NM_001013631 | p.R167W | p.R167 | Missense_Mutation | Hotspot |
| Gastric Adenocarcinoma | HNRNPCL1 | 1 | 12907847 | SNP | C | T | T | Oncomine | NM_001013631 | p.R99Q | p.R99 | Missense_Mutation | Hotspot |
| Lung Adenocarcinoma | HNRNPCL1 | 1 | 12907643 | SNP | G | A | A | Oncomine | NM_001013631 | p.R167L | p.R167 | Missense_Mutation | Hotspot |
| Cutaneous Melanoma | HNRNPCL1 | 1 | 12907847 | SNP | C | T | T | Oncomine | NM_001013631 | p.R99Q | p.R99 | Missense_Mutation | Hotspot |
| Cutaneous Melanoma | HNRNPCL1 | 1 | 12907865 | SNP | C | T | T | Oncomine | NM_001013631 | p.G93E | p.G93 | Missense_Mutation | Hotspot |
| Cutaneous Melanoma | HNRNPCL1 | 1 | 12907971 | SNP | C | T | T | Oncomine | NM_001013631 | p.D58N | p.D58 | Missense_Mutation | Hotspot |
| Prostate Adenocarcinoma | HRCT1 | 9 | 35906559 | SNP | A | C | C | Oncomine | NM_001039792 | p.H92P | p.H92 | Missense_Mutation | Hotspot |
| Glioblastoma | HRCT1 | 9 | 35906348 | DEL | CTG | — | — | Oncomine | NM_001039792 | p.L22_in_frame_del | p.L22_in_frame_del | In_Frame_Del | Hotspot |
| Ductal Breast Carcinoma | HRCT1 | 9 | 35906348 | DEL | CTG | CTG | — | Oncomine | NM_001039792 | p.L22_in_frame_del | p.L22_in_frame_del | In_Frame_Del | Hotspot |
| Cervical Squamous Cell Carcinoma | HRCT1 | 9 | 35906559 | SNP | A | C | C | Oncomine | NM_001039792 | p.H92P | p.H92 | Missense_Mutation | Hotspot |
| Gastric Adenocarcinoma | HRCT1 | 9 | 35906584 | DEL | CCA | — | — | Oncomine | NM_001039792 | p.L100_in_frame_del | p.L100_in_frame_del | In_Frame_Del | Hotspot |
| Cutaneous Melanoma | HRCT1 | 9 | 35906348 | DEL | CTG | — | — | Oncomine | NM_001039792 | p.L22_in_frame_del | p.L22_in_frame_del | In_Frame_Del | Hotspot |
| Cutaneous Melanoma | HRCT1 | 9 | 35906559 | SNP | A | C | C | Oncomine | NM_001039792 | p.H92P | p.H92 | Missense_Mutation | Hotspot |
| Papillary Renal Cell Carcinoma | HRCT1 | 9 | 35906584 | DEL | CCA | — | — | Oncomine | NM_001039792 | p.L100_in_frame_del | p.L100_in_frame_del | In_Frame_Del | Hotspot |
| Papillary Renal Cell Carcinoma | HRCT1 | 9 | 35906559 | SNP | A | C | C | Oncomine | NM_001039792 | p.H92P | p.H92 | Missense_Mutation | Hotspot |
| Thyroid Gland Carcinoma, NOS | HRCT1 | 9 | 35906584 | DEL | CCA | — | — | Oncomine | NM_001039792 | p.L100_in_frame_del | p.L100_in_frame_del | In_Frame_Del | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Colorectal Adenocarcinoma | IL3 | 5 | 131425967 | SNP | G | A | A | Oncomine | NM_000588 | p.A90T | p.A90 | Missense_Mutation | Hotspot |
| Gastric Adenocarcinoma | IL3 | 5 | 131398068 | SNP | G | A | A | Oncomine | NM_000588 | p.A90T | p.A90 | Missense_Mutation | Hotspot |
| Pancreatic Ductal Adenocarcinoma | JAM3 | 11 | 134014849 | SNP | G | A | G | Oncomine | NM_032801 | p.R191H | p.R191 | Missense_Mutation | Hotspot |
| Lobular Breast Carcinoma | JAM3 | 11 | 134014849 | SNP | G | G | A | Oncomine | NM_032801 | p.R191H | p.R191 | Missense_Mutation | Hotspot |
| Gastric Adenocarcinoma | JAM3 | 11 | 134014848 | SNP | C | T | T | Oncomine | NM_032801 | p.R191C | p.R191 | Missense_Mutation | Hotspot |
| Cutaneous Melanoma | KCNK9 | 8 | 140631316 | SNP | C | T | T | Oncomine | NM_016601 | p.D104N | p.D104 | Missense_Mutation | Hotspot |
| Endometrial Endometrioid Adenocarcinoma | KCNK9 | 8 | 140630833 | SNP | C | C | T | Oncomine | NM_016601 | p.A265T | p.A265 | Missense_Mutation | Hotspot |
| Lung Adenocarcinoma | KCNK9 | 8 | 140630832 | SNP | G | A | A | Oncomine | NM_016601 | p.A265V | p.A265 | Missense_Mutation | Hotspot |
| Squamous Cell Lung Carcinoma | KCNK9 | 8 | 140630833 | SNP | C | T | T | Oncomine | NM_016601 | p.A265T | p.A265 | Missense_Mutation | Hotspot |
| Cutaneous Melanoma | KCNK9 | 8 | 140631316 | SNP | C | T | T | Oncomine | NM_016601 | p.D104N | p.D104 | Missense_Mutation | Hotspot |
| Glioblastoma | KLK6 | 19 | 51466671 | SNP | C | T | T | Oncomine | NM_002774 | p.R111H | p.R111 | Missense_Mutation | Hotspot |
| Colorectal Mucinous Adenocarcinoma | KLK6 | 19 | 56158484 | SNP | G | A | A | Oncomine | NM_002774 | p.R111C | p.R111 | Missense_Mutation | Hotspot |
| Endometrial Endometrioid Adenocarcinoma | KLK6 | 19 | 51466671 | SNP | C | C | T | Oncomine | NM_002774 | p.R111H | p.R111 | Missense_Mutation | Hotspot |
| Cutaneous Melanoma | KLK6 | 19 | 51462556 | SNP | G | A | A | Oncomine | NM_002774 | p.P200L | p.P200 | Missense_Mutation | Hotspot |
| Prostate Adenocarcinoma | KLK6 | 19 | 51462556 | SNP | G | A | A | Oncomine | NM_002774 | p.P200L | p.P200 | Missense_Mutation | Hotspot |
| Clear Cell Renal Cell Carcinoma | KLK6 | 19 | 51462556 | SNP | G | A | A | Oncomine | NM_002774 | p.P200L | p.P200 | Missense_Mutatopm | Hotspot |
| Colorectal Adenocarcinoma | KRTAP12-4 | 21 | 44898950 | SNP | T | G | G | Oncomine | NM_198698 | p.T4P | p.T4 | Missense_Mutation | Hotspot |
| Ovarian Serous Adenocarcinoma | KRTAP12-4 | 21 | 44898949 | SNP | G | G | A | Oncomine | NM_198698 | p.T4I | p.T4 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Cutaneous Melanoma | KRTAP4-11 | 17 | 39274424 | SNP | G | C | C | Oncomine | NM_033059 | p.S48R | p.S48 | Missense_Mutation | Hotspot |
| Cutaneous Melanoma | KRTAP4-11 | 17 | 39274206 | SNP | C | T | T | Oncomine | NM_033059 | p.R121K | p.R121 | Missense_Mutation | Hotspot |
| Lung Adenocarcinoma | KRTAP4-11 | 17 | 39274150 | SNP | T | A | A | Oncomine | NM_033059 | p.S140C | p.S140 | Missense_Mutation | Hotspot |
| Lung Adenocarcinoma | KRTAP4-11 | 17 | 39274206 | SNP | C | T | T | Oncomine | NM_033059 | p.R121K | p.R121 | Missense_Mutation | Hotspot |
| Glioblastoma | KRTAP4-11 | 17 | 39274424 | SNP | G | C | C | Oncomine | NM_033059 | p.S48R | p.S48 | Missense_Mutation | Hotspot |
| Oligodendroglioma | KRTAP4-11 | 17 | 39274087 | SNP | G | C | C | Oncomine | NM_033059 | p.L161V | p.L161 | Missense_Mutation | Hotspot |
| Ductal Breast Carcinoma | KRTAP4-11 | 17 | 39274087 | SNP | G | C | C | Oncomine | NM_033059 | p.L161V | p.L161 | Missense_Mutation | Hotspot |
| Cervical Squamous Cell Carcinoma | KRTAP4-11 | 17 | 39274424 | SNP | G | C | C | Oncomine | NM_033059 | p.S48R | p.S48 | Missense_Mutation | Hotspot |
| Cervical Squamous Cell Carcinoma | KRTAP4-11 | 17 | 39274087 | SNP | G | C | C | Oncomine | NM_033059 | p.L161V | p.L161 | Missense_Mutation | Hotspot |
| Cervical Squamous Cell Carcinoma | KRTAP4-11 | 17 | 39274150 | SNP | T | A | A | Oncomine | NM_033059 | p.S140C | p.S140 | Missense_Mutation | Hotspot |
| Head and Neck Squamous Cell Carcinoma | KRTAP4-11 | 17 | 39274424 | SNP | G | C | C | Oncomine | NM_033059 | p.S48R | p.S48 | Missense_Mutation | Hotspot |
| Head and Neck Squamous Cell Carcinoma | KRTAP4-11 | 17 | 39274206 | SNP | C | T | T | Oncomine | NM_033059 | p.R121K | p.R121 | Missense_Mutation | Hotspot |
| Head and Neck Squamous Cell Carcinoma | KRTAP4-11 | 17 | 39274087 | SNP | G | C | C | Oncomine | NM_033059 | p.L161V | p.L161 | Missense_Mutation | Hotspot |
| Head and Neck Squamous Cell Carcinoma | KRTAP4-11 | 17 | 39274150 | SNP | T | A | A | Oncomine | NM_033059 | p.S140C | p.S140 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Head and Neck Squamous Cell Carcinoma | KRTAP4-11 | 17 | 39274291 | SNP | T | C | C | Oncomine | NM_033059 | p.M93V | p.M93 | Missense_Mutation | Hotspot |
| Head and Neck Squamous Cell Carcinoma | KRTAP4-11 | 17 | 39274416 | SNP | C | T | T | Oncomine | NM_033059 | p.R51K | p.R51 | Missense_Mutation | Hotspot |
| Lung Adenocarcinoma | KRTAP4-11 | 17 | 39274424 | SNP | G | C | C | Oncomine | NM_033059 | p.S48R | p.S48 | Missense_Mutation | Hotspot |
| Lung Adenocarcinoma | KRTAP4-11 | 17 | 39274206 | SNP | C | T | T | Oncomine | NM_033059 | p.R121K | p.R121 | Missense_Mutation | Hotspot |
| Cutaneous Melanoma | KRTAP4-11 | 17 | 39274150 | SNP | T | A | A | Oncomine | NM_033059 | p.S140C | p.S140 | Missense_Mutation | Hotspot |
| Cutaneous Melanoma | KRTAP4-11 | 17 | 39274206 | SNP | C | T | T | Oncomine | NM_033059 | p.R121K | p.R121 | Missense_Mutation | Hotspot |
| Cutaneous Melanoma | KRTAP4-11 | 17 | 39274424 | SNP | G | C | C | Oncomine | NM_033059 | p.S48R | p.S48 | Missense_Mutation | Hotspot |
| Cutaneous Melanoma | KRTAP4-11 | 17 | 39274087 | SNP | G | C | C | Oncomine | NM_033059 | p.L161V | p.L161 | Missense_Mutatopm | Hotspot |
| Cutaneous Melanoma | KRTAP4-11 | 17 | 39274416 | SNP | C | T | T | Oncomine | NM_033059 | p.R51K | p.R51 | Missense_Mutation | Hotspot |
| Clear Cell Renal Cell Carcinoma | KRTAP4-11 | 17 | 39274291 | SNP | T | C | C | Oncomine | NM_033059 | p.M93V | p.M93 | Missense_Mutation | Hotspot |
| Clear Cell Renal Cell Carcinoma | KRTAP4-11 | 17 | 39274206 | SNP | C | T | T | Oncomine | NM_033059 | p.R121K | p.R121 | Missense_Mutation | Hotspot |
| Clear Cell Renal Cell Carcinoma | KRTAP4-11 | 17 | 39274150 | SNP | T | A | A | Oncomine | NM_033059 | p.S140C | p.S140 | Missense_Mutation | Hotspot |
| Papillary Renal Cell Carcinoma | KRTAP4-11 | 17 | 39274087 | SNP | G | C | C | Oncomine | NM_033059 | p.L161V | p.L161 | Missense_Mutation | Hotspot |
| Thyroid Gland Papillary Carcinoma | KRTAP4-11 | 17 | 39274424 | SNP | G | C | C | Oncomine | NM_033059 | p.S48R | p.S48 | Missense_Mutation | Hotspot |
| Papillary Renal Cell Carcinoma | KRTAP4-7 | 17 | 39240900 | SNP | T | G | G | Oncomine | NM_033061 | p.L148V | p.L148 | Missense_Mutation | Hotspot |
| Cutaneous Melanoma | LAD1 | 1 | 201354881 | SNP | C | T | T | Oncomine | NM_005558 | p.R360Q | p.R360 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Cutaneous Melanoma | LAD1 | 1 | 201352246 | SNP | C | T | T | Oncomine | NM_005558 | p.E448K | p.E448 | Missense_Mutation | Hotspot |
| Clear Cell Renal Cell Carcinoma | LAD1 | 1 | 201354881 | SNP | C | A | A | Oncomine | NM_005558 | p.R360L | p.R360 | Missense_Mutation | Hotspot |
| Cutaneous Melanoma | LELP1 | 1 | 153177244 | SNP | C | T | T | Oncomine | NM_001010857 | p.P21S | p.P21 | Missense_Mutation | Hotspot |
| Cutaneous Melanoma | LELP1 | 1 | 153177437 | SNP | C | T | T | Oncomine | NM_01010857 | p.S85F | p.S85 | Missense_Mutation | Hotspot |
| Cutaneous Melanoma | LELP1 | 1 | 153177245 | SNP | C | T | T | Oncomine | NM_001010857 | p.P21L | p.P21 | Missense_Mutation | Hotspot |
| Cutaneous Melanoma | LELP1 | 1 | 153177244 | SNP | C | T | T | Oncomine | NM_001010857 | p.P21S | p.P21 | Missense_Mutation | Hotspot |
| Cutaneous Melanoma | LOC100509575 | X | 47972582 | SNP | G | A | A | Oncomine | NM_001205103 | p.R96H | p.R96 | Missense_Mutation | Hotspot |
| Lobular Breast Carcinoma | LOC100509575 | X | 47972582 | SNP | G | A | A | Oncomine | NM_001205103 | p.R96H | p.R96 | Missense_Mutation | Hotspot |
| Endometrial Endometrioid Adenocarcinoma | LOC100509575 | X | 47972581 | SNP | C | T | T | Oncomine | NM_001205103 | p.R96C | p.R96 | Missense_Mutation | Hotspot |
| Glioblastoma | MUC4 | 3 | 195516064 | SNP | C | T | T | Oncomine | NM_018406 | p.R796Q | p.R796 | Missense_Mutation | Hotspot |
| Ductal Breast Carcinoma | MUC4 | 3 | 195516064 | SNP | C | T | T | Oncomine | NM_018406 | p.R796Q | p.R796 | Missense_Mutation | Hotspot |
| Lung Adenocarcinoma | MUC4 | 3 | 195516064 | SNP | C | T | T | Oncomine | NM_018406 | p.R796Q | p.R796 | Missense_Mutation | Hotspot |
| Glioblastoma | NAB2 | 12 | 57485446 | SNP | T | C | C | Oncomine | NM_005967 | p.F208L | p.F208 | Missense_Mutation | Hotspot |
| Oligodendroglioma | NAB2 | 12 | 57485446 | SNP | P | T | C | Oncomine | NM_005967 | p.F208L | p.F208 | Missense_Mutation | Hotspot |
| Head and Neck Squamous Cell Carcinoma | NAB2 | 12 | 57485446 | SNP | T | C | C | | | p.F208L | p.F208 | | |
| Lung Adenocarcinoma | NAB2 | 12 | 57485446 | SNP | T | C | C | Oncomine | NM_005967 | p.F208L | p.F208 | Missense_Mutation | Hotspot |
| Cutaneous Melanoma | NAB2 | 12 | 57485446 | SNP | T | C | C | Oncomine | NM_005967 | p.F208L | p.F208 | Missense_Mutation | Hotspot |
| Glioblastoma | NBPF10 | 1 | 145324371 | SNP | T | C | C | Oncomine | NM_001039703 | p.V1189A | p.V1189 | Missense_Mutation | Hotspot |
| Astrocytoma | NBPF10 | 1 | 145360584 | SNP | G | A | A | Oncomine | NM_001039703 | p.G3070E | p.G3070 | Missense_Mutation | Hotspot |
| Cutaneous | NBPF10 | 1 | 145360584 | SNP | G | A | A | Oncomine | NM_001039703 | p.G3070E | p.G3070 | Missense_Mutation | Hotspot |

TABLE 11-continued

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Melanoma Cutaneous | NSFL1C | 20 | 1426360 | SNP | G | A | A | Oncomine | NM_016143 | p.R301W | p.R301 | Missense_Mutation | Hotspot |
| Melanoma Cutaneous | NSFL1C | 20 | 1374360 | SNP | G | A | A | Oncomine | NM_016143 | p.R301W | p.R301 | Missense_Mutation | Hotspot |
| Colorectal Adenocarcinoma | NSFL1C | 20 | 1426360 | SNP | G | G | A | Oncomine | NM_016143 | p.R301W | p.R301 | Missense_Mutation | Hotspot |
| Endometrial Endometrioid Adenocarcinoma | NSFL1C | 20 | 1426360 | SNP | G | A | A | Oncomine | NM_016143 | p.R301W | p.R301 | Missense_Mutation | Hotspot |
| Head and Neck Squamous Cell Carcinoma | OBP2B | 9 | 136081795 | SNP | A | G | G | Oncomine | NM_014581 | p.S133P | p.S133 | Missense_Mutation | Hotspot |
| Medulloblastoma | OBP2B | 9 | 136081795 | SNP | A | G | G | Oncomine | NM_014581 | p.S133P | p.S133 | Missense_Mutation | Hotspot |
| Head and Neck Squamous Cell Carcinoma | OBP2B | 9 | 136081795 | SNP | A | G | G | Oncomine | NM_014581 | p.S133P | p.S133 | Missense_Mutation | Hotspot |
| Lung Adenocarcinoma | OR2L13 | 1 | 248262729 | SNP | C | A | A | Oncomine | NM_175911 | p.P18T | p.P18 | Missense_Mutation | Hotspot |
| Cutaneous Melanoma | OR2L13 | 1 | 248263173 | SNP | C | T | T | Oncomine | NM_175911 | p.P166S | p.P166 | Missense_Mutation | Hotspot |
| Lung Adenocarcinoma | OR2L13 | 1 | 248263401 | SNP | A | G | G | Oncomine | NM_175911 | p.T242A | p.T242 | Missense_Mutation | Hotspot |
| Small Cell Lung Carcinoma | OR2L13 | 1 | 248262832 | SNP | C | A | A | Oncomine | NM_175911 | p.P52H | p.P52 | Missense_Mutation | Hotspot |
| Head and Neck Squamous Cell Carcinoma | OR2L13 | 1 | 248262831 | SNP | C | T | T | Oncomine | NM_175911 | p.P52S | p.P52 | Missense_Mutation | Hotspot |
| Lung Adenocarcinoma | OR2L13 | 1 | 248263401 | SNP | A | T | T | Oncomine | NM_175911 | p.T242S | p.T242 | Missense_Mutation | Hotspot |
| Lung Adenocarcinoma | OR2L13 | 1 | 248263401 | SNP | A | G | G | Oncomine | NM_175911 | p.T242A | p.T242 | Missense_Mutation | Hotspot |
| Squamous Cell Lung Carcinoma | OR2L13 | 1 | 248262831 | SNP | C | T | T | Oncomine | NM_175911 | p.P52S | p.P52 | Missense_Mutation | Hotspot |
| Cutaneous Melanoma | OR2L13 | 1 | 248262371 | SNP | G | A | A | Oncomine | NM_175911 | p.G232R | p.G232 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Cutaneous Melanoma | OR2L13 | 1 | 248263171 | SNP | C | T | T | Oncomine | NM_175911 | p.P166L | p.P166 | Missense_Mutation | Hotspot |
| Cutaneous Melanoma | OR2L13 | 1 | 248263173 | SNP | C | T | T | Oncomine | NM_175911 | p.P166S | p.P166 | Missense_Mutation | Hotspot |
| Cutaneous Melanoma | OR2L13 | 1 | 248262730 | SNP | C | T | T | Oncomine | NM_175911 | p.P18L | p.P18 | Missense_Mutation | Hotspot |
| Cutaneous Melanoma | OR2L13 | 1 | 248262721 | SNP | C | A | A | Oncomine | NM_175911 | p.P18T | p.P18 | Missense_Mutation | Hotspot |
| Ovarian Serous Adenocarcinoma | OR2L13 | 1 | 246329995 | SNP | G | A | A | Oncomine | NM_175911 | p.G232E | p.G232 | Missense_Mutation | Hotspot |
| Colorectal Adenocarcinoma | OR2T27 | 1 | 246880778 | SNP | C | T | T | Oncomine | NM_001001824 | p.D11N | p.D11 | Missense_Mutation | Hotspot |
| Endometrial Serous Adenocarcinoma | OR2T27 | 1 | 248813822 | SNP | G | G | A | Oncomine | NM_001001824 | p.R122C | p.R122 | Missense_Mutation | Hotspot |
| Gastric Adenocarcinoma | OR2T27 | 1 | 248813821 | SNP | C | T | T | Oncomine | NM_001001824 | p.R122H | p.R122 | Missense_Mutation | Hotspot |
| Gastric Adenocarcinoma | OR2T27 | 1 | 248813773 | SNP | C | T | T | Oncomine | NM_001001824 | p.R138H | p.R138 | Missense_Mutation | Hotspot |
| Head and Neck Squamous Cell Carcinoma | OR2T27 | 1 | 248813773 | SNP | C | G | G | Oncomine | NM_001001824 | p.R138P | p.R138 | Missense_Mutation | Hotspot |
| Lung Adenocarcinoma | OR2T27 | 1 | 248814155 | SNP | C | A | A | Oncomine | NM_001001824 | p.D11Y | p.D11 | Missense_Mutation | Hotspot |
| Lung Adenocarcinoma | OR2T27 | 1 | 248813773 | SNP | C | A | A | Oncomine | NM_001001824 | p.R138L | p.R138 | Missense_Mutation | Hotspot |
| Cutaneous Melanoma | OR2Z1 | 19 | 8841458 | SNP | C | T | T | Oncomine | NM_001004699 | p.S23L | p.S23 | Missense_Mutation | Hotspot |
| Glioblastoma | OR2Z1 | 19 | 8841802 | SNP | C | T | T | Oncomine | NM_001004699 | p.R138C | p.R138 | Missense_Mutation | Hotspot |
| Gastric Adenocarcinoma | OR2Z1 | 19 | 8841802 | SNP | C | T | T | Oncomine | NM_001004699 | p.R138C | p.R138 | Missense_Mutation | Hotspot |
| Lung Adenocarcinoma | OR2Z1 | 19 | 8841458 | SNP | C | T | T | Oncomine | NM_001004699 | p.S23L | p.S23 | Missense_Mutation | Hotspot |
| Cutaneous Melanoma | OR2Z1 | 19 | 8841889 | SNP | C | T | T | Oncomine | NM_001004699 | p.P167S | p.P167 | Missense_Mutation | Hotspot |
| Cutaneous Melanoma | OR4E2 | 14 | 22133748 | SNP | G | A | A | Oncomine | NM_001001912 | p.G151E | p.G151 | Missense_Mutation | Hotspot |
| Cutaneous Melanoma | OR4E2 | 14 | 22133973 | SNP | G | A | A | Oncomine | NM_001001912 | p.R226Q | p.R226 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Cutaneous Melanoma | OR4E2 | 14 | 22133747 | SNP | G | A | A | Oncomine | NM_001001912 | p.G151R | p.G151 | Missense_Mutation | Hotspot |
| Cutaneous Melanoma | OR4E2 | 14 | 22133748 | SNP | G | A | A | Oncomine | NM_001001912 | p.G151E | p.G151 | Missense_Mutation | Hotspot |
| Cutaneous Melanoma | OR51B2 | 11 | 5345263 | SNP | C | T | T | Oncomine | NM_033180 | p.E89K | p.E89 | Missense_Mutation | Hotspot |
| Cutaneous Melanoma | OR51B2 | 11 | 5345040 | SNP | G | A | A | Oncomine | NM_033180 | p.S163L | p.S163 | Missense_Mutation | Hotspot |
| Lung Adenocarcinoma | OR51B2 | 11 | 5344773 | SNP | G | T | T | Oncomine | NM_033180 | p.T252K | p.T252 | Missense_Mutation | Hotspot |
| Glioblastoma | OR51B2 | 11 | 5344773 | SNP | G | A | A | Oncomine | NM_033180 | p.T252I | p.T252 | Missense_Mutation | Hotspot |
| Head and Neck Squamous Cell Carcinoma | OR51B2 | 11 | 5344774 | SNP | T | C | C | Oncomine | NM_033180 | p.T252A | p.T252 | Missense_Mutation | Hotspot |
| Squamous Cell Lung Carcinoma | OR51B2 | 11 | 5345101 | SNP | C | T | T | Oncomine | NM_033180 | p.G143R | p.G143 | Missense_Mutation | Hotspot |
| Squamous Cell Lung Carcinoma | OR51B2 | 11 | 5345100 | SNP | C | A | A | Oncomine | NM_033180 | p.G143V | p.G143 | Missense_Mutation | Hotspot |
| Cutaneous Melanoma | OR51B2 | 11 | 5345163 | SNP | C | T | T | Oncomine | NM_033180 | p.E89K | p.E89 | Missense_Mutation | Hotspot |
| Cutaneous Melanoma | OR51B2 | 11 | 5345040 | SNP | G | A | A | Oncomine | NM_033180 | p.S163L | p.S163 | Missense_Mutation | Hotspot |
| Glioblastoma | OR51B2 | 11 | 5345100 | SNP | C | T | T | Oncomine | NM_033180 | p.G143E | p.G143 | Missense_Mutation | Hotspot |
| Cutaneous Melanoma | OR52A1 | 11 | 5172692 | SNP | G | A | A | Oncomine | NM_012375 | p.R303H | p.R303 | Missense_Mutation | Hotspot |
| Cutaneous Melanoma | OR52A1 | 11 | 5172911 | SNP | C | A | A | Oncomine | NM_012375 | p.R230C | p.R230 | Missense_Mutation | Hotspot |
| Cutaneous Melanoma | OR52A1 | 11 | 5172693 | SNP | C | T | T | Oncomine | NM_012375 | p.R303C | p.R303 | Missense_Mutation | Hotspot |
| Prostate Adenocarcinoma | OR52A1 | 11 | 5172911 | SNP | C | T | T | Oncomine | NM_012375 | p.R230H | p.R230 | Missense_Mutation | Hotspot |
| Cutaneous Melanoma | OR5AN1 | 11 | 59132584 | SNP | C | A | A | Oncomine | NM_001004729 | p.S218F | p.S218 | Missense_Mutation | Hotspot |
| Cutaneous Melanoma | OR6T1 | 11 | 123814182 | SNP | G | A | A | Oncomine | NM_001005187 | p.R122C | p.R122 | Missense_Mutation | Hotspot |
| Ductal Breast Carcinoma | OR6T1 | 11 | 123813896 | SNP | G | T | T | Oncomine | NM_001005187 | p.S217Y | p.S217 | Missense_Mutation | Hotspot |
| Colorectal Adenocarcinoma | OR6T1 | 11 | 123318974 | SNP | C | T | T | Oncomine | NM_001005187 | p.R261H | p.R261 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Colorectal Mucinous Adenocarcinoma | OR6T1 | 11 | 123319221 | SNP | G | A | A | Oncomine | NM_001005187 | p.R179C | p.R179 | Missense_Mutation | Hotspot |
| Colorectal Adenocarcinoma | OR6T1 | 11 | 123319106 | SNP | G | T | T | Oncomine | NM_001005187 | p.S217Y | p.S217 | Missense_Mutation | Hotspot |
| Cutaneous Melanoma | OR6T1 | 11 | 123813765 | SNP | G | A | A | Oncomine | NM_001005187 | p.R261C | p.R261 | Missense_Mutation | Hotspot |
| Cutaneous Melanoma | OR6T1 | 11 | 123814011 | SNP | G | A | A | Oncomine | NM_001005187 | p.R179C | p.R179 | Missense_Mutation | Hotspot |
| Cutaneous Melanoma | OR6T1 | 11 | 123813896 | SNP | G | A | A | Oncomine | NM_001005187 | p.S217F | p.S217 | Missense_Mutation | Hotspot |
| Cutaneous Melanoma | OR6T1 | 11 | 123814182 | SNP | G | A | A | Oncomine | NM_001005187 | p.R122C | p.R122 | Missense_Mutation | Hotspot |
| Clear Cell Renal Cell Carcinoma | OR6T1 | 11 | 123814182 | SNP | G | T | T | Oncomine | NM_001005187 | p.R122S | p.R122 | Missense_Mutation | Hotspot |
| Cutaneous Melanoma | OTUD5 | X | 48792073 | SNP | C | T | T | Oncomine | NM_017602 | p.R274Q | p.R274 | Missense_Mutation | Hotspot |
| Colorectal Adenocarcinoma | OTUD5 | X | 48668111 | SNP | G | A | A | Oncomine | NM_017602 | p.R412W | p.R412 | Missense_Mutation | Hotspot |
| Colorectal Adenocarcinoma | OTUD5 | X | 48677018 | SNP | G | A | A | Oncomine | NM_017602 | p.R274W | p.R274 | Missense_Mutation | Hotspot |
| Endometrial Endometrioid Adenocarcinoma | OTUD5 | X | 48792074 | SNP | G | A | A | Oncomine | NM_017602 | p.R274W | p.R274 | Missense_Mutation | Hotspot |
| Endometrial Endometrioid Adenocarcinoma | OTUD5 | X | 48783167 | SNP | G | A | A | Oncomine | NM_017602 | p.R412W | p.R412 | Missense_Mutation | Hotspot |
| Lung Adenocarcinoma | OTUD5 | X | 48783166 | SNP | C | A | A | Oncomine | NM_017602 | p.R412L | p.R412 | Missense_Mutation | Hotspot |
| Cutaneous Melanoma | OXA1L | 14 | 23235902 | SNP | C | T | T | Oncomine | NM_005015 | p.P58S | p.P58 | Missense_Mutation | Hotspot |
| Cutaneous Melanoma | OXA1L | 14 | 23235899 | SNP | C | T | T | Oncomine | NM_005015 | p.L57F | p.L57 | Missense_Mutation | Hotspot |
| Cutaneous Melanoma | OXA1L | 14 | 23235902 | SNP | C | T | T | Oncomine | NM_005015 | p.P58S | p.P58 | Missense_Mutation | Hotspot |
| Cervical Squamous Cell Carcinoma | PBX2 | 6 | 32155509 | SNP | T | A | A | Oncomine | NM_002586 | p.Y262F | p.Y262 | Missense_Mutation | Hotspot |
| Gastric Adenocarcinoma | PBX2 | 6 | 32155509 | SNP | T | A | A | Oncomine | NM_002586 | p.Y262F | p.Y262 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Head and Neck Squamous Cell Carcinoma | PBX2 | 6 | 32155509 | SNP | T | A | A | Oncomine | NM_002586 | p.Y262F | p.Y262 | Missense_Mutation | Hotspot |
| Squamous Cell Lung Carcinoma | PBX2 | 6 | 32155509 | SNP | T | A | A | Oncomine | NM_002586 | p.Y262F | p.Y262 | Missense_Mutation | Hotspot |
| Clear Cell Renal Cell Carcinoma | PBX2 | 6 | 32155509 | SNP | T | A | A | Oncomine | NM_002586 | p.Y262F | p.Y262 | Missense_Mutation | Hotspot |
| Prostate Adenocarcinoma | PDHA2 | 4 | 96761513 | SNP | G | A | A | Oncomine | NM_005390 | p.R71H | p.R71 | Missense_Mutation | Hotspot |
| Melanoma | PDHA2 | 4 | 96761738 | SNP | G | A | A | Oncomine | NM_005390 | p.G146E | p.G146 | Missense_Mutation | Hotspot |
| Cutaneous Melanoma | PDHA2 | 4 | 96761737 | SNP | G | A | A | Oncomine | NM_005390 | p.G146R | p.G146 | Missense_Mutation | Hotspot |
| Glioblastoma | PDHA2 | 4 | 96761557 | SNP | C | T | T | Oncomine | NM_005390 | p.R86C | p.R86 | Missense_Mutation | Hotspot |
| Colorectal Adenocarcinoma | PDHA2 | 4 | 96980580 | SNP | C | T | T | Oncomine | NM_005390 | p.R86C | p.R86 | Missense_Mutation | Hotspot |
| Endometrial Serous Adenocarcinoma | PDHA2 | 4 | 96761738 | SNP | G | G | A | Oncomine | NM_005390 | p.G146E | p.G146 | Missense_Mutation | Hotspot |
| Lung Adenocarcinoma | PDHA2 | 4 | 96761513 | SNP | G | A | A | Oncomine | NM_005390 | p.R71H | p.R71 | Missense_Mutation | Hotspot |
| Cutaneous Melanoma | PDHA2 | 4 | 96761854 | SNP | G | A | A | Oncomine | NM_005390 | p.D185N | p.D185 | Missense_Mutation | Hotspot |
| Cutaneous Melanoma | PDHA2 | 4 | 96761738 | SNP | G | A | A | Oncomine | NM_005390 | p.G146E | p.G146 | Missense_Mutation | Hotspot |
| Thyroid Gland Carcinoma, NOS | PDHA2 | 4 | 96761513 | SNP | G | A | A | Oncomine | NM_005390 | p.R71H | p.R71 | Missense_Mutation | Hotspot |
| Thyroid Gland Papillary Carcinoma | PDHA2 | 4 | 96761557 | SNP | C | T | T | Oncomine | NM_005390 | p.R86C | p.R86 | Missense_Mutation | Hotspot |
| Lung Adenocarcinoma | POTEC | 18 | 14543019 | SNP | T | C | C | Oncomine | NM_001137671 | p.M43V | p.M43 | Missense_Mutation | Hotspot |
| Glioblastoma | POTEC | 18 | 14543019 | SNP | T | C | C | Oncomine | NM_001137671 | p.M43V | p.M43 | Missense_Mutation | Hotspot |
| Astrocytoma | POTEC | 18 | 14513734 | SNP | C | T | T | Oncomine | NM_001137671 | p.G487E | p.G487 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Head and Neck Squamous Cell Carcinoma | POTEC | 18 | 14513734 | SNP | C | T | T | Oncomine | NM_001137671 | p.G487E | p.G487 | Missense_Mutation | Hotspot |
| Head and Neck Squamous Cell Carcinoma | POTEC | 18 | 14543019 | SNP | T | C | C | Oncomine | NM_001137671 | p.M43V | p.M43 | Missense_Mutation | Hotspot |
| Lung Adenocarcinoma | POTEC | 18 | 14513734 | SNP | C | T | T | Oncomine | NM_001137671 | p.G487E | p.G487 | Missense_Mutation | Hotspot |
| Cutaneous Melanoma | POTEC | 18 | 14543019 | SNP | T | C | C | Oncomine | NM_001137671 | p.M43V | p.M43 | Missense_Mutation | Hotspot |
| Cutaneous Melanoma | POTEC | 18 | 14542791 | SNP | C | T | T | Oncomine | NM_001137671 | p.A119T | p.A119 | Missense_Mutation | Hotspot |
| Clear Cell Renal Cell Carcinoma | POTEC | 18 | 14542791 | SNP | C | T | T | Oncomine | NM_001137671 | p.A119T | p.A119 | Missense_Mutation | Hotspot |
| Glioblastoma | POTEM | 14 | 20010235 | SNP | A | G | G | Oncomine | NM_001145442 | p.V308A | p.V308 | Missense_Mutation | Hotspot |
| Head and Neck Squamous Cell Carcinoma | POTEM | 14 | 20010235 | SNP | A | G | G | Oncomine | NM_001145442 | p.V308A | p.V308 | Missense_Mutation | Hotspot |
| Cutaneous Melanoma | POTEM | 14 | 20019948 | SNP | C | T | T | Oncomine | NM_001145442 | p.M91I | p.M91 | Missense_Mutation | Hotspot |
| Gastric Adenocarcinoma | PPIL1 | 6 | 36842542 | SNP | C | T | T | Oncomine | NM_016059 | p.A3T | p.A3 | Missense_Mutation | Hotspot |
| Ovarian Serous Adenocarcinoma | PPIL1 | 6 | 36950519 | SNP | G | G | A | Oncomine | NM_016059 | p.A3V | p.A3 | Missense_Mutation | Hotspot |
| Papillary Renal Cell Carcinoma | PPIL1 | 6 | 36842542 | SNP | C | T | T | Oncomine | NM_016059 | p.A3T | p.A3 | Missense_Mutation | Hotspot |
| Cutaneous Melanoma | PRAMEF20 | 1 | 13743091 | SNP | C | T | T | Oncomine | NM_001099852 | p.R94C | p.R94 | Missense_Mutation | Hotspot |
| Glioblastoma | PRAMEF20 | 1 | 13743092 | SNP | G | A | A | Oncomine | NM_001099852 | p.R94H | p.R94 | Missense_Mutation | Hotspot |
| Melanoma | PRB3 | 12 | 11420548 | SNP | C | T | T | Oncomine | NM_006249 | p.G212E | p.G212 | Missense_Mutation | Hotspot |
| Cutaneous Melanoma | PRB3 | 12 | 11420963 | SNP | G | A | A | Oncomine | NM_006249 | p.R74C | p.R74 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Head and Neck Squamous Cell Carcinoma | PRB3 | 12 | 11420963 | SNP | G | A | A | Oncomine | NM_006249 | p.R74C | p.R74 | Missense_Mutation | Hotspot |
| Cutaneous Melanoma | PRB3 | 12 | 11420548 | SNP | C | T | T | Oncomine | NM_002723 | p.G212E | p.G212 | Missense_Mutation | Hotspot |
| Cutaneous Melanoma | PRB4 | 12 | 11461597 | SNP | C | T | T | Oncomine | NM_002723 | p.G107E | p.G107 | Missense_Mutation | Hotspot |
| Cutaneous Melanoma | PRB4 | 12 | 11461475 | SNP | C | T | T | Oncomine | NM_002723 | p.G148R | p.G148 | Missense_Mutation | Hotspot |
| Cutaneous Melanoma | PRB4 | 12 | 11461474 | SNP | C | T | T | Oncomine | NM_002723 | p.G148E | p.G148 | Missense_Mutation | Hotspot |
| Cutaneous Melanoma | PROL1 | 4 | 71275418 | SNP | C | T | T | Oncomine | NM_021225 | p.P125S | p.P125 | Missense_Mutation | Hotspot |
| Cutaneous Melanoma | PROL1 | 4 | 71275418 | SNP | C | T | T | Oncomine | NM_021225 | p.P125S | p.P125 | Missense_Mutation | Hotspot |
| Cutaneous Melanoma | PROL1 | 4 | 71275428 | SNP | C | A | A | Oncomine | NM_021225 | p.P128H | p.P128 | Missense_Mutation | Hotspot |
| Cutaneous Melanoma | PROL1 | 4 | 71275427 | SNP | C | T | T | Oncomine | NM_021225 | p.P128S | p.P128 | Missense_Mutation | Hotspot |
| Cutaneous Melanoma | PRSS37 | 7 | 141536973 | SNP | C | T | T | Oncomine | NM_001008270 | p.G169E | p.G169 | Missense_Mutation | Hotspot |
| Cutaneous Melanoma | PRSS37 | 7 | 141540847 | SNP | C | T | T | Oncomi | NM_001008270 | p.M1I | p.M1 | Missense_Mutation | Hotspot |
| Cutaneous Melanoma | PRSS37 | 7 | 141536973 | SNP | C | T | T | Oncomine | NM_001008270 | p.G169E | p.G169 | Missense_Mutation | Hotspot |
| Cutaneous Melanoma | PRSS37 | 7 | 141540847 | SNP | C | T | T | Oncomine | NM_001008270 | p.M1I | p.M1 | Missense_Mutation | Hotspot |
| Cutaneous Melanoma | RAB39A | 11 | 107832799 | SNP | C | G | G | Oncomine | NM_017516 | p.R119G | p.R119 | Missense_Mutation | Hotspot |
| Colorectal Adenocarcinoma | RAB39A | 11 | 107738009 | SNP | C | T | T | Oncomine | NM_017516 | p.R119W | p.R119 | Missense_Mutation | Hotspot |
| Cutaneous Melanoma | RAB39A | 11 | 107832799 | SNP | C | T | T | Oncomine | NM_017516 | p.R119W | p.R119 | Missense_Mutation | Hotspot |
| Head and Neck Squamous Cell Carcinoma | RALB | 2 | 121036297 | SNP | G | A | A | Oncomine | NM_002881 | p.M19I | p.M19 | Missense_Mutation | Hotspot |
| Cutaneous Melanoma | RALB | 2 | 121036296 | SNP | T | C | C | Oncomine | NM_002881 | p.M19T | p.M19 | Missense_Mutation | Hotspot |
| Cutaneous Melanoma | RALB | 2 | 121036296 | SNP | T | A | A | Oncomine | NM_002881 | p.M19K | p.M19 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Medulloblastoma | RANGAP1 | 22 | 41652800 | SNP | A | C | C | Oncomine | NM_002883 | p.V268G | p.V268 | Missense_Mutation | Hotspot |
| Cervical Squamous Cell Carcinoma | RANGAP1 | 22 | 41652800 | SNP | A | C | C | Oncomine | NM_002883 | p.V268G | p.V268 | Missense_Mutation | Hotspot |
| Head and Neck Squamous Cell Carcinoma | RANGAP1 | 22 | 41652800 | SNP | A | C | C | Oncomine | NM_002883 | p.V268G | p.V268 | Missense_Mutation | Hotspot |
| Lung Adenocarcinoma | RANGAP1 | 22 | 41652800 | SNP | A | C | C | Oncomine | NM_002883 | p.V268G | p.V268 | Missense_Mutation | Hotspot |
| Clear Cell Renal Cell Carcinoma | RANGAP1 | 22 | 41652800 | SNP | A | C | C | Oncomine | NM_002883 | p.V268G | p.V268 | Missense_Mutation | Hotspot |
| Gastric Adenocarcinoma | RAP1B | 12 | 69042539 | SNP | G | A | A | Oncomine | NM_015646 | p.G12E | p.G12 | Missense_Mutation | Hotspot |
| Head and Neck Squamous Cell Carcinoma | RAP1B | 12 | 69042539 | SNP | G | A | A | Oncomine | NM_015646 | p.G12E | p.G12 | Missense_Mutation | Hotspot |
| Acute Myeloid Leukemia | RAP1B | 12 | 67328806 | SNP | G | G | A | Oncomine | NM_015646 | p.G12E | p.G12 | Missense_Mutation | Hotspot |
| Cutaneous Melanoma | RBMY1D | Y | 23702641 | SNP | C | T | T | Oncomine | NM_001006120 | p.P124L | p.P124 | Missense_Mutation | Hotspot |
| Squamous Cell Lung Carcinoma | RBMY1D | Y | 23702641 | SNP | C | A | A | Oncomine | NM_001006120 | p.P124H | p.P124 | Missense_Mutation | Hotspot |
| Cutaneous Melanoma | RBMY1D | Y | 23702640 | SNP | C | T | T | Oncomine | NM_001006120 | p.P124S | p.P124 | Missense_Mutation | Hotspot |
| Prostate Adenocarcinoma | RQCD1 | 2 | 219447749 | SNP | C | G | G | Oncomine | NM_005444 | p.S87C | p.S87 | Missense_Mutation | Hotspot |
| Cutaneous Melanoma | RQCD1 | 2 | 219447749 | SNP | C | G | G | Oncomine | NM_005444 | p.S87C | p.S87 | Missense_Mutation | Hotspot |
| Cutaneous Melanoma | RQCD1 | 2 | 219449406 | SNP | C | T | T | Oncomine | NM_005444 | p.P131L | p.P131 | Missense_Mutation | Hotspot |
| Cutaneous Melanoma | RQCD1 | 2 | 219447748 | SNP | T | C | C | Oncomine | NM_005444 | p.S87P | p.S87 | Missense_Mutation | Hotspot |
| Cutaneous Melanoma | S100A7L2 | 1 | 153409566 | SNP | C | T | T | Oncomine | NM_001045479 | p.G103R | p.G103 | Missense_Mutation | Hotspot |
| Cutaneous Melanoma | S100A7L2 | 1 | 153409565 | SNP | C | T | T | Oncomine | NM_001045479 | p.G103R | p.G103 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Cutaneous Melanoma | S100A7L2 | 1 | 153409565 | SNP | C | T | T | Oncomine | NM_001045479 | p.G103E | p.G103 | Missense_Mutation | Hotspot |
| Non-Small Cell Lung Carcinoma, NOS | S100A8 | 1 | 153362715 | SNP | T | C | C | Oncomine | NM_002964 | p.K49R | p.K49 | Missense_Mutation | Hotspot |
| Glioblastoma | S100A8 | 1 | 153362715 | SNP | T | C | C | Oncomine | NM_002964 | p.K49R | p.K49 | Missense_Mutation | Hotspot |
| Head and Neck Squamous Cell Carcinoma | S100A8 | 1 | 153362715 | SNP | T | C | C | Oncomine | NM_002964 | p.K49R | p.K49 | Missense_Mutation | Hotspot |
| Thyroid Gland Papillary Carcinoma | S100A8 | 1 | 153362715 | SNP | T | C | C | Oncomine | NM_002964 | p.K49R | p.K49 | Missense_Mutation | Hotspot |
| Oligodendroglioma | SAA2 | 1 | 18269491 | SNP | G | A | A | Oncomine | NM_030754 | p.S23L | p.S23 | Missense_Mutation | Hotspot |
| Lung Adenocarcinoma | SDR16C5 | 8 | 57228627 | SNP | C | A | A | Oncomine | NM_138969 | p.A94S | p.A94 | Missense_Mutation | Hotspot |
| Gastric Adenocarcinoma | SDR16C5 | 8 | 57228626 | SNP | G | T | T | Oncomine | NM_138969 | p.A94D | p.A94 | Missense_Mutation | Hotspot |
| Cutaneous Melanoma | SDR16C5 | 8 | 57228829 | SNP | C | T | T | Oncomine | NM_138969 | p.M26I | p.M26 | Missense_Mutation | Hotspot |
| Cutaneous Melanoma | SDR16C5 | 8 | 57228854 | SNP | G | A | A | Oncomine | NM_138969 | p.S18L | p.S18 | Missense_Mutation | Hotspot |
| Clear Cell Renal Cell Carcinoma | SDR16C5 | 8 | 57228627 | SNP | C | G | G | Oncomine | NM_138969 | p.A94P | p.A94 | Missense_Mutation | Hotspot |
| Cutaneous Melanoma | SHH | 7 | 155596253 | SNP | G | A | A | Oncomine | NM_000193 | p.R244C | p.R244 | Missense_Mutation | Hotspot |
| Lung Adenocarcinoma | SHH | 7 | 155596253 | SNP | G | A | A | Oncomine | NM_000193 | p.R244C | p.R244 | Missense_Mutation | Hotspot |
| Cutaneous Melanoma | SHH | 7 | 155596253 | SNP | G | A | A | Oncomine | NM_000193 | p.R244C | p.R244 | Missense_Mutation | Hotspot |
| Prostate Adenocarcinoma | SLC35G3 | 17 | 33520323 | SNP | C | T | T | Oncomine | NM_152462 | p.R335K | p.R335 | Missense_Mutation | Hotspot |
| Infiltrating Bladder Urothelial Carcinoma | SLC35G3 | 17 | 33520323 | SNP | C | T | T | Oncomine | NM_152462 | p.R335K | p.R335 | Missense_Mutation | Hotspot |
| Glioblastoma | SLC35G3 | 17 | 33520323 | SNP | C | T | T | Oncomine | NM_152462 | p.R335K | p.R335 | Missense_Mutation | Hotspot |
| Gastric Adenocarcinoma | SLC35G3 | 17 | 33520323 | SNP | C | T | T | Oncomine | NM_152462 | p.R335K | p.R335 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Head and Neck Squamous Cell Carcinoma | SLC35G3 | 17 | 33520392 | SNP | G | C | C | Oncomine | NM_152462 | p.A312G | p.A312 | Missense_Mutation | Hotspot |
| Lung Adenocarcinoma | SLC35G3 | 17 | 33520323 | SNP | C | T | T | Oncomine | NM_152462 | p.R335K | p.R335 | Missense_Mutation | Hotspot |
| Cutaneous Melanoma | SLC35G3 | 17 | 33520392 | SNP | G | C | C | Oncomine | NM_152462 | p.A312G | p.A312 | Missense_Mutation | Hotspot |
| Cutaneous Melanoma | SLC35G3 | 17 | 33520323 | SNP | C | T | T | Oncomine | NM_152462 | p.R335K | p.R335 | Missense_Mutation | Hotspot |
| Cutaneous Melanoma | SPATA8 | 15 | 97326937 | SNP | G | A | A | Oncomine | NM_173499 | p.E18K | p.E18 | Missense_Mutation | Hotspot |
| Head and Neck Squamous Cell Carcinoma | SPATA8 | 15 | 97326937 | SNP | G | A | A | Oncomine | NM_173499 | p.E18K | p.E18 | Missense_Mutation | Hotspot |
| Cutaneous Melanoma | SPATA8 | 15 | 97326937 | SNP | G | A | A | Oncomine | NM_173499 | p.E18K | p.E18 | Missense_Mutation | Hotspot |
| Cervical Squamous Cell Carcinoma | SPINK13 | 5 | 147665577 | SNP | G | A | A | Oncomine | NM_001040129 | p.R84H | p.R84 | Missense_Mutation | Hotspot |
| Cutaneous Melanoma | SPINK13 | 5 | 147665576 | SNP | C | T | T | Oncomine | NM_001040129 | p.R84C | p.R84 | Missense_Mutation | Hotspot |
| Cutaneous Melanoma | ST6GAL2 | 2 | 107459497 | SNP | C | T | T | Oncomine | NM_032528 | p.E313K | p.E313 | Missense_Mutation | Hotspot |
| Colorectal Adenocarcinoma | ST6GAL2 | 2 | 106816941 | SNP | G | A | A | Oncomine | NM_032528 | p.S346L | p.S346 | Missense_Mutation | Hotspot |
| Endometrial Endometrioid Adenocarcinoma | ST6GAL2 | 2 | 107460402 | SNP | C | C | T | Oncomine | NM_032528 | p.R11Q | p.R11 | Missense_Mutation | Hotspot |
| Lung Adenocarcinoma | ST6GAL2 | 2 | 107459730 | SNP | C | A | A | Oncomine | NM_032528 | p.G235V | p.G235 | Missense_Mutation | Hotspot |
| Lung Adenocarcinoma | ST6GAL2 | 2 | 107460276 | SNP | G | A | A | Oncomine | NM_032528 | p.P53L | p.P53 | Missense_Mutation | Hotspot |
| Squamous Cell Lung Carcinoma | ST6GAL2 | 2 | 107460166 | SNP | G | A | A | Oncomine | NM_032528 | p.H90Y | p.H90 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Squamous Cell Lung Carcinoma | ST6GAL2 | 2 | 107459731 | SNP | C | A | A | Oncomine | NM_032528 | p.G235W | p.G235 | Missense_Mutation | Hotspot |
| Squamous Cell Lung Carcinoma | ST6GAL2 | 2 | 107423361 | SNP | C | T | T | Oncomine | NM_032528 | p.E455K | p.E455 | Missense_Mutation | Hotspot |
| Cutaneous Melanoma | ST6GAL2 | 2 | 107459497 | SNP | C | T | T | Oncomine | NM_032528 | p.E313K | p.E313 | Missense_Mutation | Hotspot |
| Cutaneous Melanoma | ST6GAL | 2 | 107460402 | SNP | C | T | T | Oncomine | NM_032528 | p.R11Q | p.R11 | Missense_Mutation | Hotspot |
| Cutaneous Melanoma | ST6GAL2 | 2 | 107450509 | SNP | G | A | A | Oncomine | NM_032528 | p.S346L | p.S346 | Missense_Mutation | Hotspot |
| Cutaneous Melanoma | ST6GAL2 | 2 | 107423361 | SNP | C | T | T | Oncomine | NM_032528 | p.E455K | p.E455 | Missense_Mutation | Hotspot |
| Cutaneous Melanoma | ST6GAL2 | 2 | 107459496 | SNP | T | A | A | Oncomine | NM_032528 | p.E313V | p.E313 | Missense_Mutation | Hotspot |
| Cutaneous Melanoma | ST6GAL2 |  | 107459731 | SNP | C | T | T | Oncomine | NM_032528 | p.G235R | p.G235 | Missense_Mutation | Hotspot |
| Cutaneous Melanoma | ST6GAL2 | 2 | 107460166 | SNP | G | A | A | Oncomine | NM_032528 | p.H90Y | p.H90 | Missense_Mutation | Hotspot |
| Cutaneous Melanoma | SYPL1 | 7 | 105739611 | SNP | G | A | A | Oncomine | NM_006754 | p.P81S | p.P81 | Missense_Mutation | Hotspot |
| Cutaneous Melanoma | SYPL1 | 7 | 105739611 | SNP | G | A | A | Oncomine | NM_006754 | p.P8S1 | p.P81 | Missense_Mutation | Hotspot |
| Cutaneous Melanoma | SYT1 | 12 | 79689912 | SNP | C | T | T | Oncomine | NM_005639 | p.P180S | p.P180 | Missense_Mutation | Hotspot |
| Melanoma | SYT1 | 12 | 79679683 | SNP | G | A | A | Oncomine | NM_005639 | p.E95K | p.E95 | Missense_Mutation | Hotspot |
| Head and Neck Squamous Cell Carcinoma | SYT1 | 12 | 79611355 | SNP | C | T | T | Oncomine | NM_005639 | p.A19V | p.A19 | Missense_Mutation | Hotspot |
| Acute Myeloid Leukemia | SYT1 | 12 | 78135485 | SNP | G | G | A | Oncomine | NM_005639 | p.A19T | p.A19 | Missense_Mutation | Hotspot |
| Cutaneous Melanoma | SYT1 | 12 | 79689912 | SNP | C | T | T | Oncomine | NM_005639 | p.P180S | p.P180 | Missense_Mutation | Hotspot |
| Cutaneous Melanoma | SYT1 | 12 | 79679683 | SNP | G | A | A | Oncomine | NM_005639 | p.E95K | p.E95 | Missense_Mutation | Hotspot |
| Prostate Adenocarcinoma | SYT1 | 12 | 79611355 | SNP | C | T | T | Oncomine | NM_005639 | p.A19V | p.A19 | Missense_Mutation | Hotspot |
| Lung Adenocarcinoma | TCEAL8 | X | 102508844 | SNP | G | T | T | Oncomine | NM_153333 | p.R22S | p.R22 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Head and Neck Squamous | TCEAL8 | X | 102508843 | SNP | C | T | T | Oncomine | NM_153333 | p.R22H | p.R22 | Missense_Mutation | Hotspot |
| Clear Cell Renal Cell Carcinoma | TCEAL8 | X | 102508844 | SNP | G | A | A | Oncomine | NM_153333 | p.R22C | p.R22 | Missense_Mutation | Hotspot |
| Prostate Adenocarcinoma | TMEM147 | 19 | 36037641 | SNP | C | T | T | Oncomine | NM_032635 | p.A92V | p.A92 | Missense_Mutation | Hotspot |
| Glioblastoma | TMEM147 | 19 | 36037641 | SNP | C | T | T | Oncomine | NM_032635 | p.A92V | p.A92 | Missense_Mutation | Hotspot |
| Cutaneous Melanoma | WFDC5 | 20 | 43739300 | SNP | G | A | A | Oncomine | NM_145652 | p.R68C | p.R68 | Missense_Mutation | Hotspot |
| Ductal Breast Carcinoma | WFDC5 | 20 | 43739300 | SNP | G | A | A | Oncomine | NM_145652 | p.R68C | p.R68 | Missense_Mutation | Hotspot |
| Chromophobe Renal Cell Carcinoma | WFDC5 | 20 | 43739299 | SNP | C | T | T | Oncomine | NM_145652 | p.R68H | p.R68 | Missense_Mutation | Hotspot |
| Clear Cell Renal Cell Carcinoma | ZFAND2B | 2 | 220072989 | SNP | T | C | C | Oncomine | NM_138802 | p.I149T | p.I149 | Missense_Mutation | Hotspot |
| Papillary Renal Cell Carcinoma | ZFAND2B | 2 | 220072989 | SNP | T | G | G | Oncomine | NM_138802 | p.I149S | p.I149 | Missense_Mutation | Hotspot |
| Non-Small Cell Lung Carcinoma, NOS | ZNF780A | 19 | 40581109 | SNP | T | C | C | Oncomine | NM_001010880 | p.I414V | p.I414 | Missense_Mutation | Hotspot |
| Lung Adenocarcinoma | ZNF780A | 19 | 40581529 | SNP | C | T | T | Oncomine | NM_001010880 | p.V274I | p.V274 | Missense_Mutation | Hotspot |
| Lung Adenocarcinoma | ZNF780A | 19 | 40581535 | SNP | A | C | C | Oncomine | NM_001010880 | p.S272A | p.S272 | Missense_Mutation | Hotspot |
| Oligoastrocytoma | ZNF780A | 19 | 40580552 | SNP | T | G | G | Oncomine | NM_001010880 | p.Q599H | p.Q599 | Missense_Mutation | Hotspot |
| Cervical Squamous Cell Carcinoma | ZNF780A | 19 | 40580552 | SNP | T | G | G | Oncomine | NM_001010880 | p.Q599H | p.Q599 | Missense_Mutation | Hotspot |
| Gastric Adenocarcinoma | ZNF780A | 19 | 40581529 | SNP | C | T | T | Oncomine | NM_001010880 | p.V274I | p.V274 | Missense_Mutation | Hotspot |
| Head and Neck Squamous Cell Carcinoma | ZNF780A | 19 | 40581109 | SNP | T | C | C | Oncomine | NM_001010880 | p.I414V | p.I414 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Head and Neck Squamous Cell Carcinoma | ZNF780A | 19 | 40580552 | SNP | T | G | G | Oncomine | NM_001010880 | p.Q599H | p.Q599 | Missense_Mutation | Hotspot |
| Head and Neck Squamous Cell Carcinoma | ZNF780A | 19 | 40581529 | SNP | C | T | T | Oncomine | NM_001010880 | p.V274I | p.V274 | Missense_Mutation | Hotspot |
| Lung Adenocarcinoma | ZNF780A | 19 | 40581109 | SNP | T | C | C | Oncomine | NM_001010880 | p.I414V | p.I414 | Missense_Mutation | Hotspot |
| Squamous Cell Lung Carcinoma | ZNF780A | 19 | 40581535 | SNP | A | C | C | Oncomine | NM_001010880 | p.S272A | p.S272 | Missense_Mutation | Hotspot |
| Cutaneous Melanoma | ZNF780A | 19 | 40581535 | SNP | A | C | C | Oncomine | NM_001010880 | p.S272A | p.S272 | Missense_Mutation | Hotspot |
| Cutaneous Melanoma | ZNF780A | 19 | 40581109 | SNP | T | C | C | Oncomine | NM_001010880 | p.I414V | p.I414 | Missense_Mutation | Hotspot |
| Thyroid Gland Follicular Carcinoma | ZNF780A | 19 | 40581535 | SNP | A | C | C | Oncomine | NM_001010880 | p.S272A | p.S272 | Missense_Mutation | Hotspot |
| Thyroid Gland Papillary Carcinoma | ZNF780A | 19 | 40580552 | SNP | T | G | G | Oncomine | NM_001010880 | p.Q599H | p.Q599 | Missense_Mutation | Hotspot |
| Lung Adenocarcinoma | ZNF844 | 19 | 12187394 | SNP | T | C | C | Oncomine | NM_001136501 | p.F487L | p.F487 | Missense_Mutation | Hotspot |
| Glioblastoma | ZNF844 | 19 | 12187394 | SNP | T | C | C | Oncomine | NM_001136501 | p.F487L | p.F487 | Missense_Mutation | Hotspot |
| Glioblastoma | ZNF844 | 19 | 12187275 | SNP | G | C | C | Oncomine | NM_001136501 | p.R447P | p.R447 | Missense_Mutation | Hotspot |
| Cervical Squamous Cell Carcinoma | ZNF844 | 19 | 12187394 | SNP | T | C | C | Oncomine | NM_001136501 | p.F487L | p.F487 | Missense_Mutation | Hotspot |
| Head and Neck Squamous Cell Carcinoma | ZNF844 | 19 | 12187275 | SNP | G | C | C | Oncomine | NM_001136501 | p.R447P | p.R447 | Missense_Mutation | Hotspot |

TABLE 11-continued

Gain of Function mutations

| Cancer Type | Gene Symbol | Chromosome | Start Position | Variant Type | Reference Allele | Tumor Seq Allele 1 | Tumor Seq Allele 2 | CBI Annotation Source | Transcript | Variant Change | Variant Position | Variant Classification | Pan-Disease CBI Variant Category |
|---|---|---|---|---|---|---|---|---|---|---|---|---|---|
| Lung Adenocarcinoma | ZNF844 | 19 | 12187275 | SNP | G | C | C | Oncomine | NM_001136501 | p.R447P | p.R447 | Missense_Mutation | Hotspot |
| Cutaneous Melanoma | ZNF844 | 19 | 12187275 | SNP | G | C | C | Oncomine | NM_001136501 | p.R447P | p.R447 | Missense_Mutation | Hotspot |
| Cutaneous Melanoma | ZNF844 | 19 | 12187394 | SNP | T | C | C | Oncomine | NM_001136501 | p.F487L | p.F487 | Missense_Mutation | Hotspot |
| Oligodendroglioma | ZNF845 | 19 | 53855196 | SNP | T | C | C | Oncomine | NM_138374 | p.M423T | p.M423 | Missense_Mutation | Hotspot |
| Thyroid Gland Papillary Carcinoma | ZNF845 | 19 | 53855196 | SNP | T | C | C | Oncomine | NM_138374 | p.M423T | p.M423 | Missense_Mutation | Hotspot |
| Thyroid Gland Papillary Carcinoma | ZNF845 | 19 | 53855197 | SNP | G | A | A | Oncomine | NM_138374 | p.M423I | p.M423 | Missense_Mutation | Hotspot |

The disclosure provides novel gene variants and gene variant-disease state associations. The gene variants can have one or more mutations that result in a variant protein. The gene variants provided herein are associated with certain cancers. The gene variants result in protein variants. The disclosure further provides probes, such as amplification primer sets and detection probes, as well as methods of detection, diagnosis, and treatment and kits that include or detect the gene variants disclosed herein.

The variants are shown as amino acid variants in Tables 7 and 11 with the accession no. or the Entrez nucleotide and/or protein sequence of the parent or wildtype gene provided. The associations with various cancers are shown in Tables 7 and 11. Tables 7 and 11 provide a list of more than 99 genes that were identified using the methods outlined in Example 2. The variations or mutations were not found in the corresponding normal tissue. This is important because in a typical patient, a tumor sample can have 10's-100's of tumor specific variations. However, variations that occur at the same place in multiple patients (and not in the normal tissue) are more significant. 4445 samples (from 4445 patients) were analyzed and list of hotspots was prepared. A number of recurrent mutations were found at the same position in 15-20 different cancer types.

Diagnostics and Kits

Methods of diagnosing, treating, and detecting gene variants and associated disease are contemplated herein. The methods can include detecting gene fusions and/or gene variants in a subject sample. Any number and combination of gene fusions and/or gene variants can be detected in any of the reaction mixtures, compositions, and kits disclosed herein.

In one embodiment, the disclosure provides a composition and a kit comprising a set of probes that specifically recognize the nucleotide sequence that encodes a gene variant selected from Table 7 and/or Table 11. The set of probes can be, for example a set of amplification primers. In another embodiment, provided herein is a composition that includes a set of primers that flank a gene variant that encodes one or more variants in Table 7 and/or Table 11. The reaction mixture of this embodiment can further include a detector probe that binds to a nucleotide sequence including a gene variant selected from Table 7 and/or Table 11. The reaction mixture that includes a detector probe or does not include a detector probe, can further include a polymerase, dNTPs, and/or a uracil DNA deglycosylase (UDG). The polymerase and UDG are typically not from a human origin. The reaction mixture can further include a target nucleic acid, for example a human target nucleic acid. The human target nucleic acid can be, for example, isolated from a biological sample from a person suspected of having a cancer. The cancer can be selected from: BLCA=bladder carcinoma, BRCA=breast carcinoma, CESC=cervical cell carcinoma, COAD=colon adenocarcinoma, GBM=glioblastoma multiforme, HNSC=head and neck squamous cell carcinoma, KIRK=clear cell renal cell carcinoma, KIRP=kidney renal papillary cell carcinoma, LAML=acute myeloid leukemia, LGG=brain lower grade glioma, LIHC=liver hepatocellular carcinoma, LUAD=lung adenocarcinoma, LUSC=squamous cell lung carcinoma, OV=ovarian serous adenocarcinoma, PRAD=prostate adenocarcinoma, READ=rectal adenocarcinoma, SKCM=cutaneous melanoma, STAD=stomach adenocarcinoma, THCA=thyroid carcinoma, and UCEC=uterine corpus endometrioid carcinoma.

In some embodiments a kit is provided, wherein the kit encompasses one or more probes. In some embodiments, the kit encompasses probes for 1, 2, 3, 4, 5, 6, 7, 8, 9, 10, 11, 12, 13, 14, 15, 16, 17, 18, 19, 20, 25, 50, 75, 100, 150, 200, 250, 500 or more fusion genes. In some embodiments the probe is detectably labeled. In some embodiments the probe hybridizes to the breakpoint present in the gene fusion.

In some embodiments the detection of any one of the gene variants disclosed in Tables 7 and 11 can be combined with the detection of another of the gene variants disclosed in those tables or any of the gene fusions disclosed herein. That is, 2, 3, 4, 5, 6, 7, 8, 9, 10, 11, 12, 13, 14, 15, 16, 17, 18, 19, 20, 25, 50, 75, 100, 150, 200, 250, 500 or more of the gene variants can be detected in the same reaction. In some embodiments the detected gene variants are those disclosed in Tables 4-6, 7 and 11, 20, and 23 and can be combined with the detection of another of the gene fusion disclosed in those tables. That is, 2, 3, such that 4, 5, 6, 7, 8, 9, 10, 11, 12, 13, 14, 15, 16, 17, 18, 19, 20, 25, 50, 75, 100, 150, 200, 250, 500 or more of the gene fusions of can be detected in the same reaction.

The nucleotide sequence that encodes one or more gene variants in Table 7 and/or Table 11 can be any size that encompasses the variation. For example, the nucleotide sequence can be any size that can be easily copied using a primer and/or detected using a probe.

In another embodiment, a set of probes that specifically recognize a nucleic acid coding for a gene variant selected from Table 7 and/or Table 11 (gene variants) is provided. In another embodiment, provided herein is a set of primers that specifically amplify a target nucleic acid that codes for a gene variant selected from Table 7 and/or Table 11. In another embodiment, provided herein is a qPCR assay, such as a TaqMan™ assay or a Molecular Beacons™ assay that specifically amplifies and detects a target nucleic acid that codes for a gene variant selected from Table 7 and/or Table 11.

The disclosure also provides an isolated nucleic acid comprising at least one sequence that includes the variation found in one or more gene variants selected from Table 7 and/or Table 11. The isolated nucleic acid can include a first primer on a 5' end. Furthermore, the nucleic acid can be single stranded or double stranded.

The disclosure, in other embodiments, provides a kit that includes a detector probe and/or a set of probes, for example, a set of amplification primers that specifically recognize a nucleic acid that codes for a gene variant selected from Table 7 and/or Table 11. For example, in certain embodiments the detector probe or set of amplification primers are designed to amplify and/or detect a nucleic acid that includes at least one of a nucleic acid coding for a gene variant in Table 7 and/or Table 11. The kit can further include, in a separate or in the same vessel, a component from an amplification reaction mixture, such as a polymerase, typically not from human origin, dNTPs, and/or UDG. Furthermore, the kit can include a control nucleic acid. For example the control nucleic acid can include a sequence that includes the gene variant selected from Table 7 and/or Table 11.

A method of detecting a cancer is provided comprising amplifying a nucleic acid that encodes a gene variant selected from Table 7 and/or Table 11, for example the nucleic can include a sequence from one of the accession numbers in Table 7 and/or Table 11 except that the sequence contains the variant that codes for the gene variants in Table 7 and/or Table 11, and detecting the presence of the nucleic acid, wherein the presence of the nucleic acid indicates a cancer is present in the sample. In another method, provided herein is a method of detecting a cancer that includes generating an amplicon that includes a sequence selected from a sequence coding for a gene variant in Table 7 and/or Table 11, and detecting the presence of the nucleic acid, wherein the presence of the nucleic acid indicates bladder, head and neck, or lung squamous cell carcinoma is present in the sample. The amplicon typically includes primers that are extended to form the amplicon. The cancer is selected from bladder carcinoma, breast carcinoma, cervical cell carcinoma, colon adenocarcinoma, glioblastoma multiforme, head and neck squamous cell carcinoma, clear cell renal cell carcinoma, kidney renal papillary cell carcinoma, acute myeloid leukemia, brain lower grade glioma, liver hepatocellular carcinoma, lung adenocarcinoma, squamous cell lung carcinoma, ovarian serous adenocarcinoma, prostate adenocarcinoma, rectal adenocarcinoma, cutaneous melanoma, stomach adenocarcinoma, thyroid carcinoma, and uterine corpus endometrioid carcinoma.

A kit comprising a set of probes, for example, a set of amplification primers that specifically recognize a nucleic In another embodiment, a gene variant is provided comprising at least one of the gene variants in Table 7 and/or Table 11.

In another embodiment is a method to detect a cancer selected from bladder carcinoma, breast carcinoma, cervical cell carcinoma, colon adenocarcinoma, glioblastoma multiforme, head and neck squamous cell carcinoma, clear cell renal cell carcinoma, kidney renal papillary cell carcinoma, acute myeloid leukemia, brain lower grade glioma, liver hepatocellular carcinoma, lung adenocarcinoma, squamous cell lung carcinoma, ovarian serous adenocarcinoma, prostate adenocarcinoma, rectal adenocarcinoma, cutaneous melanoma, stomach adenocarcinoma, thyroid carcinoma, and uterine corpus endometrioid carcinoma in a sample by detecting the presence of a gene variant selected from Table 7 and/or Table 11. Gene variants, for example, can include, but are not limited to ZNF479 variants R110, R295K, R295T, R2951, R3451, R345T, K438T, and T466K (see Table 8).

TABLE 18

| Cancer Type | Gene Symbol | Druggability | KM evidence |
| --- | --- | --- | --- |
| Astrocytoma | CXCR2 | Y | |
| Endometrial Endometrioid Adenocarcinoma | CXCR2 | Y | |
| Squamous Cell Lung Carcinoma | CXCR2 | Y | |
| Cutaneous Melanoma | CXCR2 | Y | |
| Cutaneous Melanoma | CXCR2 | Y | |
| Colorectal Adenocarcinoma | IL3 | Y | |
| Gastric Adenocarcinoma | IL3 | Y | |
| Cutaneous Melanoma | KCNK9 | Y | favorable outcome |
| Endometrial Endometrioid Adenocarcinoma | KCNK9 | Y | |
| Lung Adenocarcinoma | KCNK9 | Y | |
| Squamous Cell Lung Carcinoma | KCNK9 | Y | poor outcome |
| Non-Small Cell Lung Carcinoma, NOS | S100A8 | Y | |
| Glioblastoma | S100A8 | Y | |
| Head and Neck Squamous Cell Carcinoma | S100A8 | Y | |
| Thyroid Gland Papillary Carcinoma | S100A8 | Y | |
| Cutaneous Melanoma | SHH | Y | |
| Lung Adenocarcinoma | SHH | Y | |
| Cutaneous Melanoma | CCDC61 | | poor outcome |
| Cutaneous Melanoma | CCDC61 | | poor outcome |
| Cutaneous Melanoma | CNTN5 | | poor outcome |
| Cutaneous Melanoma | CNTN5 | | poor outcome |
| Cutaneous Melanoma | CNTN5 | | poor outcome |
| Cutaneous Melanoma | CNTN5 | | poor outcome |
| Colorectal Adenocarcinoma | CNTN5 | | poor outcome |
| Colorectal Adenocarcinoma | CNTN5 | | poor outcome |
| Cutaneous Melanoma | CNTN5 | | poor outcome |
| Cutaneous Melanoma | CNTN5 | | poor outcome |
| Cutaneous Melanoma | CNTN5 | | poor outcome |
| Cutaneous Melanoma | EDDM3A | | poor outcome |
| Cutaneous Melanoma | FABP1 | | poor outcome |
| Lung Adenocarcinoma | OR2L13 | | poor outcome |
| Cutaneous Melanoma | OR4E2 | | poor outcome |
| Cutaneous Melanoma | OR4E2 | | poor outcome |
| Cutaneous Melanoma | OR4E2 | | poor outcome |
| Cutaneous Melanoma | PRSS37 | | poor outcome |
| Cutaneous Melanoma | PRSS37 | | poor outcome |
| Cutaneous Melanoma | SPINK13 | | poor outcome |
| Endometrial Endometrioid Adenocarcinoma | ST6GAL2 | | poor outcome | acid comprising a gene variant from Table 7 and/or Table 11 is provided. The kit can further include, in a separate or in the same vessel, a component from an amplification reaction mixture, such as a polymerase, typically not from human origin, dNTPs, and/or UDG. Furthermore, the kit can include a control nucleic acid. For example the control nucleic acid can include a sequence that includes the gene variant from Table 7 and/or Table 11. In certain embodiments, a set of probes that specifically recognize a nucleic acid comprising a gene variant from Table 7 and/or Table 11 is provided.

Table 18 provides druggablility or prognostic associations that were filtered from Table 11. Table 18 provides the cancer type, gene symbol, druggability (Y=yes), and KM evidence for the genes identified in Table 11 as druggable. The KM Evidence column provides the Kaplan-Meier evidence. The KM evidence indicates if the event type supports good or poor prognosis in the particular cancer type.

Targeted Treatment

In at least one embodiment, the gene fusions and/or gene variants can be used to identify targeted therapies. Targeted therapies can include the identification of agents that specifically interact with the gene fusion and/or gene variant. Targeted therapies can include, but are not limited to, antibody therapies, antisense therapies and small molecule therapies. Antisense therapies are discussed in more detail under the heading "antisense."

Compositions and methods for inactivating nucleic acid molecules involve, in part, the use of molecules with nucleic acid regions with sequence complementarity to the nucleic acid molecule which is the subject of desired inactivation (i.e., a target nucleic acid molecule). Methods of the invention can be used for inactivation of gene fusions and/or gene variants associated with specific cancers. Thus, antisense molecules can be identified that are complementary to any of the gene fusions or gene variants identified herein.

Small molecules are low molecular weight (<800 Daltons) organic compounds that may serve as enzyme substrates or regulators of biological processes, with a size on the order of $10^{-9}$ m. In pharmacology, the term is usually used for a molecule that binds to a protein or nucleic acid, and acts as an effector, altering the activity or function of the protein or nucleic acid. Small molecules can be tested for effector functions by expressing a gene fusion or variant in a cellular assay and identifying small molecules that inhibit expression or activity of the gene fusion or variant.

Druggability is a term used in drug discovery to describe a biological target such as a protein that is known to bind or is predicted to bind with high affinity to a drug. Furthermore, the binding of the drug to a druggable target alters the function of the target with a therapeutic benefit to the patient. The term "drug" herein includes small molecules (low molecular weight organic substances) but also has been extended to include biologic medical products such as therapeutic monoclonal antibodies. In at least one embodiment, the gene fusion or gene variant can be used to identify a druggable target. Table 8 provides a list of druggable targets that have been identified from Tables 1-3 and 7. For example, the TPM1/ALK gene fusion is a druggable target because, as shown in Table 8, diseases for which ALK is involved can be treated with crizotinib. Thus, if a gene fusion includes ALK, the cancer may be treatable with crizotinib. Further if a gene variant includes a mutation in ALK, the cancer may be treatable with crizotinib.

Similarly, Table 21 provides a list of druggable targets that have been identified from Table 19 and Table 24 a list of druggable targets that have been identified from Table 22.

TABLE 8

Druggable genes from Table 1

| Druggable Gene | Approved | Pre-registration (pre-approval) | Phase III | Phase II | Phase I | Preclinical |
|---|---|---|---|---|---|---|
| ALK | crizotinib | N | N | AP-26113; RG-7853; LDK-378; TSR-011 | X-396; ASP-3026 | NMS-E628; aurora kinase + ALK inhibitor (Sareum, AstraZeneca); ALK inhibitors (AstraZeneca, Cephalon, Aurigene); ARN-5032; DLX-521 |
| CASR | cincacalcet hydrochloride | N | N | N | N | N |
| EGFR | erlotinib; panitumumab; cetuximab; nepidermin; gefitinib; nimotuzumab; vandetanib; lapatinib ditosylate; icotinib hydrochloride; | Afatinib | zalutumumab; neratinib; dovitinib lactate; XL-647; rindopepimut; necitumumab; dacomitinib | BMS-690514; varlitinib; AC-480; AZD-8931; Sym-004; imgatuzumab; AVL-301; AVL-301; poziotinib; MEHD-7945A; PR-610; | marizomib; CUDC-101; MM-151; AL-6802; S-222611; ABT-806; antroquinonol; GT-MAB 5.2-GEX; epitinib; theliatinib; cipatinib; AMG-595 | STP-503; SN-29966; MT-062; STP-801 |
| FGFR3 | ponatinib | Masitinib | dovitinib lactate | ENMD-2076; AZD-4547 | JNJ-42756493; BGJ-398; LY-2874455; S-49076 | N |
| GNAS | N | N | N | N | N | N |
| JAK2 | ruxolitinib (for idiopathic myelofibrosis) | N | SAR-302503; pacritinib | AT-9283; momelotinib; gandotinib; BMS-911543; NS-018 | AC-430; SB-1317 | ON-044580; INCB-16562; NVP-BSK805; TP-0413; MRLB-11055; CPL-407-22 |
| NOTCH1 | N | N | N | N | OMP-52M51 | Debio-0826; TR-4; Notch antibody (AVEO); Notch1 inhibitors (Interprotein) |

TABLE 8-continued

Druggable genes from Table 1

| Druggable Gene | Approved | Pre-registration (pre-approval) | Phase III | Phase II | Phase I | Preclinical |
|---|---|---|---|---|---|---|
| NTRK1 | N | N | N | milciclib maleate | N | tyrosine kinase inhibitors (Bristol-Myers Squibb); PLX-7486 |
| PIK3CA | N | N | perifosine; buparlisib; | ZSTK-474; PX-866; pictilisib; XL-765; XL-147; BEZ-235; PKI-587; PF-04691502; PF-04691502; BAY-80-6946; BYL-719; | INK-1117; GSK-2126458; CUDC-907; GDC-0032; PWT-33597; DS-7423; GDC-0084; BAY-1082439; PI3 kinase/mTOR inhibitor (Lilly) | LOR-220; AEZS-129; SB-2343; WX-037; PI3/Mnk kinase inhibitors (Progenics); AEZS-132; CLR-1401; PI3/mTOR kinase inhibitors (Amgen); AEZS-136; HM-032; AMG-511; anticancer therapy (Sphaera Pharma); HMPL-518; GNE-317; mTOR inhibitor/PI3 kinase inhibitor (Lilly); CUDC908; PF-06465603; AEZS-134; |
| RET | sorafenib; vandetanib; sunitinib malate; cabozantinib; regorafenib | N | motesanib diphosphate; SAR-302503; apatinib | | N | MG-516; RET kinase inhibitor; NMS-173 |
| ROS1 | crizotinib | N | N | N | N | N |
| ALK | crizotinib | N | N | AP-26113; RG-7853; LDK-378; TSR-011; NMS-E628 | X-396; ASP-3026 | NMS-E628; aurora kinase + ALK inhibitor (Sareum, AstraZeneca); ALK inhibitors (AstraZeneca, Cephalon, Aurigene); ARN-5032; DLX-521 |
| NTRK1 | N | N | N | milciclib maleate | N | tyrosine kinase inhibitors (Bristol-Myers Squibb); PLX-7486 |
| VIM | N | N | N | pritumumab | N | N |
| PTK2 | | | | PF-04554878 | GSK-2256098; BI-853520; VS-4718 | CFAK-C4; FAK inhibitors (Varastem, Takeda); CTX-0294945; CTX-0294945 |
| BRS3 | N | N | N | N | N | N |
| TP53 | Gendicine | N | N | quinacrine; APR-246; ISA-102 | RG-7388; SGT-53; CBLC-137; SAR-405838 | PXN-527; ORCA-010; TR-2; ALT-802; OBP-702 |
| STAT3 | N | N | N | brivudine; OPB-31121; anatabine citrate; ISIS-STAT3Rx | OPB-51602 | CLT-005; GLG-101; GLG-202; GLG-302; GLG-401; PNT-500 |

TABLE 8-continued

Druggable genes from Table 1

| Druggable Gene | Approved | Pre-registration (pre-approval) | Phase III | Phase II | Phase I | Preclinical |
|---|---|---|---|---|---|---|
| NOTCH2 | N | N | N | OMP-59R5 | N | N |
| MET | cabozantinib; crizotinib | N | tivantinib; rilotumumab; onartuzumab; | MGCD-265; foretinib; ficlatuzumab; BMS-777607; golvatinib; INCB-028060; LY-2875358 | AMG-208; TAS-115; volitinib; SAR-125844; S-49076 | X-379; metatinib; PRS-110; ASP-08001; ARGX-111; DCC-2701; DCC-2721; MG-516; AL-2846; CG-206481; T-1840383; cMet-EGFR dual inhibitors (CrystalGenomics); bispecific antibodies (Hoffmann-La Roche) |
| CDH1 | N | N | N | N | N | N |
| TOP1 | belotecan hydrochloride; irinotecan hydrochloride; topotecan | N | cositecan; irinotecan, HyACT; irinotecan, PharmaEngine; etirinotecan pegol | gimatecan; camptothecin, Calando; irinotecan HCl + floxuridine, Celator; firtecan pegol; TLC-388 hydrochloride; hRS7-SN-38; irinotecan bead, Biocompatibles | irinotecan, liposomal, Yakult; HM-30181A; namitecan; camptothecin prodrug, Mersana; labetuzumab-SN-38; Genz-644282; simmitecan hydrochloride prodrug | camptothecin (Aphios); irinotecan (BioAlliance); cisplatin + irinotecan (Celator); APH-0804; irinotecan (Champions); SER-203; SN-38; topotecan + vincristine (LipoCure); topotecan (EnduRx Pharmaceuticals) |
| RARA | tamibarotene | N | N | IRX-5183 | N | N |
| ERBB2 | trastuzumab; trastuzumab emtansine; pertuzumab; lapatinib ditosylate; catumaxomab; afatinib | trastuzumab, Enhanze | neratinib; XL-647; dacomitinib; nelipepimut-S; trastuzumab (Celltrion, Biocad, Biocon, Synthon, Harvest Moon, Aryogen) | lapuleucel-T; AVX-901; AE-37; BMS-690514; MVA-BN-HER2; varlitinib; MM-111; AC-480; ovarian cancer vaccine (Generex); margetuximab; poziotinib; PR-610 | Her-VAXX; VM-206; ARRY-380; JNJ-26483327; S-222611; doxorubicin (Merrimack); cipatinib; TrasGEX; trastuzumab (Hanwha Chemical); trastuzumab (Pfizer); IDN-6439 | Lovaxin B; TH-1 (Algeta); trastuzumab-antibody conjugates (Synthon); CUDC-101; Her-2/neu Stradobody (Gliknik); ARX-788; Etbx-021; SN-34003; IBI-302; NT-004; ICT-140; ONS-1050; Sym-013; anti-HER2 X anti-CD3 (Emergent Biosolutions); Z-650; breast cancer vaccine (Cel-Sci); JNJ-28871063; trastuzumab (PlantForm, BioXpress, biOasis Technologies, Stada, Natco, Curaxys, Oncobiologics, Alteogen, Mabion) |

TABLE 8-continued

Druggable genes from Table 1

| Druggable Gene | Approved | Pre-registration (pre-approval) | Phase III | Phase II | Phase I | Preclinical |
|---|---|---|---|---|---|---|
| ALK | crizotinib | N | N | AP-26113; RG-7853; LDK-378; TSR-011; NMS-E628 | X-396; ASP-3026 | NMS-E628; aurora kinase + ALK inhibitor (Sareum, AstraZeneca); ALK inhibitors (AstraZeneca, Cephalon, Aurigene); ARN-5032; DLX-521 |
| NTRK1 | N | N | N | milciclib maleate | N | tyrosine kinase inhibitors (Bristol-Myers Squibb); PLX-7486 |
| LTK | crizotinib | N | N | N | N | N |
| BRAF | pazopanib; vemurafenib; dabrafenib | N | N | RAF-265; XL-281; LGX-818 | ARQ-761; ARQ-736 | AB-024; b-raf inhibitors (Sareum); BRAF kinase inhibitor (Selexagen Therapeutics); BeiGene-283; DP-4978; TL-241 |

Table 8 provides a list of 11 druggable targets that were identified in the gene fusions in Tables 1-3 or gene variants in Tables 7 and 11. Tables 16 and 17 provide an analysis of other druggable targets within Tables 1-3 or gene variants in Tables 7 and 11. Tables 8, 16 and 17 provide information about druggable targets including the gene name whether the drug has been approved (N=no) by the U.S. Food and Drug Administration (FDA), if the drug has not been approved, which phase the clinical trial is in (Pre-registration, Phase III, Phase II, Phase I, and preclinical). For example, the drug associated with the NOTCH1 gene has not been approved, but is in Phase 1 of clinical trials (see OMP-52M51) as of this writing.

Approved drugs include, but are not limited to, crizotinib for diseases having ALK gene fusions and cincacalcet hydrochloride for diseases having CASR gene fusions. A number of approved drugs have been identified for gene fusions having EGFR, including, but not limited to, erlotinib; panitumumab; cetuximab; nepidermin; gefitinib; nimotuzumab; vandetanib; lapatinib ditosylate; and icotinib hydrochloride. The approved drug ponatinib has been identified for diseases having FGFR3, ruxolitinib has been identified for diseases having JAK2 gene fusions. A number of approved drugs have been identified for gene fusions having RET, including but not limited to, sorafenib; vandetanib; sunitinib malate; cabozantinib; and regorafenib. The approved drug crizotinib has been identified for diseases having ROS1. Additional drugs that may prove useful include, but are not limited to, zrizotinib, afatinib, masitinib, zalutumumab, neratinib, dovitinib lactate, XL647, rindopepimut, nectumumab, dacomitinib, SAR-302503, pacritinib, perifosine, buparlisib, motesinib diphosphate, and apatinib.

Methods provided herein can include delivering a drug to a subject or a patient. The drug can be an approved drug according to a governmental drug regulatory authority, such as the FDA, or the drug can be in any of the stages before the approved stage. In illustrative aspects, the drug is an FDA-approved drug. In other aspects the drug can be in a pre-clinical, Phase I, Phase II, Phase III, or pre-approval stage. In certain aspects, the methods provided herein include delivering one or more than one of the drugs listed in Tables 8, 16 and 17 to a subject. Where genetic events are identified in a subject that involve more than one gene listed in Tables 8, 16 and 17, methods provided herein can include delivering more than one drug, particularly delivering drugs associated with the different genes affected by the identified genetic events.

Antisense

Antisense technology has been applied to inhibit the expression of various oncogenes. For example, Craf-1 cDNA fragments in an antisense orientation, brought under the control of an adenovirus 2 late promoter introduced into a human squamous carcinoma resulted in a greatly reduced tumorigenic potential relative to cells transfected with control sense transfectants. Similarly, a Cmyc antisense construct accelerated differentiation and inhibited $G_1$ progression in Friend Murine Erythroleukemia cells. Antisense methodology takes advantage of the fact that nucleic acids tend to pair with "complementary" sequences. Complementary sequences are those polynucleotides which are capable of base-pairing according to the standard Watson-Crick complementarity rules. Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense can be under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

In certain instances, an antisense expression construct will comprise a virus or engineered construct derived from a viral genome. Where a cDNA insert is employed, a polyadenylation signal to effect proper polyadenylation of the gene transcript may be included. The nature of the polyadenylation signal is not believed to be crucial and any such sequence may be employed. A terminator can be used to enhance message levels and to minimize read through from the cassette into other sequences.

Antisense constructs may be designed to bind to the promoter and other control regions, exons, introns or even exon-intron boundaries of a gene fusion or gene variant disclosed herein. The most effective antisense constructs include regions complementary to intron/exon splice junctions. One embodiment includes an antisense construct with complementarity to regions within 50-200 bases of an intron-exon splice junction. It has been observed that some exon sequences can be included in the construct without seriously affecting the target selectivity thereof. The amount of exonic material included will vary, depending on the particular exon and intron sequences used. One can readily test whether too much exon DNA is included simply by testing the constructs in vitro to determine whether normal cellular function is affected or whether the expression of related genes having complementary sequences is affected.

The word "complementary" with respect to antisense means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

In vivo, ex vivo or in vitro delivery of antisense can involve the use of vectors. One effective vector for antisense delivery is an adenovirus expression vector. "Adenovirus expression vector" is meant to include those constructs containing adenovirus sequences sufficient to support packaging of the construct and to express an antisense polynucleotide that has been cloned therein. The expression vector can include a genetically engineered form of adenovirus. Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging.

Adenovirus is easy to grow and manipulate and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus, demonstrating their safety and therapeutic potential as in vivo gene transfer vectors.

The retroviruses are a group of single-stranded RNA viruses characterized by an ability to convert their RNA to double-stranded DNA in infected cells by a process of reverse-transcription. The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome.

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed. When a recombinant plasmid containing a human cDNA, together with the retroviral LTR and packaging sequences is introduced into a cell line (by calcium phosphate precipitation for example), the packaging sequence allows the RNA transcript of the recombinant plasmid to be packaged into viral particles, which are then secreted into the culture media. The recombinant retrovirus is then collected, optionally concentrated, and used for gene transfer. Retroviral vectors are able to infect a broad variety of cell types. However, integration and stable expression require the division of host cells.

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

Other viral vectors may be employed as expression vectors. Vectors derived from viruses such as vaccinia virus, adeno-associated virus (AAV) and herpes viruses may be employed.

In order to effect expression of sense or antisense gene constructs, the expression vector may be delivered into a cell. This delivery may be accomplished in vitro, as in laboratory procedures for transforming cells lines, or in vivo or ex vivo, as in the treatment of certain disease states. As described above, one mechanism for delivery is via viral infection where the expression construct is encapsidated in an infectious viral particle.

Several non-viral methods for the transfer of expression constructs into cultured mammalian cells also are contemplated. These include calcium phosphate precipitation DEAE-dextran, electroporation, direct microinjection, DNA-loaded liposomes, and lipofectamine-DNA complexes, cell sonication, gene bombardment using high velocity microprojectiles, and receptor-mediated transfection. Some of these techniques may be successfully adapted for in vivo or ex vivo use.

Pharmaceutical Compositions—Where clinical applications are contemplated, pharmaceutical compositions can be produced—either gene delivery vectors or engineered cells—in a form appropriate for the intended application. Generally, this entails preparing compositions that are essentially free of pyrogens, as well as other impurities that could be harmful to humans or animals.

Appropriate salts and buffers are used to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated.

The expression vectors and delivery vehicles may be administered via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

Therapeutic Kits—All the essential materials and reagents required for inhibiting tumor cell proliferation may be assembled together in a kit. This generally will comprise selected expression vectors, viruses or cells. Also included may be various media for replication of the expression vectors and host cells for such replication. Such kits will comprise distinct containers for each individual reagent. The kits may also include an instruction sheet defining (i) administration of the antisense expression vector construct; (ii) the antisense expressing viruses; and (iii) the antisense expressing cells.

In some embodiments, an interfering (iRNA or siRNA) is provided. In some embodiments the iRNA is complementary to the breakpoint of a fusion gene.

Methods Associated with Clinical Outcome Discoveries

Tables 15 and 39 provided herein, contain more than 100 genetic events, including gain-of-function mutations, loss-of-function mutations, in-peak gene amplification/deletions, and fusion events for various cancer types that are associated with a clinical outcome with high statistical significance (q<0.1). Accordingly, provided herein are methods for delivering a treatment to a subject, methods for determining whether a subject receives a treatment, methods for determining whether to deliver a treatment, and methods for delivering a report. The treatment, in certain illustrative embodiments, is a drug. As non-limiting examples, the drug can be a drug listed in Tables 8, 16 and 17, especially where the method involves a genetic event that affects the gene listed for the drug in Tables 8, 16 and 17. In other examples, the drug can be any drug approved by a regulatory agency, or any drug in a stage of development before approval, as discussed herein.

Accordingly, in another embodiment, a method of delivering a treatment to a subject is provided, wherein the method includes detecting a genetic event identified in Table 15, and treating the subject, wherein the treatment is believed to positively affect the clinical outcome of cancer patients having the genetic event and/or is believed to affect a biological pathway associated with the genetic event. This embodiment can be considered a method for determining if a subject receives a treatment or a method for determining whether to deliver or perform a treatment to or on a subject. Thus, provided herein is a method for determining if a subject receives a drug, the method includes detecting a genetic event identified in Table 15 and/or 39, and then delivering a drug to the subject if the detected genetic event is listed in Table 15 and/or 39, wherein the drug is believed to positively affect the clinical outcome of patients having the genetic event. In illustrative aspects of these embodiments, the genetic event is associated with a gene found in Tables 8, 16 and 17, and the drug is listed in Tables 8, 16 and 17, as a companion for that gene. The subject is typically a subject that has a cancer of the type listed in Table 15 and/or 39. In illustrative aspects of this embodiment the genetic event is associated with a poor prognosis for the subject, who is afflicted with a cancer, typically the cancer listed in Table 15 and/or 39 for which the poor prognosis is associated with that genetic event.

In another embodiment, provided herein is a method of delivering a report, wherein the method includes detecting a genetic event identified in Table 15 and/or 39 and delivering to a medical professional, a report that provides a predicted clinical outcome associated with that genetic event for a cancer of the subject. The medical professional can be, as non-limiting examples, a physician, genetic counselor, or other medical professional. Typically, the physician, genetic counselor, or other medical professional have a professional relationship with the subject, such as a patient/doctor relationship. The report can be a paper report or can be an electronic report delivered to the medical professional over a computer network. The method and report can include one or more of the genetic events and associated prognosis identified in Table 15 and/or 39.

In another embodiment, provided herein is a method for determining which treatment to administer to a subject, the method includes detecting a genetic event listed in Table 15, and administering the treatment depending on the genetic event that is detected. In illustrative embodiments, the treatment is an aggressive treatment, such as a treatment that will involve more pain and suffering for the patient as a result of the treatment, if the detected genetic event is associated with a poor prognosis. In related embodiments the treatment is a more aggressive treatment if the detected genetic event is associated with a poor prognosis and a less aggressive treatment if the detected genetic event is another genetic event, especially if the detected genetic event is identified in Table 15 and/or 39 as indicating a good prognosis. For example, if a AADAC gene deletion, an amplification of the CHD1L gene, the FMO5 gene, or the PRKAB2 gene, or a combination thereof, is detected in a lung cancer adenocarcinoma patient, the patient may be treated with an aggressive chemotherapeutic drug regimen. If these genetic events are not detected in the patient, then the patient may be monitored but the chemotherapeutic drug may not be administered.

In another embodiment, provided herein is a method for determining whether to treat a cancer patient, the method includes detecting a genetic event listed in Table 15 and/or 39, and treating the subject if a genetic event is detected that is associated in Table 15 with a poor prognosis. In another embodiment, provided herein is a method for determining whether to treat a cancer patient, the method includes detecting a genetic event listed in Table 15 and/or 39, and not treating the subject if a genetic event is detected that is associated in Table 15 and/or 23 with a good prognosis. In another embodiment, provided herein is a method for determining whether to treat or monitor a cancer patient, the method includes detecting a genetic event listed in Table 15 and/or 39, and monitoring, but not treating the subject if a genetic event is detected that is associated in Table 15 and/or 39 with a good prognosis. Treatment may be administered at a later time if the monitoring detects recurrence or progression of the cancer.

In certain aspects of these embodiments of the invention that relate to methods provided herein based on the clinical outcomes associated with genetic events in Table 15 and/or 39, for example methods for delivering a treatment to a subject or determining whether to deliver a treatment to a subject, or determining which treatment to administer or deliver, or methods for delivering a report, the subject can be identified as having any of the types of genetic events and any of the specific genetic events listed in Table 15 and/or 39. For example, the genetic event can be a gain-of-function mutation, loss-of-function mutation, a gene amplification or deletion, typically an in-peak gene amplification/deletion, or a fusion event. In certain illustrative embodiments the genetic event is identified in Table 15 and/or 39 of having a q-value of $1 \times 10^{-3}$ or less, $1 \times 10^{-4}$ or less, or $1 \times 10^{-5}$ or less. In certain aspects, the genetic event is listed in Table 15 and/or 39 as involving a druggable gene. For example, the genetic event can be a genetic event listed in Table 15 and/or 39 associated with a gene that is a preclinical drug target. As a non-limiting example, provided herein is a method for determining which treatment or course of treatment to administer to a patient who has ovarian cancer, for example ovarian serous cystadenocarcinoma, wherein the method includes detecting or otherwise determining an amplification of the ID1 or BCL2L1 gene and administering the treatment. The treatment in illustrative embodiments, is an approved treatment for BCL2L1, such as a currently FDA-approved BCL2L1 treatment, wherein a BCL2L1 amplification is detected.

Methods are known to skilled artisans for detecting the types of genetic events listed in Table 15 and/or 39. Those methods can include nucleic acid sequencing methods or amplification methods, such as PCR or isothermal amplification methods, or combinations thereof. Those methods can include providing a primer that is designed to bind to a gene identified in Table 15 and/or 39 or bind upstream of a gene identified in Table 15 and/or 39. Thus, provided herein are reaction mixtures and kits that include a nucleic acid sample for a subject and one or more primers that bind to, or upstream from, a gene identified in Table 15 and/or 39. Typically, the gene is associated with a genetic event in Table 15 and/or 39, and the subject has a cancer identified in Table 15 and/or 39 as having a prognosis associated with the genetic event. The kit can also include a control nucleic acid that is bound by the primer as disclosed herein for various embodiments of the invention. The reaction mixture can also include a polymerase as disclosed herein for various embodiments of the invention.

In certain aspects of these embodiments of the invention that relate to methods provided herein based on the clinical outcomes associated with genetic events in Table 15 and/or 39, for example methods for delivering a treatment to a subject or determining whether to deliver a treatment to a subject, methods for determining which treatment to deliver, or methods for delivering a report to a medical professional, the genetic event can include more than one of the genetic events identified in Table 15 and/or 39. In certain aspects, a method according to this embodiment detects 2, 3, 4, 5, 6, 7, 8, 9, 10, or more of the genetic events identified in Table 15, especially those identified with the same prognosis for a given cancer type. For example, the method can include detecting a genetic event in a breast cancer patient and administering a treatment to the patient, where the detected genetic event includes a gene amplification of two or more of the BRF2, ERLIN2, GPR124, PROSC, and TAB11FI genes. In another example, the method includes detecting two or more genetic events in a subject afflicted with a lower grade glioma and administering a treatment to the subject, wherein the genetic event is at least two of an amplification of the EGFR or SEC61G gene, an amplification of the CDK4, CYP27B1, MARCH9, TSPAN31, or AGAP2 gene, a gain of function mutation in the EGFR gene, or a deletion of the CDKN2A, CDKN2B, or MTAP gene. In another aspect, the method includes detecting a genetic event associated with a poor prognosis and the genetic event is identified in Tables 8, 16, 17, Table 15 and/or 39 as being a target for a current drug in pre-clinical trials or an approved drug, such as an FDA approved drug.

In certain aspects of these embodiments of the invention that relate to methods provided herein based on the clinical outcomes associated with genetic events in Table 15 and/or 39, for example methods for delivering a treatment to a subject or determining whether to deliver a treatment to a subject, or determining which treatment to administer or deliver, or methods for delivering a report, the genetic event can be a specific genetic event identified in one of the other tables herein. A skilled artisan can identify which general type of genetic event in Table 15 and/or 39 a specific genetic event in one of the other tables will fall under.

Computer Implemented Systems

Computer systems can be utilized to in certain embodiments of the disclosure. In various embodiments, computer system can include a bus or other communication mechanism for communicating information, and a processor coupled with bus for processing information. In various embodiments, computer system 100 can also include a memory, which can be a random access memory (RAM) or other dynamic storage device, coupled to bus for determining base calls, and instructions to be executed by processor. Memory also can be used for storing temporary variables or other intermediate information during execution of instructions to be executed by processor. In various embodiments, computer system can further include a read only memory (ROM) or other static storage device coupled to bus for storing static information and instructions for processor. A storage device, such as a magnetic disk or optical disk, can be provided and coupled to bus for storing information and instructions.

In various embodiments, computer system can be coupled via bus to a display, such as a cathode ray tube (CRT) or liquid crystal display (LCD), for displaying information to a computer user. An input device, including alphanumeric and other keys, can be coupled to bus for communicating information and command selections to processor. Another type of user input device is a cursor control, such as a mouse, a trackball or cursor direction keys for communicating direction information and command selections to processor and for controlling cursor movement on display. This input device typically has two degrees of freedom in two axes, a first axis (i.e., x) and a second axis (i.e., y), that allows the device to specify positions in a plane.

A computer system can perform the present teachings. Consistent with certain implementations of the present teachings, results can be provided by computer system 100 in response to processor executing one or more sequences of one or more instructions contained in memory. Such instructions can be read into memory from another computer-readable medium, such as storage device. Execution of the sequences of instructions contained in memory can cause processor to perform the processes described herein. Alternatively hard-wired circuitry can be used in place of or in combination with software instructions to implement the present teachings. Thus implementations of the present teachings are not limited to any specific combination of hardware circuitry and software.

In various embodiments, the term "computer-readable medium" as used herein refers to any media that participates in providing instructions to processor for execution. Such a medium can take many forms, including but not limited to, non-volatile media, volatile media, and transmission media. Examples of non-volatile media can include, but are not limited to, optical or magnetic disks, such as storage device. Examples of volatile media can include, but are not limited to, dynamic memory, such as memory. Examples of transmission media can include, but are not limited to, coaxial cables, copper wire, and fiber optics, including the wires that comprise bus.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In accordance with the teachings and principles embodied in this application, methods, systems, and computer readable media that can efficiently collect, analyze, store, transfer, retrieve, and/or distribute information across multiple sites and/or entities, including genomic and/or patient information, are provided.

In one embodiment, a system is provided for determining whether one or more gene fusion and/or variant is present in a sample. The system can further determine identify a disease state, such as cancer, associated with the one or more gene fusion and/or gene variant, as well as an appropriate treatment in accordance with the mutation status. In certain embodiments, the system comprises a processor in communication with a sequencing instrument that receives sequencing data.

In some embodiments, the processor can execute one or more variant calls. In some embodiments, the processor can provide, filter, and/or annotate predictions.

EXAMPLES

In the following examples, methods were used to identify gene fusions and gene variants associated with a panel of 19 cancers in 4,225 cancer patient samples. The gene fusions and gene variants are then used to produce diagnostic methods to identify a predisposition for cancer, to diagnose cancer, to stage cancer, to provide a prognosis and to identify a druggable cancer. Methods are provided to provide targeted therapy for the cancer based on the identification of gene fusions.

Example 1: High-Throughput Systematic Analysis of Paired-End Next-Generation Sequencing Data to Characterize the Gene Fusion Landscape in Cancer 4,225 cancer patient samples across 19 diseases were processed with deFuse McPherson et al. "deFuse: an algorithm for gene fusion discovery in tumor RNASeq data" *PLoS Comp. Bio.* 2011. and TopHat (Kim et al. "TopHat-Fusion: an algorithm for discovery of novel fusion transcripts" *Genome Biology* 2011) gene fusion calling software using a cloud-based computation infrastructure. Filtering criteria were identified for gene fusion events that enriched for high confidence, chemically validated gene fusion events.

Gene fusions encode oncogenic drivers in hematologial and solid tumors and are often associated with dramatic clinical responses with the appropriate targeted agents. Massively parallel paired-end sequencing can identify structural rearrangements in tumor genomes and transcriptomes. However, computational methods to identify gene fusions are varied, still evolving and largely trained on cell line data. Systematic methods were developed to characterize known oncogenic gene fusions and to discover novel gene fusions in cancer. RNASeq data for approximately 3,400 clinical cases from 16 cancer types was obtained from the Cancer Genomics Hub (CGHub) of the Cancer Genome Atlas (TCGA). The performance of several gene fusion callers was surveyed and two were chosen (deFuse and TopHat) for further method development with the goal of supporting both single and paired end data. An analysis pipeline was developed and executed in parallel on a high-performance computing cluster. Filtering and annotation was conducted on aggregated data as a post-processing step to enable exploratory analyses of various filters. Filtering approaches were optimized on datasets that included known standards (e.g., TMPRSS2.ERG in prostate adenocarcinoma, PML.RARA in acute myeloid leukemia, etc.) to enrich for these and other gene fusions with correct 5'-3' orientation while excluding cases with ambiguous breakpoints and spanning reads, alignment errors, and read through transcripts from adjacent genes. Predicted fusions were summarized based on the occurrence of unique genes participating in fusion with multiple partners and of unique gene pairs, each within specific diseases. Elevated expression was observed after the predicted breakpoint of the 3' gene in cases positive for predicted fusions and added important confirmatory evidence. Pan-disease fusions and multi-partner fusion events broadened the clinical population scope of gene fusion events.

All single-end data was processed using TopHat and all paired-end data was processed using deFuse. TopHat has been shown to be effective with longer 75 bp single-end data. The deFuse algorithm is not compatible with single-end data and has been designed to leverage read pairs. The pre-processing data and Detect fusions: deFuse TopHat steps were executed in parallel for all samples on a high-performance computing cluster. The filtering and annotation was conducted on the aggregated data as a post-processing step to enable filtering criteria to minimize false positive fusions. The list of priority fusions was validated with RNASeq Exon Expression data.

TCGA Data Source: All RNASeq data for gene fusion analysis was obtained from the Cancer Genomics Hub (CGHub), the current repository for TCGA genomic data—cghub.ucsc.edu. Table 9 lists the TCGA sample counts downloaded and processed for M2 and M3:

ensure proper mate pairing and consistent mate pair ordering in the output FASTQ files, both of which are input requirements for the fusion callers.

There were 3 cancer types (COAD, READ, UCEC) only available as single-end RNASeq data. For single-end BAM file conversion the program BamTools (github.com/pezmaster31/bamtools) was used to generate FASTQ files.

Integration—FIG. 1 diagrams the relative levels of result filtering done by both callers. As part of the analysis "Level I" data was integrated—the output from TopHat-Fusion Post's potential_fusion.txt file and the output from deFuse's results.classify.tsv file. The integration steps involved converting the reported breakpoints to ones based on the genomic coordinate system and consolidation into a common file format.

TABLE 9

TCGA samples processed

| Cancer Type | Cancer Type Abbreviation | Samples | Center | Instrument |
|---|---|---|---|---|
| Bladder Urothelial Carcinoma | BLCA | 122 | UNC-LCCC | Illumina HiSeq 2000 |
| Breast invasive carcinoma | BRCA | 841 | UNC-LCCC | Illumina HiSeq 2000 |
| Cervical squamous cell carcinoma and endocervical adenocarcinoma | CESC | 88 | UNC-LCCC | Illumina HiSeq 2000 |
| Colon adenocarcinoma | COAD* | 196 | UNC-LCCC | Illumina GA IIx |
| Glioblastoma multiforme | GBM | 167 | UNC-LCCC | Illumina HiSeq 2000 |
| Head and Neck squamous cell carcinoma | HNSC | 302 | UNC-LCCC | Illumina HiSeq 2000 |
| Kidney Chromophobe | KICH | 66 | UNC-LCCC | Illumina HiSeq 2000 |
| Kidney renal clear cell carcinoma | KIRC | 480 | UNC-LCCC | Illumina HiSeq 2000 |
| Kidney renal papillary cell carcinoma | KIRP | 76 | UNC-LCCC | Illumina HiSeq 2000 |
| Acute Myeloid Leukemia | LAML | 179 | BCCAGSC | Illumina GA IIx |
| Brain Lower Grade Glioma | LGG | 184 | UNC-LCCC | Illumina HiSeq 2000 |
| Liver hepatocellular carcinoma | LIHC | 34 | UNC-LCCC | Illumina HiSeq 2000 |
| Lung adenocarcinoma | LUAD | 345 | UNC-LCCC | Illumina HiSeq 2000 |
| Lung squamous cell carcinoma | LUSC | 221 | UNC-LCCC | Illumina HiSeq 2000 |
| Ovarian serous cystadenocarcinoma | OV | 417 | BCCAGSC | Illumina HiSeq 2000 |
| Pancreatic adenocarcinoma | PAAD | 31 | UNC-LCCC | Illumina HiSeq 2000 |
| Prostate adenocarcinoma | PRAD | 140 | UNC-LCCC | Illumina HiSeq 2000 |
| Rectum adenocarcinoma | READ* | 71 | UNC-LCCC | Illumina GA IIx |
| Skin Cutaneous Melanoma | SKCM | 267 | UNC-LCCC | Illumina HiSeq 2000 |
| Stomach adenocarcinoma | STAD | 41 | BCCAGSC | Illumina HiSeq 2000 |
| Thyroid carcinoma | THCA | 373 | UNC-LCCC | Illumina HiSeq 2000 |
| Uterine Corpus Endometrioid Carcinoma | UCEC* | 317 | UNC-LCCC | Illumina GA IIx |

*Single-end TCGA disease
BAM files were downloaded from CGHub using its Gene Torrent Software With the goal of supporting both single and paired-end data, 4,374 paired-end samples were processed with deFuse and 584 single-end samples with TopHat.

Broadly, the analysis pipeline consisted of 5 main steps: 1. Pre-process the raw data to obtain FASTQ files 2. Run fusion callers 3. Filter breakpoints to gene regions of interest 4. Annotate the breakpoints with the Oncomine transcript set and 5. Summarize and prioritize potentially interesting novel fusions.

The input to the fusion callers consisted of RNASeq reads in FASTQ format, which required conversion of the BAM file provided by TOGA to one or two FASTQ files for single or paired end data (respectively).

A custom SamToFastq converter was developed to generate FASTQ files from a TOGA BAM file. In addition to allowing conversion of all paired-end RNASeq TOGA BAMs systematically, the SamToFASTQ converter had other advantages over other conversion tools. First, it was written in C and compiled to run faster and reduce processing time. Second, it incorporated several validation steps to Breakpoint Filtering—The ~5.5 million predictions from the "Level I" output of the callers were filtered to only retain those calls where each breakpoint was either in the 5'UTR or CDS region of a RefSeq transcript (refGene circa Jul. 18, 2012, obtained from UCSC). This was done to enrich the predicted fusions for those containing functional gene regions. Breakpoints predicted to occur in intronic sequences were also excluded, resulting in a set of 423,587 predicted chimeras.

Breakpoint Annotation—For each pair of breakpoints, only one transcript per Entrez ID was retained. This ensured consistency in annotating breakpoints at the same location. However, predicted breakpoints at different locations for the same gene partners may still result in multiple transcripts representing a pair of genes—possible evidence of alternative transcripts.

Basic annotation from the callers was discarded, as it was based on the default annotation source of each respective caller. However, certain output fields from both TopHat and deFuse were retained to help prioritize the predicted fusions.

Additionally, certain annotation properties that weren't explicitly reported by the callers were inferred from other caller properties.

Inferred Properties—Supporting and Spanning read counts were obtained from each caller and summarized in to Reads Span and Reads Span Support. The latter is a sum of reads spanning the fusion and those supporting the fusion. The breakpoint sequence reported by the callers was trimmed to include 50 bases on each side of the fusion and consolidated as Breakpoint Sequence. The fusion breakpoint is delineated by a "I". Since neither of the callers provides a definitive '5-prime' or '3-prime' flag, the relative 5'-3' orientation of the fusion partners was inferred by combining a caller parameter with the gene strand annotation. A Valid Orientation field was labeled as "Y" if there was an inferred 5' and 3' partner for a given gene fusion call.

RepeatMasker Annotation—Each predicted breakpoint location was also annotated with RepeatMasker features in the neighborhood of the breakpoint. This was done to identify breakpoints in highly repetitive genomic regions, where alignment errors were likely to affect the prediction of the chimeric transcript. For each fusion prediction, a RepeatMasker Overlap field was set to 1 if either of the breakpoint flank sequences overlaps with a RepeatMasker element by 12 or more bases. The frequency of overlapping fusion calls is used in the Oncomine Prioritization described below such that gene fusion predictions with a lower frequency of overlap are considered higher quality.

Fusion Exon Expression Imbalance—Recurrent Oncomine Priority Fusions were vizualized using RNASeq exon expression data downloaded using the GDAC Firehose tool to provide secondary evidence of true positive fusion events by searching for exon expression imbalance before and after the breakpoint call. Specifically, if the 3' partner's expression is impacted by the 5' partner's promoter region, then exon expression should increase post the predicted breakpoint. This effect is especially visible when viewing fused versus non-fused patient samples.

RPKM RNASeq values are listed for each patient as Gene Annotation Format (GAF) features corresponding to a composite of UCSC exons from several different gene definitions including Refseq. Compendia processed fusion breakpoints were mapped to the GAF features. 80.8% of the 396,298 Refseq exons map perfectly to GAF features in the plot shown below. The Refseq exon and GAF feature pair that resulted in the largest overlap was selected and reported on.

A value called rg_pct provides a metric of the mapping quality of a given Refseq exon with a GAF feature based on the following formula: rg_pct=overlap/length$_{refseq}$*overlap/length$_{GAF\ feature}$ Mappings with an rg_pct value of 1 overlap perfectly, while values less than 1 indicate the refseq exon or GAF feature did not map to the exact same genomic regions and the RPKM value may be suspect. RNASeq V2 data was selected for all diseases except OV, STAD, and LAML due to disease coverage shown in the barplot.

Fusion exon expression was manually reviewed for expression imbalance of a subset of Oncomine Priority fusions meeting the following criteria: 1. Recurrent Oncomine Priority Fusions 2. Oncomine Priority Fusions that are listed in the Mitelman Database 3. One fusion partner is an Oncomine Gain of Function Oncogene and involved in at least 3 Oncomine Priority Fusions and 4. One fusion partner is listed in the Sanger Cancer Gene Census (www.sanger.ac.uk/genetics/CGP/Census) and involved in at least 3 Oncomine Priority Fusions.

A total of 994 gene fusions meet these criteria and were manually reviewed for exon expression imbalance by assigning a "supported", "refuted", "neutral" or "not tested" rating to the gene fusion call.

Experts used the following criteria to assign ratings: Supported: Fused samples had a highly expressed 3' fusion partner post-breakpoint such that fused samples were outliers of the patient population. Prior to the breakpoint, the 3' partner's expression should be low compared to post-breakpoint. Refuted: Extremely low average expression of the 5' partner (<5 RPKM) or average expression of one partner is much lower than the other (~1/10). Neutral: Neither Support or Refute criteria are met. Fusions that were not manually reviewed were assigned a rating of Not Tested.

Fusion Summarization—Fusions were summarized within a disease based on the occurrence of unique gene pairs, and based on the occurrence of individual genes, possibly with multiple partners.

Fusion-Level Summary—For a unique fusion pair (unique by Entrez ID pair), the number of samples within a disease with at least one prediction of that fusion by either caller is the Fused Sample Count. Since multiple breakpoints for the same pair of genes may be reported in one sample and across the samples, the number of unique fusion pairs within each disease represented by the 424K+ fusion calls was 49,588. Table 10 shows the properties that were summarized for a given fusion partner pair across the individual predictions:

TABLE 10

| Property | Summary Method |
|---|---|
| DEFUSE_EVERSION | % of total fusion calls = 'Y' |
| DEFUSE_VALID_ORIENTATION | % of total fusion calls = 'Y' |
| DEFUSE_NUM_MULTI_MAP | % of total fusion calls > 0 |
| TOPHAT_VALID_ORIENTATION | % of total fusion calls = 'Y' |
| 3P/5P_REPEATMASKER_OVERLAP | % of total fusion calls = 1 |

The Adjacent flag is set for a fusion if the genes are <1 Mb apart on the genome and the defuse_eversion flag is set in ≤75% of the individual fusion prediction for these fusion partners.

Mitelman Cross-reference—Individual unique fusion pairs were cross-referenced to the Mitelman database of genomic aberrations (cgap.nci.nih.gov/Chromosomes/Mitelman downloaded Feb. 25, 2013). The match was done based on gene names and not disease type. Therefore, gene fusions reported in Mitelman in a certain disease may have occurred in a different disease type in the TCGA datasets. Gene fusions summarized at the gene level were cross-referenced to the Mitelman database based on gene name. Thus, there is more potential for the gene as reported in Mitelman to be of different histology or altogether different aberration type (for example a large chromosome-level deletion instead of a fusion) than the predicted unique fusion pairs.

Normal Sample Fusion Blacklist—To reduce the number of false positive fusions, 344 paired-end normal samples were processed across 10 diseases using the same deFuse pipeline described above. A total of 56,579 total fusion calls consisting of 6,024 unique fusions were observed. Of the 49,588 unique gene fusion events, 11,801 of these calls were observed in normal samples. These normal sample fusion calls were used to generate a blacklist and thereby remove these false positives from the Oncomine Priority gene fusions.

Paralogous Fusion Partner Blacklist—A blacklist of fusions between paralogous gene family members was assembled using two strategies: 1) manually inspecting high frequency fusion partner gene names and 2) comparing the first 3 characters of all Priority Fusion partner gene names. In the latter strategy, fusion partners were verified to be "paralogous" using HomoloGene, Ensembl, and SIMAP before inclusion in the final blacklist. This blacklist consists of 375 unique paralogous gene fusions and was used to remove false positives from the Oncomine Priority gene fusions.

Example 2: NGS Mutation Methods for Identifying Gene Variants Associated with Cancer The goal of the data integration for gene variants was to create the most complete set of mutation data currently available from the TOGA.

Data Sources—For this release, the following were integrated: TOGA mutation data from the Broad GDAC Mutation_Packager 2013_02_22 stddata build, Level 2 (public, experimentally un-validated) data available from the TOGA DCC as of Mar. 1 2013, and, for prostate adenocarcinoma, mutation data generated by Compendia from TOGA primary data.

Compendia (CBI) Mutation Calls—There was concern that the prostate adenocarcinoma mutation calls available from TOGA were of low quality and resulted in false-positive 'Gain of Function' predictions. Therefore, all calls for this disease were sourced from Compendia's own mutation calling pipeline, which closely parallels the process used by the TOGA cancer type working groups to generate the publically-available mutation calls.

TABLE 12

Data Source Selection

| Cancer Type | TCGA Disease | Mutation Packager (2013 Feb. 22) | DCC (2013 Mar. 1) | Compendia | TOTAL |
|---|---|---|---|---|---|
| Bladder Urothelial Carcinoma | BLCA | 28 | | | |
| Breast Invasive Carcinoma | BRCA | 772 | | | |
| Cervical Squamous Cell Carcinoma and Endocervical Adenocarcinoma | CESC | 39 | | | |
| Colon Adenocarcinoma | COAD | 153 | | | |
| Glioblastoma Multiforme | GBM | 290 | | | |
| Head and Neck Squamous Cell Carcinoma | HNSC | | 306 | | |
| Kidney Renal Clear Cell Carcinoma | KIRC | 293 | | | |
| Kidney Renal Papillary Cell Carcinoma | KIRP | 100 | | | |
| Acute Myeloid Leukemia | LAML | 196 | | | |
| Brain Lower Grade Glioma | LGG | 169 | | | |
| Lung Adenocarcinoma | LUAD | | 379 | | |
| Lung Squamous Cell Carcinoma | LUSC | 178 | | | |
| Ovarian Serous Cystadenocarcinoma | OV | 316 | | | |
| Pancreatic Adenocarcinoma | PAAD | 34 | | | |
| Prostate Adenocarcinoma | PRAD | | | 170 | |
| Rectal Adenocarcinoma | READ | 68 | | | |
| Skin Cutaneous Melanoma | SKCM | 252 | | | |
| Stomach Adenocarcinoma | STAD | | 136 | | |
| Thyroid Carcinoma | THCA | 323 | | | |
| Uterine Corpus Endometrioid Carcinoma | UCEC | 235 | | | |
| | | | | | 4,437 |

Data Cleaning—some simple clean-up operations were performed to remove duplicate mutation records present in the source data. Duplicate mutations from various tumor/normal aliquots pairs of the same patient sample were removed. A total of 25 "ultra-mutator" samples (mutation count of >5,000 per sample) were also excluded from the downstream analysis pipelines. In certain diseases, such as uterine corpus endometrioid carcinoma, several highly-mutated samples may dominate the overall mutation counts and dilute the results of mutation recurrence analysis necessary for the Compendia mutation and gene classification scheme.

Mutation Annotation: A. Compendia Annotation—Compendia's approach to defining mutations relied on accurate variant annotation hence; the mutations were re-annotated using a standard annotation pipeline which ensured that mutations across disease types were evaluated consistently and were subject to common interpretation during the nomination of potential oncogenes or tumor suppressor genes.

Mutations obtained from TCGA were processed by Compendia according to the following general steps: 1. Each mutation was first re-annotated using the Compendia transcript set. Successfully annotated mutations received Compendia-derived annotation, while the rest retain annotation obtained from the TCGA. Annotation includes: Variant classification, Variant position, Variant change. 2. Redundant annotations of a mutation in multiple transcripts were removed. 3. Mutations located outside of gene regions of interest were removed. 4. Mutations without a valid gene Entrez ID were removed.

"Mutation" is defined herein as a specific change at a genomic location, i.e.: Chromosome, start, stop, reference base, alternate base, variant type (SNP, INS, DEL) etc.

"Annotation" is defined herein as a transcript-specific set of properties that describe the effect of the mutation, i.e.: Gene, transcript, variant classification, variant change, variant codon position, etc.

In the Mutation Annotation step, the mutations obtained from TOGA were re-annotated against a standard transcript set compiled by Compendia. This transcript set included RefGene transcripts from hg18 and hg19 genome builds, obtained from UCSC.

Each mutation was individually mapped against a contig in the CBI Transcript Set within the specified genome build. SNP mutations were mapped directly to their start location, while for small insertion (INS) and deletion (DEL) mutations a position of interest is selected for mapping.

For a mutation successfully mapped to a transcript, the CBI mutation annotation was inferred with respect to that transcript. For mutations that fail to map, the more limited TOGA annotation was retained, and a variant position for Hotspot calculations was constructed based on the genomic coordinate.

Below is a description of the criteria used in annotating the mutations that map to the CBI Transcript Set:

Variant Classification:

For each mutation successfully mapped to a transcript, the variant classification was inferred using the location and the sequence variant type of the mutation. This approach identified the following main mutation variant classifications:

TABLE 13 main mutation variant classifications:

| Variant Classification | Transcript Region |
|---|---|
| Splice_Site | exon or intron |
| 3'UTR, 5'UTR | UTR exon |
| Intron | intron |

TABLE 13-continued main mutation variant classifications:

| Variant Classification | Transcript Region |
|---|---|
| Missense, Nonsense, Nonstop, Silent | coding exon |
| Frame_Shift_Ins/Del | coding exon |
| In_Frame_Ins/Del | coding exon |
| Non_Coding_Exon | exon of a non-coding gene |

Variant Position:

The variant position of a mutation is the location used to identify genes with Hotspot mutations, which are mutations of a certain classification that are observed at the same location in multiple tumor samples. To effectively identify recurrence and define a hotspot for each mutation, a mutation spot identifier was constructed that encompassed the mutation position, the identity of the amino acid or base affected, and the variant classification. Mutations that occurred at the same location irrespective of the specific base change they generated were aggregated. Therefore, only the reference base or amino acid was used to define the variant position. This ensured that mutations affecting the same codon or genomic position would be counted towards a possible hotspot, even if the alternate alleles they generated were different. For example, for a given gene, missense mutations V600E, V600F and V600G would all have a variant position of V600 and would thus be aggregated together when identifying hotspot mutations. When the amino-acid level position was not available, the RNA-level or genomic-level position was utilized.

For mutations that do not map to the CBI Transcript Set, and hence do not have a transcript-based location, the genomic location (start position) and the reference nucleotide (reference allele) was used as the variant position irrespective of the coding region or splice site proximity. The TOGA-annotated variant classification was then added as a suffix. The variant change (see below) for these mutations was not defined.

Variant Change:

The variant change provides HGVS-like information about the alternate allele change of the mutation (e.g. V600E). For SNP mutations in the coding region, the variant change was a full HGVS protein-level sequence variant description, indicating the alternate amino acid. For SNPs outside of the coding region, the alternate allele nucleotide base was provided. For mutations that do not map to the CBI Transcript Set, the variant classification from TOGA was retained.

Transcript Filtering:

To avoid retrieving multiple transcripts, and hence, multiple annotations for a single mutation within a gene, only one transcript per mutation per gene (unique Entrez ID) were kept. If a mutation mapped to several transcripts of a gene, only one was chosen. However, if a mutation mapped to several genes, then only one transcript per gene was selected. It was thus possible for a mutation to receive two different annotations, but only if they stemmed from transcripts with different Entrez IDs. In effect, any mutation of the same variant classification at the same genomic location was always assigned to the same transcript, and hence would be in the same frame of reference when computing recurrence for hotspot identification.

Gene Region Filtering:

All mutations were further filtered by variant type and class to avoid including mutations of minor interest to gene function analysis. Mutations were filtered out that were not resolved to a gene region, either because they fell significantly far outside of a transcript, or because they were in a location not associated with a Ref Seq gene. These mutations were evident either by their lack of gene identifier, or membership in the following variant classes: Intron, 5'Flank, IGR, and miRNA. Mutations were also filtered out with variant type of DNP, TNP, ONP, Complex_substitution, and Indel, as their annotation was not supported by the pipeline Classifying Mutations as Hotspot, Deleterious, or Other—The next step in the analysis pipeline identified recurring mutations in multiple samples based on their variant position, and categorized them into Hotspot, Deleterious or Other variant categories. For this step, and the subsequent frequency calculations, mutations for each disease type were processed independently. Only mutations of the same variant classification were tallied together, so, for example, a missense mutation and a silent mutation at the same position was counted separately.

To identify driver events, each mutation for a given Entrez Gene Id was categorized as "Deleterious" or "Hotspot". A mutation was deemed 'recurrent' if it was observed in the same variant position in 3 or more tumor samples. A mutation belonged to the "Hotspot" variant category if it was recurrent and was annotated with one of the following variant classifications: In-frame insertion/deletion, Nonstop, Missense, Non_Coding_Exon. A mutation belonged to the "Deleterious" category if it was: annotated with one of the following variant classifications: Frame shift insertion/deletion, Nonsense. A mutation was considered in the "Other" variant category if it did not fit the above criteria.

Nominating "Gain of Function" and "Loss of Function" Genes—Individual genes were classified into predicted functional classes, namely "Gain of Function", "Recurrent Other", and "Loss of Function" to reflect their relative enrichment in potential activating or deleterious mutations.

Frequency of Mutations:

Mutation frequencies for each gene were calculated with respect to a given variant classification and variant category across all samples within a disease type. Overall mutation frequency for a gene within a disease was calculated by combining all the mutations.

Mutation Significance:

The Hotspot p-values for each gene within a disease were calculated by selecting the most recurrent mutation m and using sampling to determine the probability p of observing r or more mutations at that position. More specifically: $p=100,000-\Sigma_{m=1}^{r-1} c_m/100,000$, where $c_m$ is the count of replicates with maximum multiplicity m. P-values for transcripts with a maximum multiplicity of one are defined as 1.0. P-value for transcripts with a maximum multiplicity that is never observed is defined as 1 e-5.

Hotspot Q-values were calculated within each disease by counting the number of transcripts mutated at least once (N) and calculating the rank of each p-value. The q-value for a given p-value is then Q=p*N/rank.

To assess whether a gene was significantly enriched for deleterious mutations compared with other genes, given the background mutation rate, Fisher's exact test was performed comparing the deleterious mutation frequency of the gene in question to that of other genes. Nonsense mutations, frame shift insertions and frame shift deletions were classified as deleterious mutations, while mutations of any other type (missense, etc., but non-intergenic) counted as others.

Deleterious Q-values were calculated within each disease, by counting the number of genes with deleterious mutations (N), and calculating the rank of each association. The q-value for a given p-value was then Q=p*N/rank.

Figure 2:
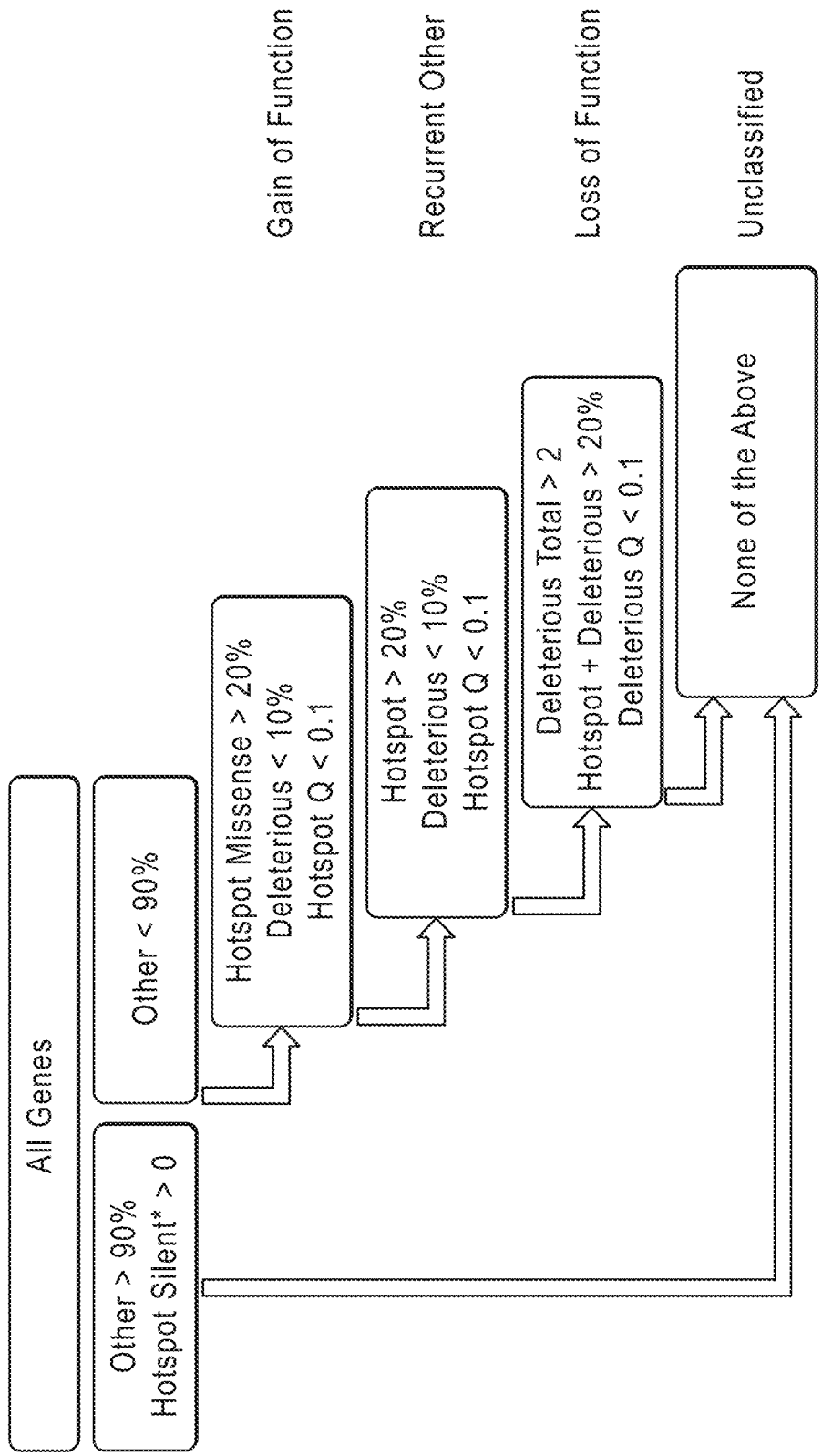
FIG. 2 shows the classification scheme for gene variants for Gain of Function and Loss of Function genes.

Gene Classification:

Once the mutations were classified, individual genes were nominated to one of three classes—"Gain of Function," "Loss of Function," and "Recurrent Other." The classification is based on the combination of relative frequencies and the significance of the mutations observed in the gene. The significance of the mutations per gene is assessed by a p-value. The classification scheme in FIG. 2 specifies the criteria for Gain of Function and Loss of Function genes.

A "Gain of Function" gene will have a relatively high frequency of Hotspot Missense mutations and a low frequency of Deleterious mutations, while a "Loss of Function" gene contains a large fraction of Deleterious mutations. "Recurrent Other" tend to contain recurrent insertion/deletion mutations, some of which—for example recurrent frame shift indels of 1 base—exhibit signs of potential false-positive calls that may arise from local alignment errors.

Pan-Cancer Analysis—To summarize mutations across diseases identical calculations were performed as for within-disease analyses, but without stratifying the mutation records by disease. For the pan-disease gene classification, the genes (unique by Entrez ID) were summarized across all cancer types.

Example 3: Diagnostic Assay for the Identification of Gene Fusions and/or Gene Variants in Cancer Library Preparation PCR Amplify Genomic DNA Targets The disclosed variant and fusion polynucleotides can be detected by the sequencing of nucleic acids. This can be accomplished by next generation sequencing, the description of which follows. The source of the nucleic acid for next generation sequencing can include a Fresh-Frozen Paraffin-Embedded (FFPE) sample.

A multiplex polymerase chain reaction is performed to amplify 384 individual amplicons across a genomic DNA sample. A pool of greater than 32,000 primers is developed covering more than 100 gene variants or fusion polynucleotides. Each primer in the primer pool was designed to contain at least one uridine nucleotide near the terminus of each primer. Each primer is also designed to selectively hybridize to, and promote amplification, by forming a primer pair, with a specific gene, gene variant, or fusion polypeptide of a nucleic acid sample.

To a single well of a 96-well PCR plate is added 5 microliters of the Primer Pool containing 384 primer pairs at a concentration of 15 µM in TE, 10-50 ng genomic DNA and 10 microliters of an amplification reaction mixture (2× AmpliSeq HiFi Master Mix) that can include glycerol, dNTPs, and Platinum® Taq High Fidelity DNA Polymerase (Invitrogen, Catalog No. 11304) to a final volume of 20 microliters with DNase/RNase Free Water (Life Technologies, CA, Part No. 600004).

The PCR plate is sealed and loaded into a thermal cycler (GeneAmp® PCR system 9700 Dual 96-well thermal cycler (Life Technologies, CA, Part No. N8050200 and 4314445)) and run using the following temperate profile to generate the preamplified amplicon library.

An initial holding stage is performed at 98° C. for 2 minutes, followed by 16 cycles of denaturing at 98° C. for 15 seconds and an annealing and extending stage at 60° C.

for 4 minutes. After cycling, the preamplified amplicon library is held at 4° C. until proceeding to the purification step outlined below.

Purify the Amplicons from Input DNA and Primers

Two rounds of Agencourt® AMPure® XP Reagent (Beckman Coulter, CA) binding, wash, and elution at 0.6× and 1.2× volume ratios are found to remove genomic DNA and unbound or excess primers. The amplification and purification step outlined herein produces amplicons of about 100 bp to about 600 bp in length.

In a 1.5 ml LoBind tube (Eppendorf, Part No. 022431021), the preamplified amplicon library (20 microliters) is combined with 12 microliters (0.6× volumes) of Agencourt® AMPure® XP reagent (Beckman Coulter, CA). The bead suspension is pipetted up and down to thoroughly mix the bead suspension with the preamplified amplicon library. The sample is then pulse-spin and incubated for 5 minutes at room temperature.

The tube containing the sample is placed on a magnetic rack such as a DynaMag™-2 spin magnet (Life Technologies, CA, Part No. 123-21 D) for 2 minutes to capture the beads. Once the solution cleared, the supernatant is transferred to a new tube, where 24 microliters (1.2× volume) of AgenCourt® AMPure® XP beads (Beckman Coulter, CA) is added to the supernatant. The mixture is pipetted to ensure that the bead suspension is mixed with the preamplified amplicon library. The sample is then pulse-spun and incubated at room temperature for 5 minutes. The tube containing the sample is placed on a magnetic rack for 2 minutes to capture the beads. Once the solution clears, the supernatant is carefully discarded without disturbing the bead pellet. The desired preamplified amplicon library is then bound to the beads. Without removing the tube from the magnetic rack, 200 microliters of freshly prepared 70% ethanol is introduced into the sample. The sample is incubated for 30 seconds while gently rotating the tube on the magnetic rack. After the solution clears, the supernatant is discarded without disturbing the pellet. A second ethanol wash is performed and the supernatant discarded. Any remaining ethanol is removed by pulse-spinning the tube and carefully removing residual ethanol while not disturbing the pellet. The pellet is air-dried for about 5 minutes at room temperature.

Once the tube is dry, the tube is removed from the magnetic rack and 20 microliters of DNase/RNase Free Water is added (Life Technologies, CA, Part No. 600004). The tube is vortexed and pipetted to ensure the sample is mixed thoroughly. The sample is pulse-spun and placed on the magnetic rack for two minutes. After the solution clears, the supernatant containing the eluted DNA is transferred to a new tube.

Phosphorylate the Amplicons

To the eluted DNA (~20 microliters), 3 microliters of DNA ligase buffer (Invitrogen, Catalog No. 15224041), 2 microliters dNTP mix, and 2 microliters of FuP reagent are added. The reaction mixture is mixed thoroughly to ensure uniformity and incubated at 37° C. for 10 minutes.

Ligate Adapters to the Amplicons and Purify the Ligated Amplicons

After incubation, the reaction mixture proceeds directly to a ligation step. Here, the reaction mixture now containing the phosphorylated amplicon library is combined with 1 microliter of A/P1 Adapters (20 μm each)(sold as a component of the Ion Fragment Library Kit, Life Technologies, Part No. 4466464) and 1 microliter of DNA ligase (sold as a component of the Ion Fragment Library Kit, Life Technologies, Part No. 4466464), and incubated at room temperature for 30 minutes.

After the incubation step, 52 microliters (1.8× sample volume) of AgenCourt® AMPure® Reagent (Beckman Coulter, CA) is added to the ligated DNA. The mixture is pipetted thoroughly to mix the bead suspension with the ligated DNA. The mixture is pulse-spun and incubated at room temperature for 5 minutes. The samples undergo another pulse-spin and are placed on a magnetic rack such as a DynaMag™-2 spin magnet (Life Technologies, CA, Part No. 123-21D) for two minutes. After the solution clears, the supernatant is discarded. Without removing the tube from the magnetic rack, 200 microliters of freshly prepared 70% ethanol is introduced into the sample. The sample is incubated for 30 seconds while gently rotating the tube on the magnetic rack. After the solution clears, the supernatant is discarded without disturbing the pellet. A second ethanol wash is performed and the supernatant is discarded. Any remaining ethanol is removed by pulse-spinning the tube and carefully removing residual ethanol while not disturbing the pellet. The pellet is air-dried for about 5 minutes at room temperature.

The pellet is resuspended in 20 microliters of DNase/RNase Free Water (Life Technologies, CA, Part No. 600004) and vortexed to ensure the sample is mixed thoroughly. The sample is pulse-spun and placed on the magnetic rack for two minutes. After the solution clears, the supernatant containing the ligated DNA is transferred to a new Lobind tube (Eppendorf, Part No. 022431021).

Nick Translate and Amplify the Amplicon Library and Purify the Library

The ligated DNA (~20 microliters) is combined with 76 microliters of Platinum® PCR SuperMix High Fidelity (Life Technologies, CA, Part No. 12532-016, sold as a component of the Ion Fragment Library Kit, Life Technologies, Part No. 4466464) and 4 microliters of Library Amplification Primer Mix (5 μM each)(Life Technologies, CA, Part No. 602-1068-01, sold as a component of the Ion Fragment Library Kit, Life Technologies, Part No. 4466464), the mixture is pipetted thoroughly to ensure a uniformed solution. The solution is applied to a single well of a 96-well PCR plate and sealed. The plate is loaded into a thermal cycler (GeneAmp® PCR system 9700 Dual 96-well thermal cycler (Life Technologies, CA, Part No. N8050200 and 4314445)) and run on the following temperate profile to generate the final amplicon library.

A nick-translation is performed at 72° C. for 1 minute, followed by an enzyme activation stage at 98° C. for 2 minutes, followed by 5-10 cycles of denaturing at 98° C. for 15 seconds and an annealing and extending stage at 60° C. for 1 minute. After cycling, the final amplicon library is held at 4° C. until proceeding to the final purification step outlined below.

In a 1.5 ml LoBind tube (Eppendorf, Part No. 022431021), the final amplicon library (~100 microliters) is combined with 180 microliters (1.8× sample volume) of Agencourt® AMPure® XP reagent (Beckman Coulter, CA). The bead suspension is pipetted up and down to thoroughly mix the bead suspension with the final amplicon library. The sample is then pulse-spun and incubated for 5 minutes at room temperature.

The tube containing the final amplicon library is placed on a magnetic rack such as a DynaMag™-2 spin magnet (Life Technologies, CA, Part No. 123-21D) for 2 minutes to capture the beads. Once the solution clears, the supernatant is carefully discarded without disturbing the bead pellet.

Without removing the tube from the magnetic rack, 400 microliters of freshly prepared 70% ethanol is introduced into the sample. The sample is incubated for 30 seconds while gently rotating the tube on the magnetic rack. After the solution clears, the supernatant is discarded without disturbing the pellet. A second ethanol wash is performed and the supernatant is discarded. Any remaining ethanol is removed by pulse-spinning the tube and carefully removing residual ethanol while not disturbing the pellet. The pellet is air-dried for about 5 minutes at room temperature.

Once the tube is dry, the tube is removed from the magnetic rack and 20 microliters of Low TE was added (Life Technologies, CA, Part No. 602-1066-01). The tube is pipetted and vortexed to ensure the sample is mixed thoroughly. The sample is pulse-spin and placed on the magnetic rack for two minutes. After the solution clears, the supernatant containing the final amplicon library is transferred to a new Lobind tube (Eppendorf, Part No. 022431021).

Assess the Library Size Distribution and Determine the Template Dilution Factor

The final amplicon library is quantitated to determine the library dilution (Template Dilution Factor) that results in a concentration within the optimized target range for Template Preparation (e.g., PCR-mediated addition of library molecules onto Ion Sphere™ Particles). The final amplicon library is typically quantitated for downstream Template Preparation procedure using an Ion Library Quantitation Kit (qPCR) (Life Technologies, Part No. 4468802) and/or a Bioanalyzer™ (Agilent Technologies, Agilent 2100 Bioanalyzer) to determine the molar concentration of the amplicon library, from which the Template Dilution Factor is calculated. For example, instructions to determine the Template Dilution Factor by quantitative real-time PCR (qPCR) can be found in the Ion Library Quantitation Kit User Guide (Life Technologies, Part No. 4468986), hereby incorporated by reference in its entirety.

In this example, 1 microliter of the final amplicon library preparation is analyzed on the 2100 Bioanalyzer™ with an Agilent High Sensitivity DNA Kit (Agilent Technologies, Part No. 5067-4626) to generate peaks in the 135-205 bp size range and at a concentration of about $5 \times 10^9$ copies per microliter.

Proceed to Template Preparation

An aliquot of the final library is used to prepare DNA templates that are clonally amplified on Ion Sphere™ Particles using emulsion PCR (emPCR). The preparation of template in the instant example is prepared according to the manufacturer's instructions using an Ion Xpress Template Kit (Life Technologies, Part No. 4466457), hereby incorporated by reference in its entirety. Once template-positive Ion Sphere Particles are enriched, an aliquot of the Ion Spheres are loaded onto an Ion 314™ Chip (Life Technologies, Part No. 4462923) as described in the Ion Sequencing User Guide (Part No. 4467391), hereby incorporated in its entirety, and subjected to analysis and sequencing as described in the Ion Torrent PGM Sequencer User Guide (Life Technologies, Part No. 4462917), hereby incorporated in its entirety.

Example 4: Oncomine NGS Integrative Analysis Methods to Identify Genetic Events Associated with Clinical Outcomes The Oncomine NGS Integrative Analysis was designed to bring together the largest possible set of core NGS data to enable scientific workflows that interrogate relationships across data types and diseases, summarizing the analyses at multiple biological levels of abstraction, such as genes and pathways.

Data Sources (Oncomine is available from Life Technologies/Compendia Biosciences—Ann Arbor, Mich. and www.oncomine.org).

The data for the Integrative Analysis was taken from the below sources:

Fusions: Oncomine driver fusions
Mutations: Oncomine pan-cancer driver mutations
CNVs: Peak amplification and deletion data derived from Oncomine-processed copy number data
DNA: Oncomine-processed DNA-seq continuous data
RNA: Normalized gene-level RNAseq continuous data
Clinical: Oncomine-curated clinical and outcome metadata
Pathways: Oncomine pathway definitions Fusions Data and Filtering Fusion data for integrative analysis was obtained from Oncomine NGS Fusion data. Oncomine Prioritized Fusion is a priority scheme developed at Compendia to capture attributes of known true positive fusion events and characterize a subset of observed gene fusions as high-confidence priority fusions. Criteria used to define priority fusions include: valid 5' to 3' orientation, non-adjacent fusion partners, uniquely mapping spanning reads, non-paralogous fusion partners, not observed in normal tissue, and non-overlapping with redundant regions in the genome.

Fusions were included and considered driver fusions if they were called by deFuse or Tophat, had exon expression evidence that was "supported" or "neutral" and met one of the following 4 criteria:

Oncomine Prioritized Fusion+Recurrent
Oncomine Prioritized Fusion+Mitelman Annotated
Oncomine Prioritized Fusion+One partner is an Oncomine Gain of Function gene involved in 3 or more Pan-Disease Priority Fusions
Oncomine Prioritized Fusion+One partner is a Sanger Oncogene (goo.gl/JQBw9) involved in 3 or more Pan-Disease Priority Fusions Mutations Data and Filtering Mutation data for Integrative Analysis was obtained from Oncomine NGS Mutation data. Individual genes are classified into predicted functional classes, namely "Gain of Function" and "Loss of Function" to reflect their relative enrichment in potential activating or deleterious mutations. This classification is based on the combination of relative frequencies and the significance of the mutations observed in the gene assessed by a p-value. A "Gain of Function" gene will have a relatively high frequency of Hotspot Missense mutations and a low frequency of Deleterious mutations, while a "Loss of Function" gene contains a large fraction of Deleterious mutations.

Copy Number Segmentation and Quantification

DNA copy number data for each TCGA sample was obtained from Oncomine.

Measurements from multiple reporters for a single gene were averaged.

Minimum Common Region (MCR) Peak Generation

In genes that were recurrently amplified (4 or more copies) or deleted (1 or less copy), peaks were identified independently in 25 cancer types by applying MCR analysis on Oncomine clinical samples. To define peaks, contiguous genomic regions with multiple genes that were significantly aberrant (common regions) were identified first. In every common region, a Peak is defined as one or more genes whose aberrant sample count meets or exceeds a peak threshold. In every cancer, common regions are defined as regions whose aberrant sample count meet or exceed a common region threshold. The baseline, average number of aberrant samples observed across all genes, is calculated for every arm of every chromosome in every cancer.

mRNA Gene Expression

Expression data was obtained from the Broad GDAC's TCGA Standard Data.

Clinical Data Curation

Patient clinical data was obtained from TCGA and curated by Compendia. Curated data types included demographics, major clinical and histological disease subtypes, and clinical outcome data. All properties were standardized to be consistent across the diseases.

Construction of Clinically Relevant Subsets

Curated clinical data obtained from TCGA and Oncomine NGS data was used and the rules in Table 14 were applied to define the Clinical Subsets:

consistency. The unique identifier for a gene is the gene Entrez ID. The unique identifier for a patient is the TCGA Patient Barcode (first 12 digits of the TCGA barcode).

Driver Event Definition

Mutation, fusion and copy number events are defined based on the following criteria for genomic events:

Fusions: Oncomine recurrent priority fusions

Mutations: Oncomine driver mutations from pan cancer driver genes

CNVs: CBI identified peaks, and gene amp/del within peaks

Genetic Event Definition and Roll-up

A genetic event is a genomic aberration, representing either an individual mutation, fusion, or copy number event, or a combination of events at the gene or pathway level. The events are 'rolled-up' according to the flowchart shown in FIG. 4. When multiple events are combined to construct rolled up events, the set of measured patients for the rolled

TABLE 14

Rules to define the Clinical Subsets

| Disease | Clinical Subtype | Source | Rules |
|---|---|---|---|
| Invasive Breast Carcinoma | Triple Negative | Phenomic Data | ERBB2 Status = ERBB2 Negative<br>Estrogen Receptor Status = Estrogen Receptor Negative<br>Progesterone Receptor Status = Progesterone Receptor Negative |
|  | ER Positive | Phenomic Data | Estrogen Receptor Status = Estrogen Receptor Positive |
|  | ER Positive and HER2 Negative | Phenomic Data | Estrogen Receptor Status = Estrogen Receptor Positive<br>ERBB2 Status = ERBB2 Negative |
| Gastric Adenocarcinoma | Hyper-Mutator | Oncomine NGS Data | Patient Mutation Count >= 400 |
| Lung Adenocarcinoma | KRAS Mutation (No ALK Fusion and No EGFR Mutation) | Oncomine NGS Data | Oncomine Mutation Classification = Hotspot |
|  | Triple Negative | Oncomine NGS Data | No EGER Mutation (AND) No KRAS Mutation (AND)<br>No ALK Fusion |
| Rectal Adenocarcinoma | KRAS Mutation | Oncomine NGS Data | Oncomine Mutation Classification = Hotspot |
|  | KRAS Mutation, Stage 3 or 4 | Oncomine NGS Data/<br>Phenomic Data | Oncomine Mutation Classification = Hotspot (AND)<br>Stage = Stage III (OR) Stage IV |
|  | KRAS Wildtype | Oncomine NGS Data | No KRAS Mutation |

Pathways

Manually curated Compendia pathway definitions were used to summarize gene-level aberrations in the integrative analysis. The pathways represent clinically relevant pathway modules, and several modules may cover a major biological pathway, and a single gene may be present in one or more pathway module definitions.

Data Integration

Figure 3:
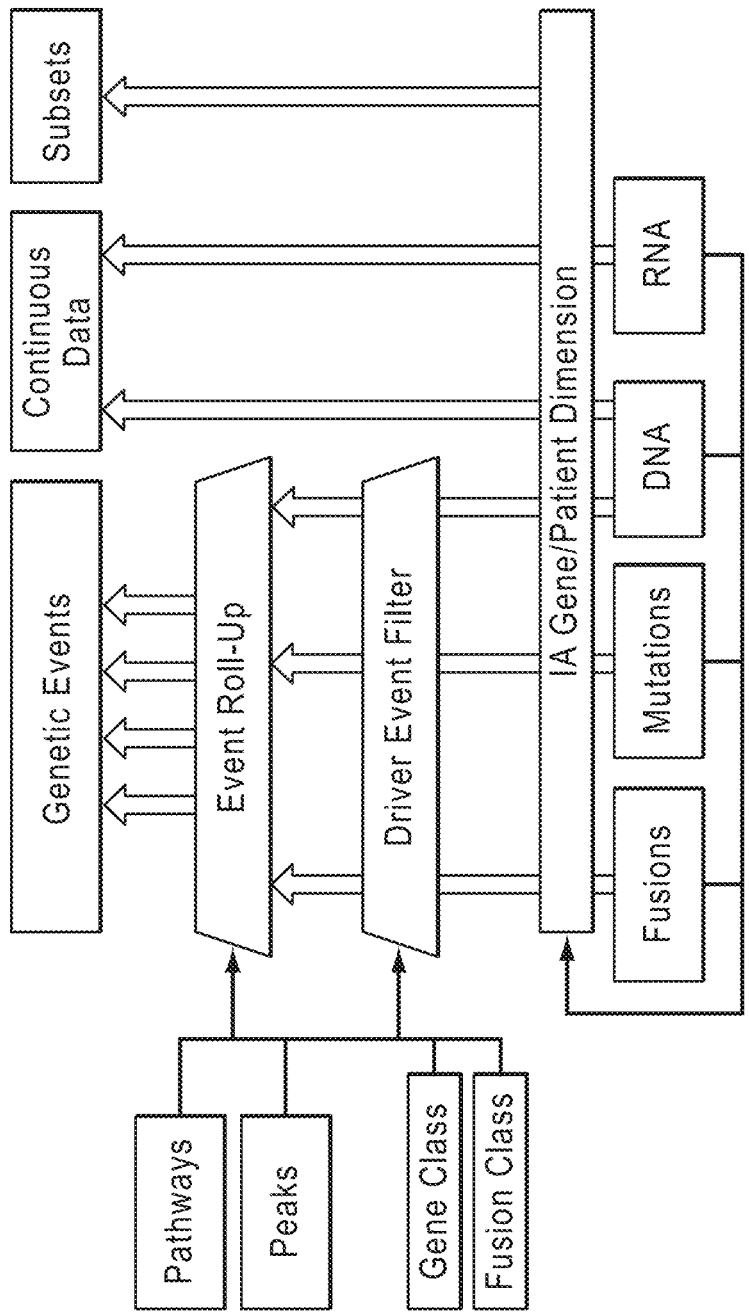
FIG. 3 summarizes the data flow that integrates the various data types into a Genetic Event Database (GEDB).

The diagram in FIG. 3 summarizes the data flow that integrates the various data types into a Genetic Event Database (GEDB). All further analyses are conducted using the GEDB. The process has 4 main steps.

Map the data to the internal IA gene and patient dimension

Define events and driver events in each data type

Roll-up individual events to the gene and pathway level

Combine the events into the Genetic Events Database.

Gene and Patient Dimensions

A single gene and patient dimension was constructed which encompassed all patients and genes measured across all disease and data types. The genes and patients were given internal identifiers, and all data in the IA was referenced against these identifiers for gene name and patient barcode up event becomes the intersection of the patients measured for all 3 data types. Patients positive are only included if fully measured.

Analyses

Once all the driver genetic events are constructed, a set of analyses is performed on each genetic event, calculating frequencies, associations and relationships within diseases (and pan-cancer where appropriate). The following are short descriptions of each analysis:

Frequency

Frequency is the occurrence of a driver event among the patients in which it was measured. Frequencies are calculated within disease and pan-cancer.

Clinical Association Analysis

Each driver event is tested for association against a set of available clinical subtypes. Each association is tested using a Fischer's exact test by comparing the occurrences of the genetic event in patients of one clinical subtype versus another. For example a Loss of Function mutation may be tested for over-representation in Smokers versus Non-Smokers, or in Stage I versus Stage II lung cancer. A total of 136 subtype pairs are tested against each event, the properties that define the subtypes are listed below (some properties may be disease-specific). At least 4 patients total, with at least 1 patient in each class are required to perform the test.

Clinical Outcome Analysis

Each driver event is tested for association with clinical outcome using log-rank test. Only the set of patients with available clinical data are used for the calculation, so the number of patients included in the test may be less than the number of patients measured for the driver event. At least 4 patients positive for driver event are required to perform the test. Survival time is presented in years, and individual alive/dead events are clearly marked on a Kaplan-Meier curve. P-values were corrected for multiple testing (q-values). Events with a q-value less than 0.1 were considered.

The results of the analysis are shown in Tables 15 and 39. In Tables 15 and 39, the columns provide the following information:

The "Subset" column provides the clinically relevant cancer type.

The p-value column is the p-value.

The q-value column is the corrected p-value. Events with q<0.1 are included in the table.

The no. positive column is the number of patients positive for an event type.

The Total no. of patients column is the total number patients assessed.

The Cytoband column is the chromsomal location of the gene(s).

The Genes (Entrez ID) column is a List of gene(s) and corresponding Entrez id.

The Druggable genes column indicates if any gene(s) are targets for drugs in active trials, approved, or otherwise commercially available.

The KM Evidence column provides the Kaplan-Meier evidence. The KM evidence indicates if the event type supports good or poor prognosis in the particular cancer type.

Tables 15 and 39 contains more than 100 gain-of-function mutations, loss-of-function mutations, in-peak gene amplification/deletions, and fusion events for various cancer types with a q<0.1. Gene(s) within each event and cancer type are included along with their chromosomal locations, druggability information and clinical outcome associations, as indicated in the column information above.

Example 5—Integrated Data Analysis

Oncomine NGS Integrated Analysis. The Oncomine NGS Integrative Analysis was designed to bring together the largest possible set of core integrated genomic and phenomic data to enable scientific workflows that interrogate relationships across data types and cancer types, summarizing the analyses at multiple biological levels of abstraction, such as genes and pathways.

Terminology:

Aberration—A genomic structural variation or alteration of DNA; Examples include: mRNA over/under-expression, copy number amplification/deletion, mutation, and gene fusion.

Driver—Aberration identified as a potential cancer driver by Oncomine methodology described in this document; examples include gain of function mutations, gene amplifications in a peak amplification region, or gene fusions Roll-up—A summary of all mutation, fusion, or copy-number aberrations for the gene or pathway; Only patients measured for all three aberration types are included in the rolled-up.

Hotspot Mutation—A mutation that is recurrent (n≥3), and classified as either an in-frame insertion/deletion, non-stop or missense.

Patient null set—The set of patients measured for a genetic aberration.

Patient positive set—The set of patients harboring the genetic aberration.

Gene null set—The set of genes measured by the experimental platform used to assess the genetic aberration.

Mitelman—Database of Chromosome Aberrations and Gene Fusions in Cancer manually curated from literature (goo.gl/PnXMT).

RPKM—"Reads Per Kilobase per Million"; a method for RNASeq data quantification that normalizes for total read length and number of sequencing reads (Mortazavi et al. 2008).

RSEM—"RNA-Seq by Expectation Maximization" a method for RNASeq data quantification that estimates the best probable distribution of reads among the expected transcripts provides relative transcript abundances as a fraction of the total read pool. (Li and Dewey 2011)

Data Sources.

An effort was made to collect the largest overlapping set of data available for each sample. The data in this release of the NGS Integrative Analysis Browser was obtained from The Cancer Genome Atlas (TCGA), the Cancer Cell Line Encyclopedia (CCLE), COSMIC Cell Lines Project, and a number of research publications, either directly or after being subjected to Oncomine processing and analysis methods. Due to the uneven coverage of all data types across the source datasets, some cancer types have a greater number of patients covered in multiple data types.

The Oncomine NGS Mutations release used in the Integrative Analysis contained a number of hand-curated datasets obtained from NGS mutation studies in peer-reviewed publications. For a full list of publications that contributed mutation data to integrative analysis, please see the Oncomine NGS Mutations methods documentation. The following datasets contained multi-dimensional NGS data, providing both, mutations and copy number data. Copy number data for these datasets was processed in the same way as the copy number data obtained from TCGA.

Cell line data includes mutation, fusion, and copy number datasets. Cell line data was processed in the same way as the clinical tumor data—with mutation and fusion cell line data obtained from the Oncomine™ NGS Mutation and Oncomine™ NGS Fusion Power Tools, respectively. Copy number data for cell lines was processed using the standard Oncomine copy number pipeline. Although there were two disparate cell line datasets used—CCLE and COSMIC—our standardization of cell line disease types and names has enabled us to cross reference the two datasets and combine the CCLE copy number data, COSMIC mutation data and Oncomine fusions calls (based on CCLE RNASeq data). Therefore, numerous cell lines in this release have had their exomes systematically characterized for all three types of aberrations. Cell line data was summarized using the Oncomine cancer type definitions to be directly comparable to tumor data, although the summarization was performed separately for tumor and cell lines.

Phenomic Data

Clinical Patient Metadata Curation.

Patient clinical data was obtained from primary sources and curated by Compendia. Curated data types include demographics, major clinical and histological disease subtypes, and clinical outcome data. All cancer type-independent properties (such as age or survival) were standardized for consistency across cancer types. Certain disease stages were merged to obtain higher patient counts within a stage. For example, Stage Ia and Ib may be combined as Revised Stage I.

Following is the list of most populated properties and corresponding values captured by the curation process. Not all properties were available for all patients.

| Property Name | Property Value |
|---|---|
| Age | 10-14 Years |
| | 15-19 Years |
| | 20-29 Years |
| | 30-39 Years |
| | 30-39 Years |
| | 40-49 Years |
| | 50-59 Years |
| | 60-69 Years |
| | 70-79 Years |
| | 80-89 Years |
| | 90+ Years |
| ERBB2 Status | ERBB2 Negative |
| | ERBB2 Positive |
| Estrogen Receptor Status | Estrogen Receptor Negative |
| | Estrogen Receptor Positive |
| FAB Subtype | FAB Subtype M0 |
| | FAB Subtype M1 |
| | FAB Subtype M2 |
| | FAB Subtype M3 |
| | FAB Subtype M4 |
| | FAB Subtype M5 |
| | FAB Subtype M6 |
| | FAB Subtype M7 |
| Gleason Score | Gleason Score 10 |
| | Gleason Score 6 |
| | Gleason Score 7 |
| | Gleason Score 8 |
| | Gleason Score 9 |
| Grade | Grade 1 |
| | Grade 2 |
| | Grade 3 |
| | Grade 3-4 |
| | Grade 4 |
| Hepatitis Virus Infection Status | Hepatitis B Virus Positive |
| | Hepatitis C Virus Positive |
| Human Papillomavirus Infection Status | HPV Negative |
| | HPV Positive |
| | HPV Type 16 and 52 Positive |
| | HPV Type 16 Positive |
| | HPV Type 45 Positive |
| | HPV Type 58 Positive |
| Metastatic Event Status | Metastatic Event |
| Microsatellite Status | Microsateilite Instable |
| | Microsateilite Stable |
| Overall Survival Status | Alive |
| | Dead |
| Overall Survival Status (Detailed) | Alive |
| | Alive With Disease |
| | Alive Without Disease |
| | Dead |
| | Dead With Disease |
| | Dead Without Disease |
| Patient Treatment Response | Unknown Therapy Complete Response |
| | Unknown Therapy Partial Response |
| | Unknown Therapy Progressive Disease |
| | Unknown Therapy Stable Disease |
| Progesterone Receptor Status | Progesterone Receptor Negative |
| | Progesterone Receptor Positive |
| Race/Ethnicity | American Indian or Alaska Native |
| | Asian |
| | Black or African American |
| | Hispanic or Latino |
| | Native Hawaiian or Other Pacific |
| | White |
| Recurrence Status | Biochemical Recurrence |
| | No Biochemical Recurrence |
| | Recurrence |

-continued

| Property Name | Property Value |
|---|---|
| Recurrence Status (Detailed) | Local Recurrence |
| | Metastatic Recurrence |
| | Recurrence |
| Revised M Stage | M0 |
| | M1 |
| Revised N Stage | N0 |
| | N1 |
| | N2 |
| | N3 |
| Revised Smoking Status | Never Smoker |
| | Smoker |
| Revised Stage | FIGO Stage I |
| | FIGO Stage II |
| | FIGO Stage III |
| | FIGO Stage IV |
| | Stage I |
| | Stage II |
| | Stage III |
| | Stage IV |
| Revised T Stage | T |
| | T0 |
| | T1 |
| | T11 |
| | T12 |
| | T2 |
| | T21 |
| | T22 |
| | T3 |
| | T4 |
| Sex | Female |
| | Male |
| *TCGA PAM50 Subtype | Basal-like |
| | HER2-enriched |
| | Luminal A |
| | Luminal B |
| | Normal-like |
| *TCGA RPPA Subtype | Basal |
| | Her2 |
| | Luminal A |
| | Luminal A/B |
| | Reactive I Group |
| | Reactive II Group |
| *TCGA Subtype | Basal |
| | CIN |
| | Classical |
| | Invasive |
| | Mesenchymal |
| | MSI/CIMP |
| | Neural |
| | Primitive |
| | Proneural |
| | Secretory |
| Metastatic Event Follow-up Time | (Days) |
| Overall Survival Follow-up Time | (Days) |
| Recurrence Follow-up Time | (Days) |

Properties prefixed by "TOGA" were obtained and curated from the TOGA publications that defined the molecular subtypes for invasive breast carcinoma, glioblastomasquamous cell lung carcinoma and colorectal cancers.

Genomic Event Data: Fusions Data Filtering.

Fusion data for the Integrative Analysis Browser was obtained from Oncomine NGS Fusion data released in November, 2013. Only fusions identified as Oncomine Priority Fusions were included in the Integrative Analysis Browser.

Oncomine Prioritized Fusion is a priority scheme developed at Compendia to capture attributes of known true positive fusion events and characterize a subset of observed gene fusions as high-confidence priority fusions. Criteria used to define priority fusions include: valid 5' to 3' orientation, non-adjacent fusion partners, uniquely mapping spanning reads, non-paralogous fusion partners, not observed in normal tissue, and non-overlapping with redundant regions in the genome.

The patient null set for the fusion data is the full set of patient tumor samples processed in the fusion analysis; data for only one tumor sample (preferably the primary, non-recurrent tumor) per patient was retained. The gene null set is the set of genes in RefGene as of May 2012. Fusions were included in the Integrative Analysis Browser if they were an Oncomine Priority Fusion, had exon expression evidence that was "supported" or "neutral", and met one of the following criteria:

Recurrent (occurred in 2 or more patients)

Annotated in the Mitelman database of known structural variations

Contained a gene partner that is an Oncomine Gain of Function gene that is involved in 3 or more Pan-Disease Priority Fusions Contained a gene partner that is a Sanger Oncogene (goo.gl/JQBw9) that is involved in 3 or more Pan-Disease Priority Fusions.

Mutation Data Filtering.

Mutation data for Integrative Analysis was obtained from Oncomine NGS Mutation data released in November, 2013. Only non-silent mutations in coding gene regions were included in the Integrative Analysis Browser.

The patient null set is the full set of patients processed in the mutation analysis; data for only one tumor sample (preferably the primary, non-recurrent tumor) per patient was retained. The gene null set is the set of genes in Ref Gene as of March 2012.

Mutations with the following variant classifications were not included in the Integrative Analysis Browser: Silent, 5' UTR, 3' UTR, RNA, Non-Coding Exon.

Calling Amplifications/Deletions.

DNA copy number data for each sample was obtained from the 2013 Q4 Oncomine Standard Data Build, in which all copy number data available from TCGA and the hand-curated publications as of October 2013 was standardized.

The patient null set for this analysis was the set of patients measured for copy number data as of October 2013 and the set of patients measured in the hand-curated publications. Data for only one tumor sample (preferably the primary, non-recurrent tumor) per patient was retained. The gene null set for this data was the Oncomine DNA Copy Number platform, based on RefSeq coordinates (hg18) provided by UCSC RefGene build July 2009, and measures 18,796 genes. Measurements from multiple reporters for a single gene were averaged.

The $\log_2$ of the estimated copy value was used to make amplification/deletion (amp/del) calls, with cutoffs of >1.0 and <−1.0, respectively. No amp/del calls were made $\log_2$ (estimated copies) that were ≥−1.0 or ≤+1.0.

Genomic Continuous Data: Copy Number Segmentation and Quantification.

DNA copy number data for each sample was obtained from the 2013 Q4 Oncomine Standard Data Build, in which all copy number data available from TCGA as of September 2013 and all copy number data from the hand-curated publications was standardized.

The patient null set for this analysis was the set of TCGA patients measured for copy number data as of October 2013 and the set of patients measured in the hand-curated publications. Data for only one tumor sample (preferably the primary, non-recurrent tumor) per patient was retained. The gene null set for this data was the Oncomine DNA Copy Number platform, based on RefSeq coordinates (hg18) provided by UCSC Ref Gene build July 2009, and measures 18,796 genes. Measurements from multiple reporters for a single gene were averaged.

Copy number data was segmented and quantified using the standard Oncomine processing pipeline. Segmentation is a method used to identify contiguous regions of amplification or deletion. These regions or "segments" can include multiple genes or single genes. A copy number value is computed for each segment based on the mean value for the reporters contained in the segment. Genes are mapped to segments and assigned a value. This gene level data is then reported. Please see the Oncomine DNA Processing Pipeline White Paper for more information.

mRNA Expression Data.

Expression data was obtained from the Broad GDAC's TOGA Standard Data build from September, 2013.

The patient null set for this data was the set of patients with available RNASeq data in the Broad GDAC 2013_08_09 stddata build; data for only one tumor sample (preferably the primary, non-recurrent tumor) per patient was retained. The gene null set for this data was different per disease and corresponded to the TOGA Gene Annotation Files (GAFs) used for the RNASeq quantification.

The TOGA currently employs two methods of RNASeq quantification—V1 (RPKM) and V2 (RSEM)—which are not directly numerically comparable. To avoid a potentially inaccurate numerical conversion, we use data from a single quantification method on a per-disease basis, choosing the format based on maximal coverage. In line with efforts by the TOGA to process (and re-process) all available RNASeq data using RSEM (V2), RSEM (V2) data was available for most samples. An exception is Gastric Adenocarcinoma where RPKM (V1) data was used. Normalized, gene-level quantification values were obtained for both RSEM and RPKM and converted to $\log_2$ values (minimum non-zero RPKM or RSEM values were set at −12). A gene was considered to be expressed if it had a $\log_2$ value>−12.

Oncomine Driver Reference Data: Minimum Common Region (MCR) Peak Generation and Gene Selection.

In order to identified cancer driver genes subject to amplifications and deletions, a peak-clustering method was performed to select genes frequently aberrant across multiple cancer types. First copy number peaks were defined across the largest-available set of copy number data (i.e data beyond what is included in the Integrative Analysis) within many cancer types. Next, the gene lists defined by the peaks were clustered in order to identify genes appearing in copy number peaks in multiple samples and multiple diseases. The parts of the method are described in more detail below.

An aberration may be classified as a "driver" aberration—or one that is considered potentially interesting according to one of the data type-specific Oncomine classification methods. Driver aberrations will be captured as events independently of other aberrations (non-driver aberrations are termed "any"). For example, a patient who has a "driver" mutation will be positive for two aberrations—a "driver" mutation, and an "any" mutation. Each of the measured data types has a set of rules for determining the driver events.

A set of continuous genomic regions subject to amplification or deletion were identified using the Oncomine MCR analysis by applying it to Oncomine's 10,249 clinical samples grouped into 25 cancers.

The patient null set for the peak definition was 10,249 clinical samples from Oncomine (See Table below). The gene null set for this data was the Oncomine DNA Copy Number platform, based on Ref Seq coordinates (hg18) provided by UCSC ref Gene build July 2009, and measures 18,796 genes.

Data for the minimal common region (MCR) analysis was sourced from Oncomine DNA copy number browser that contains >20,000 clinical specimens, xenografts and cell lines across diverse cancer types. MCR analysis identifies regions of recurrent copy number amplifications or deletions by analyzing the data at three levels—pan-cancer (across all cancer types), general cancer type (across cancer types), and intermediate cancer type or specific cancer sub-types. Briefly, the method first computes a common region (CR) defined as a contiguous genomic region that is amplified or deleted in 2 or more samples. The minimum thresholds for amplifications and deletions were set at log $2 \geq 0.9$ (3.7 copies or more) and log 2-0.9 (1 copy or less) respectively. Then the peak regions within these common regions are defined as—(i) one or more genes that are aberrant in the highest number of samples (n) and also those that are aberrant in one less than the highest number (n−1) and (ii) genes that are aberrant in 90% of the highest aberrant sample count.

Cluster Analysis to Identify Common Peaks Regions.

MCR analysis was performed. Peak regions identified by the MCR analysis were further filtered across the three analysis types (that is, pan-cancer, general cancer type, and specific cancer type analyses) using the criteria listed in table below. Note that only selected number (~40) of intermediate or specific cancer types (also listed further below) were included.

Filtering criteria to identify highly amplified/deleted regions from MCR analysis:

|  | Pan-cancer | General cancer type | Intermediate or specific cancer type |
| --- | --- | --- | --- |
| Aberrant sample count | $\geq 4$ | $\geq 4$ | $\geq 4$ |
| Maximum log2 copy number- Amplifications | $\geq 2$ (8 or more copies) | $\geq 2$ (8 or more copies) | $\geq 2$ (8 or more copies) |
| Maximum log2 copy number- Deletions |  | $\leq -1$ (1 or less copies) | $\leq -1$ (1 or less copies) |
| Median frequency | $\geq 0.5\%$ | $\geq 0.5\%$ | $\geq 1.0\%$ |
| Intermediate or specific cancer types | Include all | Include all | Selected ICTs (see Table 6) |

Selected intermediate or specific cancer types included in the filtering criteria described above:

| General Cancer Type | Intermediate or specific cancer types |
| --- | --- |
| Bladder | Bladder Urothelial Carcinoma |
| Brain and CNS | Glioblastoma; Medulloblastoma; Neuroblastoma |
| Breast | N/A |
| Cervical | Cervical Adenocarcinoma; Cervical Squamous cell carcinoma |
| Colorectal Cancer | Colorectal Adenocarcinoma |
| Esophageal | Esophageal Adenocarcinoma; Esophageal squamous cell carcinoma |
| Gastric | Gastric Adenocarcinoma |
| Head and Neck | Head-Neck Squamous Cell Carcinoma; Thyroid gland follicular carcinoma; Thyroid Gland Papillary Carcinoma |
| Kidney | Clear Cell Renal Cell Carcinoma; Papillary Renal Cell Carcinoma |
| Leukemia | Acute Lymphoblastic Leukemia; Acute Myeloid Leukemia; Chronic Lymphocytic Leukemia; Chronic Myelogenous Leukemia; Myelodysplastic Syndrome |
| Liver | Hepatocellular Carcinoma |
| Lung Cancer | Lung Adenocarcinoma; Small Cell Lung Carcinoma; Squamous Cell Lung Carcinoma |
| Lymphoma | Burkitt's Lymphoma; DLBCL; Follicular Lymphoma; Hodgkin's Lymphoma; Mantle Cell Lymphoma; |
| Melanoma | Cutaneous Melanoma; Multiple Myeloma |
| Other | Endometrial Endometrioid Adenocarcinoma |
| Ovarian | Ovarian Clear Cell Adenocarcinoma; Ovarian Serous Adenocarcinoma |
| Pancreas | Pancreatic Ductal Adenocarcinoma; Prostate Adenocarcinoma |
| Sarcoma | GIST |

Figure 11:
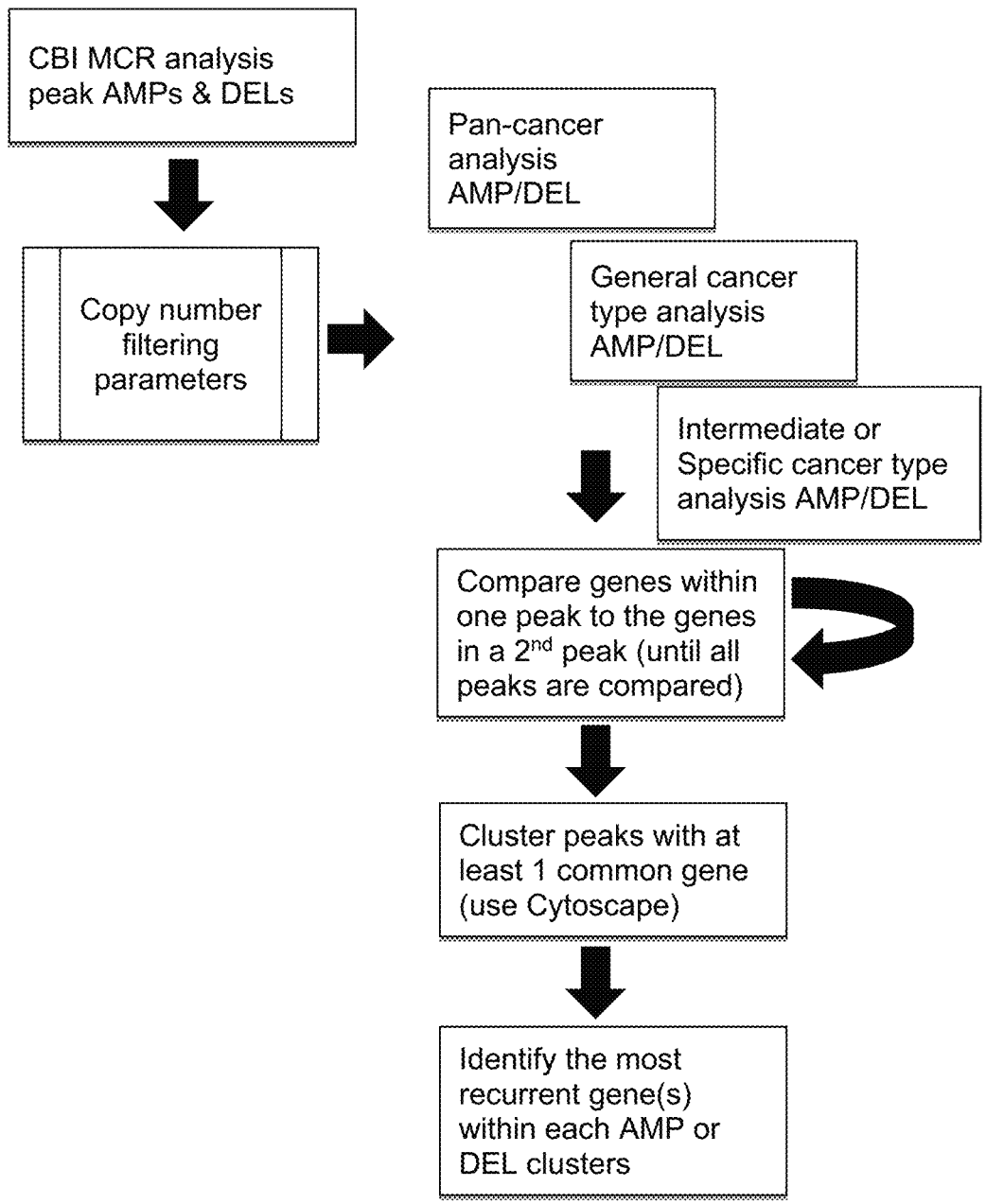
FIG. 11 shows an exemplary process for identifying potential cancer driver genes.

Next, to identify the most recurrent peak regions and genes across multiple cancer types we used Cytoscape 2.8.3 [Markiel et al. 2003; Smoot et al. 2001] to build network clusters. Briefly, the analysis compares every gene in a given peak region to genes in other peak regions and clusters peaks with at least one common gene. The most recurrent amplified or deleted gene(s) within each cluster was then considered as a potential candidate driver gene. The process is shown in FIG. 11.

Identification and Creation of Clinically Relevant Cancer Subtypes. In order to provide subsets of patients for more focused analysis, several clinically relevant cancer subtypes were identified and curated using a combination of clinical phenomic, and categorical genomic data. The phenomic data was sourced from the TCGA Web Portal or the Supplementary Methods of the hand-curated publications.

The following rules were applied to define the Clinical Subsets:

| Cancer Type | Clinical Subtype | Data Source | Data Interpretation Rules for Inclusion in Subtype |
|---|---|---|---|
| Invasive Breast Carcinoma | Triple Negative | TCGA Web Portal | ERBB2 Status = "ERBB2 Negative" Estrogen Receptor Status = "Estrogen Receptor Negative" Progesterone Receptor Status = "Progesterone Receptor Negative" |
| | ER Positive | Phenomic | Estrogen Receptor Status = "Estrogen Receptor Positive" |
| | HER2 Positive | Phenomic | ERBB2 Status = "ERBB2 Positive" |
| | ER Positive and HER2 Positive | Phenomic | Estrogen Receptor Status = "Estrogen Receptor Positive" ERBB2 Status = "ERBB2 Positive" |
| | ER Positive and HER2 Negative | Phenomic | Estrogen Receptor Status = "Estrogen Receptor Positive" ERBB2 Status = "ERBB2 Negative" |
| Gastric Adenocarcinoma | Diffuse | Phenomic | Cancer Type = "Diffuse Gastric Adenocarcinoma" |
| | Intestinal | Phenomic | Cancer Type = "Gastric Intestinal Type Adenocarcinoma" |
| | Hyper-Mutator | Oncomine NGS | Patient Mutation Count ≥ 400 |
| Head and Neck Squamous Cell Carcinoma | HPV Positive | Phenomic | Human Papillomavirus Infection Status = "HPV Positive" |
| | HPV Negative | Phenomic | Human Papillomavirus Infection Status = "HPV Negative" |
| Cervical Squamous Cell Carcinoma | HPV Positive | Phenomic | Human Papillomavirus Infection Status = "HPV Positive" |
| Lung Adenocarcinoma | EGFR Mutation | Oncomine NGS Mutation | Oncomine Mutation Classification = "Hotspot" |
| | KRAS Mutation (No ALK Fusion and No EGFR Mutation) | Oncomine NGS Mutation and Fusion | Oncomine Mutation Classification = "Hotspot" |
| | ALK Fusion | Oncomine NGS Fusion | Have Oncomine Driver ALK fusions |
| | Triple Negative | Oncomine NGS Mutation and Fusion | No EGFR Mutation AND No KRAS Mutation AND No ALK Fusion |
| Colon and Rectal Adenocarcinoma | KRAS Mutation | Oncomine NGS Mutation | Oncomine Mutation Classification = "Hotspot" |
| | KRAS Mutation, Stage 3 or 4 | Oncomine NGS Mutation and Phenomic | Oncomine Mutation Classification = "Hotspot" AND Stage = "Stage III" OR "Stage IV" |
| | KRAS Wildtype | Oncomine NGS Mutation and Fusion | Oncomine Mutation Classification = "Hotspot" AND No KRAS Fusion |
| | Microsatellite Stable | Phenomic | Microsatellite Status = "Microsatellite Stable" |
| | Microsatellite Instable | Phenomic | Microsatellite Status = "Microsatellite Instable" |
| Endometrial Endometrioid Carcinoma | Microsatellite Stable | Phenomic | Microsatellite Status = "Microsatellite Stable" |
| | Microsatellite Instable | Phenomic | Microsatellite Status = "Microsatellite Instable" |

Pathways.

Manually curated Compendia pathway definitions were used to summarize gene-level aberrations in the Integrative Analysis Browser. The pathways represent clinically relevant pathway modules, and several modules may cover a major biological pathway. A single gene may be present in one or more pathway definitions, but care was taken to eliminate largely redundant pathways, in which one module is a complete subset of another. There are 67 total pathways, ranging in size from 42 genes (e.g. MAPK pathway) to 2 genes (e.g. IGF1/IGF1R and several others).

Data Integration.

This section summarizes the data flow that integrates the primary data onto common patient and gene dimensions and constructs the Genetic Event Database (GEDB), which is comprised of all the aberrations which will be subject to Integrative Analyses. The process has 4 main steps: (1) Integrate primary data using universal gene and patient dimensions, (2) Call aberration events for each data type and define driver aberrations (3) Roll-up individual events to the gene and pathway level and integrate events, and (4) Construct the Genetic Event Database by defining patient status for each event.

Constructing and Mapping to the Gene and Patient Dimensions.

The varied data types included in the Integrative Analysis may have been measured on different experimental platforms and on sets of patients that are not perfectly overlapping. Therefore, care was taken to include all patients and genes measured while avoiding duplicate or conflicting entries.

For each data type, a gene and patient "dimension" was constructed, enumerating the genes and patients measured in the data. The dimension for each data type may be different, as indicated by the patient dimension overlap diagram below (numbers for illustration only), in this case, for Invasive Breast Carcinoma.

Gene and patient dimensions were gathered from each cancer and data type, and a non-redundant superset of all the patient and gene identifiers in the Integrative Analysis was constructed. The bars in the figure below represent blocks of patient identifiers (if sorted by said identifier) for patients measured for the certain aberration types.

Redundancy for patients was determined based on the unique patient identifier—currently the first 12 characters of the TCGA Tumor Sample Barcode (e.g., TCGA-AB-1234).

Redundancy for genes was determined based on the unique gene identifier—currently the Entrez Gene ID. The genes were also compared against the Oncomine gene set, and when a gene symbol conflict was found—one Entrez ID assigned two or more gene symbols—the gene symbol from Oncomine was used. Several (12) of the measured genes contained Entrez ID that have been discontinued and thus may not represent the most accurate gene model. The gene symbols for these genes were marked with the word "discontinued".

Once constructed, the non-redundant gene and patient dimensions were indexed to provide a consistent internal identifier for each gene and patient in the dataset. All the unique patient and gene identifiers in the primary data were then mapped to the dimension patient and gene identifiers. Gene and patient metadata, such as gene symbols and patient clinical data, are thus always mapped through the respective dimensions, providing consistency in naming and annotation. The total number of unique genes and patients in the Integrative Analysis is as follows:

| Genes | 23,340 |
|---|---|
| Patients | 11,476 |

The patient dimension along with the dataset-specific mapping of the patients helps correctly identify fully wild-type patients—those who are measured for all aberration types but do not contain any aberrations.

A patient could thus be measured for any number of aberrations, and can only be aberrant for those events measured. The aberrations a patient is measured for determined the types of analyses that patient would be included in:

| | Patient "X" Measured for: | Patient "X" Excluded from: | Patient "Y" Measured for: | Patient "Y" Excluded from: |
|---|---|---|---|---|
| Clinical* | | Clinical | ✓ | DNA vs. RNA |
| Mutations | ✓ | Associations, | ✓ | Correlation, |
| Fusions | ✓ | Clinical | ✓ | Differential |
| Copy Number | ✓ | Outcome | ✓ | Expression, |
| Expression | ✓ | Associations | | Expressed Frequency |

*"Measured for: Clinical" indicates clinical metadata was present for patient.

Event Model.

Each genomic aberration from the mutation, fusion, and copy number data sets was identified as an aberration event—a term used to define an event of interest that will be subject to the various pre-defined Integrative Analyses. Each aberration is part of three broad levels of events—data type-specific events, gene-specific but data type independent events, and pathway-specific but gene or data type independent events. The latter two levels are considered "rolled-up" events.

The specific rules for aberration event definition as well as the "level" and "driver" schemes are described below.

Mutation Event Caller.

Oncomine Pan-Cancer Mutation Classification: A mutation is classified as a "Hotspot" if it is: Recurrent (occurs in 3 or more samples at the same amino acid position) AND Annotated with one of the following variant classifications: In-Frame insertion/deletion, Nonstop, Missense. A mutation is classified as "Deleterious" if it is: Not recurrent AND Annotated with one of the following variant classifications: Frame-Shift insertion/deletion, Nonsense. Recurrence is measured across all cancer types analyzed as part of the Oncomine NGS Mutation Browser.

Oncomine Pan-Cancer Gene Classification.

As part of the Oncomine NGS Mutation Browser pipeline, individual genes are classified into predicted functional classes, namely "Gain of Function" and "Loss of Function" to reflect their relative enrichment in potential activating or deleterious mutations. This classification is based on the combination of relative frequencies and the significance of the mutations observed in the gene assessed by a p-value. A "Gain of Function" gene will have a relatively high frequency of hotspot (recurrent in 3 or more samples) missense mutations and a low frequency of deleterious mutations, while a "Loss of Function" gene contains a large fraction of deleterious mutations. Pan-cancer gene classifications are based on the mutations observed across all cancer types.

Mutation Aberration Events.

For each patient gene mutation (as defined by the Mutation Data Filtering section), either one or two mutation events will be created, depending on whether the mutation is classified as a driver aberration. A driver mutation aberration is defined as a "Hotspot" mutation present in a "Gain of Function" gene, or a "Hotspot" or "Deleterious" mutation present in a "Loss of Function" gene. For driver mutations, both a driver event and an any event is created. For non-driver mutations, only an any event is created. Pan-Cancer mutation and gene classification was used for all analysis subsets; so, gene classifications may sometimes differ between Integrative Analysis and Oncomine NGS Mutation Browser.

The table below gives the description and examples of mutation events that could be created for each gene:

| Event Type | Description of Event | Example Aberration Name | Driver Status |
|---|---|---|---|
| Gain of Function Mutation | A "Hotspot" mutation and a "Gain of Function" gene classification | EGFR Gain of Function Mutation | driver |
| Loss of Function Mutation | A "Hotspot" or "Deleterious" mutation in a "Loss of Function" gene | APC Loss of Function Mutation | driver |
| Any Gene Mutation | Any mutation in a gene | TTN <Any Gene Mutation> | any |

Fusion Event Caller.

Only Oncomine Priority fusions are included in the Integrative Analysis. Of the Priority Fusions, the driver fusions were defined as those labeled known oncogenes by the Mitelman database OR fusions that either did not have sufficient exon expression data and are recurrent, OR fusions that have exon expression data and a significant p-value for exon expression imbalance of the two gene partners (See Oncomine NGS Fusions Methods Documentation for details of exon imbalance classification). For each gene, an event will created for each unique observed 5'-3' combination of the gene partners. For example, for PML-RARA balanced translocation both isoforms are observed and hence two fusion events will be called—for PML-RARA end RARA-PML respectively.

| Event Type | Description of Event | Example Aberration Name | Driver Status |
|---|---|---|---|
| Fusion | Driver fusion involving gene | PML-RARA Fusion | driver |
| Any Fusion | Any fusion involving gene | FRS2-LYZ Fusion | any |

Copy Number Event Caller.

Each Amp/Del (see Calling Amp/Dels) that was called was defined as an any event for the aberrant gene. If the amp/del occurred in a gene that was part of a peak definition (see MCR Peak Generation) in a certain cancer type, a driver ampdel event was also created for that gene. The driver definition for copy number events is thus cancer type specific.

The following are the copy number aberration events that may be be called for a gene amplification or deletion:

| Event Type | Description of Event | Example Aberration Name | Driver Status |
|---|---|---|---|
| In-Peak Gene Amplification | An amplification in a gene observed in an Amplification Peak within the same cancer type | EGFR In-Peak Gene Amplification | driver |
| In-Peak Gene Deletion | A deletion in a gene observed in a Deletion Peak within the same cancer type | CDKN1A In-Peak Gene Deletion | driver |
| Any Gene Amplification | An amplification in a gene | ERBB2 <Any Gene Amplification> | any |
| Any Gene Deletion | A deletion in a gene | FGFR <Any Gene Deletion> | any |

Genetic Event Roll-Up.

Both driver and any events are "rolled-up" to gene-level and pathway-level events to capture a data type-independent aberration statistics and associations. For example, it may be interesting to see the association of any aberrations in a tumor suppressor gene with clinical outcome, not just the association of the deleterious mutations.

A gene-level aberration event is created for each gene that has at least one aberration of any data type. A pathway-level aberration event is created for each pathway in which at least one of the component genes has an aberration of any data type. Driver and any aberrations are rolled-up independently into gene-level or pathway-level driver or any events. The diagram below shows the hierarchical relationships between the various aberration event types.

Patient Event Status.

A patient can be measured for any number of aberrations but can only be aberrant for those events measured. Patient status for each event-level aberration is thus recorded as aberrant, wild type, or not measured.

The patient dimension along with the data set-specific mapping of the patients helps correctly identify fully wild-type patients—those who are measured for all aberration types but don't contain any aberrations.

When gene-level and pathway-level events are defined, only the patients measured for all 3 genetic data types—mutations, fusion, and copy number—are marked as "aberrant" or "wild type" for the event. This assumption has the effect of potentially reducing the number of patients summarized for a gene or pathway-level aberrations as compared to the data type-specific event-level aberrations. A patient is considered aberrant for a gene-level event if the patient is aberrant for at least one of the event-level aberration types (Fusion, Mutation, Amplification, or Deletion). A patient is considered aberrant for a pathway-level event if the patient has an aberration in at least one gene that is part of the pathway definition. In each case, the patient must have been measured for all the event types.

In the case of the Gain of Function and Fusion, the aberration frequency is ~50%. For the Driver Gene Aberration event the aberration frequency is also ~50% but only half as many patients are included in the numerator and denominator of the frequency.

Analysis.

Once all the driver genetic events are constructed, a set of analyses is performed on each genetic event, calculating frequencies, associations, and relationships within cancer types, clinically relevant subtypes, and among cancer types (pan-cancer). The following are short descriptions of each analysis, including which data is used, and what constraints, if any, are put on the reported results: frequency, expressed frequency, co-occurrence and mutual exclusivity, clinical association analysis, etc.

Frequency.

Frequency is the occurrence of an aberration among the patients in which it was measured. Frequencies are calculated within cancer types, clinically relevant cancer subtypes, and pan-cancer. All events with at least one aberrant patient are reported.

Expressed Frequency.

Expressed frequency is the frequency at which the gene(s) is expressed among the event-positive patients. For each event, expression level of the gene(s) is used to ascertain the expressed frequencies. Frequencies are calculated within cancer types and clinically relevant cancer subtypes, but not pan-cancer.

Co-Occurrence and Mutual Exclusivity.

Co-occurrence and mutual exclusivity is calculated for each pair of events using a Fischer's Exact test. At least 2 patients positive for each event and 5 patients measured for the events in total are required for the calculation. Co-occurrence or exclusivity of two individual copy number deletion or amplification events is not calculated. Also, co-occurrence and mutual exclusivity is not calculated between pairs of events with "any" driver status (i.e. only drivers vs. drivers and drivers vs. any are compared). Associations are calculated within cancer types and clinically relevant cancer subtypes, but not pan-cancer.

Clinical Association Analysis.

Each driver event is tested for association against a set of available clinical subtypes. Each association is tested using a Fischer's exact test by comparing the occurrences of the genetic event in patients of one clinical subtype versus another. For example, a Loss of Function mutation may be tested for over-representation in Smokers versus Non-Smokers, or in Stage I versus Stage II lung cancer. A total of 136 subtype pairs are tested against each event, and the properties that define the subtypes are listed below (some properties may be disease-specific). At least 4 patients total, with at least 1 patient in each class are required to perform the test. Associations are calculated within cancer types, clinically relevant cancer subtypes, and pan-cancer.

Clinical Subtype Property Names:
Race/Ethnicity
Revised Smoking Status
ERBB2 Status
Estrogen Receptor Status
Progesterone Receptor Status
TCGA PAM50 Subtype
BRAF Mutation Status
Revised T Stage
Revised N Stage
Revised M Stage
Revised Stage
KRAS Mutation Status
EGFR Amplification Status
TCGA Subtype
Microsatellite Status
Human Papillomavirus Infection Status Clinical Outcome Analysis.

Each event is tested for association with clinical outcome using the Logrank test. Only the set of patients with available clinical data are used for the calculation, so the number of patients included in the test may be less than the number of patients measured for the driver event. At least 4 patients aberrant for an event are required to perform the test. Survival time is presented in years, and individual alive/dead events are clearly marked on a Kaplan-Meier curve. Associations are calculated within cancer types and clinically relevant cancer subtypes, but not pan-cancer.

DNA-RNA Correlation Analysis.

For each gene, the RNA expression and DNA copy number values are tested for correlation among all patients within a disease who were measured for these data types using Pearson's correlation. Correlations are calculated within cancer types and clinically relevant cancer subtypes, but not pan-cancer.

Differential Expression Analysis.

For each event, each gene associated with the event was tested for differential expression in event-positive patients vs. event-negative patients using Student's T-Test. For events involving several genes—such as fusions—each gene was tested. Differential expression is calculated within cancer types and clinically relevant cancer subtypes, but not pan-cancer.

TABLE 15

Events associate with cancer prognosis

| Table 15 Subset | event type | p-value | q-value | No. positive | Total no. of patients | Cytoband |
|---|---|---|---|---|---|---|
| Hepatocellular Carcinoma | In-Peak Gene Amplification | 3.31E−02 | 9.93E−02 | 4 | 65 | 1q21.2 |
| Hepatocellular Carcinoma | In-Peak Gene Deletion | 2.47E−02 | 9.89E−02 | 4 | 65 | 13q14.2 |
| Squamous Cell Lung Carcinoma | Loss of Function Mutation | 1.60E−02 | 9.59E−02 | 7 | 175 | 4q31.3 |
| Squamous Cell Lung Carcinoma | Loss of Function Mutation | 3.14E−02 | 9.42E−02 | 7 | 175 | 9q34.3 |
| Squamous Cell Lung Carcinoma | Loss of Function Mutation | 7.73E−03 | 9.28E−02 | 5 | 175 | 1p35.3 |

TABLE 15-continued

Events associate with cancer prognosis

| | | | | | | |
|---|---|---|---|---|---|---|
| Clear Cell Renal Cell Carcinoma | In-Peak Gene Deletion | 7.12E−03 | 9.25E−02 | 8 | 493 | 9p21 |
| Invasive Breast Carcinoma:ER Positive | In-Peak Gene Amplification | 2.17E−03 | 9.13E−02 | 15 | 635 | 17q11.2 |
| Ovarian Serous Cystadenocarcinoma | In-Peak Gene Amplification | 1.00E−03 | 8.99E−02 | 10 | 557 | 19q13.1-q13.2 |
| Clear Cell Renal Cell Carcinoma | Loss of Function Mutation | 2.44E−02 | 8.55E−02 | 14 | 293 | 3p21 |
| Ovarian Serous Cystadenocarcinoma | In-Peak Gene Amplification | 5.45E−04 | 8.39E−02 | 89 | 557 | 19q12 |
| Lung Adenocarcinoma | In-Peak Gene Amplification | 6.80E−03 | 8.16E−02 | 4 | 320 | 1q12 |
| Lung Adenocarcinoma | In-Peak Gene Amplification | 6.80E−03 | 8.16E−02 | 4 | 320 | 1q21.1 |
| Lung Adenocarcinoma | In-Peak Gene Amplification | 8.57E−03 | 7.71E−02 | 9 | 320 | 12p12.1 |
| Invasive Breast Carcinoma:Triple Negative | In-Peak Gene Amplification | 8.10E−03 | 7.29E−02 | 5 | 88 | 8p12 |
| Head and Neck Squamous Cell Carcinoma | In-Peak Gene Amplification | 1.02E−02 | 6.93E−02 | 8 | 316 | 5q35 |
| Rectal Adenocarcinoma | In-Peak Gene Deletion | 2.08E−03 | 6.86E−02 | 4 | 145 | 16p13.3 |
| Lung Adenocarcinoma | In-Peak Gene Deletion | 9.37E−03 | 6.09E−02 | 5 | 320 | 3q25.1 |
| Hepatocellular Carcinoma | In-Peak Gene Deletion | 3.03E−02 | 6.06E−02 | 4 | 65 | 8p21.2 |
| Ovarian Serous Cystadenocarcinoma | In-Peak Gene Amplification | 5.58E−04 | 6.02E−02 | 22 | 557 | 20q11 |
| Rectal Adenocarcinoma:KRAS Wildtype | Loss of Function Mutation | 2.69E−02 | 5.38E−02 | 11 | 28 | 5q21-q22 |
| Papillary Renal Cell Carcinoma | In-Peak Gene Amplification | 2.68E−02 | 5.35E−02 | 6 | 100 | 17q21.1 |
| Acute Myeloid Leukemia | PML + RARA Fusion | 1.26E−02 | 5.03E−02 | 15 | 169 | 17q and 15q |
| Rectal Adenocarcinoma:KRAS Wildtype | In-Peak Gene Amplification | 4.55E−02 | 4.96E−02 | 10 | 27 | 20q |
| Gastric Adenocarcinoma | Loss of Function Mutation | 4.09E−03 | 4.50E−02 | 4 | 131 | 6p21 |
| Endometrial Endometrioid Adenocarcinoma | In-Peak Gene Deletion | 1.36E−02 | 4.43E−02 | 6 | 446 | 16Q24 |
| Lung Adenocarcinoma | In-Peak Gene Deletion | 3.15E−03 | 4.09E−02 | 8 | 320 | 19q13.4 |
| Head and Neck Squamous Cell Carcinoma | In-Peak Gene Amplification | 1.45E−03 | 3.82E−02 | 6 | 316 | 20p12 |
| Lung Adenocarcinoma:Triple Negative | In-Peak Gene Amplification | 8.80E−04 | 3.78E−02 | 6 | 174 | 7q31 |
| Endometrial Endometrioid Adenocarcinoma | In-Peak Gene Deletion | 1.09E−02 | 3.77E−02 | 4 | 446 | 3Q26 |
| Cutaneous Melanoma | Loss of Function Mutation | 3.74E−03 | 3.74E−02 | 16 | 148 | 17q11 |
| Acute Myeloid Leukemia | CBFB + MYH11 Fusion | 1.83E−02 | 3.67E−02 | 11 | 169 | 16Q22 and 16P13.11 |
| Head and Neck Squamous Cell | In-Peak Gene | 6.01E−04 | 2.86E−02 | 5 | 316 | 7p12 |

TABLE 15-continued

| Events associate with cancer prognosis | | | | | | |
|---|---|---|---|---|---|---|
| Carcinoma | Amplification | | | | | |
| Lung Adenocarcinoma | In-Peak Gene Amplification | 1.28E−03 | 2.76E−02 | 7 | 320 | 7q31 |
| Head and Neck Squamous Cell Carcinoma | In-Peak Gene Amplification | 3.00E−03 | 2.31E−02 | 80 | 316 | 11q13 |
| Gastric Adenocarcinoma | In-Peak Gene Amplification | 1.89E−04 | 2.14E−02 | 4 | 172 | 18q11 |
| Invasive Breast Carcinoma | In-Peak Gene Deletion | 2.27E−03 | 1.82E−02 | 11 | 863 | 10q23.31, q23.2 |
| Head and Neck Squamous Cell Carcinoma | In-Peak Gene Amplification | 1.89E−03 | 1.55E−02 | 6 | 316 | 2q32 |
| Colon Adenocarcinoma | In-Peak Gene Deletion | 2.27E−04 | 1.48E−02 | 4 | 412 | 3Q26 |
| Gastric Adenocarcinoma:Hyper-Mutator | Loss of Function Mutation | 5.32E−04 | 1.22E−02 | 4 | 32 | 2q31 |
| Glioblastoma | Loss of Function Mutation | 1.23E−03 | 1.11E−02 | 6 | 276 | Xq25 |
| Head and Neck Squamous Cell Carcinoma | Gain of Function Mutation | 2.61E−03 | 1.04E−02 | 13 | 304 | 2q31 |
| Endometrial Endometrioid Adenocarcinoma | In-Peak Gene Amplification | 9.20E−04 | 1.03E−02 | 7 | 446 | 1q21 |
| Endometrial Endometrioid Adenocarcinoma | In-Peak Gene Deletion | 2.47E−03 | 9.17E−03 | 7 | 446 | 16p13 |
| Hepatocellular Carcinoma | In-Peak Gene Amplification | 2.57E−03 | 8.89E−03 | 4 | 65 | 1q21.3 |
| Clear Cell Renal Cell Carcinoma | In-Peak Gene Deletion | 3.16E−04 | 8.23E−03 | 8 | 493 | 9p21 |
| Glioblastoma | Gain of Function Mutation | 2.72E−03 | 8.15E−03 | 14 | 276 | 2q33 |
| Lung Adenocarcinoma:KRAS Mutation (No ALK Fusion and No EGFR Mutation) | In-Peak Gene Amplification | 2.56E−03 | 5.98E−03 | 4 | 78 | 12p12.1 |
| Endometrial Endometrioid Adenocarcinoma | In-Peak Gene Amplification | 4.40E−04 | 5.55E−03 | 6 | 446 | 1q22 |
| Colon Adenocarcinoma:KRAS Mutation | Gain of Function Mutation | 4.97E−03 | 4.97E−03 | 17 | 53 | 3q26 |
| Head and Neck Squamous Cell Carcinoma | Loss of Function Mutation | 1.79E−04 | 3.95E−03 | 161 | 304 | 17p13 |
| Head and Neck Squamous Cell Carcinoma | In-Peak Gene Amplification | 6.41E−05 | 3.81E−03 | 4 | 316 | 22q11 |
| Gastric Adenocarcinoma | Loss of Function Mutation | 2.14E−04 | 3.53E−03 | 5 | 131 | 17q22 |
| Lower Grade Glioma | Loss of Function Mutation | 3.00E−04 | 2.70E−03 | 5 | 166 | 17q11.2 |
| Lung Adenocarcinoma:Triple Negative | Gain of Function Mutation | 5.06E−04 | 2.53E−03 | 11 | 175 | 3q26.3 |
| Lung Adenocarcinoma | Loss of Function Mutation | 5.24E−05 | 9.96E−04 | 4 | 283 | 5q21-q22 |
| Bladder Urothelial Carcinoma | In-Peak Gene Amplification | 8.34E−05 | 9.31E−04 | 5 | 125 | 5p15.33 |
| Endometrial Endometrioid Adenocarcinoma | In-Peak Gene Deletion | 1.12E−04 | 8.32E−04 | 9 | 446 | 10q23 |

TABLE 15-continued

| Events associate with cancer prognosis | | | | | | |
|---|---|---|---|---|---|---|
| Lower Grade Glioma | In-Peak Gene Amplification | 5.69E−04 | 6.74E−04 | 5 | 206 | 1q32.1 |
| Ovarian Serous Cystadenocarcinoma | In-Peak Gene Deletion | 1.05E−06 | 6.28E−04 | 7 | 557 | 9q22 |
| Endometrial Endometrioid Adenocarcinoma | In-Peak Gene Amplification | 8.93E−06 | 3.01E−04 | 25 | 446 | 8q24 |
| Acute Myeloid Leukemia | Loss of Function Mutation | 2.35E−05 | 9.42E−05 | 12 | 184 | 17P |
| Colon Adenocarcinoma | In-Peak Gene Amplification | 3.93E−06 | 6.24E−05 | 7 | 412 | 12p13 |
| Gastric Adenocarcinoma | Loss of Function Mutation | 8.74E−07 | 2.88E−05 | 4 | 131 | 2q31 |
| Lower Grade Glioma | Gain of Function Mutation | 9.38E−08 | 2.81E−07 | 130 | 166 | 2q33.3 |
| Lower Grade Glioma | In-Peak Gene Amplification | 1.31E−08 | 3.48E−08 | 14 | 206 | 7p11.2 |
| Lower Grade Glioma | In-Peak Gene Amplification | 1.48E−10 | 1.18E−09 | 5 | 206 | 12q14.1 |
| Lower Grade Glioma | Gain of Function Mutation | 1.09E−10 | 6.56E−10 | 6 | 166 | 7p12 |
| Lung Adenocarcinoma | In-Peak Gene Amplification | 1.30E−12 | 4.66E−11 | 4 | 320 | 12p11 |
| Lower Grade Glioma | In-Peak Gene Deletion | 4.57E−12 | 6.85E−12 | 21 | 206 | 9p21 |
| Endometrial Endometrioid Adenocarcinoma | In-Peak Gene Amplification | 2.00E−15 | 1.01E−13 | 4 | 446 | 17q21 |
| Astrocytoma | Loss of Function Mutation | | 3.88E−03 | 34 | 59 | 17p13.1 |
| Astrocytoma | Loss of Function Mutation | | 8.15E−03 | 22 | 59 | Xq21.1 |
| Breast Carcinoma | In-Peak Gene Deletion | | 8.14E−03 | 4 | 36 | 8p23.2 |
| Colorectal Adenocarcinoma | In-Peak Gene Amplification | | 5.71E−02 | 12 | 407 | 8q24.3 |
| Colorectal Adenocarcinoma | In-Peak Gene Amplification | | 9.18E−02 | 17 | 407 | 13q34 |
| Colorectal Mucinous Adenocarcinoma | Gain of Function Mutation | | 8.10E−03 | 8 | 32 | 3q26.3 |
| Cutaneous Melanoma | In-Peak Gene Amplification | | 2.60E−06 | 6 | 231 | 8q22.3 |
| Cutaneous Melanoma | In-Peak Gene Amplification | | 1.54E−04 | 7 | 231 | 8q24.3 |
| Cutaneous Melanoma | In-Peak Gene Amplification | | 7.21E−03 | 8 | 231 | 8q21 |
| Cutaneous Melanoma | In-Peak Gene Amplification | | 7.59E−03 | 6 | 231 | 11q13.3 |
| Cutaneous Melanoma | In-Peak Gene Amplification | | 1.82E−02 | 4 | 231 | 1q44 |
| Cutaneous Melanoma | In-Peak Gene Amplification | | 9.36E−02 | 6 | 231 | 1q21.3 |
| Ductal Breast Carcinoma | In-Peak Gene Amplification | | 2.77E−03 | 4 | 665 | 3q29 |

TABLE 15-continued

| Events associate with cancer prognosis | | | | | |
|---|---|---|---|---|---|
| Ductal Breast Carcinoma | In-Peak Gene Amplification | 2.28E−02 | 7 | 665 | 6q23.3 |
| Ductal Breast Carcinoma | In-Peak Gene Amplification | 2.64E−02 | 8 | 665 | 3q26.3 |
| Ductal Breast Carcinoma:ER Positive and HER2 Negative | In-Peak Gene Amplification | 7.92E−06 | 6 | 263 | 1q21.3 |
| Ductal Breast Carcinoma:ER Positive and HER2 Negative | In-Peak Gene Amplification | 4.02E−02 | 7 | 263 | 1q32 |
| Ductal Breast Carcinoma:ER Positive and HER2 Negative | In-Peak Gene Deletion | 4.35E−02 | 4 | 263 | 8p11.2 |
| Ductal Breast Carcinoma:ER Positive and HER2 Positive | In-Peak Gene Deletion | 7.48E−02 | 4 | 84 | 9q22 |
| Ductal Breast Carcinoma:HER2 Positive | In-Peak Gene Deletion | 4.47E−02 | 4 | 116 | 15q13.1 |
| Ductal Breast Carcinoma:HER2 Positive | In-Peak Gene Deletion | 5.17E−02 | 4 | 116 | 9p21 |
| Ductal Breast Carcinoma:Triple Negative | In-Peak Gene Amplification | 2.58E−02 | 5 | 75 | 1q23.3 |
| Ductal Breast Carcinoma:Triple Negative | In-Peak Gene Amplification | 7.21E−02 | 8 | 75 | 1q21 |
| Endometrial Endometrioid Adenocarcinoma:Microsatellite Stable | Loss of Function Mutation | 5.55E−02 | 19 | 113 | 5q13.1 |
| Endometrial Serous Adenocarcinoma | In-Peak Gene Amplification | 6.37E−04 | 4 | 52 | 19p13.2 |
| Gastric Adenocarcinoma:Hyper-Mutator | In-Peak Gene Deletion | 9.05E−02 | 8 | 106 | 9p21 |
| Glioblastoma | In-Peak Gene Deletion | 2.58E−02 | 300 | 565 | 9p21 |
| Glioblastoma | In-Peak Gene Amplification | 8.80E−02 | 189 | 565 | 7p11.2 |
| Lung Adenocarcinoma | Fusion | 5.79E−02 | 7 | 343 | 17q23.1 |
| Lung Adenocarcinoma:Triple Negative | Loss of Function Mutation | 1.31E−03 | 4 | 99 | 7q36.1 |
| Oligoastrocytoma | Loss of Function Mutation | 1.97E−02 | 38 | 53 | 17p13.1 |
| Oligodendroglioma | Loss of Function Mutation | 5.90E−02 | 6 | 89 | 9q34.3 |
| Oligodendroglioma | Loss of Function Mutation | 6.62E−02 | 15 | 89 | 1p31.1 |
| Ovarian Serous Adenocarcinoma | In-Peak Gene Amplification | 1.15E−02 | 17 | 562 | 19q13.1 |
| Ovarian Serous Adenocarcinoma | In-Peak Gene Amplification | 6.59E−02 | 17 | 562 | 20q11.2-13.2 |
| Ovarian Serous Adenocarcinoma | In-Peak Gene Deletion | 7.86E−02 | 7 | 562 | 17p13.1 |
| Ovarian Serous Adenocarcinoma | In-Peak Gene Amplification | 8.43E−02 | 53 | 562 | 19q12 |
| Squamous Cell Lung Carcinoma | In-Peak Gene Amplification | 7.93E−02 | 63 | 320 | 3q26.2 |

TABLE 15-continued

| Events associate with cancer prognosis | | | |
|---|---|---|---|
| Table 15 Subset | Genes (Entrez ID) | Druggable genes | KM Evidence |
| Hepatocellular Carcinoma | ADAMTSL4 (54507), MCL1 (4170) | MCL1 | Poor prognosis |
| Hepatocellular Carcinoma | LPAR6 (10161) | N | Poor prognosis |
| Squamous Cell Lung Carcinoma | FBXW7 (55294) | N | Poor prognosis |
| Squamous Cell Lung Carcinoma | NOTCH1 (4851) | NOTCH1 | Poor prognosis |
| Squamous Cell Lung Carcinoma | ARID1A (8289) | N | Poor prognosis |
| Clear Cell Renal Cell Carcinoma | CDKN2B (1030) | No | Poor prognosis |
| Invasive Breast Carcinoma:ER Positive | TIAF1 (9220), MYO18A (399687), CRYBA1 (1411) | N | Poor prognosis |
| Ovarian Serous Cystadenocarcinoma | PSG2 (5670), PSG5 (5673), CEACAM1 (634), CEACAM8 (1088), CXCL17 (284340), RABAC1 (10567), ATP1A3 (478) | CEACAM1 (Preclinical) | Poor prognosis |
| Clear Cell Renal Cell Carcinoma | BAP1 (8314) | No | Poor prognosis |
| Ovarian Serous Cystadenocarcinoma | C19orf2 (8725) | N | Poor prognosis |
| Lung Adenocarcinoma | CHD1L (1105) | N | Poor prognosis |
| Lung Adenocarcinoma | FMO5 (2330), PRKAB2 (5565) | N | Poor prognosis |
| Lung Adenocarcinoma | KRAS (3845), CASC1 (55259), LYRM5 (144363), LRMP (4033) | KRAS (Preclinical) | Poor prognosis |
| Invasive Breast Carcinoma:Triple Negative | BRF2 (55290), ERLIN2 (11160), GPR124 (25960), PROSC (11212), RAB11FIP1 (80223), ZNF703 (80139) | N | Poor prognosis |
| Head and Neck Squamous Cell Carcinoma | THOC3 (84321) | No | Poor prognosis |
| Rectal Adenocarcinoma | A2BP1 (54715) | N | Poor prognosis |
| Lung Adenocarcinoma | AADAC (13) | N | Poor prognosis |
| Hepatocellular Carcinoma | GNRH1 (2796) | GNRH1 | Poor prognosis |
| Ovarian Serous Cystadenocarcinoma | ID1 (3397), BCL2L1 (598), COX4I2 (84701) | ID1 (Preclinical), BCL2L1 | Poor prognosis |
| Rectal Adenocarcinoma:KRAS Wildtype | APC (324) | N | Poor prognosis |
| Papillary Renal Cell Carcinoma | CCL3L3 (414062), CCL3L1 (6349) | N | Poor prognosis |
| Acute Myeloid Leukemia | RARA (5914), PML (5371) | Y | Good prognosis |
| Rectal Adenocarcinoma:KRAS | ACOT8 (10005), ADA (100), | ADA, CD40 | Poor prognosis |

TABLE 15-continued

| | | | |
|---|---|---|---|
| Events associate with cancer prognosis | | | |
| | Wildtype | C20orf111 (51526), C20orf123 (128506), C20orf165 (128497), CD40 (958), CDH22 (64405), CTSA (5476), DBNDD2 (55861), DNTTIP1 (116092), ELMO2 (63916), FITM2 (128486), GDAP1L1 (78997), GTSF1L (149699), HNF4A (3172), IFT52 (51098), JPH2 (57158), KCNK15 (60598), KCNS1 (3787), L3MBTL (26013), MATN4 (8785), MMP9 (4318), MYBL2 (4605), NCOA5 (57727), NEURL2 (140825), PABPC1L (80336), PCIF1 (63935), PI3 (5266), PIGT (51604), PKIG (11142), PLAGL2 (5326), PLTP(5360), POFUT1 (23509), R3HDML (140902), RBPJL (11317), RIMS4 (140730), SDC4 (6385), SEMG1(6406) SEMG2 (6407), SERINC3 (10955), SFRS6 (6431), SGK2 (10110), SLC12A5 (57468), SLC13A3 (64849), SLC35C2 (51006), SLPI (6590), SNAI1 (6615), SNX21 (90203), SPINLW1 (57119), SPINT3 (10816), SPINT4 (391253), STK4 (6789), SYS1 (90196), TM9SF4 (9777), TNNC2 (7125), TOMM34 (10953), | (958), MMP9, PI3 | |

TABLE 15-continued

Events associate with cancer prognosis

| | | | |
|---|---|---|---|
| | TOX2 (84969), TP53RK (112858), TP53TG5 (27296), TTPAL (79183), UBE2C (11065), WFDC10A (140832), WFDC10B (280664), WFDC11 (259239), WFDC12 (128488), WFDC13 (164237), WFDC2 (10406), WFDC3 (140686), WFDC5 (149708), WFDC6 (140870), WFDC8 (90199), WFDC9 (259240), WISP2 (8839), YWHAB (7529), ZNF334 (55713), ZNF335 (63925), ZSWIM1 (90204), ZSWIM3 (140831) | | |
| Gastric Adenocarcinoma | HLA-B (3106) | Yes | Poor prognosis |
| Endometrial Endometrioid Adenocarcinoma | SLC7A5 (8140), CTU2 (66965), FAM38A (9780), CDT1 (81620), APRT (353), GALNS (2588) | SLC7A5 (preclinical) | Poor prognosis |
| Lung Adenocarcinoma | KIR2DS4 (3809) | N | Poor prognosis |
| Head and Neck Squamous Cell Carcinoma | C20orf94 (128710), JAG1 (182), MKKS (8195), SNAP25 (6616) | JAG1 (Preclinical) | Poor prognosis |
| Lung Adenocarcinoma:Triple Negative | MET (4233), CAPZA2 (830) | MET | Poor prognosis |
| Endometrial Endometrioid Adenocarcinoma | APOD (347) | No | Poor prognosis |
| Cutaneous Melanoma | NF1 (4763) | No | Poor prognosis |
| Acute Myeloid Leukemia | CBFB (865), MYH11 (4629) | N | Good prognosis |
| Head and Neck Squamous Cell Carcinoma | ABCA13 (154664), C7orf57 (136288), C7orf65 (401335), C7orf69 (80099), C7orf72 (100130988), DDC (1644), FIGNL1 (63979), GRB10 (2887), HUS1 (3364), IKZF1 (10320), PKD1L1 (168507), SUN3 (256979), TNS3 (64759), UPP1 | No | Poor prognosis |

TABLE 15-continued

| Events associate with cancer prognosis | | | |
|---|---|---|---|
| | (7378), VWC2 (375567), ZPBP (11055) | | |
| Lung Adenocarcinoma | MET (4233), CAPZA2 (830) | MET | Poor prognosis |
| Head and Neck Squamous Cell Carcinoma | FADD (8772), PPFIA1 (8500), ANO1 (55107), CTTN (2017) | No | Poor prognosis |
| Gastric Adenocarcinoma | GATA6 (2627) | No | Poor prognosis |
| Invasive Breast Carcinoma | ATAD1 (84896), KILLIN (100144748) | N | Poor prognosis |
| Head and Neck Squamous Cell Carcinoma | GLS (2744), MYO1B (4430), NAB1(4664), STAT1 (6772), STAT4 (6775), TMEM194B (100131211) | No | Poor prognosis |
| Colon Adenocarcinoma | APOD (347) | No | Poor prognosis |
| Gastric Adenocarcinoma:Hyper-Mutator | HOXD8 (3234) | No | Poor prognosis |
| Glioblastoma | STAG2 (10735) | No | Poor prognosis |
| Head and Neck Squamous Cell Carcinoma | NFE2L2 (4780) | NO | Poor prognosis |
| Endometrial Endometrioid Adenocarcinoma | SSR2 (6746), ARHGEF2 (9181), UBQLN4 (56893) | No | Poor prognosis |
| Endometrial Endometrioid Adenocarcinoma | LOC339047 (339047) | No | Poor prognosis |
| Hepatocellular Carcinoma | DCST1 (149095), ADAM15 (8751), EFNA4 (1945), EFNA3 (1944), EFNA1 (1942), RAG1AP1 (55974), DPM3 (54344), KRTCAP2 (200185), TRIM46 (80128), MUC1 (4582), THBS3 (7059), MTX1 (4580), GBA (2629) | ADAM15, MUC1 | Poor prognosis |
| Clear Cell Renal Cell Carcinoma | CDKN2A (1029) | Yes | Poor prognosis |
| Glioblastoma | IDH1 (3417) | preclinical | Good prognosis |
| Lung Adenocarcinoma:KRAS Mutation (No ALK Fusion and No EGFR Mutation) | LYRM5 (144363), KRAS (3845), CASC1 (55259) | KRAS (Preclinical) | Poor prognosis |
| Endometrial Endometrioid Adenocarcinoma | ROBLD3 (28956), RAB25 (57111), MEX3A (92312) | No | Poor prognosis |
| Colon Adenocarcinoma:KRAS Mutation | PIK3CA (5290) | Yes | Poor prognosis |
| Head and Neck Squamous Cell Carcinoma | TP53 (7157) | TP53 | Poor prognosis |

TABLE 15-continued

| Events associate with cancer prognosis | | | |
|---|---|---|---|
| Head and Neck Squamous Cell Carcinoma | CRKL (1399), PI4KA (5297), SERPIND1 (3053), SNAP29 (9342) | No | Poor prognosis |
| Gastric Adenocarcinoma | RNF43 (54894) | No | Poor prognosis |
| Lower Grade Glioma | NF1 (4763) | N | Poor prognosis |
| Lung Adenocarcinoma:Triple Negative | PIK3CA (5290) | Y | Poor prognosis |
| Lung Adenocarcinoma | APC (324) | N | Poor prognosis |
| Bladder Urothelial Carcinoma | PLEKHG4B (153478), LRRC14B (389257), CCDC12 (151903), SDHA (6389), PDCD6 (10016), AHRR (57491), C5orf55 (116349), EXOC3 (11336), SLC9A3 (6550), CEP72 (55722), TPPP (11076), BRD9 (65980), TRIP13 (9319), NKD2 (85409), SLC12A7 (10723), SLC6A19 (340024), SLC6A18 (348932), TERT (7015), CLPTM1L (81037), SLC6A3 (6531), LPCAT1 (79888), MRPL36 (64979), NDUFS6 (4726) | AHRR, TERT | Poor prognosis |
| Endometrial Endometrioid Adenocarcinoma | PTEN (5728), ANKRD22 (118932), STAMBPL1 (57559), ACTA2 (59), FAS (355), ATAD1 (84896), KILLIN (100144748), RNLS (55328) | Yes | Poor prognosis |
| Lower Grade Glioma | C1orf157 (284573), ETNK2 (55224), GOLT1A (127845), KISS1 (3814), LAX1 (54900), LRRN2 (10446), MDM4 (4194), PIK3C2B (5287), PLEKHA6 (22874), | MDM4 (Preclinical) | Poor prognosis |

TABLE 15-continued

| Events associate with cancer prognosis | | | |
|---|---|---|---|
| | PPP1R15B (84919), REN (5972), SNRPE (6635), SOX13 (9580), ZC3H11A (9877) | | |
| Ovarian Serous Cystadenocarcinoma | FAM75C1 (441452) | N | Poor prognosis |
| Endometrial Endometrioid Adenocarcinoma | MYC (4609), TAF2 (6873), DSCC1 (79075), DEPDC6 (64798) | No | Poor prognosis |
| Acute Myeloid Leukemia | TP53 (7157) | Y | Poor prognosis |
| Colon Adenocarcinoma | CCND2 (894), TULP3 (7289), TEAD4 (7004), TSPAN9 (10867), PRMT (563418), EFCAB4B (84766), PARP11 (57097), C12orf5 (57103), FGF23 (8074), FGF6 (2251), FKBP4 (2288), ITFG2 (55846), NRIP2 (83714), FOXM1 (2305) | No | Poor prognosis |
| Gastric Adenocarcinoma | HOXD8 (3234) | No | Poor prognosis |
| Lower Grade Glioma | IDH1 (3417) | IDH1 (Preclinical) | Good prognosis |
| Lower Grade Glioma | EGFR (1956), SEC61G (23480) | EGFR | poor prognosis |
| Lower Grade Glioma | CDK4 (1019), CYP27B1 (1594), MARCH9 (92979), TSPAN31 (6302), AGAP2 (116986), AVIL (10677), CTDSP2 (10106), FAM119B (25895), METTL1 4234), OS9 (10956), TSFM (10102) | CDK4 | Poor prognosis |
| Lower Grade Glioma | EGFR (1956) | EGFR | Poor prognosis |
| Lung Adenocarcinoma | LOC100133893 (100133893), MRPS3 (604885), REP15 (387849) | N | Poor prognosis |
| Lower Grade Glioma | CDKN2A (1029), CDKN2B (1030), MTAP (4507) | CDKN2A (1029) | Poor prognosis |
| Endometrial Endometrioid Adenocarcinoma | CCL3L3 (414062), CCL3L1 (6349) | No | Poor prognosis |
| Astrocytoma | TP53 (7157) | TP53 | favorable outcome |
| Astrocytoma | ATRX (546) | no | favorable outcome |

TABLE 15-continued

Events associate with cancer prognosis

| | | | |
|---|---|---|---|
| Breast Carcinoma | CSMD1 (64478) | no | poor outcome |
| Colorectal Adenocarcinoma | PARP10 (84875), MAPK15 (225689), PTK2 (5747), KHDRBS3 (10656) | PTK2 | poor outcome |
| Colorectal Adenocarcinoma | FAM70B (348013) | no | poor outcome |
| Colorectal Mucinous Adenocarcinoma | PIK3CA (5290) | PIK3CA | poor outcome |
| Cutaneous Melanoma | ODF1 (4956) | no | poor outcome |
| Cutaneous Melanoma | PARP10 (84875), MAPK15 (225689), PTK2 (5747), KHDRBS3 (10656) | PTK2 | poor outcome |
| Cutaneous Melanoma | HEY1 (23462) | no | poor outcome |
| Cutaneous Melanoma | FADD (8772), CCND1 (595), ORAOV1 (220064), FGF19 (9965) | CCND1 | poor outcome |
| Cutaneous Melanoma | OR2T27 (403239) | no | poor outcome |
| Cutaneous Melanoma | LCE1E (353135) | no | poor outcome |
| Ductal Breast Carcinoma | OSTalpha (200931) | no | poor outcome |
| Ductal Breast Carcinoma | AHI1 (54806) | no | poor outcome |
| Ductal Breast Carcinoma | PIK3CA (5290), SOX2 (6657), ATP11B (23200) | PIK3CA | poor outcome |
| Ductal Breast Carcinoma:ER Positive and HER2 Negative | ADAMTSL4 (54507), MCL1 (4170), ENSA (2029) | MCL1 | poor outcome |
| Ductal Breast Carcinoma:ER Positive and HER2 Negative | MDM4 (4194) | MDM4 (pre-clinical) | poor outcome |
| Ductal Breast Carcinoma:ER Positive and HER2 Negative | FKSG2 (59347) | no | poor outcome |
| Ductal Breast Carcinoma:ER Positive and HER2 Positive | FAM75C1 (441452) | no | poor outcome |
| Ductal Breast Carcinoma:HER2 Positive | CHRFAM7A (89832) | no | poor outcome |
| Ductal Breast Carcinoma:HER2 Positive | CDKN2B (1030) | CDKN2B (pre-clinical) | poor outcome |
| Ductal Breast Carcinoma:Triple Negative | APOA2 (336), SDHC (6391), FCGR2B (2213) | no | poor outcome |
| Ductal Breast Carcinoma:Triple Negative | ACP6 (51205), ECM1 (1893), ADAMTSL4 (54507), MCL1 (4170), ENSA (2029) | MCL1 | poor outcome |
| Endometrial Endometrioid Adenocarcinoma:Microsatellite Stable | PIK3R1 (5295) | no | poor outcome |
| Endometrial Serous Adenocarcinoma | DNMT1 (1786) | DNMT1 | poor outcome |

TABLE 15-continued

Events associate with cancer prognosis

| | | | |
|---|---|---|---|
| Gastric Adenocarcinoma:Hyper-Mutator | CDKN2A (1029), CDKN2B (1030) | CDKN2A, CDKN2B (pre-clinical) | poor outcome |
| Glioblastoma | CDKN2A (1029), CDKN2B (1030) | CDKN2A, CDKN2B (pre-clinical) | poor outcome |
| Glioblastoma | SEC61G (23480) | no | poor outcome |
| Lung Adenocarcinoma | RPS6KB1 (6198), VMP1 (81671) | RPS6KB1 | poor outcome |
| Lung Adenocarcinoma:Triple Negative | MLL3 (58508) | no | poor outcome |
| Oligoastrocytoma | TP53 (7157) | TP53 | favorable outcome |
| Oligodendroglioma | NOTCH1 (4851) | NOTCH1 | poor outcome |
| Oligodendroglioma | FUBP1 (8880) | no | poor outcome |
| Ovarian Serous Adenocarcinoma | FCGBP (8857), PAK4 (10298) | PAK4 (pre-clinical) | poor outcome |
| Ovarian Serous Adenocarcinoma | ZNF217 (7764), MYLK2 (85366), KIF3B (9371) | no | poor outcome |
| Ovarian Serous Adenocarcinoma | ATP1B2 (482) | no | poor outcome |
| Ovarian Serous Adenocarcinoma | CCNE1 (898) | CCNE1 | poor outcome |
| Squamous Cell Lung Carcinoma | MECOM (2122) | no | favorable outcome |

Example 5: Additional Fusion Methods

Clinical Data Sources.

All RNASeq data for gene fusion analysis was obtained from the Cancer Genomics Hub (CGHub), the current repository for TOGA genomic data—cghub.ucsc.edu.

Cell Line Data Sources.

All COLE RNASeq data for gene fusion analysis was obtained from the Cancer Genomics Hub (CGHub), the current repository for COLE NGS data—cghub.ucsc.edu.

BAM to FASTQ Conversion.

The input to the fusion callers consists of RNASeq reads in FASTQ format, which required conversion of the BAM file provided by TOGA to one or two FASTQ files for single or paired end data (respectively).

BAM files varied in provenance and processing, and many required special handling. For example, older BAM files provided by UNC were aligned using BWA (Burrows-Wheeler Aligner), while newer BAMs contained reads aligned by MapSplice. TOGA recently updated the RNASeq pipeline to support alternative gene expression reporting. (The former pipeline relied on the RPKM measurements for gene expression, while the latter uses RSEM.) These different RNASeq analysis pipelines are referred to by UNC as V1 and V2 respectively (wiki.nci.nih.gov/display/TCGA/RNASeq+Version+2). We used the following BAM prioritization pipeline to select a single "primary BAM" when both formats are available for the same TOGA sample: 1) V2 BAMs were chosen over V1 BAMs and 2) BAMs with newer upload dates were selected when multiple files for the same case were present.

The custom SamToFastq converter described above was used to generate FASTQ files from a TOGA BAM file.

There were 2 cancer types (COADREAD and UCEC) only available as single-end RNASeq data. For single-end BAM file conversion, the program BamTools (github.com/pezmaster31/bamtools) was used to generate FASTQ files.

With the goal of supporting both single and paired-end data, we processed all single-end data using TopHat and all paired-end data using deFuse.

Broadly, our analysis pipeline consists of 5 main steps:

Pre-process the raw data to obtain FASTQ files

Run fusion callers

Filter breakpoints to gene regions of interest

Annotate the breakpoints with the Oncomine transcript set

Summarize and prioritize potentially interesting novel fusions

Steps 1 and 2 were executed in parallel for all samples on a high-performance cloud computing cluster. The filtering and annotation was conducted on the aggregated data as a post-processing step, to enable exploratory analyses of effects of various filters and annotation schemes. After finalizing filtering criteria to minimize false positive fusions (Step 5), the list of Oncomine Prioritized Fusions is validated with RNASeq Exon Expression data.

TopHat.

TopHat-Fusion was obtained from the authors (tophat.cbcb.umd.edu). Software and reference data dependencies were configured as specified by the TopHat documentation:

Software:

TopHat: 2.0.4, includes TopHat-Fusion Post (release Apr. 9, 2012)

bowtie: 0.12.8 (release May 6, 2012)

samtools: 0.1.18 (release Sep. 2, 2011)

blast (2.2.26) (release Mar. 3, 2012)
blast+ (2.2.26) (release Oct. 21, 2011)
Reference and Annotation:
Reference Genome: UCSC hq19 (downloaded May 2012)
Gene Models: refGene, ensGene (downloaded May 2012)
BLAST DB: nt, human, other (downloaded May 2012)
Parameters:

We ran TopHat with largely default parameters on single and paired-end TOGA Illumina data as specified in the TopHat documentation. The following is a list of parameters used.

TABLE 25

| TopHat Parameter | Value Used |
| --- | --- |
| --fusion-search | Flag |
| --keep-fasta-order | Flag |
| --no-coverage-search | Flag |
| --mate-inner-dist | 0 |
| --mate-std-dev | 80 |
| --min-anchor-length | 8 |
| --splice-mismatches | 0 |
| --min-intron-length | 70 |
| --max-intron-length | 500,000 |
| --max-insertion-length | 3 |
| --max-deletion-length | 3 |
| --num-threads | 4 |
| --max-multihits | 20 |
| --transcriptome-mismatches | 2 |
| --genome-read-mismatches | 2 |
| --read-mismatches | 2 |
| --segment-mismatches | 2 |
| --segment-length | 25 |
| --fusion-min-dist | 100,000 |
| --fusion-anchor-length | 13 |
| --fusion-read-mismatches | 2 |
| --fusion-multireads | 2 |
| --fusion-multipairs | 2 |
| --fusion-ignore-chromosomes | chrM |

The —mate-inner-dist and —mate-std-dev parameters have no default values. The first parameter specifies an expected insert size for the RNASeq paired-end reads, while the second parameters specifies the expected standard deviation of that value. The values of 0 and 80 are recommended by TopHat authors for most data sets.

TABLE 26

| TopHat-Fusion Post Parameter | Value Used | Explanation of Values |
| --- | --- | --- |
| --num-fusion-reads | 3 | Recommended value |
| --num-fusion-pairs | 0 | Set to 0 to not penalize low-evidence, but potentially important fusions |
| --num-fusion-both | 0 | |

TopHat-Fusion was executed on one sample at a time, immediately followed by TopHat-Fusion Post. We retained both, unfiltered TopHat-Fusion output and filtered TopHat-Fusion Post output, to enable deeper analyses.

deFuse.

deFuse was obtained from the authors: defuse.sf.net. Software and reference data dependencies were configured as specified by the deFuse documentation:

Software:
deFuse: 0.5.0 (released Apr. 7, 2012)
bowtie: 0.12.8 (release May 6, 2012)
R 2.15.0 (release Mar. 30, 2012)
blat, faToTwoBit (obtained on May 1, 2012)

Reference and Annotation

Reference Genome: Ensembl GRCh37.62 fa (downloaded May 2012)
Gene Models: Ensembl gtf (downloaded May 2012)
Genomic Data:
UCSC EST fasta, EST alignments, and repeats (downloaded May 2012)
NCBI UniGene (downloaded May 2012)
Parameters:

We ran deFuse with default parameters, as specified in the deFuse program documentation.

TABLE 27

| deFuse Parameter | Value Used |
| --- | --- |
| -bowtie_quals | phred33-quals |
| -max_insert_size | 500 |
| -discord_read_trim | 50 |
| -clustering_precision | 0.95 |
| -span_count_threshold | 5 |
| -split_count_threshold | 3 |
| -percent_identity_threshold | 0.90 |
| -max_dist_pos | 600 |
| -num_dist_genes | 500 |
| -split_min_anchor | 4 |
| -max_concordant_ratio | 0.1 |
| -splice_bias | 10 |
| -denovo_assembly | No |
| -probability_threshold | 0.5 |
| -covariance_sampling_density | 0.01 |
| -reads_per_job | 1,000,000 |
| -regions_per_job | 20 |
| -p | 4 | deFuse was executed on one sample at a time. We kept both the filtered and unfiltered results of deFuse output to enable deeper analysis.

Integration.

We integrated the "Level I" data—the output from TopHat-Fusion Post's potential_fusion.txt file and the output from deFuse's results.classify.tsv file. deFuse reports many more potential calls at this level than TopHat, and thus may also report more false-positive predictions. The Level I data was chosen to strike a balance between utilizing the caller's built-in filtering and allowing through enough results to identify potentially real fusions with somewhat weaker evidence.

As each caller provided a different level of annotation and supporting evidence for the fusion calls, the breakpoints of the predicted fusions from both callers were extracted and integrated into a common format for filtering and annotation. The integration steps consisted of converting the reported breakpoints to ones-based genomic coordinate system, and consolidation into a common file format.

Breakpoint Filtering.

The predicted fusions from the "Level I" output of the callers were filtered to only retain those calls where each breakpoint was either in the 5'UTR or CDS region of a RefSeq transcript (refGene circa Jul. 18, 2012, obtained from UCSC). This was done to enrich the predicted fusions for those containing functional gene regions, filtering out, for example, fusions calls where the 3'UTR of one gene is predicted to be fused to a 3'UTR of another gene. Although at the genomic DNA level breakpoints may occur in introns, in RNASeq data such breakpoints would be observed at the nearest exon-intron boundary. Therefore, breakpoints predicted to occur in intronic sequences were also excluded.

Breakpoint Annotation.

After excluding fusions outside of the 5'UTR or CDS region of a RefSeq transcript, the annotation from the RefSeq transcripts was transferred to the remaining breakpoints with some predictions annotated against multiple Entrez IDs.

For each pair of breakpoints, only one transcript per Entrez ID was retained. In case of multiple transcripts, the transcript with the shortest transcript accession was chosen; further ties were broken by sorting the accessions alphanumerically and retaining the first accession. This scheme ensured consistency in annotating breakpoints at the same location. However, predicted breakpoints at different locations for the same gene partners may still result in multiple transcripts representing a pair of genes—possible evidence of alternative transcripts.

Basic annotation coming from the callers themselves was discarded, as it was based on the default annotation source of each respective caller. However, certain output fields from both TopHat and deFuse were retained to help prioritize the predicted fusions. Additionally, certain annotation properties that weren't explicitly reported by the callers were inferred from other caller properties.

Inferred Properties.

Supporting and Spanning read counts were obtained from each caller and summarized in two columns—Reads Span and Reads Span Support. The latter column is a sum of reads spanning the fusion and those supporting the fusion (not to be confused with TopHat's count of "spanning mate pairs where one end spans a fusion," which is sometimes referred to as 'spanning and supporting reads').

The breakpoint sequence reported by the callers was trimmed to include 50 bases on each side of the fusion and consolidated into one column—Breakpoint Sequence. The fusion breakpoint is delineated by a "|". Note that this is the breakpoint sequence as inferred by the caller, and is not simply obtained from the reference genome. Because the inferred sequence may reflect actual sequence observed by the spanning reads, this sequence may represent the complement of the reference genome sequence.

Since neither of the callers provides a definitive '5-prime' or '3-prime' flag, we infer the relative 5'-3' orientation of the fusion partners by combining a caller parameter with the gene strand annotation. For deFuse, the orientation was inferred for each partner based on the following combination of the gene strand and the deFuse output property 'genomic_strand:'

TABLE 28

| Gene | deFuse_genomic_strand | |
|---|---|---|
| Strand | + | − |
| + | 5' | 3' |
| − | 3' | 5' |

TopHat reports a different metric—the relative orientation of reads mapped to the gene partners, so a different rule set is required for inferring 5'-3' order for a pair of genes:

TABLE 29

| Gene A/B Strand | tophat_orientation | | | |
|---|---|---|---|---|
| | ff | fr | rr | Rf |
| +/+ | 5'-3' | | 3'-5' | |
| +/− | | 5'-3' | | 3'-5' |
| −/− | 3'-5' | | 5'-3' | |
| −/+ | | 3'-5' | | 5'-3' |

A Valid Orientation field was labeled as "Y" if there was an inferred 5' and 3' partner for a given gene fusion call.

RepeatMasker Annotation.

Each predicted breakpoint location was also annotated with RepeatMasker features in the neighborhood of the breakpoint. This was done to identify breakpoints in highly repetitive genomic regions, where alignment errors were likely to affect the prediction of the chimeric transcript.

Specifically, a 25 bp sequence upstream or downstream of the 5' and the 3' partner breakpoint respectively was selected as a 'breakpoint flank'. These flanks were intersected against the RepeatMasker elements set (www.repeatmasker.org) downloaded from UCSC Table Browser on Aug. 24, 2012. We reported the element name, element length, and amount of overlap with the 26 base breakpoint flank region for each breakpoint. Currently, the RepeatMasker elements are not filtered for specific element types (LINES, SINES, simple repeats, etc.).

For each fusion prediction, we set a RepeatMasker Overlap field to equal the number of bases the breakpoint flank sequences overlaps with a RepeatMasker element, and considered overlaps of 12 or more bases to be significant. The frequency of significantly overlapping fusion calls is used in the Oncomine Prioritization described below such that gene fusions with a lower frequency of overlap are considered higher quality.

Fusion Exon Expression Imbalance.

Fusions were visualized using RNASeq exon expression data to provide secondary evidence of true positive fusion events by searching for exon expression imbalance before and after the breakpoint call. Specifically, if the 3' partner's expression is impacted by the 5' partner's promoter region, then exon expression should increase post-predicted breakpoint. This effect is especially visible when viewing fused versus non-fused patient samples.

TCGA Exon Expression Data.

TOGA exon expression data was downloaded from the Broad's GDAC Firehose site. The RPKM RNASeq values are listed for each patient as Gene Annotation Format (GAF) features corresponding to a composite of UCSC exons from several different gene definitions including RefSeq. After downloading data for 21 diseases, we found that 4 different sets of GAF features were used to annotate RPKM expression. Finally, availability of patient expression data varied per disease in V1 and V2 RNASeq analysis pipelines described above.

To address these challenges we first mapped UCSC RefSeq exons to available GAF features and calculated the percentage overlap between each RefSeq exon and GAF feature. This step is critical since all CBI processed fusion breakpoints are mapped to UCSC Refgene definitions downloaded on Jul. 18, 2012 and these breakpoints must in turn be mapped to GAF features. 80.8% of the 396,298 RefSeq exons map perfectly to GAF features in the plot shown below. We selected and reported on the RefSeq exon and GAF feature pair that resulted in the largest overlap.

A value called rg_pct provides a metric of the mapping quality of a given RefSeq exon with a GAF feature based on the following formula:

$$rg\_pct = overlap/length_{refseq} * overlap/length_{GAF\ feature}$$

Mappings with an rg_pct value of 1 overlap perfectly, while values less than 1 indicate the RefSeq exon or GAF feature did not map to the exact same genomic regions and the RPKM value may be suspect.

We selected RNASeq V2 data for all diseases except STAD due to non-availability of V2 data.

Cell Line Exon Expression Data.

Exon expression data for cell line samples was generated from the COLE BAM files obtained from CGHub. The method employed was similar to Step 18 as described in the "TOGA mRNA-seq Pipeline for UNC data" method available here: webshare.bioinf.unc.edu/public/mRNAseq_TCGA/UNC_m RNAseq_summary.pdf.

A difference between the UNC method and our method is the use of RefSeq Exons BED in our method instead of a composite exons BED used by the TOGA.

Exon Expression Imbalance Calculation.

Each sample was systematically analyzed for evidence of potential 5' promoter-induced imbalance in 3' partner expression. Expression levels for each gene were first converted to a log scale, and then z-score normalized across each disease's sample cohort. This normalization was performed at the exon level to account for population-wide trends such as 3' bias or poor RefSeq exon/GAF feature match (see below).

Raw RPKM expression values (top) vs. z-score normalized values for PLXNB21 and COL7A1 in Ovarian Serous Carcinoma patients (See FIG. 8 A-D). The population-wide dips in PLXNB1 expression at exons 12, 17 and 23 are smoothed out in the normalized data. A sample predicted to harbor a fusion between these genes is highlighted in red; wild-type patients are shown in blue. The red diamond indicates the caller-predicted breakpoint exon.

Prior to normalization, samples that were considered wild-type for the fusion under consideration but that were predicted to harbor other fusions involving one of the gene partners were removed from the wild-type population, so as not to contaminate z-score calculations.

After normalization, each sample was assigned a p-value calculated via one-sided Student's t-test on the hypothesis that the sample's post-breakpoint normalized expression values (Population A) have a higher mean than the pre-breakpoint values ($H_0$: $\mu_A \leq \mu_B$). The caller-predicted breakpoint was used to separate the expression populations for samples identified by either fusion caller.

P-values were also calculated for each wild-type sample to facilitate analysis of p-values for fusion-positive samples in the context of the overall population. This allows us to discard fusions involving genes that exhibit population-wide exon imbalance trends that are not fusion-induced. Any sample whose p-value did not rank within the top fraction of wild-type sample p-values was discarded. The breakpoint that maximized the difference between pre- and post-breakpoint expression levels was used for wild-type sample p-value calculation.

Fusion Summarization.

Fusions were summarized within a disease based on the occurrence of unique gene pairs, and based on the occurrence of individual genes, possibly with multiple partners.

For a unique fusion pair (unique by Entrez ID pair), the number of samples within a disease with at least one prediction of that fusion by either caller is the Fused Sample Count. Since multiple breakpoints for the same pair of genes may be reported in one sample and across the samples, the number of unique fusion pairs within each disease is much less than the total number of fusion calls. In order to filter and prioritize fusions at the gene pair level rather than the fusion call level, several of the fusion caller properties were summarized. The following table shows the properties that were summarized for a given fusion partner pair across the individual predictions:

TABLE 30

| Property | Summary Method |
|---|---|
| DEFUSE_EVERSION | % of total fusion calls = 'Y' |
| DEFUSE_VALID_ORIENTATION | % of total fusion calls = 'Y' |
| DEFUSE_NUM_MULTI_MAP | % of total fusion calls >0 |
| TOPHAT_VALID_ORIENTATION | % of total fusion calls = 'Y' |
| 3P/5P_REPEATMASKER_OVERLAP | % of total fusion calls ≥12 |

The Adjacent flag is set for a fusion if the genes are <1 Mb apart on the genome and the defuse_eversion flag is set in 75% of the individual fusion prediction for these fusion partners.

Gene-Level Summary.

Fused sample counts were also summarized at the gene level (unique by Entrez gene ID) within each disease type and across diseases (pan-cancer). This summarization approach was irrespective of inferred orientation within the fusion. In addition, fused sample counts were tallied for only the Oncomine Priority fusions (described below).

Individual unique fusion pairs were cross-referenced to the Mitelman database of genomic aberrations (cqap.nci.nih.gov/Chromosomes/Mitelman). The match was done based on gene names and not disease type. Therefore, gene fusions reported in Mitelman in a certain disease may have occurred in a different disease type in the TOGA datasets.

Gene fusions summarized at the gene level were cross-referenced to the Mitelman database based on gene name. Thus, there is more potential for the gene as reported in Mitelman to be of different histology or altogether different aberration type (for example a large chromosome-level deletion instead of a fusion) than the predicted unique fusion pairs.

Normal Sample Fusion Blacklist.

With the assumption that all fusions called in TOGA normal samples are false positives, we asked the following questions: 1) Are fusion calls in tumor samples identified in normal samples? 2) Are Oncomine Prioritized Fusions identified in tumor samples also identified in normal samples? Answering the first question provides a baseline sense of the technical false positive rate in tumor gene fusion calls. The second question is a sanity check on how well the Oncomine Priority Fusion filter is overcoming this problem. 344 paired-end normal samples across 10 diseases were downloaded and processed using the same deFuse pipeline described above. A total of 56,579 total fusion calls consisting of 6,024 unique fusions were observed. These normal sample fusion calls were used to generate a blacklist and remove these false positives from Oncomine Priority gene fusions.

Paralogous Fusion Partner Blacklist.

A blacklist of fusions between paralogous gene family members was assembled using two strategies: 1) manually inspecting high frequency fusion partner gene names and 2) comparing the first 3 characters of all Priority Fusion partner gene names. In the latter strategy, fusion partners were verified to be "paralogous" using HomoloGene, Ensembl, SIMAP, and GeneDecks V3 before inclusion in the final blacklist. The table below shows the top 10 most commonly observed gene fusion calls between paralogous fusion partners. The entire table consists of more than 400 unique paralogous gene fusions and is used to remove these false positives from our Oncomine Priority gene fusions.

TABLE 31

| GeneA Symbol | GeneB Symbol | Observed in Normal | TCGA Cancer Types |
|---|---|---|---|
| HLA-B | HLA-C | YES | BLCA, BRCA, CESC, COAD, GBM, HNSC, KICH, KIRC, KIRP, LAML, LGG, LIHC, LUAD, LUSC, OV, PAAD, PRAD, SKCM, STAD, THCA, UCEC |
| HLA-A | HLA-B | YES | BLCA, BRCA, CESC, GBM, HNSC, KICH, KIRC, KIRP, LAML, LGG, LIHC, LUAD, LUSC, OV, PAAD, PRAD, SKCM, STAD, THCA |
| HLA-A | HLA-C | YES | BLCA, BRCA, CESC, GBM, HNSC, KICH, KIRC, KIRP, LAML, LGG, LIHC, LUAD, LUSC, OV, PAAD, PRAD, SKCM, STAD, THCA |
| TTLL12 | TTLL12 | YES | BLCA, BRCA, CESC, GBM, HNSC, KICH, KIRC, KIRP, LAML, LGG, LIHC, LUAD, LUSC, OV, PAAD, PRAD, SKCM, STAD, THCA |
| TRPV1 | TRPV1 | YES | BLCA, BRCA, CESC, GBM, HNSC, KICH, KIRC, KIRP, LAML, LGG, LIHC, LUAD, LUSC, OV, PAAD, PRAD, SKCM, STAD, THCA |
| B9D1 | B9D1 | YES | BLCA, BRCA, CESC, GBM, HNSC, KICH, KIRC, KIRP, LGG, LIHC, LUAD, LUSC, OV, PAAD, PRAD, SKCM, THCA |
| TGIF2-C20ORF24 | TGIF2-C20ORF24 | YES | BLCA, BRCA, CESC, GBM, HNSC, KICH, KIRC, KIRP, LAML, LGG, LIHC, LUAD, LUSC, OV, PRAD, SKCM, STAD, THCA |
| HLA-B | HLA-E | YES | BLCA, BRCA, CESC, COAD, GBM, HNSC, KICH, KIRC, KIRP, LAML, LGG, LIHC, LUAD, LUSC, OV, PAAD, PRAD, READ, SKCM, STAD, THCA, UCEC |
| SEC16A | SEC16A | YES | BRCA, CESC, GBM, HNSC, KICH, KIRC, KIRP, LAML, LGG, LUAD, LUSC, OV, PRAD, SKCM, THCA |
| LOC390940 | LOC390940 | YES | BLCA, BRCA, CESC, GBM, HNSC, KICH, KIRC, KIRP, LGG, LUAD, LUSC, OV, SKCM, STAD, THCA |

Fusion Prioritization—Oncomine Priority Scheme.

The Oncomine Priority scheme outlined below was designed by iterative exploration of the top results in the Level I fusion predictions and systematic elimination of suspect false-positive fusions, while retaining previously discovered 'true-positive' (Mitelman) fusions. This scheme was meant to highlight fusions that conformed to certain features expected of a 'true-positive' fusion, and conversely, lack features observed in many 'false-positive' fusions.

A fusion is an Oncomine Priority fusion if:

TABLE 32

| Fusion Summary Property | Value | Explanation |
|---|---|---|
| DEFUSE_VALID_ORIENTATIONTOPHAT_VALID_ORIENTATION | >0.75 | Most predictions in correct orientation |
| ADJACENT | 'N' | |
| REPEATMASKER_FREQUENCY | <0.25 | Minority or none of predicted breakpoints are in repetitive regions |
| DEFUSE_NUM_MULTI_MAP | >0 | Most spanning reads map uniquely to fusion breakpoint |
| PARALOGOUS_PARTNERS | Not on Paralogous Blacklist | Manually curated blacklist of predicted fusions between paralogous genes |
| OBSERVED_IN_NORMAL | Not on Normal Blacklist | List derived from processing 344 Normal samples using deFuse. |

Example 6: Oncomine NGS Mutation Methods

Mutation Integration.

The goal of the data integration was to create the most complete set of NGS mutation data currently available. We considered the following sources:
Primary Data Sources
COSMIC Cell Lines Project
TCGA Data from Broad GDAC Mutation_Packager (stddata build)
TCGA Data from DCC level 2
Compendia mutation calls based on TCGA Data
Publications containing NGS mutation data
COSMIC Cell Lines Project The Cancer Genome Project has characterized the exomes of over 1000 cancer cell lines for mutations. The database provides the mutation data, filtered for quality, in a flat-file format. The cell line data was subjected to the same Oncomine curation and annotation processes used for clinical mutation data. Cell line names were vetted against the Oncomine ontology, and cancer types were standardized to be comparable with clinical mutation data.

The dataset was obtained from the Wellcome Trust Sanger Institute Cell Lines Project website: cancersangerac.uk/cancergenome/projects/cell_lines as it appeared in November 2013.

Broad GDAC Mutation_Packager. Broad has been working since Q3 2011 on gathering and integrating mutation data from multiple sources.

docs.google.com/document/d/18XIWv-a9xLBOflNikOa9rCXOyiravMM8-PVJxAQPPo/edit

The above document details the provenance of the MAF files the Broad integrates into Mutation_Packager standard data runs. The Broad has integrated many MAF files that are maintained outside of the central TCGA DCC system, often by members of the Analysis Working Groups themselves. We have performed extensive comparisons between all MAF files available to us. It is our belief that the Broad has the most complete mutation data available.

For this release, we integrated data from the 2013_08_09 stddata build.

TCGA DCC Level 2. This is the controlled access mutation data available from the DCC. TCGA has a page on their wiki that provides additional details about the MAF files available:

wiki.nci.nih.gov/display/TCGA/TCGA+MAF+Files

For this release, we considered all MAF files available as of Sep. 15, 2013.

NGS DNASeq Mutation Calls. PRAD mutation calls available from TCGA were of low quality and resulted in false-positive 'Gain of Function' predictions. Therefore, all calls for this disease were sourced from Compendia's own mutation calling pipeline. The Compendia mutation calls were made to conform to the MAF file format for integration. Please see the Appendix: Compendia NGS DNASeq Mutation Calling for more details. Included in this release are 170 Prostate Adenocarcinoma patients.

Hand-Curation of All NGS Data. TCGA and Non-TCGA NGS datasets were sourced by the Oncomine curation team directly from their primary sources—mainly peer-reviewed cancer publications and the above publically accessible databases. Mutation data, usually available in the Supplementary Materials, was brought to the standard required for mutation re-annotation and classification as part of the overall NGS Mutation processing pipeline. Cancer types were curated using the Oncomine cancer type ontology, assigning the appropriate Oncomine Cancer Type based on the best-available clinical metadata present in the publication. Since all the published experiments claimed whole-genome ('NGS') coverage, the null gene set for each dataset was assumed to be inclusive of all human RefSeq genes. The non-TCGA data was processed in the same exact way as the TCGA MAF-file data for the rest of the mutation analysis pipeline.

Remove Duplicate Mutations. We performed some simple clean-up operations to remove duplicate mutation records present in the source data. We also performed several file-column name re-mappings, as many of the sources do not adhere to the MAF file standard. Duplicate mutations from various tumor/normal aliquot pairs of the same patient sample were removed.

Mutation Annotation. Data obtained from the TCGA and non-TCGA sources contains mutation results from datasets processed and annotated by different genome sequencing centers or authors over the course of several years. This leads to the mutation calls annotated using different gene models and using different conventions for variant classification. Since Compendia's approach to defining mutations relies on accurate variant annotation, we re-annotated the mutations against a single set of transcripts and consistent variant classification rules. A standard annotation pipeline ensured that mutations across disease types are evaluated consistently and are subject to common interpretation during the nomination of potential oncogenes or tumor suppressor genes. It also provided important annotation not consistently available from the primary sources, such as the HGVS-style mutation nomenclature (e.g., V600E).

Mutations obtained from primary sources are processed by Compendia according to the following general steps (details provided below).

We first re-annotated each mutation using Compendia's Oncomine transcript set. Successfully annotated mutations received Compendia-derived annotation, while the rest retain annotation obtained from the primary source. Annotation includes:
Variant classification
Variant position
Variant change.

Several filtering steps are implemented to remove redundant annotation in multiple transcripts, and mutations located outside of gene regions of interest.

Excluding "Ultra-mutator" Samples. In certain diseases, such as Endometrial Carcinoma, several highly-mutated samples may dominate the overall mutation counts. We also observed such "ultra-mutator" samples in Lung Adenocarcinoma, Gastric cancer, Melanoma, and Colorectal cancer. Based on a cut-off determined by analyzing ulta-mutator outliers in several cancer types, we decided on <5,000 non-silent exon mutations as the threshold for inclusion of a sample in our recurrence analysis. We therefore excluded a number of ultra-mutator samples in this dataset from our downstream analysis pipelines.

In the Mutation Annotation step, we attempted to re-annotate the mutations obtained from the primary sources against a standard transcript set compiled by Compendia. This transcript set included RefGene transcripts from hg18 and hg19 genome builds, obtained from UCSC on Feb. 19, 2012.

Each mutation is individually mapped against a contig in the Oncomine Transcript Set within the specified genome build. SNP mutations were mapped directly to their start location, while for small insertion (INS) and deletion (DEL) mutations a position of interest is selected for mapping. For insertions, the position of interest is the base at which the insertion occurred. Depending on the direction of the transcript, this can either be the start or the end coordinate of the mutation, depending on whether the gene is on the positive or negative strand respectively. For deletions, the position of interest is the deleted base if the transcript is on the positive strand or the last base deleted if the transcript is on the negative strand. This adjustment ensures that the mutation position is defined as the first base affected by the insertion/deletion with respect to the direction of the transcript translation, i.e. 5'→3'.

For a mutation successfully mapped to a transcript, the Compendia mutation annotation was inferred with respect to that transcript. For mutations that failed to map, the annotation from the primary data source was retained, and a variant position for Hotspot calculations was constructed based on the genomic coordinate (more details below). Since only the standard set of 23 chromosomes was included in our transcript set, mutations located on mitochondrial or other non-standard contigs were not mapped.

Below is a description of the criteria used in annotating the mutations that map to the Oncomine Transcript Set.

Variant Classification. For each mutation successfully mapped to a transcript, the variant classification was inferred using a combination of mutation and annotation properties. Our approach identified six main mutation variant classifications, all located within transcript. Variant classifications for mutations outside a gene region (e.g. intergenic) are currently not considered (see filtering section below). The following are the criteria used for inferring the variant classification:

TABLE 33

| Variant Classification | Criteria | Transcript Region |
|---|---|---|
| Splice_Site | Mutation is within 2 bp of a splice site | exon or intron |
| 3'UTR, 5'UTR | Mutation is in UTR region and not within 2 bp of splice site | UTR exon |
| Intron | Mutation is in an intron and is between 3 to 10 bp from a splice site | intron |
| Missense, Nonsense, Nonstop, Silent | Mutation is a SNP | coding exon |
| Frame_Shift_Ins/Del | Mutation is an INS/DEL not divisible by 3 | coding exon |
| In_Frame_Ins/Del | Mutation is an INS/DEL divisible by 3 | coding exon |
| Non_Coding_Exon | Mutation is in a non-coding transcript | non-coding exon |

This list of variant classifications is a subset of the allowed variant classification specified by the TOGA for the MAF file format.

wiki.nci.nih.gov/display/TCGA/Mutation+Annotation+Format+%28MAF %29+Specification This subset covers the mutation classes of interest for recurrence analysis and identification of potential Gain or Loss of Function genes, and is thus sufficient for the vast majority of the mutations that are mapped to the Oncomine Transcript Set. The following table describes the likely variant classification that would be assigned versus an original author classification (assuming mutation maps to the same transcript as that used in defining classification), and the relative abundance of that type of mutation in the source dataset:

TABLE 34

| Example TCGA Variant Classification | Equivalent Compendia Variant Classification | Potential Oncomine Mutation Classification (H)otspot, (D)eleterious or (O)ther |
|---|---|---|
| Missense_Mutation | Missense_Mutation | H, O |
| Nonsense_Mutation | Nonsense_Mutation | D |
| Nonstop_Mutation | Nonstop_Mutation | H, O |
| Silent | Silent | O |
| Frame_Shift_Del | Frame_Shift_Del | D |
| Frame_Shift_Ins | Frame_Shift_Ins | D |
| Translation_Start_Site | Missense_Mutation | O |
| In_Frame_Del | In_Frame_Del | H, O |
| In_Frame_Ins | In_Frame_Ins | H, O |
| 3'UTR | 3'UTR | O |
| 5'UTR | 5'UTR | O |
| Non_coding_exon (or "RNA") | Non_coding_exon | H, O |
| Splice_Site | Splice_Site | O |
| Intron | Intron | — |
| 5'Flank | --not supported by Oncomine transcript set-- | — |
| IGR | --not supported by Oncomine transcript set-- | — |
| Other (classification present in mutation list but not supported by TCGA) | | — |

Variant Position.

One of the primary goals of the current analysis is to identify genes with Hotspot mutations, which are mutations of a certain classification that are observed at the same location in multiple tumor samples. To effectively identify recurrence and define a hotspot for each mutation, we must construct a mutation spot identifier that encompasses the mutation position, the identity of the amino acid or base affected, and the variant classification. We aggregated mutations that occur at the same location irrespective of the specific base change they generate. Therefore, we only used the reference base or amino acid to define the variant position. This ensures that mutations affecting the same codon or genomic position will be counted towards a possible hotspot, even if the alternate alleles they generate are different. For example, for a given gene, missense mutations V600E, V600F and V600G would all have a variant position of V600 and would thus be aggregated together when identifying hotspot mutations. Our variant position is thus defined as follows:

Variant Position=mutation spot{base|codon}+
  reference{base|AA}+[variant classification]

If the mutation is in a coding region, then the codon number and the respective amino acid at the base of interest is used to identify the mutation spot—p.L116_in_frame_del—for example. If the mutation is in a non-coding region, such as the UTR, then the position and identity of the reference nucleotide at the base of interest is used to identify the mutation spot—c.110C—for example.

For Splice_Site mutations outside of the coding region, the variant position is specified relative to the splice boundary. The relative position is identified using a +{1 |2} or a −{1 |2} (splice site mutations are those within 2 bases of a splice junction). As with insertions and deletions, a suffix of "_Splice_Site" is added for a Splice_Site mutation. For INS and DEL mutations, a suffix indicating an in frame ("_in_frame_ins" or "_in_frame_del") or frame shift ("_frame_shift_ins" or "_frame_shift_del") is added to the variant position.

In summary, the following are examples of the different possible variant position formats:

"chr1_c.A155025094_Splice_Site". The variant change (see below) for these mutations is not defined.

Although the suffix of the variant position often implicitly incorporated the variant classification, when calculating hotspots, both the variant position and the variant classification are explicitly used for aggregating mutations. Therefore, mutations that may produce identical variant positions but have different variant classifications (such as a missense and a nonsense SNP) were tallied separately.

Variant Change.

The variant change provides HGVS-like information about the alternate allele change of the mutation. For SNP mutations in the coding region, the variant change is a full HGVS protein-level sequence variant description, indicating the alternate amino acid. For SNPs outside of the coding region, the alternate allele nucleotide base is provided.

TABLE 35

| Variant Type | Near Splice Site? | In Coding Region? | Variant Position |
|---|---|---|---|
| SNP | YES | YES | p.A42_Splice_Site |
|  |  | NO | c.42 + 1_Splice_Site |
| SNP | NO | YES | p.A42 (Missense, Nonstop, Silent) |
|  |  |  | p.Stop42 (Nonsense) |
|  |  | NO | c.*42T (3'UTR) |
|  |  |  | c.-42C (5'UTR) |
|  |  |  | c.42 (Non_coding_exon) |
| INS | YES | YES | p.A42_Splice_Site |
|  |  | NO | c.42 + 1_Splice_Site |
|  | NO | YES | p.A42_{in_frame_ins|frame_shift_ins} |
|  |  | NO | c.*42G_{in_frame_ins|frame_shift_ins} (3'UTR) |
|  |  |  | c.-42G_{in_frame_ins|frame_shift_ins} (5'UTR) |
|  |  |  | c.42 (Non_coding_exon) |
| DEL | YES | YES | p.A42_Splice_Site |
|  |  | NO | c.42 + 1_Splice_Site |
|  | NO | YES | p.A42_{in_frame_del|frame_shift_del} |
|  |  | NO | c.*42T_{in_frame_del|frame_shift_del} (3'UTR) |
|  |  |  | c.-42C_{in_frame_del|frame_shift_del} (5'UTR) |
|  |  |  | c.42 (Non_coding_exon) |

For mutations that do not map to the Oncomine Transcript Set, and hence do not have a transcript-based location, the genomic location (start position) and the reference nucleotide (reference allele) is used as the variant position irrespective of the coding region or splice site proximity. The variant classification supplied by the primary data is then added as a suffix. For example, a SNP missense mutation would have a variant position such as "chr19_c.C22952756_Missesnse_Mutation", and a splice site SNP would have a variant position For INS and DEL variant types, the variant position (see above) was used as the variant change. In these cases, the consequence of the change at the amino acid level is not inferred. As such, variant change for INS/DEL does not strictly follow HGVS specification.

The following are illustrative examples of variant changes for Compendia-derived mutation annotation:

TABLE 36

| Mutation | Variant Classification | Variant Position | Variant Change |
|---|---|---|---|
| SNP in CDS, E > K, residue 137 | Missense_Mutation | p.E137 | p.E137K |
| SNP in Intron C > 2, two bp from splice site | Splice_Site | c.4913 − 1_splice_site | c.4913 − 1 |
| INS in CDS at residue Gly 264 | Frame_Shift_ins | p.G264_frame_shift_ins | p.G264_frame_shift_ins |
| DEL of one base in a UTR | 3'UTR | c.*1007A_frame_shift_del | c.*1007A_frame_shift_del |

For mutations that do not map to the Oncomine Transcript Set, the variant classification from the primary data source was retained.

Transcript Filter.

To avoid retrieving multiple transcripts, and hence multiple annotations for a single mutation within a gene, we kept only one transcript per mutation per gene (unique Entrez ID). If a mutation mapped to several transcripts of a gene, only one was chosen. However, if a mutation mapped to several genes, then only one transcript per gene was selected. It is thus possible for a mutation to receive two different annotations, but only if they stemmed from transcripts with different Entrez IDs.

We chose the representative transcript for a mutation based on the following priority scheme:

Transcript with the most impactful variant classification:

High impact in coding: Missense, Nonsense, Nonstop, Frame-shift

Low impact in coding: In-frame, silent

Outside of coding region: Splice Site, 3' or 5' UTR, Non-coding exon

Outside of exon: Intron

If there is a tie based on priority, the transcript with the shortest (by length) RefSeq transcript accession is chosen, followed by the alphanumerically smallest transcript accession in event of further ties. For example—of the transcripts NM_003319, NM_133378, and NM_00125685 for the TTN gene, we would choose NM_003319 as the representative transcript.

These steps allowed us to repeatedly choose a consistent transcript for the same type of mutation at one location. One consequence of choosing the most impactful transcript is that multiple transcripts may be utilized for mutations at multiple locations in a single gene. However, the benefit of this scheme is that any mutations of the same variant classification at the same location are always assigned to the same transcript, and hence will be in the same frame of reference when computing recurrence for hotspot identification.

Filter by Mutation Class and Type.

All mutations were further filtered by variant type and class. To avoid including mutations of minor interest to gene function analysis, we filtered out mutations that were not resolved to a gene region, either because they fell significantly far outside of a transcript, or because they were in a location not associated with a RefSeq gene. These mutations were evident either by their lack of gene identifier (Entrez ID=0 or blank), or membership in the following variant classes: Intron, 5'Flank, IGR, and miRNA.

We also filtered out mutations with variant type DNP, TNP, ONP, Complex_substitution, and Indel, as their annotation was not supported by our pipeline Since certain data sources included extensive amounts of intronic and intergenic mutations, this filtering step significantly reduces the size of the dataset as many NGS datasets don't apply these filters pre-publication.

Classifying Mutations as Hotspot, Deleterious, or Other.

The next step in our analysis pipeline identified recurring mutations in multiple samples based on their variant position, and categorized them into Hotspot, Deleterious or Other variant categories. For this step, and the subsequent frequency calculations, mutations for each disease type were processed independently. Only mutations of the same variant classification were tallied together, so, for example, a missense mutation and a silent mutation at the same position are counted separately.

To identify driver events, each mutation for a given Entrez Gene ID was categorized as "Deleterious" or "Hotspot" depending on the following criteria:

A mutation was deemed 'recurrent' if it was observed in the same variant position in 3 or more tumor samples.

A mutation belongs to the "Hotspot" variant category if it is:

Recurrent AND

Annotated with one of the following variant classifications:

In-frame insertion/deletion

Nonstop

Missense

Non_Coding_Exon

A mutation belongs to the "Deleterious" category if it is:

Non-recurrent AND

Annotated with one of the following variant classifications:

Frame shift insertion/deletion

Nonsense

A mutation is considered in the "Other" variant category if it did not fit the above criteria.

The Oncomine Mutation Classification and the Variant Classification can be used to summarize the relative frequencies of various mutations at the gene level.

Nominating "Gain of Function" and "Loss of Function" Genes.

Individual genes were classified into predicted functional classes, namely "Gain of Function", "Recurrent Other", and "Loss of Function", to reflect their relative enrichment in potential activating or deleterious mutations. Details of the scheme used to make the classification are provided below.

Mutated Sample Frequency Calculation.

Mutation frequencies for each gene were calculated with respect to a given variant classification and variant category across all samples within a disease type. Overall mutation frequency for a gene within a disease was calculated by combining mutations of all variant classifications.

Overall Mutation Frequency.

Overall mutation frequency for a gene was obtained by dividing the total number of samples with at least one mutation of any variant classification in that gene (Mutated Sample Count) by the total number of samples in the given cancer type (Sample Count).

Hotspot Frequency.

Hotspot frequency for a gene was obtained by dividing the total number of samples with at least one mutation belonging to the "Hotspot" Oncomine Mutation Classification by the Mutated Sample Count—the total number of samples with at least one mutation for the given gene. If a sample had both Hotspot Missense and a Hotspot In-Frame Deletion, for example, it would only be counted once.

Hotspot Missense Frequency.

To obtain a Hotspot Missense Frequency for a gene, the number of samples containing at least one Missense mutation with an Oncomine Mutation Classification of "Hotspot" was divided by the Mutated Sample Count—the number samples with at least one mutation of any type in this gene. Samples with more than one mutation of such type were only counted once.

Deleterious Frequency.

To obtain the Deleterious frequency for a gene, the number of samples containing at least one mutation with an Oncomine Mutation Classification of "Deleterious" was divided by the Mutated Sample Count—the number of samples with at least one mutation for the given gene. Samples with more than one mutation of that type were only counted once.

Other Frequency.

To obtain the Other frequency for a gene, the total number of samples with at least one mutation with an Oncomine Mutation Classification "Other" was divided by the Mutated Sample Count—the total number of samples with at least one mutation for the given gene. If a sample contained both splice site and UTR mutations, for example, it would only be counted once.

Hotspot, Other, and Deleterious Frequency Consideration.

Hotspot, Other, and Deleterious frequencies should not be expected to add up to 100%, since a sample may have been counted in more than one of these categories.

Assessing Significance of Hotspot and Deleterious Mutations.

The Hotspot and Deleterious p-values for each gene within a disease are calculated by two independent methods.

Significance of Deleterious Mutation Enrichment.

To assess whether a gene was significantly enriched for deleterious mutations compared with other genes, given the background mutation rate, we performed Fisher's exact test using the following contingency table:

TABLE 37

|  | Deleterious | Other |
|---|---|---|
| Gene of Interest | A | B |
| All Other Genes | C | D | where A, B, C, and D are counts of mutations across a disease. Nonsense mutations, frame shift insertions and frame shift deletions are classified as deleterious mutations, while mutations of any other type (UTR, silent, missense, etc., but non-intergenic) count as others.

Q-values are calculated within each disease, by counting the number of genes with deleterious mutations (N), and calculating the rank of each association. The q-value for a given p-value is then Q=p*N/rank.

Significance of Recurrent Hotspot Mutations.

In order to calculate gene-specific p-values, the significance of the most recurrent hotspot on that gene is assessed. Given the assumption that each sequence position was equally likely to mutate, each gene can be tested whether the most recurrent is significantly greater than that expected using a multinomial test. This is an exact test of the sampling algorithm that has been implemented in previous versions. One of the advantages of this test is that the p-value precision is increased to 1E-16, so no flooring occurs. To obtain hotspot mutations, we filtered the mutations to remove any that did not affect the coding sequence (i.e. by removing silent, UTR, stop codon, and splice site mutations), and then removed mutation data for genes that we could not annotate with RefSeq transcript identifier. We then counted the mutations observed for each transcript in each disease. We calculated the amino acid sequence length by dividing the CDS length by three and subtracting 1.

The exact calculation of the p-value is framed as the following. Given an amino acid sequence of length x, an observed number of hotspot mutations n, what is the likelihood of observing r or more mutations at the most recurrent spot by chance For each gene, the p-value is calculated by the following formula:

$$p = Pr(y_{(X)} \geq r)$$
$$= 1 - Pr(y_1 < r, y_2 < r, \ldots, y_X < r)$$
$$= 1 - \sum_{0}^{r-1} \frac{n!}{y_1! y_2! \ldots y_X!} (1/x)^n$$

where $y_{(X)}$ is the mutation count at the most recurrent hotspot, and $y_1, \ldots, y_X$ stands for the mutation count at each spot $1, \ldots, x$.

When n and x are large, the above formula can be very slow, an approximation with Bonferroni-Mallows (BM) bounds were used:

$$1 - \frac{n!}{n^n e^{-n}} \left\{ \prod_{i=1}^{X} P(y_i \leq r-1) \right\} P(W=n)$$

where $y_i$ is a Poisson random variable with mean n/x, and $W = \sum_{i=1}^{X}$, where Y is a truncated Poisson. P(W=n) is estimated by Edgeworth Expansion. The lower and upper Bonferroni-Mallows bounds for the p-value are:

$$1 - \text{Binomial}\left(r-1, n, \frac{1}{x}\right)^x \leq p \leq x * \left(1 - \text{Binomial}\left(r-1, n, \frac{1}{x}\right)\right).$$

If the approximation falls outside of the BM bounds, either the lower bound or upper bound was used. It rarely occurred in our data, and it mostly occurred for small p-values (p<1e-16) or large p-values (p~=1).

Q-values are calculated using the Benjamini-Hochberg method, which is Q=p*N/rank, where N is the number of transcripts and rank is the rank of each p-value.

Silent Hotspot Mutations.

Recurrent silent mutations—silent hotspots—seem to be an indication of sequencing errors, occurring in regions of low sequence quality and serving as a 'canary in the coal mine' for false-positive missense mutation peaks in the neighboring nucleotides. Based on reviewing genes with silent hotspots, and the evaluation of neighboring silent peaks, we believe that these genes are subject to systematic sequencing errors, and hotspot mutations in these genes should not contribute to the gene classification.

Oncomine Gene Classification Rules.

Once the mutations have been classified, individual genes are nominated to one of three classes—"Gain of Function," "Loss of Function," and "Recurrent Other." The classification is based on the combination of relative frequencies and the significance of the mutations observed in the gene. The significance of the mutations per gene is assessed by a p-value.

Recurrent Silent Mutations.

A "Gain of Function" gene will have a relatively high frequency of Hotspot Missense mutations and a low frequency of Deleterious mutations, while a "Loss of Function" gene contains a large fraction of Deleterious mutations. "Recurrent Other" genes tend to contain recurrent insertion/deletion mutations, some of which—for example recurrent frame shift indels of 1 base—exhibit signs of potential false-positive calls that may arise from local alignment errors. In general, we are more confident about the functional importance of genes classified as Gain/Loss of Function.

Pan-Cancer Analysis.

To summarize mutations across diseases we performed identical calculations as we did for within-disease analyses, but without stratifying the mutation records by disease. All mutation records were aggregated, and frequencies, variant categories and gene classes were calculated in this pan-cancer context. For the pan-cancer summary, genes (unique by Entrez ID) are summarized across all diseases with one row per disease. However, a summary of the genes within disease is also provided, but in a pan-cancer context. This means, for example, that samples with Hotspot mutations are totaled within a disease, but only for the mutations considered Hotspots in a pan-cancer context. Cancer types with <20 samples were included in Pan-Cancer analysis, even though they were not eligible for within-disease analysis due to low sample count.

Cell Line Annotations.

Cell line mutation data was subjected to the same Oncomine curation and annotation processes described above except for mutation and gene classification. Instead, mutations from cell lines were annotated with Oncomine mutation classification and gene classifications whenever a mutation in a cell line was also observed in a clinical sample. This annotation was performed only for mutations having a Hotspot or Deleterious or Other Oncomine mutation classification. If a mutation was not observed in tumors, it would receive "Unobserved in Tumor" mutation classification.

Mutations from a cell line and a tumor sample are considered equivalent if they belong to the same gene, and have the same variant position and variant classification.

Cell lines names were vetted against internal Oncomine ontology, and cell line cancer types were standardized to be comparable with clinical mutation data. Several cell lines whose identity or cancer type could not be independently verified through databases or publications were removed from our analysis. The mutation annotation from clinical data was performed in a pan-cancer and within-disease contexts.

NGS DNASeq Mutation Calling

BAM File Selection.

We queried TCGA's CGHub to identify patients having a single tumor-normal BAM pair. We did so to remove the possibility of mutation call differences due to different tumor-normal pairs.

Reference Genome Builds.

We identified the reference genome builds used to align the reads in the BAM files by parsing the SAM headers. We located, downloaded, and indexed all the reference genome builds which are needed as inputs to the mutation caller packages.

Mutation Calling.

We employed the following somatic mutation calling packages for this analysis:

MuTect (1.0.27783), Broad Institute, Cancer Genome Analysis Group (CGA) (Cibulskis, 2013)

SomaticIndelDetector (1.6-13-g91f02df), Broad Institute, Genome Analysis Toolkit (GATK)

MuTect.

MuTect performs initial preprocessing to remove "reads with too many mismatches or very low quality scores" (MuTect documentation). Next, for a candidate mutation two log odds (LOD) scores are calculated that describe the likelihood of a mutation being present in the tumor sample ($LOD_T$) and not mutated in the normal sample ($LOD_N$):

$$LOD_T = \log_{10}\left(\frac{P(\text{observed data in tumor} \mid \text{site is mutated})}{P(\text{observed data in tumor} \mid \text{site is reference})}\right)$$

$$LOD_N = \log_{10}\left(\frac{P(\text{observed data in normal} \mid \text{site is reference})}{P(\text{observed data in normal} \mid \text{site is mutated})}\right)$$

MuTect expects somatic mutations to occur at a rate of ~1 in a Mb and requires $LOD_T \geq 6.3$. MuTect requires that a mutation not be in dbSNP and have a $LOD_N \geq 2.3$ since non-dbSNPs are expected to occur at a rate of 100 per Mb. Both cutoffs are chosen to guarantee a false positive rate less than half of the expected somatic mutation rate. Finally, additional post-processing steps are performed, including testing that the alternate allele is observed in both read directions. MuTect requires at least 14 tumor reads and 8 normal reads for a mutation to be considered.

SomaticIndelDetector (SID).

For a given mutation site, SID considers candidate indels using counts-based thresholding and an indel consensus voting scheme. The indel with the largest number of supporting reads, or votes, is chosen as the putative indel call. This call is reported if there is:

Enough coverage (default: normal >=4 reads, tumor >=6 reads),

A large fraction of reads at that site support the putative call (default: >=30%)

This fraction is sufficiently large compared to those supporting any site of the indel (default: >=70%)

Indel calls in a tumor sample are annotated as "Germline" if there is even weak evidence for the same indel in the normal sample; otherwise, they are labeled "Somatic." Calls only observed in the normal samples are ignored. SID takes BAM files as input and outputs VCF and BED formatted putative calls.

Mutation Filtering.

The callers output all candidate mutation calls, including germline mutations and other calls with low statistical confidence. We filtered the mutation caller output to only somatic mutations, mutations designated "KEEP" by MuTect and mutations occurring within the CDS of RefSeq Genes. The tables below detail the specific filters applied to MuTect and SomaticIndelDetector output:

TABLE 38

| MuTect Filter | Description |
| --- | --- |
| tumor_f > 0.1 | At least 10% of the tumor reads must be variant |
| t_alt_sum/t_alt_count > 28 | Average quality of the variant base calls > 28 |
| t_alt_count − map_Q0_reads − improper_pairs >= 3 | Conservatively require at least 3 reads where variant not in Q0 or in improperly paired reads. |

TABLE 38-continued

| | |
|---|---|
| t_alt_count > 10 *  n_alt_count  dbsnp_site NE 'DBSNP' | When MuTect allows one variant normal read, require at least 10 variant tumor reads.  Ignore variants present in dbSNP v132 |

| SomaticIndelDetector Filter | Description |
|---|---|
| T_STRAND_COUNTS_C[12]/ (..._C1 + ..._C2) > 0.1 | At least 10% of the tumor variant reads must be on each strand |
| T_AV_MAPQ_C > 28 | Average quality of the variant calls > 28 |

REFERENCES

Cibulskis, K. et al. Sensitive detection of somatic point mutations in impure and heterogeneous cancer samples. Nat Biotechnology (2013).doi:10.1038/nbt.2514

MuTect: www.broadinstitute.org/cancer/cga/muTect

SID: gatkforums.broadinstitute.org/discussion/35/somatic-indel-detection

TABLE 16

Druggability status for Table 2 genes/fusions

| Table 16 Gene | Approved | Pre-registration (pre-approval) | Phase III | Phase II | Phase I | preclinical |
|---|---|---|---|---|---|---|
| TOP1 | belotecan hydrochloride; irinotecan hydrochloride; topotecan | N | cositecan; irinotecan, HyACT; irinotecan, PharmaEngine; etirinotecan pegol | gimatecan; camptothecin, Calando; irinotecan HCl + floxuridine, Celator; firtecan pegol; TLC-388 hydrochloride; hRS7-SN-38; irinotecan bead, Biocompatibles | irinotecan, liposomal, Yakult; HM-30181A; namitecan; camptothecin prodrug, Mersana; labetuzumab-SN-38; Genz-644282; simmitecan hydrochloride prodrug | camptothecin (Aphios); irinotecan (BioAlliance); cisplatin + irinotecan (Celator); APH-0804; irinotecan (Champions); SER-203; SN-38; topotecan + vincristine (LipoCure); topotecan (EnduRx Pharmaceuticals) |
| SRD5A1 | dutasteride | N | idronoxil | N | N | N |
| VIM | N | N | N | pritumumab | N | N |
| IGFBP2 | N | N | N | N | N | OGX-225 |
| SPP1 | N | N | N | N | N | N |
| MDK | N | N | N | N | N | CAMI-103; CMS-101 |
| MUC16 | N | N | oregovomab | N | DMUC-5754A | N |
| RET | sorafenib; vandetanib; sunitinib malate; cabozantinib; regorafenib | apatinib | motesanib diphosphate; SAR-302503 | N | JNJ-26483327 | MG-516; NMS-173; RET kinase inhibitor (Bionomic) |
| MAP2K2 | trametinib | N | ARRY-438162 | selumetinib; refametinib; pimasertib; WX-554 | PD-0325901; ARRY-704; TAK-733; GDC-0623; BI-847325; AS-703988 | N |
| MAPK1 | N | N | N | N | N | AEZS-129; AEZS-136; AEZS-134; SCH-722984; SCH-772984 |
| BRAF | pazopanib; vemurafenib; dabrafenib | N | N | RAF-265; XL-281; LGX-818 | ARQ-761; ARQ-736 | AB-024; b-raf inhibitors (Sareum); BRAF kinase inhibitor |

TABLE 16-continued

Druggability status for Table 2 genes/fusions

| Table 16 Gene | Approved | Pre-registration (pre-approval) | Phase III | Phase II | Phase I | preclinical |
|---|---|---|---|---|---|---|
| | | | | | | (Selexagen Therapeutics); BeiGene-283; DP-4978; TL-241 |
| MUC16 | N | N | oregovomab | N | DMUC-5754A | N |
| MET | cabozantinib; crizotinib | N | tivantinib; rilotumumab; onartuzumab; | MGCD-265; foretinib; ficlatuzumab; BMS-777607; golvatinib; INCB-028060; LY-2875358 | AMG-208; TAS-115; volitinib; SAR-125844; S-49076 | X-379; metatinib; PRS-110; ASP-08001; ARGX-111; DCC-2701; DCC-2721; MG-516; AL-2846; CG-206481; T-1840383; cMet-EGFR dual inhibitors (CrystalGenomics); bispecific antibodies (Hoffmann-La Roche) |
| PTK2 | N | N | N | PF-04554878 | GSK-2256098; BI-853520; VS-4718 | CFAK-C4; FAK inhibitor (Verastem); CTX-0294945; CTx-0294886; FAK inhibitors (Takeda) |
| ACE* | alacepril; benazepril; delapril + manidipine (Chiesi); captopril; captopril + HCTZ; captopril slow release (Sankyo); cilazapril; delapril; delapril + indapamide (Chiesi); diltiazem, Alza; enalapril maleate; enalapril maleate + HCTZ; enalapril + nitrendipine; enalapril (KRKA); enalaprilat; felodipine + enalapril; fosinopril; imidapril; lisinopril; lisinopril + HCTZ; moexipril; perindopril; quinapril hydrochloride; quinaprilat; ramipril; felodipine + ramipril; perindopril + indapamide, Serv; saralasin acetate; spirapril; temocapril; trandolapril; zofenopril; trandolapril + verapamil, Aven; lercanidipine + enalapril (Recordati); zofenopril + HCTZ; piretanide + ramipril; benazepril + HCTZ; | N | perindopril + indapamide + amlodipine (Servier) | N | amlodipine + enalapril maleate (GlaxoSmithKline) | N |

TABLE 16-continued

Druggability status for Table 2 genes/fusions

| Table 16 Gene | Approved | Pre-registration (pre-approval) | Phase III | Phase II | Phase I | preclinical |
|---|---|---|---|---|---|---|
| | amlodipine + benazepril; moexipril + HCTZ; amlodipine + perindopril, Servier; ASA + atorvastatin + ramipril + metoprolol ER (Zydus Cadila); ramipril + hydrochlorothiazide; (S)-amlodipine + ramipril (Emcure); quinapril/hydrochlorothiazide | | | | | |
| ADAM9 | N | N | N | N | N | N |
| CDK6 | N | N | palbociclib | alvocidib; LY-2835219 | LEE-011 | N |
| IKBKB | N | N | N | N | N | EC-70124 |
| RARA | tamibarotene | N | N | IRX-5183 | N | N |
| LYN | dasatinib | N | nintedanib | bafetinib | JNJ-26483327 | Bcr-Abl/Lyn inhibitor (AB Science) |
| NTRK3 | N | N | N | N | N | PLX-7486 |
| ERBB2 | trastuzumab; trastuzumab emtansine; pertuzumab; lapatinib ditosylate; catumaxomab; afatinib | trastuzumab, Enhanze | neratinib; XL-647; dacomitinib; nelipepimut-S; trastuzumab (Celltrion, Biocad, Biocon, Synthon, Harvest Moon, Aryogen) | lapuleucel-T; AVX-901; AE-37; BMS-690514; MVA-BN-HER2; varlitinib; MM-111; AC-480; ovarian cancer vaccine (Generex); margetuximab; poziotinib; PR-610 | Her-VAXX; VM-206; ARRY-380; JNJ-26483327; S-222611; doxorubicin (Merrimack); cipatinib; TrasGEX; trastuzumab (Hanwha Chemical); trastuzumab (Pfizer); IDN-6439 | Lovaxin B; TH-1 (Algeta); trastuzumab-antibody conjugates (Synthon); CUDC-101; Her-2/neu Stradobody (Gliknik); ARX-788; Etbx-021; SN-34003; IBI-302; NT-004; ICT-140; ONS-1050; Sym-013; anti-HER2 X anti-CD3 (Emergent Biosolutions); Z-650; breast cancer vaccine (Cel-Sci); JNJ-28871063; trastuzumab (PlantForm, BioXpress, biOasis Technologies, Stada, Natco, Curaxys, Oncobiologics, Alteogen, Mabion) |
| RHOA | N | N | N | N | N | N |
| RB1 | N | N | N | N | SGT-RB94 | N |
| THRA | N | N | N | N | N | N |
| CBL | N | N | N | N | N | N |
| ALK | crizotinib | N | N | AP-26113; RG-7853; LDK-378; TSR-011; NMS-E628 | X-396; ASP-3026 | NMS-E628; aurora kinase + ALK inhibitor (Sareum, AstraZeneca); ALK inhibitors |

TABLE 16-continued

Druggability status for Table 2 genes/fusions

| Table 16 Gene | Approved | Pre-registration (pre-approval) | Phase III | Phase II | Phase I | preclinical |
|---|---|---|---|---|---|---|
| | | | | | | (AstraZeneca, Cephalon, Aurigene); ARN-5032; DLX-521 |

TABLE 17

Druggability status for Table 3 genes/fusions

| Gene | approved | Pre-registration (pre-approval) | Phase III | Phase II | Phase I | preclinical |
|---|---|---|---|---|---|---|
| ESR1 | estramustine phosphate sodium; ethinyl estradiol sulfonate; fulvestrant; raloxifene hydrochloride; tamoxifen; toremifene citrate; trilostane; | N | acolbifene | TAS-108; estradiol GTx-758; endoxifen; afimoxifene | icaritin; ARN-810 | SR-16388; VAL-201; SERM + toxin (SEEK); estradiol (BHR Pharma); NDC-1407; anticancer MAb (Shenogen) |
| RPS6KB1 | N | N | N | N | AZD-5363; AT-13148; LY-S6KAKT1 | p70S6 kinase inhibitors (Sentinel) |

TABLE 19

Gene Fusions

| Table 19 Cancer Type | 5' gene symbol | 3' gene symbol | Druggable gene |
|---|---|---|---|
| Prostate Adenocarcinoma | ABCD3 | DPYD | DPYD |
| Sarcoma | ACTG2 | ALK | ALK |
| Lung Adenocarcinoma | ADAMTS16 | TERT | TERT |
| Brain Lower Grade Glioma | ATRX | BCL2 | BCL2 |
| Gastric Adenocarcinoma | B4GALT1 | RAF1 | RAF1 |
| Gastric Adenocarcinoma | BRD3 | LCN2 | BRD3 |
| Gastric Adenocarcinoma | CASZ1 | MTOR | MTOR |
| Acute Myeloid Leukemia | CHD1 | MTOR | MTOR |
| Uterine Corpus Endometrioid Carcinoma | CPA6 | PTK2 | PTK2 |
| Breast invasive carcinoma | DAB1 | IL12RB2 | IL12RB2 |
| Lung Adenocarcinoma | DDI2 | MTOR | MTOR |
| Sarcoma | FRS2 | MDM2 | MDM2 |
| Sarcoma | GLIS3 | TERT | TERT |
| Lung Adenocarcinoma | HIF1A | PRKCH | HIF1A |
| Breast invasive carcinoma | HPRT1 | CTPS2 | HPRT1 |
| Breast invasive carcinoma | IL12RB2 | DAB1 | IL12RB2 |
| Breast invasive carcinoma | IL6R | C1orf112 | IL6R |
| Breast invasive carcinoma | KCMF1 | PRKDC | PRKDC |
| Lung Adenocarcinoma | KIF5B | MET | MET |
| Breast invasive carcinoma | MAPK14 | EFHA1 | MAPK14 |
| Sarcoma | MDM2 | SPATS2 | MDM2 |
| Thyroid carcinoma | MTMR12 | TERT | TERT |
| Bladder Urothelial Carcinoma | NOTCH2 | EIF2B3 | NOTCH2 |
| Sarcoma | NTRK1 | DYNC2H1 | NTRK1 |

TABLE 19-continued

| Gene Fusions | | | |
|---|---|---|---|
| Table 19 Cancer Type | 5' gene symbol | 3' gene symbol | Druggable gene |
| Kidney renal clear cell carcinoma | PDCD6 | TERT | TERT |
| Lung Adenocarcinoma | PHKB | PDE3A | PDE3A |
| Uterine Carcinosarcoma | RARA | SLC9A3R1 | RARA |
| Liver hepatocellular carcinoma | SLC12A7 | TERT | TERT |
| Sarcoma | SMARCA4 | EEF2 | EEF2 |
| Breast invasive carcinoma | STARD13 | TNFRSF8 | TNFRSF8 |
| Lung Adenocarcinoma | TICAM1 | IL12RB1 | IL12RB1 |
| Sarcoma | TRIO | TERT | TERT |
| Prostate Adenocarcinoma | TRPM8 | UGT1A9 | TRPM8 |
| Sarcoma | TSPAN3 | MDM2 | MDM2 |
| Breast invasive carcinoma | TTLL7 | TERT | TERT |
| Brain Lower Grade Glioma | USP46 | PDGFRA | PDGFRA |
| Gastric Adenocarcinoma | WNK2 | BRD3 | BRD3 |
| Cervical squamous cell carcinoma and endocervical adenocarcinoma | ZNF226 | AKT2 | AKT2 |

TABLE 20

Breakpoints for Gene Fusions from Table 19

| Table 20 Fusion Name | Cancer Type | TCGA Tumor Sample Barcode | 5' Gene Symbol | 5' Accession | 5' Chromosome | 5' Breakpoint | 3' Gene Symbol | 3' Accession | 3' Chromosome | 3' Breakpoint | Breakpoint Sequence | SEQ ID NO |
|---|---|---|---|---|---|---|---|---|---|---|---|---|
| PDCD6\|TERT | Clear Cell Renal Cell Carcinoma | TCGA-BP-4991-01A-01R-1334-07 | PDCD6 | 10016 | chr5 | 272852 | TERT | 7015 | chr5 | 1282548 | TTCCTGTGAACGTT TTCCAGAGGGTCGA TAAAGACAGGAGTG GAGTGAT\|ATCAGA CAGCACTTGAAGAG GGTGCAGCTGCGGG AGCTGTCCGAAGCA GA | 200 |
| TSPAN3\|MDM2 | Sarcoma | TCGA-DX-A23R-01A-11R-A26T-07 | TSPAN3 | 10099 | chr15 | 77344775 | MDM2 | 4193 | chr12 | 69202269 | ACCTCTATGCTGAGG GGTGTGAGGCTCTA GTAGTGAAGAAGCT ACAAGAA\|CAGGCA AATGTGCAATACCA ACATGTCTCTACCTA CTGATGGTGCTGTAA | 201 |
| SLC12A7\|TERT | Hepatocellular Carcinoma | TCGA-BC-A3KG-01A-11R-A213-07 | SLC12A7 | 10723 | chr5 | 1111983 | TERT | 7015 | chr5 | 1282739 | CGGAGGCTCCGGGC ACCCCCGAGGGCC CGAGCCCGAGCGCC CCAGCCCG\|GGGGT TGGCTGTGTTCCGGC CGCAGAGCACCGTC TGCGTGAGGAGATC CT | 202 |
| FRS2\|MDM2 | Sarcoma | TCGA-DX-A3M1-01A-11R-A22K-07 | FRS2 | 10818 | chr12 | 69864310 | MDM2 | 4193 | chr12 | 69202988 | GTGGTTACAGCACC ATCAGTAGTACAG ACATGTTGGTATTGC ACATTTG\|CCGTCCG CCCAGGTGCTGAGA GGGAGCAGGCGC GGGTCGGCGGGCGC GA | 203 |

TABLE 20-continued

Breakpoints for Gene Fusions from Table 19

| Table 20 Fusion Name | Cancer Type | TCGA Tumor Sample Barcode | 5' Gene Symbol | 5' Accession | 5' Chromosome | 5' Breakpoint | 3' Gene Symbol | 3' Accession | 3' Chromosome | 3' Breakpoint | Breakpoint Sequence | SEQ ID NO |
|---|---|---|---|---|---|---|---|---|---|---|---|---|
| CHD1\|MTOR | Acute Myeloid Leukemia | TCGA-AB-2939-03A-01T-0740-13 | CHD1 | 1105 | chr5 | 98199112 | MTOR | 2475 | chr1 | 11273623 | GAATGTCTAAAAGA GTATACAAATCCTGA ACAAATTAAGCAAT GGAGAAA\|GAATTC TGGGTCATGAACAC CTCAATTCAGAGCAC GATCATTCTTCTCAT | 204 |
| CHD1\|MTOR | Acute Myeloid Leukemia | TCGA-AB-2939-03A-01T-0740-13 | CHD1 | 1105 | chr5 | 98204199 | MTOR | 2475 | chr1 | 11273623 | TTCCCATTTCTGAAG AATCTGAAGAGCTG GATCAGAAGACATT CAGCATT\|GAATTCT GGGTCATGAACACC TCAATTCAGAGCAC GATCATTCTTCTCAT | 205 |
| CHD1\|MTOR | Acute Myeloid Leukemia | TCGA-AB-2939-03A-01T-0740-13 | CHD1 | 1105 | chr5 | 98199112 | MTOR | 2475 | chr1 | 11273623 | AATGAGAAGAATGA TCGTGCTTGAATTG AGGTGTTCATGACCC AGAATT\|CTTTCTC ATTGCTTAATTTGTT CAGGATTTGTATACT CTTTTAGACATT | 206 |
| MAPK14\|EFHA1 | Invasive Breast Carcinoma | TCGA-AO-A129-01A-21R-A10J-07 | MAPK14 | 1432 | chr6 | 36044379 | EFHA1 | 221154 | chr13 | 22113824 | GGGATGCATAATGG CCGAGCTGTTGACT GGAAGAACATTGTT TCCTGGTA\|AAACTT CAGTCAAGAAGCTG ACAAAAAGGACAT CGAGGATACACTGT CA | 207 |
| TICAM1\|IL12RB1 | Lung Adeno carcinoma | TCGA-05-4426-01A-01R-1206-07 | TICAM1 | 148022 | chr19 | 4831636 | IL12RB1 | 3594 | chr19 | 18180463 | GTCCTGGCCCACAG GCTGCCATTCAATGC AATACGTCATGCTCT GAGCCC\|GGGCTGC CGGCTGCCCACTG GGTCCTGGGGTCCT GGGGGCTGGGGCTTC | 208 |
| TICAM1\|IL12RB1 | Lung Adeno carcinoma | TCGA-05-4426-01A- | TICAM1 | 148022 | chr19 | 4831630 | IL12RB1 | 3594 | chr19 | 18182962 | CCACTGGTTCTGTGT GGGTGTCGGCAGGA ATGTGCCACGTCTG GTTCAGG\|GATCCG | 209 |

TABLE 20-continued

Breakpoints for Gene Fusions from Table 19

| Table 20 Fusion Name | Cancer Type | TCGA Tumor Sample Barcode | 5' Gene Symbol | 5' Accession | 5' Chromosome | 5' Breakpoint | 3' Gene Symbol | 3' Accession | 3' Chromosome | 3' Breakpoint | Breakpoint Sequence | SEQ ID NO |
|---|---|---|---|---|---|---|---|---|---|---|---|---|
| | | 01R-1206-07 | | | | | | | | | GGGCTGCCGGCTGC GCCACTGGGTCCTG GGGTCCTGGGGGCT GG | |
| DAB1\|IL12RB2 | Invasive Breast Carcinoma | TCGA-AN-A0AM-01A-11R-A034-07 | DAB1 | 1600 | chr1 | 57611102 | IL12RB2 | 3595 | chr1 | 67845789 | CCCTTCACCTTTAAA CCTCTTTATCAAAGT GGCTTCACTGCGATC CTGAC\|GGGAATTTT GTCTGCAAGGTGAG AGGCAGTGTTAAGG ATGATGAGTCCAC | 210 |
| IL12RB2\|DAB1 | Invasive Breast Carcinoma | TCGA-AN-A0AM-01A-11R-A034-07 | IL12RB2 | 3595 | chr1 | 67845806 | DAB1 | 1600 | chr1 | 57611102 | CTGCTGGTGAAAGT TCCACGAAATGA GAGGGAATTTTGTCT GCAAGGT\|CAGGAT CGCAGTGAAGCCAC TTTGATAAAGAGGTT TAAAGGTGAAGGGGT | 211 |
| IL12RB2\|DAB1 | Invasive Breast Carcinoma | TCGA-AN-A0AM-01A-11R-A034-07 | IL12RB2 | 3595 | chr1 | 67845733 | DAB1 | 1600 | chr1 | 57611052 | TCTCCCAAAATTCAC ATCCAATAAACAGCC TGCAGCCCCGAGTG ACATAT\|GTCCGGTA CAAAGCCAAATTGA TCGGGATTGATGAA GTTTCCGCAGCTCG | 212 |
| GLIS3\|TERT | Sarcoma | TCGA-DX-A3LS-01A-11R-A21T-07 | GLIS3 | 169792 | chr9 | 4117768 | TERT | 7015 | chr5 | 1282739 | CTGCTGATCCACATG AGAGTCCACTCTGG GGAGAAGCCCAACA AGTGTAC\|GGGGTT GGCTGTGTTCCGGC CGCAGAGCACCGTC TGCCGTGAGGAGATC CT | 213 |
| ADAMTS16\|TERT | Lung Adeno carcinoma | TCGA-44-2662-01A-01R-0946-07 | ADAMTS16 | 170690 | chr5 | 5191903 | TERT | 7015 | chr5 | 1282739 | GATACAGGTCTTGG ACTGGCCTTCACCAT TGCCCATGAGTCTG GACACAA\|GGGTTG GCTGTGTTCCGGCC GCAGAGCACCGTCT GCGTGAGGAGATCC TG | 214 |

TABLE 20-continued

Breakpoints for Gene Fusions from Table 19

| Table 20 Fusion Name | Cancer Type | TCGA Tumor Sample Barcode | 5' Gene Symbol | 5' Accession | 5' Chromosome | 5' Breakpoint | 3' Gene Symbol | 3' Accession | 3' Chromosome | 3' Breakpoint | Breakpoint Sequence | SEQ ID NO |
|---|---|---|---|---|---|---|---|---|---|---|---|---|
| ABCD3\|DPYD | Prostate Adeno carcinoma | TCGA-CH-5764-01A-21R-1580-07 | ABCD3 | 5825 | chr1 | 94956803 | DPYD | 1806 | chr1 | 97981497 | CTTTAGCAACGCCAA ATGGAGATGTTTG ATCCGAGACCTAAT TTTGAA\|TCACAATA TGGAGCTTCCGTTTC TGCCAAGCCTGAACT ACCCCTCTTTTA | 215 |
| SMARCA4\|EEF2 | Sarcoma | TCGA-K1-A3PO-01A-21R-A21T-07 | SMARCA4 | 6597 | chr19 | 11151982 | EEF2 | 1938 | chr19 | 3983208 | TCTGCCGGACCTCCT CTTCGATCTCCTCCA GCGTGCCCTCCTGA TGGCC\|CAACCTCAT TGACTCCCCGGGC ATGTCGACTTCTCCT CGGAGGTGACTG | 216 |
| ZNF226\|AKT2 | Cervical Squamous Cell Carcinoma | TCGA-IR-A3LH-01A-21R-A213-07 | ZNF226 | 7769 | chr19 | 44669953 | AKT2 | 208 | chr19 | 40748529 | ATTCAGCCCTGACTT CTCAAAAGCACTG CACAGAGGAGAG GCAGCAGA\|ACCCC ATGGACTACAAGTG TGGCTCCCCAGTGA CTCCTCCACGACTGAG | 217 |
| ZNF226\|AKT2 | Cervical Squamous Cell Carcinoma | TCGA-IR-A3LH-01A-21R-A213-07 | ZNF226 | 7769 | chr19 | 44669953 | AKT2 | 208 | chr19 | 40748529 | AATTCTCCCTGACTT CTCAAAAGCACTG CACAGAGGAGAG GCAGCAGA\|ACCCC ATGGACTACAAGTG TGGCTCCCCAGTGA CTCCTCCACGACTGAG | 218 |
| ACTG2\|ALK | Sarcoma | TCGA-IW-A3M6-01A-11R-A21T-07 | ACTG2 | 72 | chr2 | 74128558 | ALK | 238 | chr2 | 29446380 | GAGATGATGCCCC CGGGCTGTCTTCCC TCCATTGTGGGCGC CCTCGC\|CACCAGGA GCTGCAAGCCATGC AGATGGAGCTGCAG AGCCCTGAGTACAA | 219 |
| ACTG2\|ALK | Sarcoma | TCGA-IW-A3M6-01A-11R- | ACTG2 | 72 | chr2 | 74128564 | ALK | 238 | chr2 | 29449940 | ATGCCCCCGGGCT GTCTTCCCTCCATT GTGGGCCGCCCTCG CCACCAG\|TGATGG AAGGCCACGGGAA | 220 |

TABLE 20-continued

Breakpoints for Gene Fusions from Table 19

| Table 20 Fusion Name | Cancer Type | TCGA Tumor Sample Barcode | 5' Gene Symbol | 5' Accession | 5' Chromosome | 5' Breakpoint | 3' Gene Symbol | 3' Accession | 3' Chromosome | 3' Breakpoint | Breakpoint Sequence | SEQ ID NO |
|---|---|---|---|---|---|---|---|---|---|---|---|---|
| | | TCGA-A21T-07 | | | | | | | | | GTGAATATTAAGCAT TATCTAAACTGCAGT | 221 |
| ACTG2\|ALK | Sarcoma | TCGA-IW-A3M5-01A-22R-A21T-07 | ACTG2 | 72 | chr2 | 74128564 | ALK | 238 | chr2 | 29449940 | TGATGCCCCCGGG CTGTCTTCCCCTCCA TTGTGGCCGCCCTC GCCACC\|AGTGATG GAAGGCCACGGGGA AGTGAATATTAAGC ATTATCTAAACTGCA | 222 |
| CASZ1\|MTOR | Gastric Adeno carcinoma | TCGA-BR-8590-01A-11R-2402-13 | CASZ1 | 54897 | chr1 | 10765549 | MTOR | 2475 | chr1 | 11288975 | ATGAAGTGACACCC CCAGCTACATCCGA GGAGGTTCTAGGAC CTGCTACG\|AGCTGA CTATAGCACTAGTGA AATGCTGGTCAACAT GGGAAACTTGCCTC | 222 |
| DDI2\|MTOR | Lung Adeno carcinoma | TCGA-MP-A4SW-01A-21R-A24X-07 | DDI2 | 84301 | chr1 | 15944303 | MTOR | 2475 | chr1 | 11227574 | ATTCTAACACTCCGG CCGCTGCCTCCGGCT GCTGTAGCTTATTAT TAATG\|CTGGCTCTC GGCTGCGGGGATGC CAGACTCGAGCTCG CACAGCGCGCGGA | 223 |
| B4GALT1\|RAF1 | Gastric Adeno carcinoma | TCGA-HU-A4GH-01A-11R-A24K-31 | B4GALT1 | 2683 | chr9 | 33166756 | RAF1 | 5894 | chr3 | 12641914 | CTGGACAGGGCTGA AGGTGAGGCTGATT CGCTGTGACTTCGAA TTGCATC\|CAAGCAG CGGGGACTCCTCAG GGCAGGCGGGCAGC GACAGTGCGGTGGTG | 224 |
| HIF1A\|PRKCH | Lung Adeno carcinoma | TCGA-44-2668-01A-01R-0946-07 | HIF1A | 3091 | chr14 | 62207906 | PRKCH | 5583 | chr14 | 61995793 | AAAAATCTCATCCAA GAAGCCCTAACGTG TTATCTGTCGCTTTG AGTCAA\|AGAGATCT GAAACTGGACAATG TCCTGTTGACCACG AGGGTCACTGTAA | 225 |
| HIF1A\|PRKCH | Lung Adeno carcinoma | TCGA-44-2668- | HIF1A | 3091 | chr14 | 62207766 | PRKCH | 5583 | chr14 | 61995805 | CGAAGTCTGCCAGTT TACAGTGACCCTCGT GGTCCAACAGGACA | 226 |

TABLE 20-continued

Breakpoints for Gene Fusions from Table 19

| Table 20 Fusion Name | Cancer Type | TCGA Tumor Sample Barcode | 5' Gene Symbol | 5' Accession | 5' Chromosome | 5' Breakpoint | 3' Gene Symbol | 3' Accession | 3' Chromosome | 3' Breakpoint | Breakpoint Sequence | SEQ ID NO |
|---|---|---|---|---|---|---|---|---|---|---|---|---|
| HPRT1\|CTPS2 | Invasive Breast Carcinoma | TCGA-AR-A24W-01A-11R-A169-07 | HPRT1 | 3251 | chrX | | | | | | TTGTCC\|AGTTTCTTT ATGTATGTGGGTAG GAGATGGAGATGCA ATCATATTTTAA | |
| HPRT1\|CTPS2 | Invasive Breast Carcinoma | TCGA-AR-A24W-01A-11R-A169-07 | HPRT1 | 3251 | chrX | 133627542 | CTPS2 | 56474 | chrX | 16657355 | GATGATCTCTCAACT TTAACTGGAAAGTCT AGGTTGTTGGCAGA AGATAT\|GCCCGAG CACAACCCTGGCAAT TTGGGAGGAACAAT GAGACTGGGAATAA | 227 |
| HPRT1\|CTPS2 | Invasive Breast Carcinoma | TCGA-AR-A24W-01A-11R-A169-07 | HPRT1 | 3251 | chrX | 133609340 | CTPS2 | 56474 | chrX | 16685822 | ATAAATTCTTTGCTG ACCTGCTGATTACA TCAAAGCACTGAAT AGAAAT\|AGTGATA GAGTTTGCAAGAAA CTGCCTTAACTTGAA AGATGCTGATTCCA | 228 |
| HPRT1\|CTPS2 | Invasive Breast Carcinoma | TCGA-AR-A24W-01A-11R-A169-07 | HPRT1 | 3251 | chrX | 133609375 | CTPS2 | 56474 | chrX | 16638444 | GCACTGAATAGAAA TAGTGATAGATCCAT TCCTATGACTGTAGA TTTTAT\|GTGATGT TCCTTTTATAGAAGA AAGACACAGACATC GGTTCGAGGTAAA | 229 |
| HPRT1\|CTPS2 | Invasive Breast Carcinoma | TCGA-AR-A24W-01A-11R-A169-07 | HPRT1 | 3251 | chrX | 133627542 | CTPS2 | 56474 | chrX | 16657355 | GATGATCTCTCAACT TTAACTGGAAAGAA TGTCTTGATTGTGGA AGATAT\|GCCCGAG CACAACCCTGGCAAT TTGGGAGGAACAAT GAGACTGGGAATAA | 230 |
| HPRT1\|CTPS2 | Invasive Breast Carcinoma | TCGA-AR-A24W-01A-11R-A169-07 | HPRT1 | 3251 | chrX | 133609363 | CTPS2 | 56474 | chrX | 16685820 | GATTACATCAAAGC ACTGAATAGAAATA GTGATAGATCCATTC CTATGAC\|TGATAGA GTTTGCAAGAAACT GCCTTAACTTGAAAG ATGCTGATTCCACA | 231 |

TABLE 20-continued

Breakpoints for Gene Fusions from Table 19

| Table 20 Fusion Name | Cancer Type | TCGA Tumor Sample Barcode | 5' Gene Symbol | 5' Accession | 5' Chromosome | 5' Breakpoint | 3' Gene Symbol | 3' Accession | 3' Chromosome | 3' Breakpoint | Breakpoint Sequence | SEQ ID NO |
|---|---|---|---|---|---|---|---|---|---|---|---|---|
| IL6R\|C1orf112 | Invasive Breast Carcinoma | TCGA-E9-A1RF-01A-11R-A157-07 | IL6R | 3570 | chr1 | 154420647 | C1orf112 | 55732 | chr1 | 169790820 | GGACAGAATCCAGG AGTCCTCCAGCTGA GAACGAGGTGTCA CCCCATG\|CAGGAT AATGCTGACTACAG ATTATTTCAGAAAAC ACTCAAATTGTGTCG | 232 |
| KIF5B\|MET | Lung Adenocarcinoma | TCGA-93-A4JN-01A-11R-A24X-07 | KIF5B | 3799 | chr10 | 32304500 | MET | 4233 | chr7 | 116411617 | CCAACTCACCCAAGT GCAATTCGTGGAGG AGGTGCATTTGTTCA GAACAG\|AGGATTG ATTGCTGGTGTTGTC TCAATATCAACAGCA CTGTTATTACTAC | 233 |
| KIF5B\|MET | Lung Adenocarcinoma | TCGA-93-A4JN-01A-11R-A24X-07 | KIF5B | 3799 | chr10 | 32306145 | MET | 4233 | chr7 | 116411932 | GCACTGAAAGAAGC TAAAGAAATGCAT CTCGTGATCGCAAAC GCTATCA\|GCAAGA GTACACACTCCTCAT TTGGATAGGCTTGTA AGTGCCCGAAGTGT | 234 |
| BRD3\|LCN2 | Gastric Adenocarcinoma | TCGA-HU-A4H2-01A-11R-A251-31 | BRD3 | 8019 | chr9 | 136917428 | LCN2 | 3934 | chr9 | 130912517 | GTATGCAGGACTTC AACACCATGTTTACA AATTGTTACATTTAT AACAAG\|TTCCAGG GGAAGTGGTATGTG GTAGGCCTGGCAGG GAATGCAATTCTCAG | 235 |
| MDM2\|SPATS2 | Sarcoma | TCGA-DX-A1KZ-01A-11R-A24X-07 | MDM2 | 4193 | chr12 | 69233549 | SPATS2 | 65244 | chr12 | 49883267 | CATTGTCCATGGCAA AACAGGACATCTTAT GGCCTGCTTTACATG TGCAA\|TAGTTCCTA ATAAGACAACAAT GAAATTATCCTGGTT TTGCAGCACTTT | 236 |
| NOTCH2\|EIF2B3 | Bladder Urothelial Carcinoma | TCGA-FD-A5BS-01A-21R- | NOTCH2 | 4853 | chr1 | 120458963 | EIF2B3 | 8891 | chr1 | 45392411 | CATGCCTACTAGCCT CCCTAACCTTGCCAA GGAGGCAAAGGATG CCAAGG\|TGGAGCA GCGTGACTTCATTGG | 237 |

TABLE 20-continued

Breakpoints for Gene Fusions from Table 19

| Table 20 Fusion Name | Cancer Type | TCGA Tumor Sample Barcode | 5' Gene Symbol | 5' Accession | 5' Chromosome | 3' Gene Symbol | 3' Accession | 3' Chromosome | 3' Breakpoint | Breakpoint Sequence | SEQ ID NO |
|---|---|---|---|---|---|---|---|---|---|---|---|
| | | A26T-07 | | | | | | | | AGTGGACAGCACAG GAAAGAGGCTGCTC | |
| NTRK1\|DYNC2H1 | Sarcoma | TCGA-DX-A3LY-01B-11R-A27Q-07 | NTRK1 | 4914 | chr1 | DYNC2H1 | 79659 | chr11 | 103306708 | AACGCCACAGCATC AAGGATGTGCACGC CCGCTGCAAGCCC TGGCCCAG\|AAGAT CCCTACAATACCTG AGAGGTCTTGTTGCC CGTGCCCTTGCAATA | 238 |
| PHKB\|PDE3A | Lung Adenocarcinoma | TCGA-MN-A4N5-01A-11R-A24X-07 | PHKB | 5257 | chr16 | PDE3A | 5139 | chr12 | 20799464 | ACTTCAGATCCGTGG CGGAGACAAGCCAG CCTTGGACTTGTATC AGCTGT\|TTGGTATC TTACTACACAGCCTA TTCCAGGCCTCTCAA CTGTGATTAATG | 239 |
| USP46\|PDGFRA | Lower Grade Glioma | TCGA-CS-6665-01A-11R-1896-07 | USP46 | 64854 | chr4 | PDGFRA | 5156 | chr4 | 55143576 | GTGAAGCAACCAC TAATATAAACACCTC CCATGTATAGGAAG GCTGGAG\|CGTTTG GGAAGGTGGTTGAA GGAACAGCCTATGG ATTAAGCCCGTCCCAA | 240 |
| USP46\|PDGFRA | Lower Grade Glioma | TCGA-CS-6665-01A-11R-1896-07 | USP46 | 64854 | chr4 | PDGFRA | 5156 | chr4 | 55140771 | GGTCAATTTTGGAA ACACATGCTACTGTA ACTCCGTGCTTCAGG CATTGT\|CCTGGTTG TCATTTGGAAACAG AACCGAGTATGA AATTCGCTGGAGGG | 241 |
| MTMR12\|TERT | Thyroid Gland Carcinoma | TCGA-BJ-A4O9-01A-11R-A250-07 | MTMR12 | 54545 | chr5 | TERT | 7015 | chr5 | 1282739 | ACATGAAGTACAAA GCAGTGAGTGTCAA CGAAGGCTATAAAG TCTGTGAG\|AGGGG TTGGCTGTGTTCCGG CCCAGAAGCACCGT CTGCTGAGGAGAT CC | 242 |

TABLE 20-continued

Breakpoints for Gene Fusions from Table 19

| Table 20 Fusion Name | Cancer Type | TCGA Tumor Sample Barcode | 5' Gene Symbol | 5' Accession | 5' Chromosome | 5' Breakpoint | 3' Gene Symbol | 3' Accession | 3' Chromosome | 3' Breakpoint | Breakpoint Sequence | SEQ ID NO |
|---|---|---|---|---|---|---|---|---|---|---|---|---|
| ATRX\|BCL2 | Lower Grade Glioma | TCGA-DB-A4XF-01A-11R-A27Q-07 | ATRX | 546 | chrX | 77041468 | BCL2 | 596 | chr18 | 60795992 | AATCAAACAGAGGC CGCATGCTGGGGCC GTACAGTTCCACAAA GGCATCC\|TCATGGG CTCAGCGGTCATGTT TTCGCTTGAACGCCT TGTCGGCTTCTGT | 243 |
| TRPM8\|UGT1A9 | Prostate Adenocarcinoma | TCGA-CH-5766-01A-11R-1580-07 | TRPM8 | 79054 | chr2 | 234894509 | UGT1A9 | 54600 | chr2 | 234675680 | CATGTTATCCACCAA CATCCTGCTGGTCAA CCTGCTGGTCGCCAT GTTTG\|GGAATTTGA AGCCTACATTAATGC TTCTGGAGAACATG GAATTGTGTTT | 244 |
| KCMF1\|PRKDC | Invasive Breast Carcinoma | TCGA-EW-A1P4-01A-21R-A144-07 | KCMF1 | 56888 | chr2 | 85262227 | PRKDC | 5591 | chr8 | 48772278 | CACAGTCTTTTACTT GTCCCTATTGTGGAA AAATGGGCTATACG GAGACA\|GTACCCT GAGTGAGAAATGA GTCAATTGATTTCT CAACCGGAGTTCAG | 245 |
| CPA6\|PTK2 | Endometrial Endometrioid Adenocarcinoma | TCGA-A5-A0G5-01A-11R-A040-07 | CPA6 | 57094 | chr8 | 68536411 | PTK2 | 5747 | chr8 | 141774389 | AAACAGAAGAGGAA GCATATGCACTGAA GAAAATATCCTATCA ACTTAAG\|AAACAG ATGATTATGCTGAG ATTATAGATGAAGA AGATACTTACACCATG | 246 |
| RARA\|SLC9A3R1 | Carcinosarcoma | TCGA-N8-A4PQ-01A-11R-A28V-07 | RARA | 5914 | chr17 | 38508759 | SLC9A3R1 | 9368 | chr17 | 72758151 | ACCATCGCCGACCA GATCACCCTCCTCAA GGCTGCCTGCCTGG ACATCCT\|GCGCGAG CTTCGGCCTCGGCTC TGTACCATGAAGAA GGGCCCCAGTGGCT | 247 |
| WNK2\|BRD3 | Gastric Adenocarcinoma | TCGA-HU-A4H2-01A-11R- | WNK2 | 65268 | chr9 | 95947892 | BRD3 | 8019 | chr9 | 136910543 | ACAAGGGGTGGAC ACGGAGACCTGGGT GTGAGGTGGCCTGGT GTGAGCTG\|CAGAG GAAGATGGATGGCC | 248 |

TABLE 20-continued

Breakpoints for Gene Fusions from Table 19

| Table 20 Fusion Name | Cancer Type | TCGA Tumor Sample Barcode | 5' Gene Symbol | 5' Accession | 5' Chromosome | 5' Breakpoint | 3' Gene Symbol | 3' Accession | 3' Chromosome | 3' Breakpoint | Breakpoint Sequence | SEQ ID NO |
|---|---|---|---|---|---|---|---|---|---|---|---|---|
| TRIO\|TERT | Sarcoma | TCGA-DX-A1L3-01A-11R-A24X-07 | TRIO | 7204 | chr5 | 14420130 | TERT | 7015 | chr5 | 1282739 | GAGAGTACCCAGAC GCACAGGGCTTTGC TGC ATCGCCCACTCCAGA AGTAGCATGGAAAT GGAGGGCATCTTCA ACCACAA\|AGGGGT TGGCTGTGTTCCGGC CGCAGAGCACCGTC TGCCGTGAGGAGATCC | 249 |
| TTLL7\|TERT | Invasive Breast Carcinoma | TCGA-C8-A131-01A-11R-A115-07 | TTLL7 | 79739 | chr1 | 84464614 | TERT | 7015 | chr5 | 1282739 | CCGCTTGCAGCGGG GACGCGAGGACCCG GGCTGGGCTTTCCTC ACCCGGG\|GGTTGG CTGTGTTCCGGCCGC AGAGCACCGTCTGC GTGAGGAGATCCTGG | 250 |
| STARD13\|TNFRSF8 | Invasive Breast Carcinoma | TCGA-BH-A0C7-01B-11R-A115-07 | STARD13 | 90627 | chr13 | 33859649 | TNFRSF8 | 943 | chr1 | 12164568 | CTCACAGACCGTGTT CTTCTGCCGCCGTGCC TGGGAACTTGACAA TCATCC\|GGCTCATC CTGTAAGGAGAGCG TCTTGTAGTCTGATC AAATCGCAAGTAC | 251 |

TABLE 21

Druggability Status for Table 19 Genes/Fusions

| Table 21 Gene | approved | Pre-registration (pre-approval) | Phase III | Phase II | Phase I | Preclinical |
|---|---|---|---|---|---|---|
| AKT2 | N | N | N | N | ARQ-092; BAY-1125976 | RX-1792; NT-113; TAS-117 |
| ALK | crizotinib | N | N | AP-26113; RG-7853; LDK-378; TSR-011; NMS-E628 | X-396; ASP-3026; | NMS-E628; aurora kinase + ALK inhibitor (Sareum, AstraZeneca); ALK inhibitors (AstraZeneca, Cephalon, Aurigene); ARN-5032; DLX-521 |
| BCL2 | N | N | N | PBI-1402; PNT-2258; R-(—)-gossypol; navitoclax; RG-7601 | N | VAL-101; BP-100-1.02; sabutoclax |
| BRD3 | N | N | N | N | Y-803 | N |
| DPYD | N | N | N | eniluracil | TAS-114 | N |
| EEF2 | denileukin diftitox | N | moxetumomab pasudotox | cintredekin besudotox | N | Glioblast-13 |
| FGFR3 | ponatinib | asitinib | lenvatinib | dovitinib lactate; ENMD-2076; AZD-4547 | JNJ-42756493; BGJ-398; LY-2874455; S-49076 | N |
| HIF1A | | | | camptothecin, Calando | 2-methoxyestradiol; SPC-2968 | RX-0047; ATSP-9172; ATSP-9172; P-3971 |
| HPRT1 | Butocin | N | N | N | N | N |
| IL12RB1 | N | N | N | INXN-2001/1001; IL-12 | AS-1409; NHS-IL12 | N |
| IL12RB2 | N | N | N | IL-12 | NHS-IL-12; AS-1409 | N |
| IL6R | tocilizumab | N | ARRY-438162 | givinostat; ALX-0061 | | L-6 inhibitors, Interprotein; IL-6 antagonists, Protagonist Therapeutics; APX-007 |
| MAPK14 | pirfenidone | N | N | ralimetinib | ARRY-614; thioureidobutyronitrile | N |
| MDM2 | N | N | N | N | SAR-405838; RG-7388; RO-5503781; CGM-097; DS-3032 | p53-mdm2/mdm4 dual inhibitors, Adamed; PXN-527; ATSP-7041; MDM2 inhibitors, Amgen |
| MET | cabozantinib; crizotinib | N | tivantinib; rilotumumab; onartuzumab; | MGCD-265; foretinib; ficlatuzumab; BMS-777607; golvatinib; INCB-028060; LY-2875358; apitolisib | AMG-208; TAS-115; volitinib; SAR-125844; S-49076 | X-379; metatinib; PRS-110; ASP-08001; ARGX-111; DCC-2701; DCC-2721; MG-516; AL-2846; CG-206481; T-1840383; cMet-EGFR dual inhibitors (CrystalGenomics); bispecific antibodies (Hoffmann-La Roche) |

TABLE 21-continued

Druggability Status for Table 19 Genes/Fusions

| Table 21 Gene | approved | Pre-registration (pre-approval) | Phase III | Phase II | Phase I | Preclinical |
|---|---|---|---|---|---|---|
| MTOR | everolimus; temsirolimus | ridaforolimus | N | quinacrine; XL-765; dactolisib; PKI-587; PF-04691502; CC-223 | P-7170; CBLC-137, INK-128, AZD-2014; CC-115; PWT-33957; DS-7423; GDC-0084; DS-3078; LY-3023414; PI3 kinase/mTOR inhibitor, Lilly | nPT-MTOR; SB2343; STP-503; X-480; ABTL-0812; X-414; CC214; HMPL-518; PQR-309; PQR-401; mTOR inhibitor/PI3 kinase inhibitor, Lilly-1; PIM/PI3k/mTOR inhibitors, Inflection Biosciences |
| NOTCH2 | N | N | N | OMP-59R5 | N | N |
| NTRK1 | N | N | N | milciclib maleate | N | tyrosine kinase inhibitors (Bristol-Myers Squibb); PLX-7486 |
| PDE3A | amrinone; anagrelide hydrochloride; enoximone; cilostazol; loprinone hydrochloride; loprinone hydrochloride; loprinone hydrochloride | N | N | parogrelil hydrochloride; K-134; RPL-554; cilostazol, Genovate | CR-3465 | CLC-2001 |
| PDGFRA | imatinib mesilate; pazopanib; sunitinib, dasatinib; nilotinib; regorafenib | nintedanib | orantinib; motesanib; linifanib | ENMD-2076; olaratumab; X-82; crenolanib; | N | DCC-2618; CG-206481 |
| PRKDC | N | N | vosaroxin | N | SF-1126, Dbait; CC-115 | N |
| PTK2 | N | N | N | defactinib | GSK-2256098; CEP-37440; BI-853520; VS-4718 | CFAK-C4; FAK inhibitor, Verastem; CTX-0294945; x-0294886 |
| RAF1 | sorafenib | N | N | iCo-007; XL-281 | RO-5126766; MLN-2480 | BIB-024; STP503; DP-4978; HM-95573; TAK-632 |
| RARA | tamibarotene | N | N | IRX-5183 | N | N |
| TERT | N | N | GV-1001 | VX-001; GX-301- | TeloB-Vax | telomerase vaccine, Geron; hTERT DNA vaccine, Inovio |
| TNFRSF8 | brentuximab vedotin | N | N | AFM-13; XmAb-2513 | N | N |
| TRPM8 | N | N | N | N | D-3263 | N |

TABLE 22

Cancer Types Newly Associated with Gene Fusions

| Cancer Type | Gene A | Gene B | Orientation (5'/3') | Druggable gene | Cancer type precedent |
|---|---|---|---|---|---|
| Papillary renal cell carcinoma | FGFR3 | TACC3 | FGFR3/TACC3 | FGFR3 | Bladder cancer; Squamous cell lung cancer; Glioblastoma; Head & Neck squamous cell carcinoma; Cervical sqaumous cell carcinoma; Low grade glioma |
| Squamous cell Lung Carcinoma | SEC16A | NOTCH1 | SEC16A/NOTCH1 | NOTCH1 | Breast Cancer; Thyroid Gland Carcinoma |

TABLE 23

Breakpoints of Gene Fusions from Table 22

| Table 23 Fusion Name | Cancer Name Type | TCGA Tumor Sample Barcode | 5' Gene Symbol | 5' Accession | 5' Chromosome | 5' Breakpoint | 3' Gene Symbol | 3' Accession | 3' Chromosome | 3' Breakpoint | Breakpoint Sequence | SEQ ID NO |
|---|---|---|---|---|---|---|---|---|---|---|---|---|
| FGFR3\|TACC3 | Papillary Renal Cell Carcinoma | TCGA-A4-7287-01A-11R-2139-07 | FGFR3 | 2261 | chr4 | 1808661 | TACC3 | 10460 | chr4 | 1741429 | TCCTCACA CCTGCTCC TCAGCTCC CGGTTCTC CTCCTGTG TCGCCTTT AC\|GTCGG TGGACGTC ACGTAAG GACACGGT CCAGGTCC TCCACCAG CTGCT | 252 |
| FGFR3\|TACC3 | Papillary Renal Cell Carcinoma | TCGA-A4-7287-01A-11R-2139-07 | FGFR3 | 2261 | chr4 | 1808633 | TACC3 | 10460 | chr4 | 1741500 | GCCGCGCC CTCCCAGA GGCCCACC TTCAAGCA GCTGGTGG AGGACCTG GA\|ACTGG GGAAGATC ATGGACAG GTTCGAAG AGTTGTG TACCAGGC CATGG | 253 |
| FGFR3\|TACC3 | Papillary Renal Cell Carcinoma | TCGA-A4-7287-01A-11R-2139-07 | FGFR3 | 2261 | chr4 | 1808661 | TACC3 | 10460 | chr4 | 1741429 | AGCAGCTG GTGAGG ACCTGGAC CGTGTCCT TACCGTGA CGTCCACC GAC\|GTAA AGGCGACA CAGGAGG AGAACCGG GAGCTGAG GAGCAGGT GTGAGGA | 254 |

TABLE 23-continued

Breakpoints of Gene Fusions from Table 22

| Table 23 Fusion Name | Cancer Type | TCGA Tumor Sample Barcode | 5' Gene Symbol | 5' Accession | 5' Chromosome | 5' Breakpoint | 3' Gene Symbol | 3' Accession | 3' Chromosome | 3' Breakpoint | Breakpoint Sequence | SEQ ID NO |
|---|---|---|---|---|---|---|---|---|---|---|---|---|
| FGFR3\|TACC3 | Papillary Renal Cell Carcinoma | TCGA-A4-7287-01A-11R-2139-07 | FGFR3 | 2261 | chr4 | 1808637 | TACC3 | 10460 | chr4 | 1742650 | CGCCCTCC CAGAGGCC CACCTTCA AGCAGCTG GTGGAGG ACCTGGAC CGT\|GTCC TTCTCCGA CCTCTTCA AGCGTTTT GAGAAACA GAAAGAG GTGATCG | 255 |
| FGFR3\|TACC3 | Papillary Renal Cell Carcinoma | TCGA-A4-7287-01A-11R-2139-07 | FGFR3 | 2261 | chr4 | 1808561 | TACC3 | 10460 | chr4 | 1741689 | GAGGGCC ACCGCATG GACAAGCC CGCCAACT GCACACAC GACCTGTA CAT\|GATC ATGGACAG GTTCGAAG AGGTGTG TACCAGGC CATGGAGG AAGTTC | 256 |
| SEC16A\|NOTCH1 | Squamous Cell Lung Carcinoma | TCGA-NC-A5HK-01A-11R-A26W-07 | SEC16A | 9919 | chr9 | 139352036 | NOTCH1 | 4851 | chr9 | 139418396 | GTACGCCC AGTCCCTG GGTGCCGA GACCTGCC CCCTGCCT AGTTTCCA GG\|ACCCC AACCGTG CCTCAGCA CCCCCTGC AAGAACGC CGGGACAT GCCAC | 257 |

TABLE 24

Druggability Status of Genes/Fusions of Table 22

| Gene | approved | Pre-registration (pre-approval) | Phase III | Phase II | Phase I | preclinical |
|---|---|---|---|---|---|---|
| FGFR3 | ponatinib | masitinib | lenvatinib | dovitinib lactate; ENMD-2076; AZD-4547 | JNJ-42756493; BGJ-398; LY-2874455; S-49076 | N |
| NOTCH1 | N | N | N | N | OMP-52M51 | Debio-0826; TR-4; Notch antibody (AVEO); Notch1 inhibitors (Interprotein); BMS871; NTR-4 |

TABLE 39

| Cancer | Event type | Q | No. positive | Total no. of patients | Cytoband | Genes (Entrez ID) | Druggable genes | KM evidence |
|---|---|---|---|---|---|---|---|---|
| Endometrial Endometrioid Adenocarcinoma | Fusion | 2.18E−03 | 5 | 258 | 11p15.5, 4p13 | RPLP2 (6181), ATP8A1 (609542) | | poor outcome |
| Cervical Squamous Cell Carcinoma | Fusion | 3.56E−03 | 5 | 54 | 17q21.2 | KRT15 (3866), KRT19 (3880) | | poor outcome |
| Colorectal Adenocarcinoma: KRAS Mutation | Loss of Function Mutation | 9.69E−03 | 4 | 105 | 11q22-q23 | ATM (472) | | poor outcome |
| Ductal Breast Carcinoma: ER Positive and HER2 Negative | Fusion | 1.46E−02 | 7 | 265 | 17p11.2, 17p13 | USP22 (23326), MYH10 (160776) | | poor outcome |
| Endometrial Endometrioid Adenocarcinoma: Microsatellite Stable | In-Peak Gene Amplification | 3.40E−02 | 8 | 171 | 3q26.2 | MECOM (2122) | | poor outcome |
| Endometrial Endometrioid Adenocarcinoma | Loss of Function Mutation | 5.04E−02 | 4 | 188 | 16p13.3 | CREBBP (1387) | | poor outcome |
| Cutaneous Melanoma | Gain of Function Mutation | 6.69E−02 | 5 | 214 | 7q34 | PRSS37 (136242) | | poor outcome |
| Endometrial Serous Adenocarcinoma | In-Peak Gene Deletion | 7.52E−02 | 4 | 94 | 8p11.2 | FKSG2 (59347) | | poor outcome |
| Cutaneous Melanoma | Gain of Function Mutation | 7.94E−02 | 5 | 214 | 6p21.3 | STK19 (8859) | | poor outcome |
| Endometrial Serous Adenocarcinoma: Microsatellite Stable | Loss of Function Mutation | 8.05E−02 | 30 | 38 | 17p13.1 | TP53 (7157) | TP53 | favorable outcome |
| Colorectal Adenocarcinoma: KRAS Mutation, Stage 3 or 4 | In-Peak Gene Amplification | 8.58E−02 | 4 | 45 | 13q12.3 | CDX2 (1045) | | poor outcome |
| Colorectal Adenocarcinoma: KRAS Mutation | Loss of Function Mutation | 8.77E−02 | 4 | 105 | 18q21.1 | SMAD4 (4089) | | poor outcome |

TABLE 39-continued

| Cancer | Event type | Q | No. positive | Total no. of patients | Cytoband | Genes (Entrez ID) | Druggable genes | KM evidence |
|---|---|---|---|---|---|---|---|---|
| Colorectal Adenocarcinoma: Microsatellite Stable | Gain of Function Mutation | 9.10E−02 | 10 | 21 | 12p12.1 | KRAS (3845) | KRAS (pre-clinical) | poor outcome |

Example 7 Identification of Status of TP53

Advances in both molecular diagnostics and the understanding of cancer biology are raising the bar for clinical trial paradigms with the expectation that more effective patient stratification will improve outcome and expedite approval of effective cancer drugs.

Mutational status of TP53 has been identified as a predictive biomarker of treatment response and prognosis. For example, TP53 wild-type (WT) patients have been shown to exhibit significantly increased progression-free survival following therapies including adjuvant 5-fluorouracil and cetuximab combination treatments compared to patients harboring TP53 mutations.

TP53 mutation annotations were obtained from ONCOMINE™ NGS Mutation Browser (Compendia Biosciences, MI). In total 776 patients were assessed for TP53 mutation status; 259 patients contained at least one mutation in TP53 and were annotated as TP53 mutant while 519 patients lacked a detected TP53 mutation and were annotated as TP53 wild type. TP53 wild type and TP53 mutant annotations were then mapped at the patient level to corresponding microarray samples from the TCGA breast dataset. When mutation annotations were mapped to patients with corresponding microarray data, 327 patients were annotated as TP53 wild type and 188 were annotated as TP53 mutant. TP53 wild type and TP53 mutation signatures were generated from a differential expression analysis of the TCGA breast datasets. Gene lists were ranked by p-value according to Student's two class t-test. Genes differentially upregulated in TP53 wild type patients contributed to the TP53 wild type signature whereas genes that were upregulated in TP53 mutant patients contributed to the TP53 mutant signature. Each signature contained the top 1% of ranked genes (n=204). All genes in the TP53 wild type and TP53 mutation signature were highly significant after correcting for false discovery (Q<0.0001). The Q-value was calculated as (p-value/p-value rank)*number of genes measured.

Five ONCOMINE™ cancer types contained sufficient TP53 mutation status data to complete an analysis. Of these, significantly increased signature expression was found in TP53 WT compared to TP53 mutated clinical samples from breast ($p<0.001$; n=189 WT, 37 mutant), lung ($p=0.0003$; n=23 WT, 18 mutated), liver ($p=0.0069$; n=74 WT, 11 mutated) and ovarian ($p=0.05$; n=22 WT, 15 mutated) cancer patients and a trend was found within lymphoma patients ($p=0.068$; n=65 WT, 16 mutated) (see FIGS. 5-7 and 9-10). Table 40 contains the TP53 WT TCGA breast cancer signature.

The clinically-derived expression signature effectively distinguishes TP53 WT from mutant tumor samples.

TABLE 40

| TP53 WT Signature Genes | | | | |
|---|---|---|---|---|
| SUSD3 | BAG1 | ZNF214 | USP30 | CEP120 |
| DMXL1 | ERBB4 | SLC24A1 | MKL2 | CA12 |
| P4HTM | PCP2 | AGBL2 | SYTL4 | SLC7A2 |
| KIF12 | C1orf64 | NME5 | HEXIM2 | ANKHD1-EIF4EBP3 |
| ACBD4 | TMEM161B | RERG | BRD8 | EIF4EBP3 |
| FSIP1 | SLC16A6 | VEZF1 | LOC644189 | TMEM128 |
| CAMLG | MLPH | ZNF484 | PJA2 | HVCN1 |
| FAM47E | LRBA | FBXO38 | TCEAL5 | TCTN1 |
| C14orf25 | EXOC6 | LOC100129623 | CHIC1 | TOX4 |
| USP47 | FAM174A | WFS1 | RNF135 | SEPSECS |
| POLK | C14orf19 | TRIM4 | LOC646976 | KIAA1370 |
| SPG11 | TCEAL3 | SLC7A8 | XPC | RG9MTD2 |
| TLE3 | CCNH | ZC3H6 | MED13L | CELSR1 |
| GLIPR1L2 | ANXA9 | SFRS12 | CXXC5 | TBC1D9B |
| PCBD2 | TTC8 | LOC100131801 | C9orf68 | |
| TCEAL4 | TCEAL6 | GAMT | CACNA1D | |
| KCTD3 | MAN2B2 | ABCC8 | ANKRD42 | |
| OBFC1 | CST5 | CRY2 | LOC440459 | |
| MRFAP1L1 | SCAMP1 | LRRC48 | PCM1 | |
| GMPR2 | PTGER3 | ZNF24 | C7orf63 | |
| DDB2 | CST3 | TMEM101 | RHBDD1 | |
| TIGD6 | PTPRT | NDFIP1 | WDFY3 | |
| KIAA0232 | RAI2 | CHCHD5 | REEP5 | |
| TMEM26 | GREB1 | KCNE4 | FUT8 | |
| PCDH19 | CCDC103 | PGR | ZFYVE1 | |

Example 8

In accordance with methods of the Example 9, 8,690 clinical samples were analyzed for mutation status and 7,202 clinical samples were analyzed for fusion status.

Novel mutations and fusion events were identified. Table 44 shows novel mutations identified in CDNK2A and ALK. Table 41-43 identifies novel fusion events identified in the analysis.

The druggability of each target and available clinical trials are also provided in the Tables.

The novel mutations and fusion events provide an opportunity not only for further development for target treatments but also potential options for future targets of chemotherapeutics.

Example 9

In accordance with methods of previous Examples 1-8, 8,690 clinical samples were analyzed for mutation status and 7,202 clinical samples were analyzed for mutation status. Novel mutation and cancer association events were identified. Tables 45 and 46 show the novel mutations/cancer associations.

The druggability of each target and likely outcome are also provided in Table 45.

The novel mutation/cancer association events provide an opportunity not only for further development for target treatments but also potential options for future targets of chemotherapeutics.

Example 10

In accordance with methods of previous Examples 1-8, 8,690 clinical samples were analyzed for mutation status and 7,202 clinical samples were analyzed for mutation status Novel mutation/cancer association events are shown in Table 47.

Novel fusion events and associated cancers are shown in Table 48. breakpoints and druggability are shown in Table 49. The status of additional drugs relevant to fusion partners are shown in Table 50.

In certain embodiments, the disclosure provides:

A kit comprising a set of probes that specifically recognize at least one fusion of two genes chosen from: Table 42 or 49.

A composition comprising a set of probes that specifically recognize at least one gene fusion of two genes chosen from: Table 42 or 49.

A set of probes that specifically recognize a nucleic acid comprising at least one of SEQ ID NOs: 1-289.

An isolated nucleic acid comprising at least one sequence selected from SEQ ID NOs: 1-289.

A method of detecting bladder urothelial carcinoma, breast carcinoma, endometrial endometrioid adenocarcinoma, colon adenocarcinoma, glioblastoma multiforme, clear cell renal cell carcinoma, papillary renal cell carcinoma, acute myeloid leukemia, brain lower grade glioma, lung adenocarcinoma, ovarian serous cystadenocarcinoma, prostate adenocarcinoma, rectal cutaneous melanoma, and thyroid gland carcinoma in a sample, the method comprising: amplifying a nucleic acid comprising a sequence selected from SEQ ID NOs: 1-289; and detecting the presence of the nucleic acid comprising a sequence selected from SEQ ID NOs: 1-289; wherein detecting the nucleic acid comprising a sequence selected from SEQ ID NOs: 1-289, indicates that one or more of the above cancers is present in the sample.

A kit comprising a set of probes that specifically hybridize to at least one nucleic acid comprising a break point from Table 42 or 49.

A set of probes that specifically hybridize to at least one nucleic acid comprising a break point from Tables 42 or 49.

In the kit, the nucleic acid can be a gene fusion chosen from Table 41.

A method of detecting bladder urothelial carcinoma, breast carcinoma, endometrial endometrioid adenocarcinoma, colon adenocarcinoma, glioblastoma multiforme, clear cell renal cell carcinoma, papillary renal cell carcinoma, acute myeloid leukemia, brain lower grade glioma, lung adenocarcinoma, ovarian serous cystadenocarcinoma, prostate adenocarcinoma, rectal cutaneous melanoma, and thyroid gland carcinoma in a sample, the method comprising: amplifying a gene fusion chosen from Table 41 or 48 or a fusion gene product; and detecting the presence of the gene fusion chosen from Table 41 or 48 or fusion gene product in the sample; wherein detecting the presence of the gene fusion chosen from Table 41, indicates that one or more of the above cancers is present in the sample.

An isolated gene fusion nucleic acid of between 100 and 10,000 nucleotides in length and comprising at least 25 nucleotides on either side of one of the break points in Table 42 or 49.

The isolated gene fusion nucleic acid can have a gene fusion partner that is two genes chosen from: TPM1 and ALK, PRKAR1A and ALK, NCOA1 and ALK, LPP and CASR, MDM2 and EGFR, FGFR3 and ELAVL3, B2M and GNAS, DOCK8 and JAK2, HNF1B and NOTCH1, NFASC and NTRK1, SSBP2 and NTRK1, SQSTM1 and NTRK1, TBL1XR1 and PIK3CA, AKAP13 and RET, FKBP15 and RET, TBL1XR1 and RET, CEP85L and ROS1, CLCN6 and RAF1, TRAK1 and RAF1, PRKACA and AKT1, PRKACA and AKT2, MLL and FYN, and TTC13 and JAK2, SEC16A and NOTCH1, ERC1 and RET, GTF2IRD1 and ALK, HTATSF1 and BRS3, CDH1 and CCDC132, CCDC132 and CDH1, ERBB2 and SLC29A3, MET and TFG; TFG and MET, NOTCH2 and MNDA, IRF2BP2 and NTRK1, EIF2C2 and PTK2, RARA and HOXB3, STAT3 and ETV4, and GFAP and VIM, VIM and GFAP, TOP1 and C17orf64, and TP53 and KIAA0753.

In the above method the sample is a patient sample.

The above method can further comprise diagnosing the patient as having bladder urothelial carcinoma, breast carcinoma, endometrial endometrioid adenocarcinoma, colon adenocarcinoma, glioblastoma multiforme, clear cell renal cell carcinoma, papillary renal cell carcinoma, acute myeloid leukemia, brain lower grade glioma, lung adenocarcinoma, ovarian serous cystadenocarcinoma, prostate adenocarcinoma, rectal cutaneous melanoma, or thyroid gland carcinoma when a nucleic acid comprising a sequence selected from SEQ ID NOs: 1-289 is present in the patient sample.

A kit comprising a set of probes, wherein the set of probes specifically recognize a gene variant chosen from Table 41, Table 44, Table 45, Table 46, Table 47 or a combination thereof.

A composition comprising a set of probes that specifically recognize a gene variant from Table 41, Table 44, Table 45, Table 46, Table 47 or a combination thereof.

A set of probes that specifically recognize a gene variant from Table 41, Table 44, Table 45, Table 46, Table 47 or a combination thereof.

A method of detecting bladder carcinoma, breast carcinoma, cervical cell carcinoma, colon adenocarcinoma, glioblastoma multiforme, head and neck squamous cell carcinoma, clear cell renal cell carcinoma, kidney renal papillary cell carcinoma, acute myeloid leukemia, brain lower grade glioma, liver hepatocellular carcinoma, lung adenocarcinoma, squamous cell lung carcinoma, ovarian serous adenocarcinoma, prostate adenocarcinoma, rectal adenocarcinoma, cutaneous melanoma, stomach adenocarcinoma, thyroid carcinoma, or uterine corpus endometrioid carcinoma, the method comprising: amplifying a nucleic acid comprising a variant selected from Table 7 and/or Table 11; and detecting the presence of the variant selected from Table 41, Table 44, Table 45, Table 46, Table 47 or a combination thereof; wherein detecting the variant selected from Table 41, Table 44, Table 45, Table 46, Table 47 or a combination thereof, indicates one ore of the above cancers is present in the sample.

A kit comprising a set of probes that specifically hybridize to a variant selected from Table 41, Table 44, Table 45, Table 46, Table 47 or a combination thereof.

A set of probes that specifically hybridize to a gene variant selected from Table 41, Table 44, Table 45, Table 46, Table 47 or a combination thereof.

The method of claim 17, wherein the sample is a patient sample.

The method of claim 20, further comprising diagnosing the patient as having bladder carcinoma, breast carcinoma, cervical cell carcinoma, colon adenocarcinoma, glioblastoma multiforme, head and neck squamous cell carcinoma, clear cell renal cell carcinoma, kidney renal papillary cell carcinoma, acute myeloid leukemia, brain lower grade glioma, liver hepatocellular carcinoma, lung adenocarcinoma, squamous cell lung carcinoma, ovarian serous adenocarcinoma, prostate adenocarcinoma, rectal adenocarcinoma, cutaneous melanoma, stomach adenocarcinoma, thyroid carcinoma, or uterine corpus endometrioid carcinoma when a variant selected from Table 41, Table 44, Table 45, Table 46, Table 47 or a combination thereof is present in the patient sample.

An isolated genetic construct comprising an antisense polynucleotide sequence of a sequence selected from SEQ ID NOs:1-289.

The isolated genetic construct can further comprise a promoter operatively linked to the antisense polynucleotide.

The isolated genetic construct can be a vector. The vector can be a viral vector A method comprising contacting a cell comprising a gene fusion with a drug, wherein the gene fusion is disclosed in Table 41 or Table 49 and the drug is one or more of the drugs in Table 43 or Table 49.

A method comprising administering to a patient with a gene fusion a drug, wherein the gene fusion is disclosed in Table 41 or Table 49.

The method of claim 27, wherein the patient is diagnosed with cancer.

The method of claim 28, wherein the cancer is a cancer type disclosed in Table 41 or Table 49.

A method comprising contacting a nucleic acid sample from a patient with a reaction mixture comprising two primers, wherein a first primer is complementary to one gene and a second primer is complementary to a second gene, wherein the fusion of the first gene and the second gene is detectable by the presence of an amplicon generated by the first primer and the second primer, wherein the fusion breakpoint is one of the breakpoints of Table 42 or 49, and wherein a patient with an amplicon is administered one or more of the drugs in Table 43 or Table 49.

A method comprising performing a bioassay to detect one or more gene fusions in a sample from a subject, wherein at least one of the gene fusions is selected from those in Table 42 or Table 49, receiving the results of the bioassay into a computer system, processing the results to determine an output, presenting the output on a readable medium, wherein the output identifies therapeutic options recommended for the subject based on the presence or absence of the gene fusions.

In the above method, the bioassay can include probes specific for one or more of the breakpoints of Table 42 or Table 49.

A kit, comprising: a set of probes, wherein each probe specifically hybridizes to a nucleic acid comprising a breakpoint from Table 42 or Table 49.

In the kit, each non-naturally occurring probe can comprise: a nucleic acid sequence configured to specifically hybridize to the nucleic acid comprising the breakpoint from Table 42 or Table 49, and a detectable moiety covalently bonded to the nucleic acid sequence.

In the kit, each non-naturally occurring probe can comprise: a deoxyribonucleic acid sequence comprising at least one deoxyuridine (dU) residue in place of a deoxythymidine residue.

A method, comprising: amplifying a nucleic acid comprising at least one gene fusion from Table 41 or Table 49 from a sample; and detecting the presence of the at least one gene fusion by at least one of: contacting the composition with at least one probe, wherein each probe specifically hybridizes to the nucleic acid, or observing the presence of a non-natural or non-native chemical structure in the nucleic acid; wherein detecting the presence of the at least one gene fusion indicates that at least one cancer from Table 41 or Table 49 is present in the sample.

A system, comprising: a nucleic acid amplifier configured to amplify a nucleic acid comprising at least one gene fusion from Table 41 or Table 49 from a sample, to yield an amplified nucleic acid; a detector configured to detect the presence of the at least one gene fusion in the amplified nucleic acid by at least one of (i) contacting the composition with at least one probe, wherein each probe specifically hybridizes to the nucleic acid, or (ii) observing the presence of a non-natural or non-native chemical structure in the nucleic acid, and further configured to transmit a detection indication; and a computer system configured to receive the detection indication and determine that at least one cancer from Table 41 or Table 49 is present in the sample, based on the detection indication.

A non-transitory computer readable program storage unit encoded with instructions that, when executed by a computer, perform a method, comprising: receiving an input comprising at least a cancer type and an event type, wherein the cancer type is selected from Table 44, 45, 46 and/or 47 and the event type is selected from Table 44, 45, 46 and/or 47; querying a database for at least one entry comprising a plurality of fields, wherein the plurality of fields comprises at least one of the cancer type and the event type; transmitting an output comprising at least one field of the plurality from the at least one entry, wherein the at least one field comprises at least one gene, at least one druggable gene, at least one drug targeting the at least one druggable gene, or a prognosis.

A method, comprising: administering to a patient having at least one gene fusion selected from the gene fusions listed in Table 41 at least one drug selected from the drugs listed in Table 43.

A method, comprising: contacting a nucleic acid sample from a patient with a reaction mixture comprising a first primer complementary to a first gene and a second primer complementary to a second gene, wherein a fusion of the first gene and the second gene is detectable by the presence of an amplicon generated by the first primer and the second primer, wherein the fusion comprises a breakpoint selected from the breakpoints listed in Table 42 or Table 49.

In the above method, at least one drug can be selected from the drugs listed in Table 43, 45, 46 and/or 47 is administered to the patient, in response to a detection of the fusion.

A non-transitory computer readable program storage unit encoded with instructions that, when executed by a computer, perform a method, comprising: receiving RNA sequence data from at least one cancer cell line; running at least one gene fusion caller on the sequence data, to identify possible breakpoints between fused genes in the processed data; filtering said possible breakpoints, to retain candidate breakpoints, wherein each candidate breakpoint is in a 5' untranslated region (UTR) or a coding DNA sequence (CDS) of a functional gene region and each candidate breakpoint does not occur in an intron; annotating the candidate breakpoints with at least one annotation useful in determining a relevance of a gene fusion for at least one of cancer diagnosis, cancer prognosis, or cancer treatment, wherein the gene fusion comprises the candidate breakpoint.

In the non-transitory computer readable program storage unit, at least one gene fusion caller can be selected from TopHat and deFuse.

A non-transitory computer readable program storage unit encoded with instructions that, when executed by a computer, perform a method, comprising: receiving mutation data from at least one cancer cell line; annotating the mutation data with at least one of variant classification, variant position, or variant change, to yield annotated mutation data; filtering the annotated mutation data, to yield gene region mutation data; classifying the gene region mutation data as hotspot, deleterious, or other; and nominating a gene comprising the gene region mutation as a gain of function, loss of function, or recurrent other gene, based on the relative frequency of mutations in the gene and the classifications of all gene region mutations in the gene.

In the non-transitory computer readable program storage unit, the variant classification can be selected from splice site, 3' untranslated region (UTR), 5' UTR, intron, missense, nonsense, nonstop, silent, frame shift insertion, frame shift deletion, in-frame insertion, in-frame deletion, or non-coding exon.

In the non-transitory computer readable program storage unit, filtering the annotated mutation data can comprise excluding mutations outside of a known transcript and mutations not associated with a known gene.

In the non-transitory computer readable program storage unit, classifying the mutation as hotspot can comprise determining its presence at the same variant position in at least three cancer cell lines, wherein the variant classification is missense, nonstop, in-frame insertion, in-frame deletion, or non-coding exon.

In the non-transitory computer readable program storage unit, wherein classifying the mutation as deleterious can comprise observing the variant classification is nonsense, frame shift insertion, or frame shift deletion.

A method, comprising: detecting one or more gene fusions in a sample from a subject, to yield gene fusion detection data, wherein at least one of the gene fusions is selected from the gene fusions listed in Table 41 or 49, receiving by a computer system the gene fusion detection data, identifying by the computer system at least one therapeutic option recommended for the subject, based on the gene fusion detection data.

A system, comprising: a detector configured to (i) detect one or more gene fusions in a sample from a subject, to yield gene fusion detection data, wherein at least one of the gene fusions is selected from the gene fusions listed in Table 41 or 49 and (ii) transmit the gene fusion detection data; and a computer system configured to receive the gene fusion detection data and identify at least one therapeutic option recommended for the subject, based on the gene fusion detection data.

A gene fusion that is prepared by a process comprising: isolating an RNA molecule comprising the gene fusion; and synthesizing a complementary DNA (cDNA) molecule complementary to the isolated RNA molecule.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Reference to sequence identifiers, such as those beginning with NM_, refer to the database accession numbers and the underlying sequences as they were found on Apr. 18, 2013.

TABLE 7

| TCGA Disease | Gene Symbol | Entrez Gene ID | Start Position | Reference Allele | Tumor Seq Allele | Transcript | Variant C |
| --- | --- | --- | --- | --- | --- | --- | --- |
| READ | ANXA1 | 301 | 74965099 | G | A | NM_000700 | p.R124H |
| SKCM | ANXA1 | 301 | 75775278 | C | T | NM_000700 | p.R124C |
| UCEC | ANXA1 | 301 | 75775279 | G | A | NM_000700 | p.R124H |
| BRCA | AR | 367 | 66765161 | A | T | NM_000044 | p.Q58L |
| HNSC | AR | 367 | 66765161 | A | T | NM_000044 | p.Q58L |
| KIRP | AR | 367 | 66765161 | A | T | NM_000044 | p.Q58L |
| LGG | AR | 367 | 66765161 | A | T | NM_000044 | p.Q58L |
| LUAD | AR | 367 | 66765161 | A | T | NM_000044 | p.Q58L |
| STAD | AR | 367 | 66765161 | A | T | NM_000044 | p.Q58L |
| UCEC | AR | 367 | 66765161 | A | T | NM_000044 | p.Q58L |
| LUAD | ARAF | 369 | 47426120 | T | A | NM_001654 | p.S214T |
| LUAD | ARAF | 369 | 47426121 | C | T | NM_001654 | p.S214F |
| SKCM | ARAF | 369 | 47426121 | C | T | NM_001654 | p.S214F |
| PAAD | ATP6V1A | 523 | 113505224 | T | C | NM_001690 | p.L237P |
| SKCM | ATP6V1A | 523 | 113505224 | T | C | NM_001690 | p.L237P |
| LUAD | CDK4 | 1019 | 58145430 | C | A | NM_000075 | p.R24L |
| SKCM | CDK4 | 1019 | 58145430 | C | A | NM_000075 | p.R24L |
| SKCM | CDK4 | 1019 | 58145431 | G | T | NM_000075 | p.R24S |
| OV | CHEK2 | 11200 | 27422947 | C | T | NM_007194 | p.R346H |
| GBM | CHEK2 | 11200 | 29083962 | G | C | NM_007194 | p.R519G |
| HNSC | CHEK2 | 11200 | 29083962 | G | C | NM_007194 | p.R519G |
| KIRC | CHEK2 | 11200 | 29083962 | G | C | NM_007194 | p.R519G |
| PAAD | CHEK2 | 11200 | 29083962 | G | C | NM_007194 | p.R519G |
| HNSC | CHEK2 | 11200 | 29091840 | T | C | NM_007194 | p.K373E |
| KIRC | CHEK2 | 11200 | 29091840 | T | C | NM_007194 | p.K373E |
| LUAD | CHEK2 | 11200 | 29091840 | T | C | NM_007194 | p.K373E |
| SKCM | CHEK2 | 11200 | 29091840 | T | C | NM_007194 | p.K373E |
| BRCA | CHEK2 | 11200 | 29092948 | G | A | NM_007194 | p.R346C |
| LUSC | CHEK2 | 11200 | 29092948 | G | C | NM_007194 | p.R346G |
| HNSC | CSNK2A1 | 1457 | 470440 | T | C | NM_001895 | p.H236R |
| LUAD | CSNK2A1 | 1457 | 470440 | T | C | NM_001895 | p.H236R |
| LUSC | CSNK2A1 | 1457 | 470440 | T | C | NM_001895 | p.H236R |
| STAD | CSNK2A1 | 1457 | 470440 | T | C | NM_001895 | p.H236R |
| THCA | CSNK2A1 | 1457 | 470440 | T | C | NM_001895 | p.H236R |
| GBM | DRD5 | 1816 | 9784478 | C | A | NM_000798 | p.S275R |
| HNSC | DRD5 | 1816 | 9784478 | C | A | NM_000798 | p.S275R |
| LUSC | DRD5 | 1816 | 9784478 | C | A | NM_000798 | p.S275R |
| STAD | DRD5 | 1816 | 9784478 | C | A | NM_000798 | p.S275R |
| COAD | ERBB3 | 2065 | 54765121 | G | A | NM_001982 | p.V104M |
| COAD | ERBB3 | 2065 | 54765121 | G | A | NM_001982 | p.V104M |
| COAD | ERBB3 | 2065 | 54765121 | G | T | NM_001982 | p.V104L |
| READ | ERBB3 | 2065 | 54765121 | G | A | NM_001982 | p.V104M |
| CESC | ERBB3 | 2065 | 56478854 | 6 | A | NM_001982 | p.V104M |
| STAD | ERBB3 | 2065 | 56478854 | G | T | NM_001982 | p.V104L |
| STAD | ERBB3 | 2065 | 55478854 | G | A | NM_001982 | p.V104M |
| UCEC | ERBB3 | 2065 | 56478854 | G | A | NM_001982 | p.V104M |
| BRCA | ERBB3 | 2065 | 56482341 | G | T | NM_001982 | p.D297Y |
| UCEC | ERBB3 | 2065 | 56482341 | G | T | NM_001982 | p.D297Y |
| UCEC | ERBB3 | 2065 | 56482341 | G | A | NM_001982 | p.D297N |
| UCEC | ERBB3 | 2065 | 56482342 | A | T | NM_001982 | p.D297V |
| HNSC | FGFR3 | 2261 | 1803565 | C | G | NM_000142 | p.S249C |
| KIRP | FGFR3 | 2261 | 1803568 | C | G | NM_000142 | p.S249C |
| LUSC | FGFR3 | 2261 | 1803568 | C | G | NM_000142 | p.S249C |
| COAD | GPRC5A | 9052 | 12952538 | G | A | NM_003979 | p.V30I |

TABLE 7-continued

| TCGA Disease | Gene Symbol | Entrez Gene ID | Start Position | Reference Allele | Tumor Seq Allele | Transcript | Variant C |
|---|---|---|---|---|---|---|---|
| UCEC | GPRC5A | 9052 | 13061271 | G | A | NM_003979 | p.V30I |
| LUAD | GPX1 | 2876 | 49395482 | G | C | NM_000581 | p.P77R |
| SKCM | GPX1 | 2876 | 49395482 | G | C | NM_000581 | p.P77R |
| STAD | GPX1 | 2876 | 49395482 | G | C | NM_000581 | p.P77R |
| KIRC | HSD17B7 | 51478 | 162769603 | G | A | NM_016371 | p.S173N |
| PAAD | HSD17B7 | 51478 | 162759603 | G | A | NM_016371 | p.S173N |
| BRCA | JUN | 3725 | 59248409 | C | T | NM_002228 | p.E112K |
| LUSC | JUN | 3725 | 59248409 | C | T | NM_002228 | p.E112K |
| LUSC | JUN | 3725 | 59248409 | C | G | NM_002228 | p.E112Q |
| COAD | KDR | 3791 | 55650977 | C | T | NM_002253 | p.R1032Q |
| SKCM | KDR | 3791 | 55955863 | G | A | NM_002253 | p.S1100F |
| SKCM | KDR | 3791 | 55956220 | C | T | NM_002253 | p.R1032Q |
| LAML | KIT | 3815 | 55294077 | G | T | NM_000222 | p.D816Y |
| LAML | KIT | 3815 | 55294078 | A | T | NM_000222 | p.D816V |
| SKCM | LHCGR | 3973 | 48915500 | C | T | NM_000233 | p.R479Q |
| UCEC | LHCGR | 3973 | 48915500 | C | A | NM_000233 | p.R479L |
| SKCM | LHCGR | 3973 | 48936151 | C | T | NM_000233 | p.E206K |
| HNSC | MAP2K2 | 5605 | 4117549 | A | C | NM_030662 | p.F57L |
| SKCM | MAP2K2 | 5605 | 4117551 | A | C | NM_030662 | p.F57V |
| STAD | MAP2K2 | 5605 | 4117551 | A | C | NM_030662 | p.F57V |
| CESC | MAPK1 | 5594 | 22127164 | C | T | NM_002745 | p.E322K |
| HNSC | MAPK1 | 5594 | 22127164 | C | T | NM_002745 | p.E322K |
| COAD | MMP15 | 4324 | 56631345 | G | A | NM_002428 | p.R169H |
| SKCM | MMP15 | 4324 | 58073843 | C | T | NM_002428 | p.R169C |
| LUAD | MMP15 | 4324 | 58073844 | G | A | NM_002428 | p.R169H |
| OV | MMP3 | 4314 | 102215174 | G | A | NM_002422 | p.R316C |
| GBM | MMP3 | 4314 | 102709963 | C | T | NM_002422 | p.R316H |
| GBM | MMP3 | 4314 | 102709964 | G | A | NM_002422 | p.R316C |
| LUAD | MMP3 | 4314 | 102709964 | G | A | NM_002422 | p.R316C |
| COAD | MTOR | 2475 | 11107160 | G | T | NM_004958 | p.S2215Y |
| KIRC | MTOR | 2475 | 11184573 | G | T | NM_004958 | p.S2215Y |
| KIRP | MTOR | 2475 | 11184573 | G | T | NM_004958 | p.S2215Y |
| UCEC | MTOR | 2475 | 11184573 | G | T | NM_004958 | p.S2215Y |
| KIRC | MTOR | 2475 | 11189545 | G | C | NM_004958 | p.F1888L |
| UCEC | MTOR | 2475 | 11189845 | G | T | NM_004958 | p.F1888L |
| UCEC | MTOR | 2475 | 11189847 | A | C | NM_004958 | p.F1888V |
| OV | MTOR | 2475 | 11195525 | C | T | NM_004958 | p.A1105T |
| KIRC | MTOR | 2475 | 11217230 | C | T | NM_004958 | p.C1483Y |
| KIRC | MTOR | 2475 | 11217230 | C | A | NM_004958 | p.C1483F |
| GBM | MTOR | 2475 | 11217231 | A | G | NM_004958 | p.C1483R |
| SKCM | MTOR | 2475 | 11272938 | C | T | NM_004958 | p.A1105T |
| GBM | PIK3CB | 5291 | 138374244 | T | G | NM_006219 | p.D1067A |
| HNSC | PIK3CB | 5291 | 138374244 | T | A | NM_006219 | p.D1067V |
| THCA | PIK3CB | 5291 | 138374244 | T | A | NM_006219 | p.D1067V |
| UCEC | PIK3CB | 5291 | 138374245 | C | A | NM_006219 | p.D1067Y |
| LUAD | PIK3R2 | 5296 | 18273784 | G | A | NM_005027 | p.G373R |
| UCEC | PIK3R2 | 5296 | 18273784 | G | A | NM_005027 | p.G373R |
| COAD | POLE | 5426 | 131760362 | C | A | NM_006231 | p.V411L |
| COAD | POLE | 5426 | 131763257 | G | T | NM_006231 | p.P286H |
| UCEC | POLE | 5426 | 133250289 | C | A | NM_006231 | p.V411L |
| UCEC | POLE | 5426 | 133253184 | G | C | NM_006231 | p.P286R |
| UCEC | PPP2R1A | 5518 | 52715971 | C | G | NM_014225 | p.P179R |
| UCEC | PPP2R1A | 5518 | 52715982 | C | T | NM_014225 | p.R183W |
| HNSC | PPP2R1A | 5518 | 52715983 | G | A | NM_014225 | p.R183Q |
| STAD | PPP2R1A | 5518 | 52715983 | G | A | NM_014225 | p.R183Q |
| UCEC | PPP2R1A | 5518 | 52716323 | C | T | NM_014225 | p.S256F |
| UCEC | PPP2R1A | 5518 | 52716323 | C | A | NM_014225 | p.S256Y |
| UCEC | PPP2R1A | 5518 | 52716328 | C | T | NM_014225 | p.R258C |
| LUAD | PPP2R1A | 5518 | 52716329 | G | A | NM_014225 | p.R258H |
| COAD | PPP2R1A | 5518 | 57407794 | C | T | NM_014225 | p.R183W |
| COAD | PPP2R1A | 5518 | 57407794 | C | T | NM_014225 | p.R183W |
| OV | PPP2R1A | 5518 | 57407794 | C | T | NM_014225 | p.R183W |
| COAD | PPP2R1A | 5518 | 57408141 | G | A | NM_014225 | p.R258H |
| HNSC | PRKCA | 5578 | 64299066 | G | C | NM_002737 | p.E33Q |
| LUAD | PRKCA | 5578 | 64299066 | G | A | NM_002737 | p.E33K |
| LUSC | PRKCA | 5578 | 64299066 | G | A | NM_002737 | p.E33K |
| KIRC | PRKCH | 5583 | 61789073 | C | T | NM_006255 | p.A85V |
| PAAD | PRKCH | 5583 | 61789073 | C | T | NM_006255 | p.A85V |
| STAD | PRKCI | 5584 | 170013719 | C | A | NM_002740 | p.R480S |
| COAD | PRKCI | 5584 | 171496413 | C | T | NM_002740 | p.R480C |
| COAD | PRKCI | 5584 | 171496413 | C | T | NM_002740 | p.R480C |
| OV | PRKCI | 5584 | 171496413 | C | T | NM_002740 | p.R480C |
| COAD | RAF1 | 5894 | 12620699 | G | A | NM_002880 | p.S257L |
| COAD | RAF1 | 5894 | 12620699 | G | A | NM_002880 | p.S257L |
| LUAD | RAF1 | 5894 | 12645699 | G | A | NM_002880 | p.S257L |
| LUAD | RAF1 | 5894 | 12645699 | G | C | NM_002880 | p.S257W |
| SKCM | RAF1 | 5894 | 12645699 | G | A | NM_002880 | p.S257L |
| STAD | RAF1 | 5894 | 12645699 | G | A | NM_002880 | p.S2S7L |

TABLE 7-continued

| TCGA Disease | Gene Symbol | Entrez Gene ID | Start Position | Reference Allele | Tumor Seq Allele | Transcript | Variant C |
|---|---|---|---|---|---|---|---|
| KIRC | RHEB | 6009 | 151188050 | A | T | NM_005614 | p.Y35N |
| UCEC | RHEB | 6009 | 151188050 | A | T | NM_005614 | p.Y35N |
| STAD | RHOA | 387 | 49412898 | T | C | NM_001664 | p.Y42C |
| STAD | RHOA | 387 | 49412898 | T | G | NM_001664 | p.Y42S |
| BRCA | RHOA | 387 | 49412905 | C | G | NM_001664 | p.E40Q |
| HNSC | RHOA | 387 | 49412905 | C | G | NM_001664 | p.E40Q |
| COAD | SRC | 6714 | 35464354 | G | C | NM_005417 | p.D407H |
| OV | SRC | 6714 | 35464354 | G | C | NM_005417 | p.D407H |
| SKCM | SRCIN1 | 80725 | 36704930 | C | T | NM_025248 | p.E1045K |
| READ | SYK | 6850 | 92676932 | G | T | NM_003177 | p.K387N |
| LGG | SYK | 6850 | 93637110 | A | G | NM_003177 | p.K387R |
| SKCM | SYK | 6850 | 93637110 | A | G | NM_003177 | p.K387R |
| STAD | TOP2A | 7153 | 38552660 | T | C | NM_001067 | p.K1199E |
| THCA | TOP2A | 7153 | 38552660 | T | C | NM_001067 | p.K1199E |
| COAD | TOP2B | 7155 | 25643731 | C | T | NM_001068 | p.R651H |
| UCEC | TOP2B | 7155 | 25668727 | C | T | NM_001068 | p.R651H |
| GBM | TUBA1B | 10376 | 49523423 | C | T | NM_006082 | p.G29D |
| STAD | TUBA1B | 10376 | 49523423 | C | T | NM_006082 | p.G29D |
| HNSC | TUBA1B | 10376 | 49523424 | C | G | NM_006082 | p.G29R |
| BLCA | TXNRD1 | 7296 | 104725378 | G | A | NM_003330 | p.E439K |
| CESC | TXNRD1 | 7296 | 104725378 | G | C | NM_003330 | p.E439Q |
| UCEC | TXNRD1 | 7296 | 104725378 | G | C | NM_003330 | p.E439Q |
| HNSC | TXNRD1 | 7296 | 104725379 | A | G | NM_003330 | p.E439G |
| KIRC | TXNRD1 | 7296 | 104725379 | A | G | NM_003330 | p.E439G |
| LGG | VEGFB | 7423 | 64005040 | A | C | NM_003377 | p.T187P |
| PAAD | VEGFB | 7423 | 64005040 | A | C | NM_003377 | p.T187P |
| HNSC | VEGFB | 7423 | 64005048 | A | C | NM_001243733 | p.T156P |
| PAAD | VEGFB | 7423 | 64005048 | A | C | NM_001243733 | p.T156P |
| SKCM | VEGFB | 7423 | 64005048 | A | C | NM_001243733 | p.T156P |

BLCA Bladder Urothelial Carcinoma
BRCA Breast invasive carcinoma
CESC Cervical Squamous Cell Carcinoma
COAD colon adenocarcinoma
GBM glioblastoma
HNSC head and neck squamous cancer
KIRC Kidney Renal Clear Cell Carcinoma
KIRP Kidney Renal Papillary Cell Carcinoma
LAML acute myeloid leukemia
LGG low grade glioma
LUAD lung adenocarcinoma
LUSC lung squamous cell carcinoma
OV ovarian carcinoma
PAAD pancreatic adenoacrcinoma
READ rectal adenocarcinoma
SKCM Skin Cutaneous Melanoma
STAD stomach adenocarcinoma
THCA thyroid carcinoma
UCEC Uterine Corpus Endometrioid Carcinoma

TABLE 41

| Cancer Type | 5' gene symbol | 3' gene symbol | Druggable gene |
|---|---|---|---|
| Prostate Adenocarcinoma | ACPP | AXL | AXL |
| Prostate Adenocarcinoma | ATM | CARD18 | ATM |
| Lung Adenocarcinoma | ATXN1 | ARG1 | ARG1 |
| Lower Grade Glioma | CLU | CST3 | CLU |
| Prostate Adenocarcinoma | DHX15 | ETV1 | none |
| Lower Grade Glioma | DOT1L | TECR | DOT1L |
| Adrenal Cortex Carcinoma | EXOSC10 | MTOR | MTOR |
| Cervical Squamous Cell Carcinoma | FAT1 | NTRK3 | NTRK3 |
| Bladder Urothelial Carcinoma | FHIT | RUNX1 | none |
| Prostate Adenocarcinoma | GUCA2A | ERG | none |
| Sarcoma | KANK2 | ALK | ALK |
| Cutaneous Melanoma | LMNA | RAF1 | RAF1 |
| Prostate Adenocarcinoma | MDM2 | BRI3BP | MDM2 |
| Cervical Squamous Cell Carcinoma | MX1 | ERG | none |
| Hepatocellular Carcinoma | OXR1 | MET | MET |
| Papillary Renal Cell Carcinoma | PLS1 | PIK3CB | PIK3CB |
| Colon and Rectal Adenocarcinoma | RPS6 | FN1 | FN1 |
| Cutaneous Melanoma | RSBN1L | HGF | HGF |
| Lung Adenocarcinoma | RUNX1 | CEP76 | none |
| Sarcoma | SEC16A | RXRA | RXRA |
| Lung Adenocarcinoma | STK11 | HMHA1 | None |
| Ovarian Serous Cystadenocarcinoma | TBL1XR1 | CTNNB1 | CTNNB1 |
| Prostate Adenocarcinoma | TMPRSS2 | GUCA2A | None |
| Prostate Adenocarcinoma | TMPRSS2 | TMEM109 | None |
| Prostate Adenocarcinoma | TMPRSS2 | BRAF | BRAF |
| Colon and Rectal Adenocarcinoma | USP7 | PRKCB | PRKCB |
| Lower Grade Glioma | VEGFA | STK38 | VEGFA |

TABLE 42

| 5' Gene Symbol | 3' Gene Symbol | Cancer Type | TCGA Tumor Sample Barcode | 5' Accession | 5' Chromosome | 5' Breakpoint | 3' Accession | 3' Chromosome | 3' Breakpoint |
|---|---|---|---|---|---|---|---|---|---|
| ACPP | AXL | Prostate Adenocarcinoma | TCGA-J4-A6G3-01A-11R-A311-07 | 55 | chr3 | 132075687 | 558 | chr19 | 41745606 |
| ATM | CARD18 | Prostate Adenocarcinoma | TCGA-KK-A6E8-01A-11R-A31N-07 | 472 | chr11 | 108218092 | 59082 | chr11 | 105009805 |
| ATXN1 | ARG1 | Lung Adenocarcinoma | TCGA-55-6978-01A-11R-1949-07 | 6310 | chr6 | 1658016 | 383 | chr6 | 131897847 |
| CLU | CST3 | Lower Grade Glioma | TCGA-CS-4944-01A-01R-1470-07 | 1191 | chr8 | 27461879 | 1471 | chr20 | 23618406 |
| CLU | CST3 | Lower Grade Glioma | TCGA-PS-A72U-01A-31R-A32Q-07 | 1191 | chr8 | 27461878 | 1471 | chr20 | 23614559 |
| DHX15 | ETV1 | Prostate Adenocarcinoma | TCGA-G9-6339-01A-12R-A311-07 | 1665 | chr4 | 24585946 | 2115 | chr7 | 13975521 |
| DOT1L | TECR | Lower Grade Glioma | TCGA-TM-A7CF-02A-11R-A32Q-07 | 84444 | chr19 | 2194576 | 9524 | chr19 | 14673337 |
| DOT1L | TECR | Lower Grade Glioma | TCGA-TM-A7CF-01A-11R-A32Q-07 | 84444 | chr19 | 2194576 | 9524 | chr19 | 14673337 |
| EXOSC10 | MTOR | Adrenal Cortex Carcinoma | TCGA-OR-A5J7-01A-11R-A29S-07 | 5394 | chr1 | 11139768 | 2475 | chr1 | 11190834 |
| FAT1 | NTRK3 | Cervical Squamous Cell Carcinoma | TCGA-HM-A3JK-01A-11R-A32Y-07 | 2195 | chr4 | 187627717 | 4916 | chr15 | 88680792 |
| FHIT | RUNX1 | Bladder Urothelial Carcinoma | TCGA-LC-A66R-01A-41R-A30C-07 | 2272 | chr3 | 61237029 | 861 | chr21 | 36231788 |
| GUCA2A | ERG | Prostate Adenocarcinoma | TCGA-KC-A4BR-01A-32R-A32Y-07 | 2980 | chr1 | 42629074 | 2078 | chr21 | 39817544 |
| HMHA1 | STK11 | Lung Adenocarcinoma | TCGA-62-8395-01A-11R-2326-07 | 23526 | chr19 | 1066162 | 6794 | chr19 | 1218416 |
| STK11 | HMHA1 | Lung Adenocarcinoma | TCGA-NJ-A4YF-01A-12R-A262-07 | 6794 | chr19 | 1222005 | 23526 | chr19 | 1080254 |
| KANK2 | ALK | Sarcoma | TCGA-FX-A48G-01A-11R-A24X-07 | 25959 | chr19 | 11303507 | 238 | chr2 | 29451932 |
| LMNA | RAF1 | Cutaneous Melanoma | TCGA-EB-A55F-01A-11R-A311-07 | 4000 | chr1 | 156107492 | 5894 | chr3 | 12645651 |
| MDM2 | BRI3BP | Prostate Adenocarcinoma | TCGA-KK-A7B2-01A-12R-A320-07 | 4193 | chr12 | 69214153 | 140707 | chr12 | 125509889 |
| MX1 | ERG | Cervical Squamous Cell Carcinoma | TCGA-C5-A7CJ-01A-11R-A32P-07 | 4599 | chr21 | 42809050 | 2078 | chr21 | 39947620 |
| OXR1 | MET | Hepatocellular Carcinoma | TCGA-RC-A6M6-01A-11R-A320-07 | 55074 | chr8 | 107726213 | 4233 | chr7 | 116411552 |
| PLS1 | PIK3CB | Papillary Renal Cell Carcinoma | TCGA-G7-6793-01A-11R-1965-07 | 5357 | chr3 | 142315341 | 5291 | chr3 | 138461531 |
| RPS6 | FN1 | Colon and Rectal Adenocarcinom | TCGA-AG-3609-01A-02R-0826-07 | 6194 | chr9 | 19378859 | 2335 | chr2 | 216259394 |
| RSBN1L | HGF | Cutaneous Melanoma | TCGA-EB-A55E-01A-11R-A311-07 | 221194 | chr7 | 77326339 | 3082 | chr7 | 81381543 |
| RLINX1 | CEP76 | Lung Adenocarcinoma | TCGA-O1-A52J-01A-13R-A262-07 | 861 | chr21 | 36206707 | 79959 | chr18 | 12686449 |
| SEC16A | RXRA | Sarcoma | TCGA-DX-A3LS-01A-11R-A21T-07 | 9919 | chr9 | 139352034 | 6256 | chr9 | 137293495 |

TABLE 42-continued

| 5' Gene Symbol | 3' Gene Symbol | | | | | | Breakpoint Sequence | SEQ ID NO |
|---|---|---|---|---|---|---|---|---|
| TBL1XR1 | CTNNB1 | Ovarian Serous Cystadenocarcinoma | TCGA-24-2280-01A-01R-1568-13 | 79718 | chr3 | 176914909 | 1499 | chr3 | 41274832 | GGTTGGCCCTGTGATCCCTCAAGACTGTCCACGGAGTGTATGACCACAA\|ACAGCCAGTCCACCAGCTGGTGAAGGAACCTTCAACTCCTGCCTTCTCGT | 258 |
| TMPRSS2 | GUCA2A | Prostate Adenocarcinoma | TCGA-KC-A4BR-01A-32R-A32Y-07 | 7113 | chr21 | 42879877 | 2980 | chr1 | 42629281 | GAATATCTTGATAATGACCAGTCAGCAGAGAACTTGTACATATAGATCTAG\|ACCAACTCTTGCGTAAAAAGAAGAAGAATTTTTATCCATTCAGTGGGTGCA | 259 |
| TMPRSS2 | TMEM109 | Prostate Adenocarcinoma | TCGA-HC-8216-01A-11R-A29R-07 | 7113 | chr21 | 42860321 | 79073 | chr11 | 60687158 | AAGAGAGAAAGAGTGGATTTCAGCTGTCACGATGGTCTTGAAACACAAA\|TGGTCTGCTTGAGAAACTTAAAGAACAAGAGAGTGTGATGTGAAGGATTATG | 260 |
| TMPRSS2 | TMEM109 | Prostate Adenocarcinoma | TCGA-HC-8213-01A-11R-A29R-07 | 7113 | chr21 | 42852403 | 79073 | chr11 | 60687197 | ACAGAATTCATACGAGAAGGCGACGATGACCGACTGTGTGCCGGAGAT\|CCGCCCGCGCCAGTGGAGGCCCCATGGAGGTGTACCCGGCGGTGGAGGAGGG | 261 |
| TMPRSS2 | BRAF | Prostate Adenocarcinoma | TCGA-FC-A6HD-11R-A31N-07 | 7113 | chr21 | 42866283 | 673 | chr7 | 140481493 | CAGAATTCATACGAGAAGGCGACGATGACCGACTGTGTGCCGGAGATC\|CGCCTAGGGGTCTGTGATCAGGAGCCACAAGTGGGAATGAGGCCCTCCAAC | 262 |
| USP7 | PRKCB | Colon and Rectal Adenocarcinoma | TCGA-A6-3807-01A-01R-1022-07 | 7874 | chr16 | 9057064 | 5579 | chr16 | 24043457 | GGACCTAGGGGGAGGATTACCCCTCTGGCAAGAAGCGTGCGGGGACCATG\|GTGCCTATGATCAGGAGATTCTGGACGCAAAGACAAGGAGAAGCTGTGTTTCTTGGACAA | 263 |
| VEGFA | STK38 | Lower Grade Glioma | TCGA-TM-A7CF-02A-11R-A32Q-07 | 7422 | chr6 | 43745395 | 11329 | chr6 | 36467720 | AGTTCAGGAAGTGGATGAAATGTATGGAAAAAAAGCATGCAGAATACCA\|GTGGAGATTCTGGACGCAAAGACAAGGAGAAGCTGTGTTTCTTGGACAA | 264 |
| VEGFA | STK38 | Lower Grade Glioma | TCGA-TM-A7CF-01A-11R-A32Q-07 | 7422 | chr6 | 43745395 | 11329 | chr6 | 36467720 | AGTTCAGGAAGTGGATGAAATGTATGGAAAAAAAAGCATGCAGAATACCA\|GTGGAGATTCTGGACGCAAAGACAAGGAGAAGCTGTGTTTCTTGGACAA | 265 |
| ACPP | MTOR | | | | | | | | | ATCAACGAAATGCACCTTTTAATCCAGCAGGCCCAGGCCCCTGCT\|CAAGGCCTGCTGGACTTGGAGCAGAACTTTTTCAACTGCAGCTGTGACATCCGCTGAT | 266 |
| ATM | NTRK3 | | | | | | | | | TCCATTAGAGATGGCTCTGCGTTGTGTTTTCAAAATAGGTGAAGAGAC\|AGGCAGTTGAGGAACCTCTGAAGTATCTCCTGGGCATTGGGCTTCCTTGCAGAGAGGCTTGA | 267 |
| ATXN1 | RUNX1 | | | | | | | | | GTCCCTCAGGGCGGCCAGTGGACTGGTCCTCACTCACTCCAGGCGGCGCTCC\|GGCCCCCAGGGGCTCCCACAACTGATAAGGCTTCC | 268 |
| CLU | ERG | | | | | | | | | AGGCACACTCAAACAACGACTGGTCCTCACTCCAGGCGGCGCTCC\|CAGCCTCTGAACTTCTGAAGTATCTCCTGGGCATTCGACAGAGAGGCTTGA | 269 |
| CLU | STK11 | | | | | | | | | GCTGTGGCCTTCATGTCCTGTGCCCCAGAGATCTCCCCTCCACCCGAG\|GGAAATTCAACTACTGAGGAGGTTACGGCACAAAAATGTCATCCAGCTGG | 270 |
| DHX15 | HMHA1 | | | | | | | | | GAGTACGAACCGGCCAAGAGGTTCTCCATCCGGCAGATCCGGCAGCACAG\|GTCCCCCCGTCATGCGTCCCGGAAGAGCAGCTTCAACGTGAGTGATGTGG | 271 |
| DOM | ALK | | | | | | | | | CCGGCCCAGAGCAAGGAGAGTGTTATCATTCCAGCCACCACCTC\|TGCTCCATCGCAGCTTGCTCGTTGTGATCTTCGTTGATGCTAATCTTCTTCACCATATGGA | 272 |
| DOM | RAF1 | | | | | | | | | AAGAAGTGCCATGCGCAAGCTGGTCGCCTCAGTGTGTTGAGGAC\|ACAGCAGGATGATTGAGAATAACAACCTGAGTGCTTCTCCCAGGGCGTGG | 273 |
| EXOSC10 | BRI3BP | | | | | | | | | GGAAAATATATACCATGATCTACAGGAACTTGGTTAGTAGTCAATCAGCAG\|GCTGGGAGACCACCTGGAGACAGGGTCAGACTGCTCAACATCCGTCTCAACC | 274 |
| FAT1 | ERG | | | | | | | | | TGGAGAGGCCAAGGTCAGTTACCAGGACTACGAGATTGAGAACGGATGC\|TTCAGACTGTCCCGGACCCAGCACTCATATCAAGGAAGCCTTATCAGTT | 275 |
| FHIT | | | | | | | | | | | |
| GUCA2A | | | | | | | | | | | |
| HMHA1 | | | | | | | | | | | |
| STK11 | | | | | | | | | | | |
| KANK2 | | | | | | | | | | | |
| LMNA | | | | | | | | | | | |
| MDM2 | | | | | | | | | | | |
| MX1 | | | | | | | | | | | |

TABLE 42-continued

| | | | |
|---|---|---|---|
| OXR1 | MET | CTGAAACAATTGAGGATTCTAGTAATCAAGCAGCAGCCAGAGAATGGGAG\|TGGAAGCAAGCAATTCTTCAACCGTCCTTGGAAAAGTAATAGTTCAACC | 276 |
| PL51 | PIK3CB | TGCTCTGGTGGATATGTTTGTTTTAGCCAGTCCATCCAAGACAATCCCAC\|CGCTGTCCTGCCTTCGAGAGGCAGCTCCCACTGAGATCCAAGTACCTG | 277 |
| RPS6 | FN1 | GGTCCGAATCAGTGGTGGGAACACAAACAAGTTTCCCATGAAGCAGG\|GAAATCTTTGGAAGAAGTGTCCATGCTGATCAGAGCTCCTGCACTTTT | 278 |
| RSBN1L | HGF | GAGGAGGCACGTCTCGGTGGGCCCGAGAGGCCCGGCCGGGGCCTCCCGGG\|AGGAAAACTACTGTCGAAATCCTGAGGGGAAGAAGGGGACCCTGGTGT | 279 |
| RUNX1 | CEP76 | CCCTGAACCACTCCACTGCCTTTAACCCTCAGCCTCAGAGTCAGATGCAG\|GGATGAAAATGGGATAAATAGACCAGTCTGTTCCTATGTTAAACCACTTC | 280 |
| SEC16A | RXRA | ACGCCCAGTCCCTGGGTGCCGAGACCTGCCCCCTAGTTTCCAGTG\|AACTCCTCCCTCACCTCCCGACGGGGCGAGGCTCCATGCTGCCCCTC | 281 |
| TBL1XR1 | CTNNB1 | CAAGACGTTGACTTGGATCTGTCAGGTGAAGTCCTAAAGCTTGCATTCCA\|CCTGGAAACGTGGCCTCCAACGCCCTCCCCCCCTCCCGGGAATGGAGGC | 282 |
| TMPRSS2 | GUCA2A | AGGTCTTTGAGCTTCTCACTGACTTCCAGAGAAAAGGAGAAATTTCCATC\|CTGCCGCGCCGCCGCTCACCTCACCCGCCGCCTTTCACCTCCGCCAGGG | 283 |
| TMPRSS2 | TMEM109 | GTGTGATGGCGTGTCACAACTGCCCCGGCCGGGAGGAGGACCAGAATCGGTGTG\|ACCCAGTCATGGCAGCCTCCAGCATCAGTTCACCATGGGGAAAGCATGTG | 284 |
| TMPRSS2 | TMEM109 | GACTGGAACGAGAACTACGGGCCGGGCGCCTGCAGGGGACATGGGCTATAA\|GAAAGCATGTGTTCAAAGCCATTCTGATGGTCCTAGTGGCCCTTATCCTC | 285 |
| TMPRSS2 | BRAF | CGTCGTCTGCACCGCAGCCAGCCAAATCCCATCCGGGACAGTGTGCACCTCAA\|AAAAACACTTGGTAGACGGGACTGCAGACTGGAGTGATGATTCCTGATGG | 286 |
| USP7 | PRKCB | GAAAGCGGGCGACGCAGCAGTTGAGCGAGCCCGAGGACATGGAGAATGGAAG\|GACCCCCGCAGCAAACAAGTTTAAGATCCACACGTACTCCAGCCCAC | 287 |
| STK38 | VEGFA | TGCAATGACGAGGGCCTGGAGTGTGTGCCCACTGAGAGTCCAACATCAC\|CATGCAGACCGGGTACAACAGCTCTGTGATTGGTGTCGCTTGGGGTGA | 288 |
| STK38 | VEGFA | TGCAATGACGAGGGCCTGGAGTGTGTGCCCACTGAGAGTCCAACATCAC\|CATGCAGACCGGGTACAACAAGCTCTGTGATTGGTGTCGCTTGGGGTGA | 289 |

TABLE 43

| Gene | Approved | Pre-registration (pre-approval) | Phase III |
|---|---|---|---|
| AXL | | | |
| ARG1 | | | |
| CLU | | | custirsen |
| DOT1L | | | |
| MTOR | everolimus; temsirolimus | ridaforolimus | N |
| NTRK3 | | | |
| ALK | crizotinib | alectinib hydrochloride | ceritinib |
| RAF1 | sorafenib | N | N |
| MDM2 | N | N | N |
| MET | cabozantinib; crizotinib | N | tivantinib; rilotumumab; onartuzumab; |
| PIK3CB | | | |
| FN1 | | | |
| HGF | | | rilotumumab |
| RXRA | bexarotene, bexarotene, gel, | | |
| CTNNB1 | | | |
| PRKCB | | | |
| BRAF | vemurafenib, pazopanib, dabrafenib | | encorafenib |
| VEGFA | bevacizumab, pegaptanib octasodium, pegaptanib octasodium | | midostaurin, XL-647, bevacizumab, Biocad, bevacizumab, Actavis, bevacizumab, Reliance Life Sciences |

| Gene | Phase II | Phase I | Preclinical |
|---|---|---|---|
| AXL | foretinib, | BGB-324, S-49076, ningetinib | TP-0903, SGI-7079, Q-4, BGB-109, CEP-40783 |
| ARG1 | PEG-arginase, Bio-Cancer | | |
| CLU | | | AB-16B5, CGEN-25008 |
| DOT1L | | EPZ-01 | DOT1L inhibitors, Aurigene |
| MTOR | quinacrine; XL-765; dactolisib; PKI-587; PF-04691502; CC-223, apitolisib; gedatolisib, INK-128 PKI-587; PF-04691502; CC-223, apitolisib, gedatolisib, INK-128 | P-7170; CBLC-137, AZD-2014; CC-115; PWT-33957; DS-7423; GDC-0084; DS-3078; LY-3023414; PI3 kinase/mTOR inhibitor, Lilly, SF-1126, SB-2343 | nPT-MTOR; STP-503; X-480; ABTL-0812; X-414; CC214; HMPL-518; PQR-309; PQR-401; mTOR inhibitor/PI3 kinase inhibitor, Lilly-1; PIM/PI3k/mTOR inhibitors, Inflection Biosciences |
| NTRK3 | TSR-011 | PLX-7486 | NMS-P626 |
| ALK | AP-26113; RG-7853; TSR-011; NMS-E628, PF-06463922 | X-396; ASP-3026; CEP-37440 | NMS-E628; aurora kinase + ALK inhibitor (Sareum, AstraZeneca); ALK inhibitors (AstraZeneca, Cephalon, Aurigene); ARN-5032; DLX-521, TL-398, AZD-3463 |
| RAF1 | iCo-007; XL-281 | RO-5126766; MLN-2480, pan-Raf inhibitor, Eli Lilly | BIB-024; STP503; DP-4978; HM-95573; TAK-632 |
| MDM2 | N | DS-3032, AMG-232 | p53-mdm2/mdm4 dual inhibitors, Adamed; PXN-527; ATSP-7041; MDM2 inhibitors, Amgen, DS-5272 |
| MET | MGCD-265; foretinib; ficlatuzumab; BMS-777607; golvatinib; INCB-028060; LY-2875358; apitolisib | AMG-208; TAS-115; volitinib; SAR-125844; S-49076, metatinib, F-50064, ARGX-111, DCC-2701 | X-379; metatinib; PRS-110; ASP-08001; DCC-2721; MG-516; AL-2846; CG-206481; T-1840383; cMet-EGFR dual inhibitors( CrystalGenomics); bispecific antibodies (Hoffmann-La Roche) |
| PIK3CB | pictilisib, GS-9820, GSK-2636771 | INK-1117, BAY-1082439, SAR-260301, AZD-8186 | PQR-3xx, Piqur |
| FN1 | radretumab, darleukin | AS-1409 | |
| HGF | | HuL2G7 | NK4, Kringle |
| RXRA | | | IRX-4310 |
| CTNNB1 | PRI-724 | | β-catenin inhibitors, PhaseRx, K-756, DsiRNAs, Dicerna |
| PRKCB | sotrastaurin, | | |
| BRAF | RAF-265, XL-281, AB-024 | ARQ-761, ARQ-736, BeiGene-283 | b-raf inhibitors, Sareum, B-Raf and c-RAF dual inhibitor, Redx Pharma, PLX-8394, DP-4978, TL-241, B-Raf kinase inhibitors, Array BioPharma-1, EN-3352, EBI-907, PI3K/BET bromodomain inhibitors, SignalRx |

TABLE 43-continued

| | | | |
|---|---|---|---|
| VEGFA | squalamine, PTC-299, MP-0112, ESBA-1008 | ASC-06, PRS-050, sevacizumab, RG-7221, PAN-90806, TAS-115, bevacizumab, Pfizer | VEGF vaccine, Neovacs, CEQ-300, bevacizumab, BioXpress, bevacizumab, Natco, bevacizumab, Oncobiologics, bevacizumab, Harvest Moon, OMP-305B83, bevacizumab, Fujifilm Kyowa Kirin Biologics, bevacizumab, LG Life Sciences, bevacizumab, Biocon, bevacizumab, Mabion, bevacizumab, Aryogen, hVEGF-trunc vaccine, Immunovo, bevacizumab, Avesthagen, bevacizumab, Alteogen, bevacizumab, Nanogen |

TABLE 44

| Cancer Type | Gene Symbol | Entrez Gene ID | Reference Allele | Tumor Seq Allele1 | Tumor Seq Allele2 | Variant Change | Variant Position | Variant Class | Druggability |
|---|---|---|---|---|---|---|---|---|---|
| Gastric Adenocarcinoma | CDKN2A | 1029 | A | C | C | p.V25G | p.V25 | Missense_Mutation | Y |
| Clear Cell Renal Cell Carcinoma | CDKN2A | 1030 | A | C | C | p.V25G | p.V25 | Missense_Mutation | Y |
| Multiple Myeloma | CDKN2A | 1031 | A | C | — | p.V25G | p.V25 | Missense_Mutation | Y |
| Prostate Adenocarcinoma | CDKN2A | 1032 | A | A | C | p.V25G | p.V25 | Missense_Mutation | Y |
| Lung Adenocarcinoma | ALK | 238 | C | G | G | p.W247S | p.W247 | Missense_Mutation | Y |

TABLE 45

| Subset | Event type | Q | No. positive | Total no. of patients |
|---|---|---|---|---|
| Acute Myeloid Leukemia | Fusion | 4.03E−02 | 11 | 168 |
| Chromophobe Renal Cell Carcinoma | Loss of Function Mutation | 6.84E−02 | 18 | 65 |
| Chromophobe Renal Cell Carcinoma | Loss of Function Mutation | 6.92E−02 | 4 | 65 |
| Colorectal Adenocarcinoma: KRAS Mutation, Stage 3 or 4 | Gain of Function Mutation | 3.86E−02 | 8 | 45 |
| Colorectal Adenocarcinoma: Microsatellite Stable | Gain of Function Mutation | 9.10E−02 | 5 | 21 |
| Diffuse Gastric Adenocarcinoma | In-Peak Gene Amplification | 3.04E−02 | 4 | 52 |
| Ductal Breast Carcinoma: Triple Negative | Loss of Function Mutation | 9.90E−02 | 51 | 68 |
| Gastric Intestinal Type Adenocarcinoma | In-Peak Gene Amplification | 3.41E−02 | 4 | 44 |
| Infiltrating Bladder Urothelial Carcinoma | In-Peak Gene Amplification | 7.16E−02 | 4 | 183 |
| Leiomyosarcoma | In-Peak Gene Deletion | 1.86E−03 | 6 | 40 |
| Lung Adenocarcinoma: EGFR Mutation | Loss of Function Mutation | 9.57E−02 | 13 | 21 |
| Pancreatic Ductal Adenocarcinoma | Gain of Function Mutation | 8.78E−04 | 5 | 39 |
| Pancreatic Ductal Adenocarcinoma | Loss of Function Mutation | 5.97E−02 | 5 | 39 |
| Prostate Adenocarcinoma | Loss of Function Mutation | 1.25E−03 | 14 | 172 |
| Colorectal Adenocarcinoma: KRAS Mutation | Gain of Function Mutation | 3.39E−04 | 10 | 105 |

| Cytoband | Genes (Entrez ID) | Druggable genes | KM evidence |
|---|---|---|---|
| 17q21, 15q22 | RARA (5914), PML (5371) | RARA | favorable outcome |
| 17p13 | TP53 (7157) | TP53 | poor outcome |
| 10q23 | PTEN (5728) | PTEN | poor outcome |
| 7q32 | IRF5 (3663) | | Poor outcome |
| 22q12 | NEFH (4744) | | poor outcome |
| 11p13 | APIP (51074) | | poor outcome |
| 17p13 | TP53 (7157) | TP53 | favorable outcome |
| 10q26 | FGFR2 (2263) | FGFR2 | poor outcome |
| 20q11 | E2F1 (1869) | E2F1 | Poor outcome |
| 9p21 | CDKN2A (1029), CDKN2B (1030) | CDKN2A | poor outcome |
| 17p13 | TP53 (7157) | TP53 | poor outcome |
| 7q22 | PTCD1 (26024), ATP5J2-PTCD1 (100526740) | | poor outcome |
| 4q35 | DUX2 (26583) | | poor outcome |
| 17p13 | TP53 (7157) | TP53 | poor outcome |
| 7q32 | IRF5 (3663) | | poor outcome |

TABLE 46

| Subset | Event type | Q |
|---|---|---|
| Acute Myeloid Leukemia | Fusion | 4.03E-02 |
| Chromophobe Renal Cell Carcinoma | Loss of Function Mutation | 6.84E-02 |
| Chromophobe Renal Cell Carcinoma | Loss of Function Mutation | 6.92E-02 |
| Colorectal Adenocarcinoma: KRAS Mutation, Stage 3 or 4 | Gain of Function Mutation | 3.86E-02 |
| Colorectal Adenocarcinoma: Microsatellite Stable | Gain of Function Mutation | 9.10E-02 |
| Diffuse Gastric Adenocarcinoma | In-Peak Gene Amplification | 3.04E-02 |
| Ductal Breast Carcinoma: Triple Negative | Loss of Function Mutation | 9.90E-02 |
| Gastric Intestinal Type Adenocarcinoma | In-Peak Gene Amplification | 3.41E-02 |
| Infiltrating Bladder Urothelial Carcinoma | In-Peak Gene Amplification | 7.16E-02 |
| Leiomyosarcoma | In-Peak Gene Deletion | 1.86E-03 |
| Lung Adenocarcinoma: EGFR Mutation | Loss of Function Mutation | 9.57E-03 |
| Pancreatic Ductal Adenocarcinoma | Gain of Function Mutation | 8.78E-04 |
| Pancreatic Ductal Adenocarcinoma | Loss of Function Mutation | 5.97E-02 |
| Prostate Adenocarcinoma | Loss of Function Mutation | 1.25E-03 |
| Colorectal Adenocarcinoma: KRAS Mutation | Gain of Function Mutation | 3.39E-04 |
| Colorectal Adenocarcinoma: KRAS Mutation | Gain of Function Mutation | 1.53E-02 |

| Subset | No. positive | Total no. of patients | Cytoband | Genes (Entrez ID) |
|---|---|---|---|---|
| Acute Myeloid Leukemia | 11 | 168 | 17q21, 15q22 | RARA (5914), PML (5371) |
| Chromophobe Renal Cell Carcinoma | 18 | 65 | 17p13 | TP53 (7157) |
| Chromophobe Renal Cell Carcinoma | 4 | 65 | 10q23 | PTEN (5728) |
| Colorectal Adenocarcinoma: KRAS Mutation, Stage 3 or 4 | 8 | 45 | 7q32 | IRF5 (3663) |
| Colorectal Adenocarcinoma: Microsatellite Stable | 5 | 21 | 22q12 | NEFH (4744) |
| Diffuse Gastric Adenocarcinoma | 4 | 52 | 11p13 | APIP (51074) |
| Ductal Breast Carcinoma: Triple Negative | 51 | 68 | 17p13 | TP53 (7157) |
| Gastric Intestinal Type Adenocarcinoma | 4 | 44 | 10q26 | FGFR2 (2263) |
| Infiltrating Bladder Urothelial Carcinoma | 4 | 183 | 20q11 | E2F1 (1869) |
| Leiomyosarcoma | 6 | 40 | 9p21 | CDKN2A (1029), CDKN2B (1030) |
| Lung Adenocarcinoma: EGFR Mutation | 13 | 21 | 17p13 | TP53 (7157) |
| Pancreatic Ductal Adenocarcinoma | 5 | 39 | 7q22 | PTCD1 (26024), ATP5J2-PTCD1 (100526740) |
| Pancreatic Ductal Adenocarcinoma | 5 | 39 | 4q35 | DUX2 (26583) |
| Prostate Adenocarcinoma | 14 | 172 | 17p13 | TP53 (7157) |
| Colorectal Adenocarcinoma: KRAS Mutation | 10 | 105 | 7q32 | IRF5 (3663) |
| Colorectal Adenocarcinoma: KRAS Mutation | 4 | 105 | 5q31 | PCDHA7 (56141) |

| Subset | Druggable genes | KM evidence |
|---|---|---|
| Acute Myeloid Leukemia | RARA | favorable outcome |
| Chromophobe Renal Cell Carcinoma | TP53 | poor outcome |
| Chromophobe Renal Cell Carcinoma | PTEN | poor outcome |
| Colorectal Adenocarcinoma: KRAS Mutation, Stage 3 or 4 | | Poor outcome |
| Colorectal Adenocarcinoma: Microsatellite Stable | | poor outcome |
| Diffuse Gastric Adenocarcinoma | | poor outcome |
| Ductal Breast Carcinoma: Triple Negative | TP53 | favorable outcome |
| Gastric Intestinal Type Adenocarcinoma | FGFR2 | poor outcome |
| Infiltrating Bladder Urothelial Carcinoma | E2F1 | Poor outcome |
| Leiomyosarcoma | CDKN2A | poor outcome |
| Lung Adenocarcinoma: EGFR Mutation | TP53 | poor outcome |
| Pancreatic Ductal Adenocarcinoma | | poor outcome |
| Pancreatic Ductal Adenocarcinoma | | poor outcome |
| Prostate Adenocarcinoma | TP53 | poor outcome |
| Colorectal Adenocarcinoma: KRAS Mutation | | poor outcome |
| Colorectal Adenocarcinoma: KRAS Mutation | | poor outcome |

TABLE 47

| Cancer Type | Gene Symbol | Entrez Gene ID |
|---|---|---|
| Papillary Renal Cell Carcinoma | AR | 367 |
| Lobular Breast Carcinoma | AR | 367 |

TABLE 47-continued

| Cancer Type | | | |
|---|---|---|---|
| Adrenal Cortex Carcinoma | AR | 367 | |
| Colorectal Adenocarcinoma | AR | 367 | |
| Pancreatic Carcinoma | AR | 367 | |
| Colorectal Adenocarcinoma | AR | 367 | |
| Pancreatic Ductal Adenocarcinoma | AR | 367 | |
| Prostate Carcinoma | JAK1 | 3716 | |
| Hepatocellular Carcinoma | JAK1 | 3716 | |

| Cancer Type | Reference Allele |
|---|---|
| Papillary Renal Cell Carcinoma | — |
| Lobular Breast Carcinoma | — |
| Adrenal Cortex Carcinoma | GCAGCAGCAGCAGCAGCAGCA (SEQ ID NO: 290) |
| Colorectal Adenocarcinoma | — |
| Pancreatic Carcinoma | GCAGCAGCA |
| Colorectal Adenocarcinoma | GCAGCAGCAGCAGCAGCAGCAGCA (SEQ ID NO: 291) |
| Pancreatic Ductal Adenocarcinoma | GCAGCAGCA |
| Prostate Carcinoma | C |
| Hepatocellular Carcinoma | T |

| Cancer Type | Tumor Seq Allele 1 |
|---|---|
| Papillary Renal Cell Carcinoma | — |
| Lobular Breast Carcinoma | — |
| Adrenal Cortex Carcinoma | GCAGCAGCAGCAGCAGCAGCA (SEQ ID NO: 290) |
| Colorectal Adenocarcinoma | — |
| Pancreatic Carcinoma | GCAGCAGCA |
| Colorectal Adenocarcinoma | GCAGCAGCAGCAGCAGCAGCAGCA (SEQ ID NO: 291) |
| Pancreatic Ductal Adenocarcinoma | GCAGCAGCA |
| Prostate Carcinoma | T |
| Hepatocellular Carcinoma | T |

| Cancer Type | Tumor Seq Allele 2 | Variant Change | Variant position |
|---|---|---|---|
| Papillary Renal Cell Carcinoma | GCAGCA | p.L57_in_frame_ins | p.L57 |
| Lobular Breast Carcinoma | GCA | p.L57_in_frame_ins | p.L57 |
| Adrenal Cortex Carcinoma | — | p.L57_in_frame_del | p.L57 |
| Colorectal Adenocarcinoma | GCAGCA | p.L57_in_frame_ins | p.L57 |
| Pancreatic Carcinoma | — | p.L57_in_frame_del | p.L57 |
| Colorectal Adenocarcinoma | — | p.L57_in_frame_del | p.L57 |

TABLE 47-continued

| | | | |
|---|---|---|---|
| Pancreatic Ductal Adenocarcinoma | — | p.L57_in_frame_del | p.L57 |
| Prostate Carcinoma | — | p.E188K | p.E188 |
| Hepatocellular Carcinoma | C; A | p.E188G; p.E188V | p.E188 |

| Cancer Type | Variant Class | Pan-Cancer CBI Variant Category | Druggability |
|---|---|---|---|
| Papillary Renal Cell Carcinoma | In_Frame_Ins | Hotspot | Y |
| Lobular Breast Carcinoma | In_Frame_Ins | Hotspot | Y |
| Adrenal Cortex Carcinoma | In_Frame_Del | Hotspot | Y |
| Colorectal Adenocarcinoma | In_Frame_Ins | Hotspot | Y |
| Pancreatic Carcinoma | In_Frame_Del | Hotspot | Y |
| Colorectal Adenocarcinoma | In_Frame_Del | Hotspot | Y |
| Pancreatic Ductal Adenocarcinoma | In_Frame_Del | Hotspot | Y |
| Prostate Carcinoma | Missense_Mutation | Hotspot | Y |
| Hepatocellular Carcinoma | Missense_Mutation | Hotspot | Y |

TABLE 48

| Cancer Type | 5' gene symbol | 3' gene symbol | Druggable gene |
|---|---|---|---|
| Esophageal Carcinoma | NUP214 | ABL1 | ABL1 |
| Colon and Rectal Adenocarcinoma | SMEK2 | ALK | ALK |
| Cutaneous Melanoma | KCNQ5 | ALK | ALK |
| Colon and Rectal Adenocarcinoma | TRIM24 | BRAF | BRAF |
| Bladder Urothelial Carcinoma | CDKN2A | CAPZB | CDKN2A |
| Colon and Rectal Adenocarcinoma | PEX1 | CDK6 | CDK6 |
| Lower Grade Glioma | EGFR | C7orf72 | EGFR |
| Hepatocellular Carcinoma | ERBB2 | PPP1R1B | ERBB2 |
| Prostate Adenocarcinoma | ERBB2 | PPP1R1B | ERBB2 |
| Hepatocellular Carcinoma | FGFR2 | BICC1 | FGFR2 |
| Lower Grade Glioma | FGFR3 | FBXO28 | FGFR3 |
| Prostate Adenocarcinoma | FGFR3 | AES | FGFR3 |
| Esophageal Carcinoma | FGFR3 | TACC3 | FGFR3 |
| Cervical Squamous Cell Carcinoma | JAK2 | RCL1 | JAK2 |
| Gastric Adenocarcinoma | ZBTB17 | MTOR | MTOR |
| Endometrial Endometroid Adenocarcinoma | KAZN | MTOR | MTOR |
| Lower Grade Glioma | EPHB2 | NTRK1 | NTRK1 |
| Esophageal Carcinoma | RAF1 | C9orf153 | RAF1 |
| Pancreatic Carcinoma | RAF1 | TMEM40 | RAF1 |
| Squamous Cell Lung Carcinoma | CDKN2A | SRGAP2 | CDKN2A |
| Hepatocellular Carcinoma | SLC7A2 | TERT | TERT |

TABLE 49

| 5' Gene Symbol | 3' Gene Symbol | Cancer Type | TCGA Tumor Sample Barcode |
|---|---|---|---|
| NUP214 | ABL1 | Esophageal Carcinoma | TCGA-L5-A4OQ-01A-11R-A260-31 |
| FGFR3 | AES | Prostate Adenocarcinoma | TCGA-EJ-A7NM-01A-21R-A33R-07 |
| FGFR3 | AES | Prostate Adenocarcinoma | TCGA-EJ-A7NM-01A-21R-A33R-07 |
| FGFR3 | AES | Prostate Adenocarcinoma | TCGA-EJ-A7NM-01A-21R-A33R-07 |
| FGFR3 | AES | Prostate Adenocarcinoma | TCGA-EJ-A7NM-01A-21R-A33R-07 |
| SMEK2 | ALK | Colon and Rectal Adenocarcinoma | TCGA-F5-6864-01A-11R-1928-07 |
| KCNQ5 | ALK | Cutaneous Melanoma | TCGA-EB-A6QY-01A-12R-A32P-07 |
| FGFR2 | BICC1 | Hepatocellular Carcinoma | TCGA-ED-A7PX-01A-51R-A352-07 |
| FGFR2 | BICC1 | Hepatocellular Carcinoma | TCGA-ED-A7PX-01A-51R-A352-07 |
| EGFR | C7orf72 | Lower Grade Glioma | TCGA-E1-A7YJ-01A-11R-A34F-07 |
| RAF1 | C9orf153 | Esophageal Carcinoma | TCGA-L5-A4OS-01A-11R-A28J-31 |
| CDKN2A | CAPZB | Bladder Urothelial Carcinoma | TCGA-E7-A6MD-01A-41R-A352-07 |
| CDKN2A | CAPZB | Bladder Urothelial Carcinoma | TCGA-E7-A6MD-01A-41R-A352-07 |

TABLE 49-continued

| | | | |
|---|---|---|---|
| CDKN2A | CAPZB | Bladder Urothelial Carcinoma | TCGA-E7-A6MD-01A-41R-A352-07 |
| PEX1 | CDK6 | Colon and Rectal Adenocarcinoma | TCGA-AA-3697-01A-01R-1723-07 |
| FGFR3 | FBXO28 | Lower Grade Glioma | TCGA-TM-A84B-01A-11R-A36H-07 |
| FGFR3 | FBXO28 | Lower Grade Glioma | TCGA-TM-A84B-01A-11R-A36H-07 |
| FGFR3 | FBXO28 | Lower Grade Glioma | TCGA-TM-A84B-01A-11R-A36H-07 |
| FGFR3 | FBXO28 | Lower Grade Glioma | TCGA-TM-A84B-01A-11R-A36H-07 |
| FGFR3 | FBXO28 | Lower Grade Glioma | TCGA-TM-A84B-01A-11R-A36H-07 |
| FGFR3 | FBXO28 | Lower Grade Glioma | TCGA-TM-A84B-01A-11R-A36H-07 |
| FGFR3 | FBXO28 | Lower Grade Glioma | TCGA-TM-A84B-01A-11R-A36H-07 |
| FGFR3 | FBXO28 | Lower Grade Glioma | TCGA-TM-A84B-01A-11R-A36H-07 |
| ZBTB17 | MTOR | Gastric Adenocarcinoma | TCGA-BR-4357-01A-01R-1157-13 |
| KAZN | MTOR | Endometrial Endometrioid Adenocarcinoma | TCGA-D1-A3JQ-01A-11R-A22K-07 |
| EPHB2 | NTRK1 | Lower Grade Glioma | TCGA-TM-A84J-01A-11R-A36H-07 |
| ERBB2 | PPP1R1B | Hepatocellular Carcinoma | TCGA-KR-A7K2-01A-12R-A33R-07 |
| ERBB2 | PPP1R1B | Pancreatic Adenocarcinoma | TCGA-LB-A7SX-01A-11R-A33R-07 |
| JAK2 | RCL1 | Cervical Squamous Cell Carcinoma | TCGA-PN-A8MA-01A-11R-A36F-07 |
| JAK2 | RCL1 | Cervical Squamous Cell Carcinoma | TCGA-PN-A8MA-01A-11R-A36F-07 |
| CDKN2A | SRGAP2 | Squamous Cell Lung Carcinoma | TCGA-60-2715-01A-01R-0851-07 |
| CDKN2A | SRGAP2 | Squamous Cell Lung Carcinoma | TCGA-60-2715-01A-01R-0851-07 |
| FGFR3 | TACC3 | Esophageal Carcinoma | TCGA-LN-A5U5-01A-21R-A28J-31 |
| SLC7A2 | TERT | Hepatocellular Carcinoma | TCGA-DD-A73C-01A-12R-A33J-07 |
| RAF1 | TMEM40 | Pancreatic Adenocarcinoma | TCGA-IB-A5SS-01A-11R-A32O-07 |
| BRAF | TRIM24 | Colon and Rectal Adenocarcinoma | TCGA-F5-6464-01A-11R-1736-07 |
| TRIM24 | BRAF | Colon and Rectal Adenocarcinoma | TCGA-F5-6464-01A-11R-1736-07 |

| 5' Gene Symbol | 5' Accession | 5' Chromosome | 5' Breakpoint | 3' Accession | 3' Chromosome | 3' Breakpoint |
|---|---|---|---|---|---|---|
| NUP214 | 8021 | chr9 | 134027281 | 25 | chr9 | 133747516 |
| FGFR3 | 2261 | chr4 | 1808969 | 166 | chr19 | 3061232 |
| FGFR3 | 2261 | chr4 | 1808905 | 166 | chr19 | 3061233 |
| FGFR3 | 2261 | chr4 | 1808905 | 166 | chr19 | 3061233 |
| FGFR3 | 2261 | chr4 | 1808661 | 166 | chr19 | 3061255 |
| SMEK2 | 57223 | chr2 | 55804451 | 238 | chr2 | 29940563 |
| KCNQ5 | 56479 | chr6 | 73332315 | 238 | chr2 | 29498362 |
| FGFR2 | 2263 | chr10 | 123239533 | 80114 | chr10 | 60461846 |
| FGFR2 | 2263 | chr10 | 123244971 | 80114 | chr10 | 60461846 |
| EGFR | 1956 | chr7 | 55268106 | 100130988 | chr7 | 50143910 |
| RAF1 | 5894 | chr3 | 12627180 | 389766 | chr9 | 88844544 |
| CDKN2A | 1029 | chr9 | 21974677 | 832 | chr1 | 19671746 |
| CDKN2A | 1029 | chr9 | 21974673 | 832 | chr1 | 19666067 |
| CDKN2A | 1029 | chr9 | 21994138 | 832 | chr1 | 19671746 |

TABLE 49-continued

| | | | | | | |
|---|---|---|---|---|---|---|
| PEX1 | 5189 | chr7 | 92151518 | 1021 | chr7 | 92355063 |
| FGFR3 | 2261 | chr4 | 1808661 | 23219 | chr1 | 224340844 |
| FGFR3 | 2261 | chr4 | 1808989 | 23219 | chr1 | 224340848 |
| FGFR3 | 2261 | chr4 | 1808645 | 23219 | chr1 | 224345163 |
| FGFR3 | 2261 | chr4 | 1808645 | 23219 | chr1 | 224345163 |
| FGFR3 | 2261 | chr4 | 1808586 | 23219 | chr1 | 224340892 |
| FGFR3 | 2261 | chr4 | 1808591 | 23219 | chr1 | 224318276 |
| FGFR3 | 2261 | chr4 | 1808661 | 23219 | chr1 | 224340844 |
| FGFR3 | 2261 | chr4 | 1808582 | 23219 | chr1 | 224340949 |
| ZBTB17 | 7709 | chr1 | 16269559 | 2475 | chr1 | 11227574 |
| KAZN | 23254 | chr1 | 15251068 | 2475 | chr1 | 11206848 |
| EPHB2 | 2048 | chr1 | 23111569 | 4914 | chr1 | 156843425 |
| ERBB2 | 2064 | chr17 | 37883777 | 84152 | chr17 | 37790317 |
| ERBB2 | 2064 | chr17 | 37883798 | 84152 | chr17 | 37790337 |
| JAK2 | 3717 | chr9 | 5090911 | 10171 | chr9 | 4834141 |
| JAK2 | 3717 | chr9 | 5126446 | 10171 | chr9 | 4860125 |
| CDKN2A | 1029 | chr9 | 21994138 | 23380 | chr1 | 206634382 |
| CDKN2A | 1029 | chr9 | 21974677 | 23380 | chr1 | 206634382 |
| FGFR3 | 2261 | chr4 | 1808661 | 10460 | chr4 | 1741429 |
| SLC7A2 | 6542 | chr8 | 17354726 | 7015 | chr5 | 1282731 |
| RAF1 | 5894 | chr3 | 12632350 | 55287 | chr3 | 12791339 |
| BRAF | 673 | chr7 | 140624377 | 8805 | chr7 | 138255741 |
| TRIM24 | 8805 | chr7 | 138255748 | 673 | chr7 | 140550012 |

| 5' Gene Symbol | Breakpoint Sequence | SEQ ID NO. |
|---|---|---|
| NUP214 | CATGACTGCAGCTTCTTTCAAGAACTCTTCCACCTCCATGGTGTCCTCCT\|GAAGCTGAGCTTCACTCTTGGGATCCAGTGGTCTTTTATAAAGCAAATGC | 292 |
| FGFR3 | GGACGACTCCGTGTTTGCCCACGACCTGCTGCCCCCGGCCCCACCCAGCA\|ACTCAAATTCACCACCTCGGACTCCTGCGACCGCATCAAAGACGAATTTC | 293 |
| FGFR3 | TGTCGGCGCCTTTCGAGCAGTACTCCCCGGGTGGCCAGGACACCCCCAGC\|AACTCAAATTCACCACCTCGGACTCCTGCGACCGCATCAAAG | 294 |
| FGFR3 | TGTCGGCGCCTTTCGAGCAGTACTCCCCGGGTGGCCAGGACACCCCCAGC\|AACTCAAATTCACCACCTCGGACTCCTGCGACCGCATCAAAGACGAATTT | 295 |
| FGFR3 | GCAGCTGGTGGAGGACCTGGACCGTGTCCTTACCGTGACGTCCACCGACG\|CTCCTCGCACCTACCCCAGCAACTCAAATTCACCACCTCGGACTCCTGC | 296 |
| SMEK2 | TGAAAAGGATAATATAGTTGGATCAAACAAAAACAACACAATTTGTCCCG\|GTCATAGCTCCTTGGAATCACCAACAAACATGCCTTCTCCTTCTCCTGAT | 297 |
| KCNQ5 | CGATGGCTCTGGATCCTTGTCCCCACCATGCGACCATCTGCAGCCAGAAC\|ACGAAAGCGTGGTAGATGAACGCCCAGCCGCGGGGTCTCTCCAGCACGTT | 298 |
| FGFR2 | AGTTGGTAGAAGACTTGGATCGAATTCTCACTCTCACAACCAATGAGGAA\|ACAAATACGCAGATTGCTTGGCCATCAAAACTGAAGATCGGAGCCAAATC | 299 |
| FGFR2 | AGATCTTCACTTTAGGGGGCTCGCCCTACCCAGGGATTCCCGTGGAGGAA\|ACAAATACGCAGATTGCTTGGCCATCAAAACTGAAGATCGGAGCCAAATC | 300 |

TABLE 49-continued

| | | |
|---|---|---|
| EGFR | GATCATCGAATTCTCCAAAATGGCCCGAGACCCCCAGCGCTACCTTGTCA\|TTCAGGTTGGACAAGCCCTCTGAAAGTTACTCCCTTACAACCTCATCATG | 301 |
| RAF1 | GAGTGGTTCTCAGCAGGTTGAACAACCTACTGGCTCTGTCCTCTGGATGG\|AATTAGAGAATAAAATCCCAGCACGATGTTCCTCACTGGAGACACCAGTC | 302 |
| CDKN2A | TTGGCTATGTGTGGGGAGCAGTCACTCACAGTTTCATCCTTCTCCATCTG\|GATCGGCCTCCGACCGTAACTATTCGGTGCGTTGGGCAGCGCCCCCGCCT | 303 |
| CDKN2A | AGAGGTTTAGCATTGCTGCTTTCTCTTCAAAGCCTCCACCAGGTCATTCT\|CCACCTGGATCGGCCTCCGACCGTAACTATTCGGTGCGTTGGGCAGCGCC | 304 |
| CDKN2A | TTGGCTATGTGTGGGGAGCAGTCACTCACAGTFTCATCCTTCTCCATCTG\|GTCTTCTAGGAAGCGGCTGCTGCCCTAGACGCTGGCTCCTCAGTAGCATC | 305 |
| PEX1 | TGCTGCAGAATCAAGCTATAGAAGTGGTCTGGAGTCACCAGCCTGCATTC\|ACACCGAGTAGTGCATCGCGATCTAAAACCACAGAACATTCTGGTGACCA | 306 |
| FGFR3 | GCAGCTGGTGGAGGACCTGGACCGTGTCCTTACCGTGACGTCCACCGACG\|TGATTGATGAGATTTATCGTGTGTTGAGATATGTCAATTCTACCAGAGCC | 307 |
| FGFR3 | ACGACCTGCTGCCCCCGGCCCCACCCAGCAGTGGGGCTCGCGGACGTGA\|TTGATGAGATTTATCGTGTGTTGAGATATGTCAATTCTACCAGAGCCCCT | 308 |
| FGFR3 | CAGAGGCCCACCTTCAAGCAGCTGGTGGAGGACCTGGACCGTGTCCTTAC\|CGTGACTGTTCTCAGGCGTGAAATTTCTGAGCTTCGCACCAAAGTGCAAG | 309 |
| FGFR3 | CTTGCACTTTGGTGCGAAGCTCAGAAATTTCACGCCTGAGAACAGTCACG\|GTAAGGACACGGTCCAGGTCCTCCACCAGCTGCTTGAAGGTGGG | 310 |
| FGFR3 | CCAACTGCACACACGACCTGTACATGATCATGCGGGAGTGCTGGCATGCC\|GCCCCTCAACGAGCTCATGAAGTACTTCAAGAATTAAGGGATATATCCTC | 311 |
| FGFR3 | TGCACACACGACCTGTACATGATCATGCGGGAGTGCTGGCATGCCGCGCC\|CTCCCAAGGTGATTGATGAGATTTATCGTGTGTTGAGATATGTCAATTCT | 312 |
| FGFR3 | AGGGGCTCTGGTAGAATTGACATATCTCAACACACGATAAATCTCATCAA\|TCACGTCGGTGGACGTCACGGTAAGGACACGGTCCAGGTCCTCCACCAGC | 313 |
| FGFR3 | CCCGCCAACTGCACACACGACCTGTACATGATCATGCGGGAGTGCTGGCA\|ATGGAGTACTTTGATGAAAAGATTGTTCCAATTTTAAAGAGGAAATTACC | 314 |
| ZBTB17 | GGCCTTCGTGAACGTGGGGGACCTGTCCAAGCACATCATCATTCACACTG\|CATTAATAATAAGCTACAGCAGCCGGAGGCAGCGGCCGGAGTGTTAGAAT | 315 |
| KAZN | CCCGCGCCGGGGTTCCCCGGGTCCGAGCGGATGGCGACTGCAGCCAGCCC\|GGTCAGTGGGACAGCATGGAAGAATACACCTGTATGATCCCTCGGGACAC | 316 |
| EPHB2 | CATGTGCAAAGCAGGCTTCGAGGCCGTTGAGAATGGCACCGTCTGCCGAG\|TCCCGGCCAGTGTGCAGCTGCACACGGCGGTGGAGATGCACCACTGGTGC | 317 |
| ERBB2 | CCTGGCCACAGGTTGTCTTTTGCCCAGCAGACTGCCTGATGACCTTCAGG\|GGGGCAACGTAGCCATCAGTCTCAGAGGGCAGGGGTACTGTGGGGTCCTC | 318 |
| ERBB2 | CCCTCTGAGACTGATGGCTACGTTGCCCCCCTGACCTGCAGCCCCCAGCC\|CTGCTGGGCAAAAGACAACCTGTGGCCAGGGTCTGGAAGGGCCCTGGGAG | 319 |
| JAK2 | GACAAAGAATACTATAAAGTAAAAGAACCTGGTGAAAGTCCCATATTCTG\|ATTGTGCGACGGGGAATGCCTCCCGGAGGAGGAGGCGAAGTGGTTTTCTC | 320 |
| JAK2 | ACTTTTGAAGAATAATGGAAGATTACCAAGACCAGATGGATGCCCAGATG\|AGGATAGAATTTTTGCGGCATTTGAAGAGCTTTTTCCAGATTATGTTTAA | 321 |
| CDKN2A | CTACTGAGGAGCCAGCGTCTAGGGCAGCAGCCGCTTCCTAGAAGACCAGG\|ATATTGAGGCAACAATGAACTCGGCCCTGAATGAGCTACGGGAACTAGAA | 322 |
| CDKN2A | AGGCGGGGGCGCTGCCCAACGCACCGAATAGTTACGGTCGGAGGCCGATC\|CAGGATATTGAGGCAACAATGAACTCGGCCCTGAATGAGCTACGGGAACT | 323 |
| FGFR3 | GCAGCTGGTGGAGGACCTGGACCGTGTCCTTACCGTGACGTCCACCGACG\|TAAAGGCGACACAGGAGGAGAACCGGGAGCTGAGGAGCAGGTGTGAGGAG | 324 |
| SLC7A2 | CGCGGGCCCCGACGCGCTGCAGCCGGCAGCCCACCGCCGCCTTCTTGGC\|TGTGTTCCGGCCGCAGAGCACCGTCTGCCGTGAGGAGATCCTGGCCAAGTT | 325 |
| RAF1 | GGTGCGAGGGCAGCAGCCTCTACAAACACCTGCATGTCCAGGAGACCAAG\|GAAAAGCCATGGAGACTTCAGCATCCTCCTCCCAGCCTCAGGACAACAGT | 326 |

TABLE 49-continued

| BRAF | GGCCGGCGCCGGCGCCGGCGCCGCGGCCTCTTCGGCTGCGGACCCTGCCA\|TTCCGGATATTGACTGTTCAAGTAC TATTATGCTGGACAATATTGTGAGG | 327 |
|---|---|---|
| TRIM24 | ATTTGAGCTCACCAGTGGGAGGGTCTTATAATCTTCCCTCTCTTCCGGAT\|GTGTGGAATATCAAACAAATGATTA AGTTGACACAGGAACATATAGAGGC | 328 |

TABLE 50

| Gene | approved | Pre-registration (pre-approval) | Phase III |
|---|---|---|---|
| ABL1 | imatinib mesilate<br>bosutinib<br>nilotinib<br>ponatinib<br>radotinib | N | N |
| ALK | crizotinib<br>alectinib hydrochloride<br>ceritinib | N | N |
| BRAF | vemurafenib<br>pazopanib<br>dabrafenib | N | encorafenib |
| CDKN2A | N | N | N |
| CDK6 | N | palbociclib | LEE-011<br>LY-2835219 |
| EGFR | panitumumab<br>cetuximab<br>erlotinib<br>nepidermin<br>gefitinib<br>nimotuzumab<br>vandetanib<br>lapatinib<br>afatinib<br>icotinib | N | neratinib<br>XL-647<br>rindopepimut<br>necitumumab<br>dacomitinib<br>rociletinib<br>AZD-9291 |

| Gene | Phase II | Phase I | Preclinical |
|---|---|---|---|
| ABL1 | bafetinib | rebastinib<br>ABL-001 | ON-044580<br>SUN-K706 |
| ALK | AP-26113<br>X-396<br>PF-06463922<br>TSR-011<br>entrectinib | CEP-37440<br>EBI-215 | AZD-3463<br>ARN-5032<br>DLX-521 |
| BRAF | RAF-265<br>XL-281<br>AB-024<br>PLX-8394 | ARQ-761<br>ARQ-736<br>BeiGene-283<br>DP-4978 | Braf inhibitors, Sareum<br>B-Raf and c-RAF dual<br>inhibitor, Redx Pharma<br>PLX-8394<br>DP-4978<br>TL-241, B-Raf kinase inhibitors,<br>Array BioPharma-1<br>EN-3352<br>EBI-907<br>PI3K/BET bromodomain<br>inhibitors SignalRx<br>UAI-201<br>Nanolipolee-007<br>ASN-003 |
| CDKN2A | P16_37-63 | N | N |
| CDK6 | alvocidib | GZ38-1 | CDK4/6 inhibitors,<br>G1 Therapeutics<br>capridine Beta, AV Therapeutics<br>G1T38-1<br>G1T30-1 |
| EGFR | dovitinib<br>varlitinib<br>marizomib<br>futuximab<br>S-222611<br>AP-26113<br>antroquinonol<br>GT-MAB 5.2-GEX<br>poziotinib<br>duligotuzumab<br>LY-3016859 | JNJ-26483327<br>MM-151<br>AL-6802<br>ABT-806<br>epitinib<br>allitinib<br>theliatinib<br>ErbituxEDVsPac<br>AMG-595<br>IMGN-289<br>pyrotinib | CUDC-101<br>Sym-013<br>STI-A020X<br>SCT-200<br>pirotinib<br>PF-06459988<br>NT-004<br>larotinib<br>KL-ON113<br>JNJ-61186372<br>IRAD-425 |

TABLE 50-continued

|  |  |  |  |
|---|---|---|---|
|  | ABT-414 | TAS-121 | HL-176 |
|  | KD-020 | chimeric antigen receptor | FV-225 |
|  | ASP-8273 | T-cell therapy, | Epidermal growth |
|  | doxorubicin loaded | EGFRVIII, Novartis | factor, USV Limited |
|  | EnGeneIC delivery | GC-1118A | EM1-mAB |
|  | vehicles | LY-3164530 | EGFRvIII/CD3 |
|  | EGF-816 | AZD-3759 | CUDC-101 |
|  | EGFRvII CAR, | miR-16, EDV nanocells, | CTX-023 |
|  | Kite Pharma | EnGeneIC | BPI-4039 |
|  |  |  | BPI-0403 |
|  |  |  | bi-specific antibodies, Zyngenia |
|  |  |  | Avid Biologics-2 |
|  |  |  | Avid Biologics-1 |
|  |  |  | anticancer gene therapy, Gradalis |
|  |  |  | anti-EGFR MAbs, Kadmon |
|  |  |  | anti-EGFR biosimilar, Mabion |
|  |  |  | AFM-21 |

| Gene | approved | Pre-registration (pre-approval) | Phase III |
|---|---|---|---|
| ERBB2 | trastuzumab | N | neratinib |
|  | trastuzumab emtansine |  | XL-647 |
|  | pertuzumab; lapatinib |  | dacomitinib |
|  | ditosylate |  | nelipepimut-S |
|  | catumaxomab |  | trastuzumab |
|  | afatinib |  | (Celltrion, Biocad, |
|  | trastuzumab, Enhanze |  | Biocon, Synthon, |
|  |  |  | Harvest Moon, |
|  |  |  | Aryogen) |
|  |  |  | doxorubicin |
| FGFR2 | ponatinib | lenvatinib | N |
|  | palifermin |  |  |
| FGFR3 | ponatinib | lenvatinib | N |
|  | levetiracetam in | masitinib |  |
|  | sodium |  |  |
|  | chloride, HQ |  |  |
|  | Specialty Pharma |  |  |
| JAK2 | ruxolitinib | N | momelotinib |
|  |  |  | pacritinib |
|  |  |  | baricitinib |
| MTOR | everolimus | ridaforolimus | TCD-10023 |
|  | temsirolimus |  | voxtalisib |
|  | sirolimus |  | nab-rapamycin |
|  | zotarolimus |  | apitolisib |
|  | biolimus |  | gedatolisib |
|  | umirolimus |  |  |
| NTRK1 | N | N | MIM-D3 |
| RAF1 | sorafenib | N | N |
| TERT | N | N | GV-1001 |

| Gene | Phase II | Phase I | Preclinical |
|---|---|---|---|
| ERBB2 | lapuleucel-T | Her-VAXX | Lovaxin B |
|  | AVX-901 | VM-206 | TH-1, Algeta |
|  | AE-37 | ARRY-380 | trastuzumab-antibody |
|  | BMS-690514 | JNJ-26483327 | conjugates, Synthon |
|  | MVA-BN-HER2 | S-222611 | CUDC-101 |
|  | varlitinib | doxorubicin (Merrimack) | Her-2/neu Stradobody,Gliknik |
|  | MM-111 | cipatinib | ARX-788 |
|  | AC-480; ovarian | TrasGEX | Etbx-021 |
|  | cancer | trastuzumab (Hanwha | SN-34003 |
|  | vaccine (Generex) | Chemical); | IBI-302 |
|  | TrasGEX | trastuzumab (Pfizer) | NT-004 ICT-140 |
|  | margetuximab | IDN-6439 | ONS-1050 |
|  | poziotinib | AVX-901 | Sym-013 |
|  | PR-610 |  | anti-HER2 X anti-CD3 |
|  | KD-020 |  | (Emergent Biosolutions) |
| FGFR2 | EN MD-2076 | JNJ-42756493 | FPA-144 |
|  | lucitanib | S-49076 | keratinocyte growth |
|  | AZD-4547 | FF-284 | factor, Nanogen |
|  | BGJ-398 | BAY-1179470 |  |
|  | LY-2874455 | BAY-1163877 |  |
|  |  | ASP-5878 |  |
| FGFR3 | dovitinib lactate | JNJ-42756493 | N |
|  | ENMD-2076 | S-49076 |  |
|  | AZD-4547 | FF284 |  |
|  | BGJ-398 | BAY-1163877 |  |
|  | LY-2874455 | ASP-5878 |  |
|  |  | B-701 |  |

TABLE 50-continued

| | | | |
|---|---|---|---|
| JAK2 | BMS-911543 | AC-430 | ON-044580 |
| | NS-018 | SB-1317 | TP-0413 |
| | | PF-06263276 | VR-588 |
| | | | NMS-P953 |
| MTOR | quinacrine | P-7170 | nPT-MTOR |
| | XL-765 | CBLC-137 | STP-503 |
| | dactolisib | AZD-2014 | X-480 |
| | PKI-587 | CC-115 | ABTL-0812 |
| | PF-04691502 | PWT-33957 | X-414; CC214 |
| | INK-128 | DS-7423 | HMPL-518 |
| | AZD-2014 | GDC-0084 | PQR-401 |
| | CC-223 | DS-3078 | mTOR inhibitor/PI3 kinase |
| | | LY-3023414 | inhibitor, Lilly-1 |
| | | PI3 kinase/mTOR | PIM/PI3k/mTOR inhibitors, |
| | | inhibitor, Lilly | Inflection Biosciences |
| | | SF-1126 | LOR-220 |
| | | SB-2343 | NV-128 |
| | | omipalisib | SPR-965 |
| | | ABTL-0812 | IBL-301 |
| | | PQR-309 | PQR-316 |
| | | DCBCI-0901 | PQR-311 |
| | | | TAM-01 |
| NTRK1 | milciclib maleate | BXL-1H5 | NMS-P626 |
| | CT-327 | PLX-7486 | CT-340 |
| | NMS-E628 | LOXO-101 | FX-007 |
| | PSR-011 | DS-6051b | CRB-0089 |
| | | | pan-TRK (Merck) |
| RAF1 | iCo-007 | RO-5126766 | HM-95573 |
| | XL-281 | MLN-2480 | TAK-632 |
| | | DP-4978 | UAI-201 |
| | | | pan-RAF Novartis and Celator |
| TERT | VX-001 | TeloB-Vax | telomerase vaccine, Geron |
| | GX-301 | | hTERT DNA vaccine, Inovio |
| | | | INVAC-1 |
| | | | AST-VAC2 |

What is claimed:

1. A composition reaction mixture comprising a target nucleic acid and a set of primers that specifically hybridize to the target nucleic acid to flank a gene fusion, a recombinant thermostable polymerase, and dNTPs, wherein the set of primers specifically amplify a fusion between the KANK2 gene and the ALK gene comprising SEQ ID NO: 272, and wherein each primer is 15 to 40 nucleotides long and a deoxyribonucleic acid sequence comprising at least one deoxyuridine (dU) residue in place of a deoxythymidine residue.

2. The composition of claim 1, additionally comprising one or more additional set of primers that specifically hybridize to one or more additional target nucleic acids to flank a gene fusion, wherein the additional set(s) of primers specifically amplify at least one fusion of two genes comprising one or more sequences selected from SEQ ID NOs: 1-328.

3. A kit comprising components:
i. a set of primers that specifically hybridize to a target nucleic acid to flank a gene fusion, wherein the set of primers specifically amplify a fusion between the KANK2 gene and the ALK gene comprising SEQ ID NO: 272, and wherein each primer is 15 to 40 nucleotides long and a deoxyribonucleic acid sequence comprising at least one deoxyuridine (dU) residue in place of a deoxythymidine residue,
ii. a recombinant thermostable polymerase, and
iii. a set of dNTPs.

4. The kit of claim 3, additionally comprising one or more additional set of primers that specifically hybridize to a target nucleic acid to flank a gene fusion that specifically amplify at least one fusion of two genes comprising one or more sequences selected from SEQ ID NOs: 1-328.

5. The composition of claim 2, wherein the set of primers specifically hybridize to at least one nucleic acid comprising a break point from sequences selected from SEQ ID NOs: 1-328.

* * * * *

SEQUENCE LISTING

<160> NUMBER OF SEQ ID NOS: 328

<210> SEQ ID NO 1
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
tgcggagagg tcagtaacta aattggagaa aagcattgat gacttagaag tgtaccgccg     60
gaagcaccag gagctgcaag ccatgcagat ggagctgcag                          100

<210> SEQ ID NO 2
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
ctgagagacc catggcattc ctcagggaat actttgagag gttggagaag acctcctcca     60
tcagtgacct gaaggaggtg ccgcggaaaa acatcaccct                          100

<210> SEQ ID NO 3
<211> LENGTH: 100
<212> TYPE: DNA
<213> ORGANISM: Artificial Sequence
<220> FEATURE:

```
<223> OTHER INFORMATION: Description of Artificial Sequence: Synthetic
      polynucleotide

<400> SEQUENCE: 3
gtgcaacagg ttcaggtgtt tgctgacgtc cagtgtacag tgaatctggt aggcggctgt     60
ggggctgctc cagttcaatc tcagcgagct gttcagttgg                          100

<210> SEQ ID NO 4
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gaaactttcc tcctccacca cctcttgatg aagaggcttt caaagtacag aaggcatcac     60
aggaggcctc tgcatgatgt ggcttccaaa gactcaagga                          100

<210> SEQ ID NO 5
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gatggtgctg taaccacctc acagattcca gcttcggaac aagagaccct gtgagccaag     60
ggagtttgtg gagaactctg agtgcataca gtgccaccca                          100

<210> SEQ ID NO 6
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gccctcccag aggcccacct tcaagcagct ggtggaggac ctggaccgtg tccttggtac     60
aaatggagcc actgacgaca gcaagaccaa cctcatcgtc                          100

<210> SEQ ID NO 7
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
tagctgtgct cgcgctactc tctctttctg gcctggaggc tatccagcgt gctggagaat     60
ctggtaaaag caccattgtg aagcagatga ggatcctgca                          100

<210> SEQ ID NO 8
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
```
gagattttgg aatttccaac acgagaagta tatgtccctc acactgtgta cagtggcggc    60
atgattttgt gcacggatgg ataaaagtac ctgtgactca                         100

<210> SEQ ID NO 9
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
tgccgctctg tacacctggt acgtcagaaa gcaacgagag atcctccgac gtgagaccgt    60
ggagccgccc ccgccggcgc agctgcactt catgtacgtg                          100

<210> SEQ ID NO 10
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gggaagggcc ctgagccaga gtccgtcatc ggttactccg gagaagatta cactaacagc    60
acatctggag acccggtgga gaagaaggac gaaacacctt                          100

<210> SEQ ID NO 11
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
tccaggaggt ggagggccac caggaacacc catcatgcct agtccagcag gcccggctgt    60
gctggctcca gaggatgggc tggccatgtc cctgcatttc                          100

<210> SEQ ID NO 12
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
tttcctgaag aacgttgggg agagtgtggc agctgccctt agccctctgg acactaacag    60
cacatctgga gacccggtgg agaagaagga cgaaacacct                          100

<210> SEQ ID NO 13
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
catataaaac tactttaagg aattagatgt atggttgtcc caaagcagaa acctggaaac    60
ggtggcctcc aacgccgctc cccctcccg ggaatggagg                           100

<210> SEQ ID NO 14
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
cgccatctgc accttccata gccaaatcag ggtcattgga ctcagaactt ggttcttgga    60
aaaactctag gagaaggcga atttggaaaa gtggtcaagg                         100

<210> SEQ ID NO 15
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
aatcttacaa tggcaggacc attctgggaa ccatcatgaa tacgatcaag gaggatccaa    60
agtgggaatt ccctcggaag aacttggttc ttggaaaaac                         100

<210> SEQ ID NO 16
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
gccctatatt tgcattaaaa tggaataaga aaggaaattt catcctaagt gctggactcc    60
atggagaacc aggtctccgt ggatgccttc aagatcctgg                         100

<210> SEQ ID NO 17
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
ttaatatgcc agaaaagaa agaaaaggag ttagtaacta ccgttcagag tactcttcca    60
acccaagagg agattgaaaa tcttcctgcc ttccctcggg                         100

<210> SEQ ID NO 18
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gagaaacaca ggaggaggag gatgagattc ttccaaggaa agactatgag gatgcaattc    60
gaagtcacag cgaatcagcc tcaccttcag ccctgtccag                         100

<210> SEQ ID NO 19
<211> LENGTH: 100

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
tccagcatct gggggctgct aaggatgccc agcggcagct cacagccgag gatgcaattc     60
gaagtcacag cgaatcagcc tcaccttcag ccctgtccag                         100

<210> SEQ ID NO 20
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
agggccgcac ttggaccttg tgcggcaccc ctgagtacct ggcccctgag gtgctggagg     60
acaatgacta cggccgtgca gtggactggt gggggctggg                         100

<210> SEQ ID NO 21
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
agggccgcac ttggaccttg tgcggcaccc ctgagtacct ggcccctgag gtgctggagg     60
acaatgacta cggccgtgca gtggactggt gggggctggg                         100

<210> SEQ ID NO 22
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
agggccgcac ttggaccttg tgcggcaccc ctgagtacct ggcccctgag gtgctggagg     60
acaatgacta cggccgtgca gtggactggt gggggctggg                         100

<210> SEQ ID NO 23
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
agggccgcac ttggaccttg tgcggcaccc ctgagtacct ggcccctgag gtgctggagg     60
acaatgacta cggccgtgca gtggactggt gggggctggg                         100

<210> SEQ ID NO 24
<211> LENGTH: 100
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 24
agggccgcac ttggaccttg tgcggcaccc ctgagtacct ggcccctgag gtgctggagg    60
acaatgacta tggccgggcc gtggactggt gggggctggg                          100

<210> SEQ ID NO 25
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
ccaggaagct cgatcaaatg cccgcctaaa gcagctctca tttgcaggtg gtactttgga    60
aaacttggcc gaaaagatgc tgagcgacag ctattgtcct                          100

<210> SEQ ID NO 26
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
caaggttggg cattgggtgg aggagcagaa tttactacag catgtgattt cagggaagga    60
gattggtggg aagcccgctc cttgacaact ggagagacag                          100

<210> SEQ ID NO 27
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
cttcatatca gaggactatg caacagccca tgaagacttt cagcagtcct ctggaaattg    60
aacttagctc attaagggaa gctttgtctt tcgtgtcatt                          100

<210> SEQ ID NO 28
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
attgatttca cgaatgaggc agtggagcag gtggaagagg aggagtctgg cccgcgatgc    60
tcccagcccg gtgagacctg cctgaatggc gggaagtgtg                          100

<210> SEQ ID NO 29
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
ggacatgttg atgtgaagg agcggaaggt taatgttctt cagaagaagg aggatccaaa    60
gtgggaattc cctcggaaga acttggttct tggaaaaact                        100
```

<210> SEQ ID NO 30
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
gaatgcacct atcttaacaa atacaacatt gaacgtcata agacttgttg ttctggggat    60
tcttggagga attcttgctt tgctaattct gattctgctg                        100
```

<210> SEQ ID NO 31
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
aacatcaaag gcaattggct taagaatgtt catcatctgc atatattttc ttagcaaagc    60
aagaattcct ccaagaatcc ccagaatggc aggaatttgc                        100
```

<210> SEQ ID NO 32
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
gcaaattcct gccattctgg ggattcttgg aggaattctt gctttgctaa gaaaatatat    60
gcagatgatg aacattctta agccaattgc ctttgatgtt                        100
```

<210> SEQ ID NO 33
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
gctgcaggat ctggtttacc cacaggctga tatatatgtt ggtttccaat cggggccggc    60
tcccgagtac atggtggcgc cgccgagggg ctccggggcc                        100
```

<210> SEQ ID NO 34
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
ggccccggag cccctcggcg gcgccaccat gtactcggga gccggccccg attggaaacc    60
aacatatata tcagcctgtg ggtaaaccag atcctgcagc                        100
```

<210> SEQ ID NO 35
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
ccccggagcc cctcggcggc gccaccatgt actcgggagc cggccccggt ttctggctac      60
cctggttcac atggaatcac agccatggct ggcagcatct                           100

<210> SEQ ID NO 36
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
cgaagtacag tttttacatg ttttaattgc aaccgccaaa gctggattct ccggggccgg      60
ctcccgagta catggtggcg ccgccgaggg gctccggggc                           100

<210> SEQ ID NO 37
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
ggccccggag cccctcggcg gcgccaccat gtactcggga gccggccccg gaagtcggct      60
tggccctgag gacattattg gccactgtgg atgagaccat                           100

<210> SEQ ID NO 38
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
acacatgggc cgcaagaaca ggcctcatgt agtacctggc atactccagc gcccggggca      60
gggtctggac agaagaagcc ctgctggggt accagatact                           100

<210> SEQ ID NO 39
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gggcgctggg ggcatggtcc accacaggca ccgcagctca tctaccagga ctccctcagt      60
gccccttcgg tggcctccag attcattgat tcccacacac                           100

<210> SEQ ID NO 40
<211> LENGTH: 100
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 40
gtggcggtgg ggacctgaca ctagggctgg agccctctga agaggaggcc tgttcttgcg    60
gcccatgtgt tttctggtga agaggagctt ccccaggact                         100

<210> SEQ ID NO 41
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
ctgaggagta tctggtaccc cagcagggct tcttctgtcc agaccctgcc cagcgccctg    60
gccttcttcc tgacggccac tgtcttcctc gtgctctgca                         100

<210> SEQ ID NO 42
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
tgcagagcac gaggaagaca gtggccgtca ggaagaaggc cagggcgctg ggtgcagatg    60
gggggctggg gcagccgctc cccctttcc agcaggtcag                          100

<210> SEQ ID NO 43
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
aggagaaccg gatcaccatt cccgtgcaga ccttctccaa cctgcagatt cgaggagagc    60
aggattctct gcctcttcca aactttcct ccctgaacct                          100

<210> SEQ ID NO 44
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
acgtgcggga ggcggccagt tatcaggagg cgctggcgcg gctggaggaa atggctcgtc    60
accttcgtga ataccaagac ctgctcaatg ttaagatggc                         100

<210> SEQ ID NO 45
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 45
aggagaaccg gatcaccatt cccgtgcaga ccttctccaa cctgcagatt cgaggagagc    60
aggatttctc tgcctcttcc aaacttttcc tccctgaacc                        100

<210> SEQ ID NO 46
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
aatgtcaagc tggccctgga catcgagatc gccacctaca ggaagctgct ggaaggcgag    60
gagagcagga tttctctgcc tcttccaaac ttttcctccc                        100

<210> SEQ ID NO 47
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
atcaccattc ccgtgcagac cttctccaac ctgcagattc gagaaaccag gacactattg    60
gccgcctgca ggatgagatt cagaatatga aggaggaaat                        100

<210> SEQ ID NO 48
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
cttctccaac ctgcagattc gagggggcaa aagcaccaaa gacggggaaa tggctcgtca    60
ccttcgtgaa taccaagacc tgctcaatgt taagatggcc                        100

<210> SEQ ID NO 49
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gaaccggatc accattcccg tgcagacctt ctccaacctg cagattcgag aatctggatt    60
cactccctct ggttgatacc cactcaaaaa ggacacttct                        100

<210> SEQ ID NO 50
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
cagagatgat ggagctcaat gaccgctttg ccagctacat cgagaaggtt cgcttcctgg    60
agcagcagaa taagatcctg ctggccgagc tcgagcagct              100

<210> SEQ ID NO 51
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gaaaccagcc tggacaccaa gtctgtgtca gaaggccacc tcaagaggaa atggctcgtc    60
accttcgtga ataccaagac ctgctcaatg ttaagatggc                        100

<210> SEQ ID NO 52
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
cacgaacgag tccctggaga ggcagatgcg cgagcaggag gagcggcacg aatgagtccc    60
tggaacgcca gatgcgtgaa atggaagaga actttgccgt                        100

<210> SEQ ID NO 53
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
ggcagagaaa tcctgctctc ctcgccttcc agcagcttcc tgtaggtggc gtggcgatct    60
cgatgtccag ggccagcttg acattgagca ggtcctggta                        100

<210> SEQ ID NO 54
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
ctggcttcaa ggagacccgg gccagtgagc gggcagagat gatggagctc aatgaccgct    60
tcgccaacta catcgacaag gtgcgcttcc tggagcagca                        100

<210> SEQ ID NO 55
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
gaggagcggc acgtgcggga ggcggccagt tatcaggagg cgctggcgcg gccacctaca    60
ggaagctgct ggaaggcgag gagagcagga tttctctgcc                        100

```
<210> SEQ ID NO 56
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
catcgagatc gccacctaca ggaagctgct agagggcgag gagaaccgga gacaggtgca    60
gtccctcacc tgtgaagtgg atgcccttaa aggaaccaat                         100

<210> SEQ ID NO 57
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gaggagcggc acgtgcggga ggcggccagt tatcaggagg cgctggcgcg tgctggaagg    60
cgaggagagc aggatttctc tgcctcttcc aaacttttcc                         100

<210> SEQ ID NO 58
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
ggcagagaaa tcctgctctc ctcgccttcc agcagcttcc tgtaggtggc gatctcgatg    60
tccagggcca gcttgacatt gagcaggtcc tggtactcct                         100

<210> SEQ ID NO 59
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
aggagtacca ggacctgctc aatgtcaagc tggccctgga catcgagatc gccacctaca    60
ggaagctgct ggaaggcgag gagagcagga tttctctgcc                         100

<210> SEQ ID NO 60
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
cccgggccag tgagcgggca gagatgatgg agctcaatga ccgctttgcc ctcgagcagc    60
tcaagggcca aggcaagtcg cgcctggggg acctctacga                         100

<210> SEQ ID NO 61
<211> LENGTH: 100
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 61
cgggccagtg agcgggcaga gatgatggag ctcaatgacc gctttgccag ctacatcgac        60
aaggtgcgct tcctggagca gcagaataag atcctgctgg                              100

<210> SEQ ID NO 62
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
acgtccatgc ctccaagcgc attctcttct ccatcgtcca tgacaagtca gtgtaccgcc        60
ggaagcacca ggagctgcaa gccatgcaga tggagctgca                              100

<210> SEQ ID NO 63
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
ccatgagcga gttgtcatca tcaagaatat gtttcatcct atggattttg agatacaagg        60
cagttgtgaa gccacttgag cgacagccct ccaatgccat                              100

<210> SEQ ID NO 64
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
ctcggggccc ttcgagagca agtttaagaa ggagccggcc ctgactgcag acactaacag        60
cacatctgga gacccggtgg agaagaagga cgaaacacct                              100

<210> SEQ ID NO 65
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
aggtgtttcg tccttcttct ccaccgggtc tccagatgtg ctgttagtgt ctgcagtcag        60
ggccggctcc ttcttaaaact tgctctcgaa gggccccgag                             100

<210> SEQ ID NO 66
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 66
agaaatggtt tcaaatgaat ctgtagacta ccgagctact tttccagaag ggccacccag    60
tgctcctgca gaagatcgtt caggaacacc cgacagcatt                         100

<210> SEQ ID NO 67
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
tgtaagtgcc cgaagtgtaa gcccaactac agaaatggtt tcaaatgaat ctgcagaaga    60
tcgttcagga cacccgaca gcattgcttc ctcctcctca                          100

<210> SEQ ID NO 68
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
aatggtttca atgaatctg tagactaccg agctactttt ccagaagatc gttcaggaac     60
acccgacagc attgcttcct cctcctcagc agctcaccca                         100

<210> SEQ ID NO 69
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
tatatccagt ccattactgc aaaatactgt ccacattgac ctcagtgctc ctgcagaaga    60
tcgttcagga cacccgaca gcattgcttc ctcctcctca                          100

<210> SEQ ID NO 70
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
tattgacctt gtgaaccatt tcaagtgctc ttgcccacca ggcactcggg aatcaggaaa    60
cccaggccca acggcaggtg gatgcaagaa gaaatgttcc                         100

<210> SEQ ID NO 71
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
gtattgacct tgtgaaccat ttcaagtgct cttgcccacc aggcactcgg gaatcaggaa    60

```
acccaggccc aacggcaggt ggatgcaaga agaaatgttc                          100
```

<210> SEQ ID NO 72
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

```
ccatcgccga ccagatcacc ctcctcaagg ctgcctgcct ggacatcctg gagggagat    60 ttgtcgcctg ccgctcgctc tggggctcga tgtgaatata                         100
```

<210> SEQ ID NO 73
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

```
gtttggaaat aatggtgaag gtgctgaacc ctcagcagga gggcagtttg tagctttcca    60
cagccccacc accaggatca agaaggagcc ccagagtccc                         100
```

<210> SEQ ID NO 74
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
agcaatacca ttgacctgcc gatgtccccc cgcactttag attcattgat gcagtttgtt    60
cctgatttcc attcagaaaa cctagctttc cacagcccca                         100
```

<210> SEQ ID NO 75
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
cctgccgatg tcccccgca ctttagattc attgatgcag tttggaaata gatgtcaccg     60
ggtgcgcatc aatgtacctc cacacagagg gcttctctgg                         100
```

<210> SEQ ID NO 76
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
atcaataaaa atgttatgtc agcgtttggc ttaacagatg atcaggtttc agatcagttt    60
cctaattcat ctcagaacgg ttcatgccga caagtgcagt                         100
```

<210> SEQ ID NO 77

```
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
catccaaggt tccattaaat acatcatgct taaccctagt tcacgaatca aggtgacaaa      60
tgtgtcatgc ctggagacaa gctccagcgc cagccctgct                          100

<210> SEQ ID NO 78
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
ccaaggttcc attaaataca tcatgcttaa ccctagttca cgaatcaagg tgacaaatgt      60
gtcatgcctg agacaagct ccagcgccag ccctgctaga                           100

<210> SEQ ID NO 79
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
tggcatggcg catgagcgag tctctagcag ggctggcgct ggagcttgtc tccaggaggc      60
tctatcttga agttagcaat cctctctttg tggttatcca                          100

<210> SEQ ID NO 80
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
tcagcatatg cgattttatt atatctttga cgaacagact cctggtattt ccaatccagg      60
gaagcgtgtc accgtcgtgg aaagcacgct cccagcccga                          100

<210> SEQ ID NO 81
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
tcccaagcaa tggatgattt gatgctgtcc ccggacgata ttgaacaatg ttccctggat      60
gaaagtgtgg aacagagga aggatcagag aaaagagagg                           100

<210> SEQ ID NO 82
<211> LENGTH: 100
<212> TYPE: DNA
<213> ORGANISM: Artificial Sequence
<220> FEATURE:
```

```
<223> OTHER INFORMATION: Description of Artificial Sequence: Synthetic
      polynucleotide

<400> SEQUENCE: 82
ttcgggctgg gagcgtgctt tccacgacgg tgacacgctt ccctggattg gaaataccag      60
gagtctgttc gtcaaagata taataaaatc gcatatgctg                          100

<210> SEQ ID NO 83
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
gaactttgcc gttgaagctg ctaactacca agacactatt ggccgcctgc tcgagaaacc      60
agcctggaca ccaagtctgt gtcagaaggc cacctcaaga                          100

<210> SEQ ID NO 84
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
aaggaggaaa tggctcgtca ccttcgtgaa taccaagacc tgctcaatgt caagctggcc      60
ctggacatcg agatcgccac ctacaggaag ctgctagagg                          100

<210> SEQ ID NO 85
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ttgaagctgc taactaccaa gacactattg gccgcctgct cgagaaacca gcctggacac      60
caagtctgtg tcagaaggcc acctcaaga                                       89

<210> SEQ ID NO 86
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
aatgttaaga tggcccttga cattgagatt gccacctaca ggaagctgct agagggcgag      60
gagaaccgga tcaccattcc cgtgcagacc ttctccaacc                          100

<210> SEQ ID NO 87
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
```

```
ggtgcgcttc ctggagcagc agaataagat cctgctggcc gagctcgagc gggcactcaa    60
tgctggcttc aaggagaccc gggccagtga gcgggcagag                          100

<210> SEQ ID NO 88
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
gtgaatacca agacctgctc aatgttaaga tggcccttga cattgagatt gccacctaca    60
ggaagctgct agagggcgag gagaaccgga tcaccattcc                          100

<210> SEQ ID NO 89
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
gaaggcgagg agagcaggat ttctctgcct cttccaaact tttcctccct tggacatcga    60
gatcgccacc tacaggaagc tgctagaggg cgaggagaac                          100

<210> SEQ ID NO 90
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
ggaaggcgag gagagcagga ttctctgcct cttccaaact tttcctccct tggacatcga    60
gatcgccacc tacaggaagc tgctagaggg cgaggagaac                          100

<210> SEQ ID NO 91
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
ggggacagcg acgacgcgga ggcagagaag ggaacgcccg gcccagcccc tgtgcaccgg    60
cacagacatg aagctgcggc tccctgccag tcccgagacc                          100

<210> SEQ ID NO 92
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
ccagaaggaa gatggcggat ctggaggagc agttgtctga tgaagagaag tggtcctttg    60
gcgtgctcct ctgggagctg atgacaagag gagccccacc                          100
```

<210> SEQ ID NO 93
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
caaaatcaaa ccttcctcat ctgccaatgc catttattct ctggctgcca gggatgagga    60
gaatttctgt gccactgtgc ccaaggatgg acgttcctat                         100

<210> SEQ ID NO 94
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
tctgcgagaa cagagaaggg agctctatag tcggagtgga gaactgcaag attctcgcct    60
ctattgagct gctggcccgc tcattgccaa aaattcaccg                         100

<210> SEQ ID NO 95
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
cctgctggcc gagctcgagc agctcaaggg ccaaggcaag tcgcgcctgg ctcctggccg    60
ccgtctgggt cctggcaccc gcctctccct ggctcgaatg                         100

<210> SEQ ID NO 96
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
ctgacctctc tgaggctgcc aaccggaaca atgacgccct gcgccaggca caggagtacc    60
aggacctgct caatgtcaag ctggccctgg acatcgagat                         100

<210> SEQ ID NO 97
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
caggcaaagc aggagtccac tgagtaccgg agacaggtgc agtccctcac gtaccgctcc    60
aagtttgcag acctgacaga cgctgctgcc cgcaacgcgg                         100

<210> SEQ ID NO 98
<211> LENGTH: 100

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
tttgccgttg aagctgctaa ctaccaagac actattggcc gcctgcagga gtaccaggac    60
ctgctcaatg tcaagctggc cctggacatc gagatcgcca                         100

<210> SEQ ID NO 99
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
cattgagatt gccacctaca ggaagctgct ggaaggcgag gagagcagga gtaccaggac    60
ctgctcaatg tcaagctggc cctggacatc gagatcgcca                         100

<210> SEQ ID NO 100
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
gaactttgcc gttgaagctg ctaactacca agacactatt ggccgcctgc ttcgagaaac    60
cagcctggac accaagtctg tgtcagaagg ccacctcaag                         100

<210> SEQ ID NO 101
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
tttgccgttg aagctgctaa ctaccaagac actattggcc gcctgcagga gtaccaggac    60
ctgctcaatg tcaagctggc cctggacatc gagatcgcca                         100

<210> SEQ ID NO 102
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
tttgccgttg aagctgctaa ctaccaagac actattggcc gcctgcagga gtaccaggac    60
ctgctcaatg tcaagctggc cctggacatc gagatcgcca                         100

<210> SEQ ID NO 103
<211> LENGTH: 100
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 103
tgaaggagga atggctcgt caccttcgtg aataccaaga cctgctcaat ctagagggcg    60
aggagaaccg gatcaccatt cccgtgcaga ccttctccaa                          100

<210> SEQ ID NO 104
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
aaggaggaaa tggctcgtca ccttcgtgaa taccaagacc tgctcaatgt caagctggcc    60
ctggacatcg agatcgccac ctacaggaag ctgctagagg                          100

<210> SEQ ID NO 105
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
aatgttaaga tggcccttga cattgagatt gccacctaca ggaagctgct agagggcgag    60
gagaaccgga tcaccattcc cgtgcagacc ttctccaacc                          100

<210> SEQ ID NO 106
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
aatgttaaga tggcccttga cattgagatt gccacctaca ggaagctgct agagggcgag    60
gagaaccgga tcaccattcc cgtgcagacc ttctccaacc                          100

<210> SEQ ID NO 107
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
aatgttaaga tggcccttga cattgagatt gccacctaca ggaagctgct agagggcgag    60
gagaaccgga tcaccattcc cgtgcagacc ttctccaacc                          100

<210> SEQ ID NO 108
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108

```
aatgttaaga tggcccttga cattgagatt gccacctaca ggaagctgct agagggcgag      60
gagaaccgga tcaccattcc cgtgcagacc ttctccaacc                          100
```

<210> SEQ ID NO 109
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

```
taagatggcc cttgacattg agattgccac ctacaggaag ctgctggaag gcgggaggcg      60
gccagttatc aggaggcgct ggcgcggctg gaggaagagg                          100
```

<210> SEQ ID NO 110
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110

```
gaaggcgagg agagcaggat ttctctgcct cttccaaact tttcctccct tggacatcga      60
gatcgccacc tacaggaagc tgctagaggg cgaggagaac                          100
```

<210> SEQ ID NO 111
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111

```
gaaggcgagg agagcaggat ttctctgcct cttccaaact tttcctccct tggacatcga      60
gatcgccacc tacaggaagc tgctagaggg cgaggagaac                          100
```

<210> SEQ ID NO 112
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112

```
cctcaagagg aacatcgtgg tgaagaccgt ggagatgcgg gatggagagg gatacccact      60
caaaaaggac acttctgatt aagacggttg aaactagaga                          100
```

<210> SEQ ID NO 113
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

```
ggccacctca agaggaacat cgtggtgaag accgtggaga tgcgggatgg agatgcgtga      60
aatggaagag aactttgccg ttgaagctgc taactaccaa                          100
```

<210> SEQ ID NO 114
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
aaggccacct caagaggaac atcgtggtga agaccgtgga gatgcgggat ggagagcagg    60
atttctctgc ctcttccaaa cttttcctcc ctgaacctga                         100

<210> SEQ ID NO 115
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
caagtctgtg tcagaaggcc acctcaagag gaacatcgtg gtgaagaccg ggaggaaatg    60
gctcgtcacc ttcgtgaata ccaagacctg ctcaatgtta                         100

<210> SEQ ID NO 116
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
ttataccaat acaggctcac cagattgtaa atggaacgcc gccggctcgc gaataccaag    60
acctgctcaa tgttaagatg gcccttgaca ttgagattgc                         100

<210> SEQ ID NO 117
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
aggagaaccg gatcaccatt cccgtgcaga ccttctccaa cctgcagatt cgaggagagc    60
aggatttctc tgcctcttcc aaacttttcc tccctgaacc                         100

<210> SEQ ID NO 118
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
aggagaaccg gatcaccatt cccgtgcaga ccttctccaa cctgcagatt cgaggagagc    60
aggatttctc tgcctcttcc aaacttttcc tccctgaacc                         100

<210> SEQ ID NO 119
<211> LENGTH: 100
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 119
aggagtacca ggacctgctc aatgtcaagc tggccctgga catcgagatc gccacctaca      60
ggaagctgct ggaaggcgag gagagcagga tttctctgcc                          100

<210> SEQ ID NO 120
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
gcccgccact tgcaggagta ccaggacctg ctcaatgtca agctggccct cttgacattg      60
agattgccac ctacaggaag ctgctggaag gcgaggagag                          100

<210> SEQ ID NO 121
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
gcattttctt cccacaggtg aaaaggagg gagctgctct caggctgcgt ccagcaacag       60
tgcccaggct actaccagtc acacctagac ctggaggatc                          100

<210> SEQ ID NO 122
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
gcattttctt cccacaggtg aaaaggagg gagctgctct caggctgcgt ccagcaacag       60
tgcccaggct actaccagtc acacctagac ctggaggatc                          100

<210> SEQ ID NO 123
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
gcattttctt cccacaggtg aaaaggagg gagctgctct caggctgcgt ccagcaacag       60
tgcccaggct actaccagtc acacctagac ctggaggatc                          100

<210> SEQ ID NO 124
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 124
gcattttctt cccacaggtg gaaaaggagg gagctgctct caggctgcgt ccagcaacag    60
tgcccaggct actaccagtc acacctagac ctggaggatc                         100

<210> SEQ ID NO 125
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
gcattttctt cccacaggtg gaaaaggagg gagctgctct caggctgcgt ccagcaacag    60
tgcccaggct actaccagtc acacctagac ctggaggatc                         100

<210> SEQ ID NO 126
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
gcattttctt cccacaggtg gaaaaggagg gagctgctct caggctgcgt ccagcaacag    60
tgcccaggct actaccagtc acacctagac ctggaggatc                         100

<210> SEQ ID NO 127
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
gcattttctt cccacaggtg gaaaaggagg gagctgctct caggctgcgt ccagcaacag    60
tgcccaggct actaccagtc acacctagac ctggaggatc                         100

<210> SEQ ID NO 128
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
gcattttctt cccacaggtg gaaaaggagg gagctgctct caggctgcgt ccagcaacag    60
tgcccaggct actaccagtc acacctagac ctggaggatc                         100

<210> SEQ ID NO 129
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
gcattttctt cccacaggtg gaaaaggagg gagctgctct caggctgcgt ccagcaacag    60
tgcccaggct actaccagtc acacctagac ctggaggatc                                100

<210> SEQ ID NO 130
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
gcattttctt cccacaggtg gaaaaggagg gagctgctct caggctgcgt ccagcaacag           60
tgcccaggct actaccagtc acacctagac ctggaggatc                                100

<210> SEQ ID NO 131
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
gatgcagcag agcttggaag gatgcttcag ctcatcttag gctgtgctgt gaacttggcg          60
cccaatgacc tgcccctgct ggccatggag tactgccaag                                100

<210> SEQ ID NO 132
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
ggatgcttca gctcatctta ggctgtgctg tgaactgtga acagaagcaa gcctctgcgc          60
ttagatacct tcatgaaaac agaatcatcc atcgggatct                                100

<210> SEQ ID NO 133
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
gggagccccc accatccggg gggaccccga gtgtcatctc ttctacaatg agcagcagga          60
ggaggcagag cacagcatcg tcggaccag actcgtctca                                 100

<210> SEQ ID NO 134
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
tgagacgagt ctggtcccga cgatgctgtg ctctgcctcc tcctgctgct cattgtagaa          60
gagatgacac tcggggtccc cccggatggt gggggctccc                                100

```
<210> SEQ ID NO 135
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135
atatttacaa aggcaagccc cagcaatcat aaagtcatcc ctgtgtatgt aggagggcat      60
gccgctctcc accatccgcg aggtggcggt gctgaggcac                          100

<210> SEQ ID NO 136
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
agatcccccg ggagtccatc aagttggtga aaaggcttgg cgctgggcag tttggggtat      60
ccatagcagt tggacttgct gcttttgcct gtgtcctgtt                          100

<210> SEQ ID NO 137
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
ccacgcagca ggagaagcac cccacccacc acgagagggg ccagaagaag gtactttgtc      60
agcttcatca tccagttcca gttccacgag gcactgtgcc                          100

<210> SEQ ID NO 138
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
cctggcacag tgcctcgtgg aactggaact ggatgatgaa gctgacaaag taccttcttc      60
tggcccctct cgtggtgggt ggggtgcttc tcctgctgcg                          100

<210> SEQ ID NO 139
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
agtggatctc agaacctcag ggactccatc ctccctctcc agccccacaa attcatcatc      60
aacagcatgg aagcgagaaa ccaaacagct atttcaaaat                          100

<210> SEQ ID NO 140
<211> LENGTH: 100
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 140
attttgaaat agctgtttgg tttctcgctt ccatgctgtt gatgatgaat ttgttcttga      60
ggtcacactc tcagaggcca aggtggacat cccaggtgtg                          100

<210> SEQ ID NO 141
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
ggaactgttc aaggctacaa caatgatggt tctctcaaaa tgtcctgaag gcatcaagtg      60
gaaattccta gaacataaag gtccagtatt tgccccacca                          100

<210> SEQ ID NO 142
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142
gcgcccaact gcatcctcct ggccatgttc ctcgtccact acgggcatcg gtacagatat      60
ttggcagctt tagtacaggt ctttatcttc caactagcga                          100

<210> SEQ ID NO 143
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143
gggagaaatt ttaattactt gaaaaccggt attagaatca agaaggagg cttatttgaa       60 tacgtaactg cagccaacta ttttggagaa atcatggagt                          100

<210> SEQ ID NO 144
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144
gacgaggact tggaagttcc agttcctagc agatttaata gacgagtatc aggtagagtt      60
ggctttgtgg gacacagctg ggcaggaaga ttatgatcgc                          100

<210> SEQ ID NO 145
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 145
ctctgtgtcc cgtttgagaa aaaggacttt gtaggactgg acacagacag cagaatatga    60
cagataccta gcatctagca aaataatggc agctgcttac                          100

<210> SEQ ID NO 146
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
ccgccccgtc gtcgtctgcc ttcgcttcac ggcgccgagc cgcggtccga accctggaag    60
ctgtcctgaa tttcaaatac tctggaggcc cgggccacac                          100

<210> SEQ ID NO 147
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 147
aggaagcatt caagaacatc ctcacagaga tctaccgcat cgtgtcacag gtgatggggg    60
cacaggcacc aaagtccgcc aaggcaccct gaagaaggcg                          100

<210> SEQ ID NO 148
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148
gatcgcagac cgcgctgccc acgacgagtc cccggggaac aacgtggtgg ccatccgcgt    60
caccaagccc tgcacccca agaccaaagc aaaggccaaa                           100

<210> SEQ ID NO 149
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149
aaaacattta gaacgatgtg aacatcgaat catggaatcc cttgcatggc caagatgcca    60
cagatgattg tgaactggca gcagcagcag cgggagaact                          100

<210> SEQ ID NO 150
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150
tttatgccca gaacctcatc gatgataagc agtttgcaaa gcttcacaca aagatctgtg    60
actttggcct ggcccgtgtt gcagatccag accatgatca        100

<210> SEQ ID NO 151
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151
tgcagctgca attcctcgaa cgcccctgag cccaagtcct atgaaaaccc ctcctcagct        60
gagatgacct tccggaggcc cgcccaggcc ttcccggtca        100

<210> SEQ ID NO 152
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
gggagggctg ggcactatct cttcagaact gctgctctgg gtctcaatgg cctttcgccg        60
acaggtctgg ggcggagcag gcaggcgcag cccctgcag        100

<210> SEQ ID NO 153
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 153
caaccaccgc aaacacaaca ttccgcactt ctggcccaag ctgctgatga agagaagagg        60 cccccctgagc cccccggacc tccaccgccg ccacctccac        100

<210> SEQ ID NO 154
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 154
tccttgggaa ttatgggaac tgaaaaatgc tgtgataatt gcaggtccag agaccttttg        60
cctgaagatt ttgtggttta tacttacaac aaggaaggga        100

<210> SEQ ID NO 155
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 155
cgctatggat gatcgagagg atctggtgta ccaggcgaag ctggccgagc tggcccggag        60
gaagccggtg ctgccggcgc tcaccatcaa ccctaccatc        100

<210> SEQ ID NO 156

```
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
catggagcac ccagggaagc tactgtttgc tcctaacttg ctcttggaca gatggtctcc      60
cagcttgaag cccaaatatc tgagcttgtt gaacagttgg                          100

<210> SEQ ID NO 157
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157
cagaatgttt tgagctactt cgggtacttg gtaaaggggg ctatggaaag tgctgtcccc      60
ggcataggtc catctctgca gaagccattt caggagtacc                          100

<210> SEQ ID NO 158
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 158
gttcatatgg tccaactccc ccatggtcca tgctttcatt taactgaccc tgtggtgtgc      60
ccatttcgct tttgtggtga agcttctgcc gttgagcctc                          100

<210> SEQ ID NO 159
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159
agacctggac cagccagagg acgcgggctc tgaggatgag ctggaggagg ggtgctgtcc      60
ccggcatagg tccatctctg cagaagccat tcaggagta                           100

<210> SEQ ID NO 160
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160
aagttcatat ggtccaactc ccccatggtc catgctttca tttaactgac cctgtggtgt      60
gcccatttcg cttttgtggt gaagcttctg ccgttgagcc                          100

<210> SEQ ID NO 161
<211> LENGTH: 100
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 161
ggtactcctg aaatggcttc tgcagagatg gacctatgcc ggggacagca cttccctgtc    60
tcggaagtcc ggggctgggt aaaagccgtc ccgcctcctt                         100

<210> SEQ ID NO 162
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162
gtaacaggag caaatactgg gaaaatattt gccatgaagg tgcttaaaaa gtgctgtccc    60
cggcataggt ccatctctgc agaagccatt tcaggagtac                         100

<210> SEQ ID NO 163
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 163
gcctttcaga ctggtggaaa actctacctc atccttgagt atctcagtgg gagaaaactg    60
gttgtcctgg atgtttgaaa agttggtcgt tgtcatggtg                         100

<210> SEQ ID NO 164
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 164
agacctggac cagccagagg acgcgggctc tgaggatgag ctggaggagg ggtgctgtcc    60
ccggcatagg tccatctctg cagaagccat ttcaggagta                         100

<210> SEQ ID NO 165
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165
cagaatgttt tgagctactt cgggtacttg gtaaaggggg ctatggaaag tgctgtcccc    60
ggcataggtc catctctgca gaagccattt caggagtacc                         100

<210> SEQ ID NO 166
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166

```
atgcctttca gactggtgga aaactctacc tcatccttga gtatctcagt gggagaaaac    60
tggttgtcct ggatgtttga aaagttggtc gttgtcatgg                          100
```

<210> SEQ ID NO 167
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167

```
atatttatgg aagacactgc ctgcttttac ttggcagaaa tctccatggc acaaagttat    60
gccaaacgaa tccagcagcg gttgaactca gaggagaaaa                          100
```

<210> SEQ ID NO 168
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 168

```
tggggcattt acatcaaaag gggatcatct acagagacct gaagccggag tggtgctgtc    60
cccggcatag gtccatctct gcagaagcca tttcaggagt                          100
```

<210> SEQ ID NO 169
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169

```
tacccagccc cggacttccg agacagggaa gctgaggaca tggcaggagt acctggaggc    60
tcaacggcag aagcttcacc acaaaagcga atgggcaca                           100
```

<210> SEQ ID NO 170
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170

```
cctgtggtgt gcccatttcg cttttgtggt gaagcttctg ccgttgagcc tccaggtcta    60
tgtcaaacac tcctgccatg tcctcagctt ccctgtctcg                          100
```

<210> SEQ ID NO 171
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 171

```
aacaggagca atactggga aaatatttgc catgaaggtg cttaaaaagg actttgcctc     60
ccgggccaaa ctggcagttc aaaaactagt acagaaagtt                          100
```

<210> SEQ ID NO 172
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172
ctatttatgc agttagaaag agagggaata tttatggaag acactgcctg tgctgtcccc    60
ggcataggtc catctctgca gaagccattt caggagtacc                         100

<210> SEQ ID NO 173
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 173
tgtgcccatt tcgcttttgt ggtgaagctt ctgccgttga gcctccaggt actcctgcca    60
tgtcctcagc ttccctgtct cggaagtccg gggctgggta                         100

<210> SEQ ID NO 174
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 174
ccagaatgtt ttgagctact tcgggtactt ggtaaagggg gctatggaaa gggagaaaac    60
tggttgtcct ggatgtttga aaagttggtc gttgtcatgg                         100

<210> SEQ ID NO 175
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175
atggaaaggt ttttcaagta cgaaaagtaa caggagcaaa tactgggaaa atatttcatg    60
gccagagcag ctcgcctctc aggtgctgaa ccagatgatg                         100

<210> SEQ ID NO 176
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 176
acctggacca gccagaggac gcgggctctg aggatgagct ggaggagggg attccaaatc    60
ctttatttga tctggctgga ataacgtgtg gacactttct                         100

<210> SEQ ID NO 177
<211> LENGTH: 100

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177
acctggacca gccagaggac gcgggctctg aggatgagct ggaggagggg gactttgcct       60
cccgggccaa actggcagtt caaaaactag tacagaaagt                            100

<210> SEQ ID NO 178
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
gaaagtgtcc acacgttatt ccagccagat caaataaagg atttggaatc ccctcctcca       60
gctcatcctc agagcccgcg tcctctggct ggtccaggtc                            100

<210> SEQ ID NO 179
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179
ctggaccagc cagaggacgc gggctctgag gatgagctgg aggaggggga ctttgcctcc       60
cgggccaaac tggcagttca aaaactagta cagaaagttg                            100

<210> SEQ ID NO 180
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180
cctggaccag ccagaggacg cgggctctga ggatgagctg gaggaggggg actttgcctc       60
ccgggccaaa ctggcagttc aaaaactagt acagaaagtt                            100

<210> SEQ ID NO 181
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181
acctggacca gccagaggac gcgggctctg aggatgagct ggaggagggg gactttgcct       60
cccgggccaa actggcagtt caaaaactag tacagaaagt                            100

<210> SEQ ID NO 182
<211> LENGTH: 83
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 182
cgcgggctct gaggatgagc tggaggaggg ggactttgcc tcccgggcca aactggcagt    60
tcaaaaacta gtacagaaag ttg                                            83

<210> SEQ ID NO 183
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183
agtaacagga gcaaatactg ggaaaatatt tgccatgaag gtgcttaaaa agtgctgtcc    60
ccggcatagg tccatctctg cagaagccat ttcaggagta                         100

<210> SEQ ID NO 184
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 184
tgattgacac tctgcagcac caagtgaaat ctctggagca acagctggcc gtggggcttg    60
gcccggccca gtcctggcct ctgccaccag gtgtcaccga                         100

<210> SEQ ID NO 185
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185
tacgggacag aattgaatca gggagatatg aagcctccaa gctatgattc tgtgtaccgc    60
cggaagcacc aggagctgca agccatgcag atggagctgc                         100

<210> SEQ ID NO 186
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 186
tacgggacag aattgaatca gggagatatg aagcctccaa gctatgattc tgtgtaccgc    60
cggaagcacc aggagctgca agccatgcag atggagctgc                         100

<210> SEQ ID NO 187
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187

```
tagacctgga caccttatta aagaactttc taaagtaatt cgagcaatag agaaaacact    60
tggtagacgg gactcgagtg atgattggga gattcctgat                         100
```

<210> SEQ ID NO 188
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188

```
gacctggaca ccttattaaa gaactttcta agtaattcg agcaatagag aaaacacttg     60
gtagacggga ctcgagtgat gattgggaga ttcctgatgg                         100
```

<210> SEQ ID NO 189
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 189

```
ctgaaaagga aaatctgcaa agaactttcc tgcttacaac ctcaagtaaa aaaacacttg    60
gtagacggga ctcgagtgat gattgggaga ttcctgatgg                         100
```

<210> SEQ ID NO 190
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 190

```
tgcaggtcct gcatccaatg gatgctgccc agagatcgca gcatatcaaa gacttgatta    60
gagaccaagg atttcgtggt gatggaggat caaccacagg                         100
```

<210> SEQ ID NO 191
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191

```
ttggacaaag ggtggatgaa attgatgctg ctattcagag atcacaacag gacttgatta    60
gagaccaagg atttcgtggt gatggaggat caaccacagg                         100
```

<210> SEQ ID NO 192
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192

```
cagagaaggc tttggatacc ctaaacaaag ccattgtcat tgatcccaag gatttcgtgg    60
tgatggagga tcaaccacag gtttgtctgc taccccccct                         100
```

<210> SEQ ID NO 193
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193
accaagccag ccaattctgt cttcaccacc aaatggattt ggtattggaa gaatgaaaac      60
acttggtaga cgggactcga gtgatgattg ggagattcct                          100

<210> SEQ ID NO 194
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194
ttcacctgtc cagcatccga ccaccgaggc tggaggggga gaacacccag gacttgatta      60
gagaccaagg atttcgtggt gatggaggat caaccacagg                          100

<210> SEQ ID NO 195
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195
gtcaatattg atgacttgat tagagaccaa ggatttcgtg gtgatggagg cacccagttg      60
gagaagctga tggagaacat gcgcaatgac attgccagtc                          100

<210> SEQ ID NO 196
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196
cacctgtcca gcatccgacc accgaggctg gagggggaga cacccagga cttgattaga      60 gaccaaggat ttcgtggtga tggaggatca accacaggtt                          100

<210> SEQ ID NO 197
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 197
ggctttcaca agtacagtct acaaaaagac ctgctagagc cattattgcc ccggaaactg      60
cctgtgggtt tttactgcaa cttttgaagat ggcttctgtg                         100

<210> SEQ ID NO 198
<211> LENGTH: 100
<212> TYPE: DNA

<213> ORGANISM: Artificial Sequence
<220> FEATURE:
<223> OTHER INFORMATION: Description of Artificial Sequence: Synthetic
    polynucleotide

<400> SEQUENCE: 198 gagggtctc aggtcctgct cacgagctcc aatgagatgg gtactgttag gttgaagatg    60
cccagcacag acacgccgtg ggaccgcatc atggtgttct                         100

<210> SEQ ID NO 199
<211> LENGTH: 100
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 199
acgaggggtc tcaggtcctg ctcacgagct ccaatgagat gggtactgtt aggttgaaga    60
tgcccagcac agacacgccg tgggaccgca tcatggtgtt                         100

<210> SEQ ID NO 200
<211> LENGTH: 100
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 200
ttcctgtgga acgttttcca gagggtcgat aaagacagga gtggagtgat atcagacagc    60
acttgaagag ggtgcagctg cgggagctgt cggaagcaga                         100

<210> SEQ ID NO 201
<211> LENGTH: 100
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 201
acctctatgc tgagggtgt gaggctctag tagtgaagaa gctacaagaa caggcaaatg    60
tgcaatacca acatgtctgt acctactgat ggtgctgtaa                         100

<210> SEQ ID NO 202
<211> LENGTH: 100
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 202
cggaggctcc gggcaccccc gagggccccg agcccgagcg ccccagcccg ggggttggct    60
gtgttccggc cgcagagcac cgtctgcgtg aggagatcct                         100

<210> SEQ ID NO 203
<211> LENGTH: 100
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 203
gtggttacag caccatcagt aggtacagac atgttggtat tgcacatttg ccgtccgccc    60
aggtgctgag agggagcagg gcgcgggtcg gcgggcgcga                          100

<210> SEQ ID NO 204
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204
gaatgtctaa aagagtatac aaatcctgaa caaattaagc aatggagaaa gaattctggg    60
tcatgaacac ctcaattcag agcacgatca ttcttctcat                         100

<210> SEQ ID NO 205
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205
ttcccatttc tgaagaatct gaagagctgg atcagaagac attcagcatt gaattctggg    60
tcatgaacac ctcaattcag agcacgatca ttcttctcat                         100

<210> SEQ ID NO 206
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 206
aatgagaaga atgatcgtgc tctgaattga ggtgttcatg acccagaatt ctttctccat    60
tgcttaattt gttcaggatt tgtatactct tttagacatt                         100

<210> SEQ ID NO 207
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 207
gggatgcata atggccgagc tgttgactgg aagaacattg tttcctggta aaacttcagt    60
caagaagctg acaaaaaagg acatcgagga tacactgtca                         100

<210> SEQ ID NO 208
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208
gtcctggccc acaggctgcc attcaatgca atacgtcatg ctctgagccc gggctgccgg    60

```
ctgcgccact gggtcctggg gtcctggggg ctggggcttc                           100
```

<210> SEQ ID NO 209
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209

```
ccactggttc tgtgtgggtg tcggcaggaa tgtgccacgt ctggttcagg gatccggggc    60
tgccggctgc gccactgggt cctgggtcc tggggctgg                            100
```

<210> SEQ ID NO 210
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210

```
cccttcacct ttaaacctct ttatcaaagt ggcttcactg cgatcctgac gggaattttg    60
tctgcaaggt gagaggcagt gttaaggatg atgagtccac                          100
```

<210> SEQ ID NO 211
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211

```
ctgctggtga agttcccac ggaaatgaga gggaattttg tctgcaaggt caggatcgca    60
gtgaagccac tttgataaag aggtttaaag gtgaaggggt                          100
```

<210> SEQ ID NO 212
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212

```
tctcccaaaa ttcacatcca ataaacagcc tgcagccccg agtgacatat gtccggtaca    60
aagccaaatt gatcgggatt gatgaagttt ccgcagctcg                          100
```

<210> SEQ ID NO 213
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 213

```
ctgctgatcc acatgagagt ccactctggg gagaagccca acaagtgtac ggggttggct    60
gtgttccggc cgcagagcac cgtctgcgtg aggagatcct                          100
```

```
<210> SEQ ID NO 214
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 214
gatacaggtc ttggactggc cttcaccatt gcccatgagt ctggacacaa gggttggctg      60
tgttccggcc gcagagcacc gtctgcgtga ggagatcctg                           100

<210> SEQ ID NO 215
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 215
ctttagcaac gccaaatgga gatgttttga tccgagacct taattttgaa tcacaatatg      60
gagcttccgt ttctgccaag cctgaactac ccctctttta                           100

<210> SEQ ID NO 216
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 216
tctgccggac ctcctcttcg atctcctcca gcgtgccctc ctcgatggcc caacctcatt      60
gactcccccg ggcatgtcga cttctcctcg gaggtgactg                           100

<210> SEQ ID NO 217
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 217
attcagccct gacttctcaa aaagcactgc acagaggagg aggcagcaga accccatgga      60
ctacaagtgt ggctccccca gtgactcctc cacgactgag                           100

<210> SEQ ID NO 218
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 218
aattctccct gacttctcaa aaagcactgc acagaggagg aggcagcaga accccatgga      60
ctacaagtgt ggctccccca gtgactcctc cacgactgag                           100

<210> SEQ ID NO 219
<211> LENGTH: 100
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 219
gagatgatgc cccccgggct gtcttcccct ccattgtggg ccgccctcgc caccaggagc    60
tgcaagccat gcagatggag ctgcagagcc ctgagtacaa                          100

<210> SEQ ID NO 220
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 220 atgcccccg ggctgtcttc ccctccattg tgggccgccc tcgccaccag tgatggaagg     60
ccacggggaa gtgaatatta agcattatct aaactgcagt                          100

<210> SEQ ID NO 221
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221
tgatgccccc cgggctgtct tcccctccat tgtgggccgc cctcgccacc agtgatggaa    60
ggccacgggg aagtgaatat taagcattat ctaaactgca                          100

<210> SEQ ID NO 222
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 222
atgaagtgac accccagct acatccgagg aggttctagg acctgctacg agctgactat     60
agcactagtg aaatgctggt caacatggga aacttgcctc                          100

<210> SEQ ID NO 223
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 223
attctaacac tccggccgct gcctccggct gctgtagctt attattaatg ctggctctcg    60
gctgcgggga tgccagactc gagctcgcac agcgcgcgga                          100

<210> SEQ ID NO 224
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 224
ctggacaggg ctgaaggtga ggctgattcg ctgtgacttc gaattgcatc caagcagcgg    60
ggactcctca gggcaggcgg gcagcgacag tgcggtggtg                         100

<210> SEQ ID NO 225
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 225
aaaaatctca tccaagaagc cctaacgtgt tatctgtcgc tttgagtcaa agagatctga    60
aactggacaa tgtcctgttg gaccacgagg gtcactgtaa                         100

<210> SEQ ID NO 226
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 226
cgaagtctgc cagtttacag tgaccctcgt ggtccaacag gacattgtcc agtttcttta    60
tgtatgtggg taggagatgg agatgcaatc aatattttaa                         100

<210> SEQ ID NO 227
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 227
gatgatctct caactttaac tggaaagtct aggttgttgg cagaagatat gcccgagcac    60
aaccctggca atttgggagg aacaatgaga ctgggaataa                         100

<210> SEQ ID NO 228
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 228
ataaattctt tgctgacctg ctggattaca tcaaagcact gaatagaaat agtgatagag    60
tttgcaagaa actgccttaa cttgaaagat gctgattcca                         100

<210> SEQ ID NO 229
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 229
gcactgaata gaaatagtga tagatccatt cctatgactg tagattttat ggtgatgttc    60
cttttataga agaaagacac agacatcggt tcgaggtaaa 100

<210> SEQ ID NO 230
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230
gatgatctct caactttaac tggaaagaat gtcttgattg tggaagatat gcccgagcac 60
aaccctggca atttgggagg aacaatgaga ctgggaataa 100

<210> SEQ ID NO 231
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231
gattacatca aagcactgaa tagaaatagt gatagatcca ttcctatgac tgatagagtt 60
tgcaagaaac tgccttaact tgaaagatgc tgattccaca 100

<210> SEQ ID NO 232
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 232
ggacagaatc caggagtcct ccagctgaga acgaggtgtc caccccatg caggataatg 60 ctgactacag attatttcag aaaacactca aattgtgtcg 100

<210> SEQ ID NO 233
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233
ccaactcacc caagtgcaat tcgtggagga ggtgcatttg ttcagaacag aggattgatt 60
gctggtgttg tctcaatatc aacagcactg ttattactac 100

<210> SEQ ID NO 234
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 234
gcactgaaag aagctaaaga aaatgcatct cgtgatcgca aacgctatca gcaagagtac 60
acactcctca tttggatagg cttgtaagtg cccgaagtgt 100

<210> SEQ ID NO 235

```
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 235
gtatgcagga cttcaacacc atgtttacaa attgttacat ttataacaag ttccagggga      60
agtggtatgt ggtaggcctg gcagggaatg caattctcag                          100

<210> SEQ ID NO 236
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 236
cattgtccat ggcaaaacag gacatcttat ggcctgcttt acatgtgcaa tagttcctaa      60
taagagcaac aatgaaatta tcctggtttt gcagcacttt                          100

<210> SEQ ID NO 237
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 237
catgcctact agcctcccta accttgccaa ggaggcaaag gatgccaagg tggagcagcg      60
tgacttcatt ggagtggaca gcacaggaaa gaggctgctc                          100

<210> SEQ ID NO 238
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 238
aacgccacag catcaaggat gtgcacgccc ggctgcaagc cctggcccag aagatccctt      60
acaatacctg agaggtcttg ttgcccgtgc ccttgcaata                          100

<210> SEQ ID NO 239
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 239
acttcagatc cgtggcggag acaagccagc cttggacttg tatcagctgt ttggtatctt      60
actacacagc ctattccagg cctctcaact gtgattaatg                          100

<210> SEQ ID NO 240
<211> LENGTH: 100
<212> TYPE: DNA
<213> ORGANISM: Artificial Sequence
<220> FEATURE:
```

```
<223> OTHER INFORMATION: Description of Artificial Sequence: Synthetic
      polynucleotide

<400> SEQUENCE: 240
gtggaagcaa ccactaatat aaacacctcc catgtatagg aaggctggag cgtttgggaa      60
ggtggttgaa ggaacagcct atggattaag ccggtcccaa                          100

<210> SEQ ID NO 241
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 241
ggtcaatttt ggaaacacat gctactgtaa ctccgtgctt caggcattgt cctggttgtc      60
atttggaaac agaaaccgag gtatgaaatt cgctggaggg                          100

<210> SEQ ID NO 242
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 242
acatgaagta caaagcagtg agtgtcaacg aaggctataa agtctgtgag aggggttggc      60
tgtgttccgg ccgcagagca ccgtctgcgt gaggagatcc                          100

<210> SEQ ID NO 243
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 243
aatcaaacag aggccgcatg ctggggccgt acagttccac aaaggcatcc tcatgggctc      60
agcggtcatg ttttcgcttg aacgccttgt cggcttctgt                          100

<210> SEQ ID NO 244
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 244
catgttatcc accaacatcc tgctggtcaa cctgctggtc gccatgtttg ggaatttgaa      60
gcctacatta atgcttctgg agaacatgga attgtggttt                          100

<210> SEQ ID NO 245
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 245
```
cacagtcttt tacttgtccc tattgtggaa aaatgggcta tacggagaca gtaccctgag    60
tgaggaaatg agtcaatttg atttctcaac cggagttcag                         100

<210> SEQ ID NO 246
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 246
aaacagaaga ggaagcatat gcactgaaga aaatatccta tcaacttaag aaacagatga    60
ttatgctgag attatagatg aagaagatac ttacaccatg                         100

<210> SEQ ID NO 247
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 247
accatcgccg accagatcac cctcctcaag gctgcctgcc tggacatcct gcgcgagctt    60
cggcctcggc tctgtaccat gaagaagggc cccagtggct                         100

<210> SEQ ID NO 248
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 248
acaaggggct ggacacggag acctgggtgg aggtggcctg gtgtgagctg cagaggaaga    60
tggatggccg agagtaccca gacgcacagg gctttgctgc                         100

<210> SEQ ID NO 249
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249
atcgcccact ccagaagtag catggaaatg gagggcatct tcaaccacaa aggggttggc    60
tgtgttccgg ccgcagagca ccgtctgcgt gaggagatcc                         100

<210> SEQ ID NO 250
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 250
ccgcttgcag cggggacgcg aggacccggg ctgggctttc ctcacccggg ggttggctgt    60
gttccggccg cagagcaccg tctgcgtgag gagatcctgg                         100

<210> SEQ ID NO 251
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251
ctcacagacc gtgttcttct gcgccgtgcc tgggaacttg acaatcatcc ggctcatcct        60
gtaaggagag cgtcttgtag tctgatcaaa tcgcaagtac                            100

<210> SEQ ID NO 252
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 252
tcctcacacc tgctcctcag ctcccggttc tcctcctgtg tcgcctttac gtcggtggac        60
gtcacggtaa ggacacggtc caggtcctcc accagctgct                            100

<210> SEQ ID NO 253
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 253
gccgcgccct cccagaggcc caccttcaag cagctggtgg aggacctgga actggggaag        60
atcatggaca ggttcgaaga ggttgtgtac caggccatgg                            100

<210> SEQ ID NO 254
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 254
agcagctggt ggaggacctg gaccgtgtcc ttaccgtgac gtccaccgac gtaaaggcga        60
cacaggagga gaaccgggag ctgaggagca ggtgtgagga                            100

<210> SEQ ID NO 255
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 255
cgccctccca gaggcccacc ttcaagcagc tggtggagga cctggaccgt gtccttctcc        60
gacctcttca gcgtttttga gaaacagaaa gaggtgatcg                            100

<210> SEQ ID NO 256
<211> LENGTH: 100

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 256
gagggccacc gcatggacaa gcccgccaac tgcacacacg acctgtacat gatcatggac    60
aggttcgaag aggttgtgta ccaggccatg gaggaagttc                         100

<210> SEQ ID NO 257
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257
gtacgcccag tccctgggtg ccgagacctg cccccctgcct agtttccagg accccaaccc   60
gtgcctcagc accccctgca agaacgccgg gacatgccac                        100

<210> SEQ ID NO 258
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 258
ggttggccct gtgatccctc aagactggtc cacggagtgt atgaccacaa acagccagtc    60
caccagctgg tgaaggaacc ttcaactcct gccttctcgt                        100

<210> SEQ ID NO 259
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 259
gaatatcttg ataaatgagc agtcagcaga acttgtacat atagatctag accaactctt    60
gcgtaaaaag agaagaattt ttatccattc agtgggtgca                        100

<210> SEQ ID NO 260
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 260
aagagagaaa gagtggattt cagcctgcac ggatggtctt gaaacacaaa tggtctgctt    60
gagaaactta agaacaaga gtgtgatgtg aaggattatg                         100

<210> SEQ ID NO 261
<211> LENGTH: 100
<212> TYPE: DNA
<213> ORGANISM: Artificial Sequence
<220> FEATURE:
<223> OTHER INFORMATION: Description of Artificial Sequence: Synthetic
```

```
                        polynucleotide

<400> SEQUENCE: 261
acagaattca tacgagaagg cgacgatgac cggactgtgt gccgggagat ccgccgcgcc    60
tagtgggagg ccccatggac gccagcgtgg aggaggaggg                         100

<210> SEQ ID NO 262
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 262
cagaattcat acgagaaggc gacgatgacc ggactgtgtg ccgggagatc cgcctagggg    60
tctgtaccgg gctggcctgt gcctatcacc tcttatgcac                         100

<210> SEQ ID NO 263
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 263
ggacctaggg gaggattacc cctctggcaa gaagcgtgcg gggaccgatg gtgcctatga    60
tcagaagcca caagtgggaa tgaggccctc caaccccccc                         100

<210> SEQ ID NO 264
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 264
agttcaggaa gtggatgaaa tggtatggaa aaaagcatgc agaatacaca gtggagattc    60
tggacgcaaa gacaagggag aagctgtgtt tcttggacaa                         100

<210> SEQ ID NO 265
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 265
agttcaggaa gtggatgaaa tggtatggaa aaaagcatgc agaatacaca gtggagattc    60
tggacgcaaa gacaagggag aagctgtgtt tcttggacaa                         100

<210> SEQ ID NO 266
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 266
```

```
atcaacgaaa tgcacctttt aatccagcag gcccgagaga tgcccctgct caaggcctgg    60
catgcgtggg cagtgatgaa cttcgaagct gtgctacact                         100

<210> SEQ ID NO 267
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 267
tccattagag atggctctgg cgttggtgtt ttcaaaatag gtgaagagac aggcagttgg    60
agcagaactt tttcaactgc agctgtgaca tccgctggat                         100

<210> SEQ ID NO 268
<211> LENGTH: 96
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 268
gtccctcagg cggccaccca gtgggcacac tcccaggcgg cgctccggcc ccgagaacct    60
cgaagacatc ggcagaaact agatgatcag accaag                              96

<210> SEQ ID NO 269
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 269
aggcacactc aaacaacgac tggtcctcac tcacaactga taaggcttcc cagcctctga    60
agtatctcct gggcattggg ctccttgcag agaggcttga                         100

<210> SEQ ID NO 270
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 270
gctgtggcct tcatgtcctg tgccccagag atctgcccct cccacccgag ggaaattcaa    60
ctactgagga ggttacggca caaaaatgtc atccagctgg                         100

<210> SEQ ID NO 271
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 271
gagtacgaac cggccaagag gttctccatc cggcagatcc ggcagcacag gtccccgtc    60 atgcgtgccc ggaagagcag cttcaacgtg agtgatgtgg                         100
```

<210> SEQ ID NO 272
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 272
ccggcccaga gcaaggaagt gttatcattc cagccacctc caccacctgc tgctccatcg      60
cagcttcgct ctgtgatgct aatcttcttc accatatgga                          100

<210> SEQ ID NO 273
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 273
aagaagtggc catgcgcaag ctggtgcgct cagtgactgt ggttgaggac acagcaggat      60
gattgagaat aacaacctga gtgcttctcc cagggcgtgg                          100

<210> SEQ ID NO 274
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 274
ggaaaatata taccatgatc tacaggaact tggtagtagt caatcagcag gctggagcac      60
ctggagaagc aggtcagact gctcaacatc cgtctcaacc                          100

<210> SEQ ID NO 275
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 275
tggagaggca aggtcagtta ccaggactac gagattgaga tttcggatgc ttcagactgt      60
cccggaccca gcagctcata tcaaggaagc cttatcagtt                          100

<210> SEQ ID NO 276
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 276
ctgaaacaat tgaggattct agtaatcaag cagcagccag agaatgggag tggaagcaag      60
caatttcttc aaccgtcctt ggaaaagtaa tagttcaacc                          100

<210> SEQ ID NO 277
<211> LENGTH: 100
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 277
tgctctggtg gatatgtttg ttttagccag tccatccaag acaatcccac cgctgtcctg    60
ccttcgagag ggcagctccc actggagatc caagtacctg                         100

<210> SEQ ID NO 278
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 278
ggtccgaatc agtggtggga acgacaaaca aggtttcccc atgaagcagg gaaattcttt    60
ggaagaagtg gtccatgctg atcagagctc ctgcactttt                         100

<210> SEQ ID NO 279
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 279
gaggaggcac ggtctcggtg gggcccgaga ggccggcggg gcctcccggg aggaaaacta    60
ctgtcgaaat cctcgagggg aagaaggggg accctggtgt                         100

<210> SEQ ID NO 280
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 280
ccctgaacca ctccactgcc tttaaccctc agcctcagag tcagatgcag ggatgaaaat    60
gggataaata gaccagtctg ttcctatgtt aaaccacttc                         100

<210> SEQ ID NO 281
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281
acgcccagtc cctgggtgcc gagacctgcc ccctgcctag tttccaggtg aactcctccc    60
tcacctcccc gacggggcga ggctccatgg ctgcccctc                          100

<210> SEQ ID NO 282
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 282
caagacgttg acttggatct gtcaggtgaa gtcctaaagc ttgcattcca cctggaaacg    60
gtggcctcca acgccgctcc cccctcccgg gaatggaggc                         100

<210> SEQ ID NO 283
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 283
aggtctttga gcttcttcac tgactccaga gaaaaggaga aatttccatc ctgccgcgcc    60
gcgctcctca cacccgcttt cacctccggg cggggcaggg                         100

<210> SEQ ID NO 284
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 284
gtgtgatggc gtgtcacact gccccggcgg ggaggacgag aatcggtgtg acccagtcat    60
ggcagcctcc agcatcagtt caccatgggg aaagcatgtg                         100

<210> SEQ ID NO 285
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 285
gactggaacg agaactacgg gcgggcggcc tgcagggaca tgggctataa gaaagcatgt    60
gttcaaagcc attctgatgg tcctagtggc ccttatcctc                         100

<210> SEQ ID NO 286
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 286
cgtcgtctgc acgcagccca atccccatc cgggacagtg tgcacctcaa aaaacacttg    60
gtagacggga ctcgagtgat gattgggaga ttcctgatgg                         100

<210> SEQ ID NO 287
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 287
gaaagcgggc gagcagcagt tgagcgagcc cgaggacatg gagatggaag gaccccgca     60 gcaaacacaa gtttaagatc cacacgtact ccagccccac                          100

<210> SEQ ID NO 288
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 288
tgcaatgacg agggcctgga gtgtgtgccc actgaggagt ccaacatcac catgcagacc    60
gggtacaaca agctctgtga ttggtggtcg cttggggtga                         100

<210> SEQ ID NO 289
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 289
tgcaatgacg agggcctgga gtgtgtgccc actgaggagt ccaacatcac catgcagacc    60
gggtacaaca agctctgtga ttggtggtcg cttggggtga                         100

<210> SEQ ID NO 290
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 290
gcagcagcag cagcagcagc agca                                           24

<210> SEQ ID NO 291
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 291
gcagcagcag cagcagcagc agcagca                                        27

<210> SEQ ID NO 292
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 292
catgactgca gcttctttca agaactcttc cacctccatg gtgtcctcct gaagctgagc    60
ttcactcttg ggatccagtg gtcttttata aagcaaatgc                         100

<210> SEQ ID NO 293
<211> LENGTH: 100
<212> TYPE: DNA
<213> ORGANISM: Artificial Sequence
<220> FEATURE:
<223> OTHER INFORMATION: Synthetic polynucleotide

```
<400> SEQUENCE: 293
ggacgactcc gtgtttgccc acgacctgct gcccccggcc ccacccagca actcaaattc    60
accacctcgg actcctgcga ccgcatcaaa gacgaatttc                          100

<210> SEQ ID NO 294
<211> LENGTH: 92
<212> TYPE: DNA
<213> ORGANISM: Artificial Sequence
<220> FEATURE:
<223> OTHER INFORMATION: Synthetic polynucleotide

<400> SEQUENCE: 294
tgtcggcgcc tttcgagcag tactccccgg gtggccagga caccccagc aactcaaatt     60 caccacctcg gactcctgcg accgcatcaa ag                                  92

<210> SEQ ID NO 295
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 295
tgtcggcgcc tttcgagcag tactccccgg gtggccagga caccccagc aactcaaatt     60 caccacctcg gactcctgcg accgcatcaa agacgaattt                          100

<210> SEQ ID NO 296
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 296
gcagctggtg gaggacctgg accgtgtcct taccgtgacg tccaccgacg gctcctcgca    60
cctaccccag caactcaaat tcaccacctc ggactcctgc                          100

<210> SEQ ID NO 297
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 297
tgaaaaggat aatatagttg atcaaacaa aaacaacaca atttgtcccg gtcatagctc     60
cttggaatca ccaacaaaca tgccttctcc ttctcctgat                          100

<210> SEQ ID NO 298
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 298
cgatggctct ggatccttgt ccccaccatg cgaccatctg cagccagaac acgaaagcgt    60
ggtagatgaa cgcccagccg cggggtctct ccagcacgtt                          100

<210> SEQ ID NO 299
<211> LENGTH: 100
```

```
<212> TYPE: DNA
<213> ORGANISM: Artificial Sequence
<220> FEATURE:
<223> OTHER INFORMATION: Synthetic polynucleotide

<400> SEQUENCE: 299
agttggtaga agacttggat cgaattctca ctctcacaac caatgaggaa acaaatacgc        60
agattgcttg gccatcaaaa ctgaagatcg gagccaaatc                             100

<210> SEQ ID NO 300
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 300
agatcttcac tttaggggc tcgccctacc cagggattcc cgtggaggaa acaaatacgc         60
agattgcttg gccatcaaaa ctgaagatcg gagccaaatc                             100

<210> SEQ ID NO 301
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 301
gatcatcgaa ttctccaaaa tggcccgaga cccccagcgc taccttgtca ttcaggttgg        60
acaagccctc tgaaagttac tcccttacaa cctcatcatg                             100

<210> SEQ ID NO 302
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 302
gagtggttct cagcaggttg aacaacctac tggctctgtc ctctggatgg aattagagaa        60
taaaatccca gcacgatgtt cctcactgga gacaccagtc                             100

<210> SEQ ID NO 303
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 303
ttggctatgt gtggggagca gtcactcaca gtttcatcct tctccatctg gatcggcctc        60
cgaccgtaac tattcggtgc gttgggcagc gccccgcct                              100

<210> SEQ ID NO 304
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 304
agaggtttag cattgctgct ttctcttcaa agcctccacc aggtcattct ccacctggat        60
```

```
cggcctccga ccgtaactat tcggtgcgtt gggcagcgcc                          100
```

<210> SEQ ID NO 305
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 305

```
ttggctatgt gtggggagca gtcactcaca gtttcatcct tctccatctg gtcttctagg     60
aagcggctgc tgccctagac gctggctcct cagtagcatc                          100
```

<210> SEQ ID NO 306
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 306

```
tgctgcagaa tcaagctata gaagtggtct ggagtcacca gcctgcattc acaccgagta     60
gtgcatcgcg atctaaaacc acagaacatt ctggtgacca                          100
```

<210> SEQ ID NO 307
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 307

```
gcagctggtg gaggacctgg accgtgtcct taccgtgacg tccaccgacg tgattgatga     60
gatttatcgt gtgttgagat atgtcaattc taccagagcc                          100
```

<210> SEQ ID NO 308
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 308

```
acgacctgct gccccggcc ccacccagca gtggggctc gcggacgtga ttgatgagat      60
ttatcgtgtg ttgagatatg tcaattctac cagagcccct                          100
```

<210> SEQ ID NO 309
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 309

```
cagaggccca ccttcaagca gctggtggag gacctggacc gtgtccttac cgtgactgtt     60
ctcaggcgtg aaatttctga gcttcgcacc aaagtgcaag                          100
```

<210> SEQ ID NO 310
<211> LENGTH: 94
<212> TYPE: DNA
<213> ORGANISM: Artificial Sequence
<220> FEATURE:
<223> OTHER INFORMATION: Synthetic polynucleotide

<400> SEQUENCE: 310 cttgcactttggtgcgaagctcagaaatttcacgcctgagaacagtcacggtaaggacac 60 ggtccaggtcctccaccagctgcttgaaggtggg 94

<210> SEQ ID NO 311
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 311 ccaactgcacacacgacctgtacatgatcatgcgggagtgctggcatgccgccctcaac 60 gagctcatgaagtacttcaagaattaagggatatatcctc 100

<210> SEQ ID NO 312
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 312 tgcacacacgacctgtacatgatcatgcgggagtgctggcatgccgcgccctcccaaggt 60 gattgatgagatttatcgtgtgttgagatatgtcaattct 100

<210> SEQ ID NO 313
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 313 aggggctctggtagaattgacatatctcaacacacgataaatctcatcaatcacgtcggt 60 ggacgtcacggtaaggacacggtccaggtcctccaccagc 100

<210> SEQ ID NO 314
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 314 cccgccaactgcacacacgacctgtacatgatcatgcgggagtgctggcaatggagtact 60 ttgatgaaaagattgttccaattttaaagaggaaattacc 100

<210> SEQ ID NO 315
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 315 ggccttcgtgaacgtgggggacctgtccaagcacatcatcattcacactgcattaataat 60 aagctacagcagccggaggcagcggccggagtgttagaat 100

<210> SEQ ID NO 316

```
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 316
cccgcgccgg ggttccccgg gtccgagcgg atggcgactg cagccagccc ggtcagtggg    60
acagcatgga agaatacacc tgtatgatcc ctcgggacac                         100

<210> SEQ ID NO 317
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 317
catgtgcaaa gcaggcttcg aggccgttga gaatggcacc gtctgccgag tcccggccag    60
tgtgcagctg cacacggcgg tggagatgca ccactggtgc                         100

<210> SEQ ID NO 318
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 318
cctggccaca ggttgtcttt tgcccagcag actgcctgat gaccttcagg ggggcaacgt    60
agccatcagt ctcagagggc aggggtactg tggggtcctc                         100

<210> SEQ ID NO 319
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 319
ccctctgaga ctgatggcta cgttgccccc ctgacctgca gccccagcc ctgctgggca     60 aaagacaacc tgtggccagg gtctggaagg gccctgggag                         100

<210> SEQ ID NO 320
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 320
gacaaagaat actataaagt aaaagaacct ggtgaaagtc ccatattctg attgtgcgac    60
ggggaatgcc tcccggagga ggaggcgaag tggttttctc                         100

<210> SEQ ID NO 321
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 321
acttttgaag aataatggaa gattaccaag accagatgga tgcccagatg aggatagaat    60
```

```
ttttgcggca tttgaagagc tttttccaga ttatgtttaa                          100
```

<210> SEQ ID NO 322
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 322

```
ctactgagga gccagcgtct agggcagcag ccgcttccta aagaccagg atattgaggc      60 aacaatgaac tcggccctga atgagctacg ggaactagaa                          100
```

<210> SEQ ID NO 323
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 323

```
aggcggggc gctgcccaac gcaccgaata gttacggtcg gaggccgatc caggatattg      60
aggcaacaat gaactcggcc ctgaatgagc tacgggaact                          100
```

<210> SEQ ID NO 324
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 324

```
gcagctggtg gaggacctgg accgtgtcct taccgtgacg tccaccgacg taaaggcgac     60
acaggaggag aaccgggagc tgaggagcag gtgtgaggag                          100
```

<210> SEQ ID NO 325
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 325

```
cgcgggcccc cgacgcgctg cagccggcag cccaccgccg ccttcttggc tgtgttccgg     60
ccgcagagca ccgtctgcgt gaggagatcc tggccaagtt                          100
```

<210> SEQ ID NO 326
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 326

```
ggtgcgaggg cagcagcctc tacaaacacc tgcatgtcca ggagaccaag gaaaagccat     60
ggagacttca gcatcctcct cccagcctca ggacaacagt                          100
```

<210> SEQ ID NO 327
<211> LENGTH: 100
<212> TYPE: DNA
<213> ORGANISM: Artificial Sequence
<220> FEATURE:

<223> OTHER INFORMATION: Synthetic polynucleotide

<400> SEQUENCE: 327
ggccggcgcc ggcgccggcg ccgcggcctc ttcggctgcg gaccctgcca ttccggatat    60
tgactgttca agtactatta tgctggacaa tattgtgagg                          100

<210> SEQ ID NO 328
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 328
atttgagctc accagtggga gggtcttata atcttccctc tcttccggat gtgtggaata    60
tcaaacaaat gattaagttg acacaggaac atatagaggc                          100